(12) United States Patent
Disney

(10) Patent No.: US 9,260,476 B2
(45) Date of Patent: *Feb. 16, 2016

(54) RNA TARGETING COMPOUNDS AND METHODS FOR MAKING AND USING SAME

(71) Applicant: The Research Foundation for The State University of New York, Amherst, NY (US)

(72) Inventor: Matthew David Disney, Jupiter, FL (US)

(73) Assignee: The Research Foundation for The State University of New York, Amherst, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/073,069

(22) Filed: Nov. 6, 2013

(65) Prior Publication Data

US 2014/0212945 A1  Jul. 31, 2014

Related U.S. Application Data

(63) Continuation-in-part of application No. 12/072,291, filed on Feb. 25, 2008, which is a continuation-in-part of application No. PCT/US2008/002438, filed on Feb. 25, 2008.

(60) Provisional application No. 61/723,145, filed on Nov. 6, 2012, provisional application No. 61/004,389, filed on Nov. 27, 2007, provisional application No. 60/903,212, filed on Feb. 23, 2007.

(51) Int. Cl.
| | |
|---|---|
| C07K 4/00 | (2006.01) |
| C07K 5/08 | (2006.01) |
| C07K 14/00 | (2006.01) |
| C07K 7/06 | (2006.01) |
| C07K 7/08 | (2006.01) |
| C07K 9/00 | (2006.01) |
| G01N 33/53 | (2006.01) |

(52) U.S. Cl.
CPC ... *C07K 4/00* (2013.01); *C07K 5/08* (2013.01); *C07K 7/06* (2013.01); *C07K 7/08* (2013.01); *C07K 9/001* (2013.01); *C07K 14/00* (2013.01); *C07K 14/001* (2013.01); *C07K 14/003* (2013.01); *G01N 33/5308* (2013.01)

(58) Field of Classification Search
CPC ........................................................ C07K 4/00
USPC ....................................................... 530/326
See application file for complete search history.

(56) References Cited

U.S. PATENT DOCUMENTS

| | | | |
|---|---|---|---|
| 5,434,047 A | 7/1995 | Arnold, Jr. | |
| 5,521,063 A | 5/1996 | Summerton et al. | |
| 5,539,082 A | 7/1996 | Nielsen et al. | |
| 5,635,383 A | 6/1997 | Wu et al. | |
| 5,656,609 A | 8/1997 | Wu et al. | |
| 5,714,331 A | 2/1998 | Buchardt et al. | |
| 5,728,518 A | 3/1998 | Carmichael | |
| 5,811,387 A | 9/1998 | Simon et al. | |
| 5,831,005 A | 11/1998 | Zuckerman et al. | |
| 5,972,900 A | 10/1999 | Ferkol et al. | |
| 6,083,741 A | 7/2000 | Hart et al. | |
| 6,150,168 A | 11/2000 | Woo et al. | |
| 6,395,474 B1 | 5/2002 | Buchardt et al. | |
| 7,030,216 B2 | 4/2006 | Horn et al. | |
| 7,169,814 B2 | 1/2007 | Rothbard et al. | |
| 2003/0176670 A1 | 9/2003 | Griffin et al. | |
| 2012/0027677 A1 | 2/2012 | Peretz et al. | |

FOREIGN PATENT DOCUMENTS

| | | |
|---|---|---|
| WO | 02/14545 A2 | 2/2002 |
| WO | 2007016455 A2 | 2/2007 |

OTHER PUBLICATIONS

Prathiba, J. et al. Probing RNA-Antibiotic Interactions: A FTIR Study, Molecular Biology Reports, vol. 35, pp. 51-57. Mar. 1, 2008.
Metallo, Steven J. et al. Using Bifunctional Polymers Presenting Vancomycin and Fluorescein Groups to Direct Anti-Fluorescein Antibodies to Self-Assembled Monolayers Presenting D-Alanine-D-Alanine Groups, J. Am. Chem. Soc., vol. 125, pp. 4534-4540. Mar. 20, 2003.
Thomas, Jason R. et al. Biochemical and Thermodynamic Characterization of Compounds that Bind to RNA Hairpin Loops: Towards and Understanding of Selectivity, Biochemistry, vol. 45, No. 36, pp. 10928-10938. Sep. 1, 2006.
Kanadia et al. Reversal of RNA Missplicing and Myotonia after Muscleblind Overexpression in a Mouse poly (CUG) Model For Myotonic Dystrophy, PNAS, vol. 103, No. 31, pp. 11748-11753. Aug. 1, 2006.
Huq (Biochem 38, 5172-77, 1999).
Henklein et al., 5-Norbornene-2,3-diacarboximido Carbonochloridate. A New Stable Ragent for the Introduction of Amino-Protecting Groups, Synthesis, 1987:166-167 (1987).
Woese et al., Secondary Structure Model for Bacterial 16S Ribosomal RNA: Phylogenetic, Enzymatic and Chemical Evidence, Nucleic Acids Res., 8:2275-2293 (1980).
Zaug et al., "The Intervening Sequence RNA of Tetrahymena is an Enzyme," Science, 231:470-475 (1986).
Zuckermann et al., Efficient Method for the Preparation of Peptoids (Oligo(N-Substituted Glycines)(by Submonomer Solid-Phase Synthesis, J. Am. Chem. Soc., 114(26):10646-10647 (1992).
Joyce, "In vitro evolution of nucleic acids," Curr. Opin. Struct. Biol., 4:331-336 (1994).
Klug et al., "All You Wanted to Know About SELEX," Mot. Biol. Rep., 20:97-107 (1994).
Roestamadji et al., "Loss of Individual Electrostatic Interactions Between Aminoglycoside Antibiotics and Resistance Enzymes as an Effective Means to Overcoming Bacterial Drug Resistance," J. Am Chem. Soc., 117:11060-11069 (1995).
Fourmy et al., "Structure of the A Site of *Escherichia coli* 16S Ribosomal RNA Complexed With an Aminoglycoside Antibiotic," Science, 274:1367-1371 (1996).

(Continued)

*Primary Examiner* — David Lukton
(74) *Attorney, Agent, or Firm* — Hodgson Russ LLP

(57) ABSTRACT

Disclosed are RNA targeting compounds, methods for using the subject RNA targeting compounds to treat myotonic dystrophy and other diseases are also disclosed.

6 Claims, 32 Drawing Sheets

(56) References Cited

OTHER PUBLICATIONS

Hamy et al., "An Inhibitor of the Tat/TAR RNA Interaction That Effectively Suppresses HIV-1 Replication," Proc. Natl. Acad. Sci. U.S.A., 94:3548-3553 (1997).
Weber et al., "A Fast and Inexpensive Method for N-Terminal Fluorescein-Labeling of Peptides," Bioorg. Med. Chem. Lett., 8:597-600 (1998).
Batey et al., "Tertiary Motifs in RNA Structure and Folding," Angew. Chem., Int. Ed. Engl., 38:2326-2343 (1999).
Griffey et al., "Determinants of Aminoglycoside-Binding Specificity for rRNA by Using Mass Spectrometry," Proc. Natl. Acad. Sci. U.S. A., 96:10129-10133 (1999).
MacBeath et al., "Printing: Small Molecules as Microarrays and Detecting Protein-ligand Interactions En Masse," J. Am. Chem. Soc., 121:7967-7968 (1999).
Mathews et al., "Expanded Sequence Dependence of Thermodynamic Parameters Improves Prediction of RNA Secondary Structure," J. Mol. Bio., 288:911-940 (1999).
Disney et al., "Targeting a Pneumocystis Carinii Group I Intron With Methylphosphonate Oligonucleotides: Backbone Charge is Not Required for Binding or Reactivity," Biochemsitry, 39:6991-7000 (2000).
Doudna, "Structural Genomics of RNA," Nat. Struct. Biol., 7 (Suppl.):954-956 (2000).
Mankodi et al., "Myotonic Dystrophy in Transgenic Mice Expressing an Expanded CUG Repeat," Science, 289: 1769-1772 (2000).
Miller et al., "Recruitment of Human Muscleblind Proteins to (CUG)n Expansions Associated with Myotonic Dystrophy," EMBO J., 19:4439-4448(2000).
Satz et al., "Synthesis of Fluorescent Microgonotropens (FMGTs) and Their Interactions with dsDNA," Bioorg. Med. Chem., 8(8):1871-1880 (2000).
Tian et al., "Expanded CUG Regeat RNAs Form Hairpins That Activate the Double-Stranded RNA-Dependent Protein Kinase PKR," RNA 6:79-87 (2000).
Gallego et al., "Targeting RNA with Small Molecule Drugs: Therapeutic Promise and Chemical Challenges," Acc. Chem. Res., 34:836-843 (2001).
Kolb et al., "Click Chemistry: Diverse Chemical Function from a Few Good Reactions," Angew. Chem., Int. Ed. Engl., 40:2004-2021 (2001).
Lagos-Quintana et al., "Identification of Novel Genes Coding for Small Expressed RNAs," Science, 294:853-858 (2001).
Mankodi et al., "Muscleblind Localizes to Nuclear Foci of Aberrant RNA in Myotonic Dystrophy Types 1 and 2," Hum. Mol. Genet., 10:2165-2170 (2001).
Mankodi et al., "Myotonic Syndromes," Curr. Opin. Neurol., 15:545-552 (2002).
Swayze et al., "SAR by MS: A Ligand Based Technique for Drug Lead Discovery Against Structured Rna Targets," J. Med. Chem., 45:3816-3819 (2002).
Winkler et al., "Thiamine Derivatives Bind Messenger RNAs Directly to Regulate Bacterial Gene Expression," Nature, 419:952-956 (2002).
Carter et al., "Functional Insights From the Structure of the 30S Ribosomal Subunit and its Interactions With Antibiotics," Nature, 407:340-348 (2003).
Johnson et al., "Application of NMR SHAPES Screening to an RNA Target," J. Am. Chem. Soc., 125: 15724-15725 (2003).
Kanadia et al., "A Muscleblind Knockout Model for Myotonic Dystrophy," Science, 302:1978-1980 (2003).
Kolb et al., "The Growing Impact of Click Chemistry on Drug Discovery," Drug Discovery Today, 8: 1128-1137 (2003).
Lynch et al., "Comparison of X-ray Crystal Structure of the 30S Subunit-Antibiotic Complex with NMR Structure of Decoding Site Oligonucleotide-Paromomycin Complex," Structure, 11 :43-53 (2003).
Chan et al., "Polytriazoles as Copper(I)-Stabilizing Ligands in Catalysis," Org. Lett., 6:2853-2855 (2004).
DeNap et al., "Combating Drug-Resistant Bacteria: Small Molecule Mimics of Plasmid Incompatibility as Antiplasmid Compounds," J. Am. Chem. Soc., 126:15402-15404 (2004).
Disney et al., "Aminoglycoside Microarrays to Explore Interactions of Antibiotics with RNAs and Proteins," Chemistry, 10:3308-3314 (2004).
Disney et al., "Aminoglcoside Microarrays to Study Antibiotic Resistance," Angew. Chem. Int. Ed. Engl.,43: 1591-1594 (2004).
Disney et al., "The Use of Carbohydrate Microarrays to Study Carbohydrate-Cell Interactions and to Detect Pathogens," Chem. Biol., 11:1701-1707 (2004).
He et al., "Synthesis and Evaluation of Novel Bacterial rRNA-Binding Benzimidazoles by Mass Spectrometry," Bioorg. Med. Chem. Lett., 14:695-699 (2004).
Kaul et al., "Fluorescence based Approach for Detecting and Characterizing Antibiotic-Induced Conformational Changes in Ribosomal RNA . . . , " J. Am. Chem. Soc.,126:3447-3453 (2004).
Mathews et al., "Incorporating Chemical Modification Constraints into a Dynamic Programming Algorithm for Prediction of RNA Secondary Structure," Proc. Natl. Acad. Sci. U.S.A., 101:7287-7292 (2004).
Ratner et al., "Tools for Glycomics: Mapping Interactions of Carbohydrates in Biological Systems," ChemBioChem, 5:1375-1383 (2004).
Shandrick et al., "Monitoring Molecular Recognition of the Ribosomal Decoding Site," Angew. Chem., Int. Ed. Engl., 43:3177-3182 (2004).
Gao et al., "Regio- and Chemoselective 6'-N-Derivatization of Aminoglycosides: Bisubstrate Inhibitors as Probes to Study Aminoglycoside 6'-N-Acetyltransferases," Angew. Chem. Int. Ed., 44(42):6859-6862 (2005).
Jang et al., "Click to Fit: Versatile Polyvalent Display on a Peptidomimetic Scaffold," Org. Lett., 7:1951-1954 (2005).
Seth et al., "SAR by MS: Discovery of a New Class of RNA-binding Small Molecules for the Hepatitis C Virus: Internal Ribosome Entry Site IIA Subdomain," J. Med. Chem., 48:7099-7102 (2005).
Thomas et al., "Size-Specific Ligands for RNA Hairpin Loops," J. Am. Chem. Soc.,127:12434-12435 (2005).
Thomas et al., "The Relationship Between Aminoglycosides' RNA Binding Proclivity and Their Antiplasmid Effect on an IncB Plasmid Combating Drug-Resistant Bacteria: Small Molecule Mimics of . . . ," Biochemistry, 44:6800-6808 (2005).
Kaul et al., "Aminoglycosideinduced Reduction in Nucleotide Mobility at the Ribosomal RNA A-Site as a Potentially Key Determinant of Antibacterial Activity," J. Am. Chem. Soc., 128:1261-1271 (2006).
Lin et al., "Failure of MBNL1-Dependent Post-Natal Splicing Transitions in Myotonic Dystrophy," Hum. Mol. Genet., 15:2087-2097 (2006).
Childs-Disney et al., "A Small Molecule Microarray Platform to Select RNA Internal Loop-Ligand Interactions.," ACS Chem Bio., 2(11):745-754 (2007).
Disney et al., "An Aminoglycoside Microarray Platform for Directly Monitoring and Studying Antibiotic Resistance," Biochemistry, 40:11223-11230 (2007).
Disney et al., "Using Selection to Identify and Chemical Microarray to Study the RNA Internal Loops Recognized by 6'-N-Acylated Kanamycin A," ChemBioChem, 8(6):649-656 (2007).

43a R=n-propyl; n=4
43b R=n-propyl; n=8
43c R=n-propyl; n=12
43d R=n-propyl; n=16
44  R=methyl;   n=16

RNA TARGETING COMPOUNDS AND METHODS FOR MAKING AND USING SAME

This application is a continuation-in-part of U.S. patent application Ser. No. 12/072,291, filed Feb. 25, 2008, which claims the benefit of U.S. Provisional Patent Application No. 61/004,389, filed Nov. 27, 2007, and U.S. Provisional Patent Application No. 60/903,212, filed Feb. 23, 2007, the disclosures of each of which are incorporated herein by reference in their entirety. This application is a continuation-in-part of 371 International Application PCT/US2008/002438, filed Feb. 25, 2008, which claims the benefit of U.S. Provisional Patent Application No. 61/004,389, filed Nov. 27, 2007, and U.S. Provisional Patent Application No. 60/903,212, filed Feb. 23, 2007, the disclosures of each of which are incorporated herein by reference in their entirety. This application also claims the benefit of U.S. Provisional Patent Application No. 61/723,145, filed Nov. 6, 2012, the disclosure of which is incorporated herein by reference in its entirety.

FIELD OF THE INVENTION

The present invention relates to methods and materials for systematically identifying RNA-ligand interactions, and, more particularly, to methods and materials that can be used to identify small molecules that target particular RNA motifs.

The present application cites a number of references, some or all of which are cited by number in square brackets. The references thus cited are listed in a section entitled "References" immediately before the claims. Each reference cited in this application, whether by number or otherwise, is hereby incorporated in its entirety, by reference.

BACKGROUND OF THE INVENTION

RNA forms complex tertiary structures that impart diverse functions [1, 2]. For example, RNA catalyzes reactions [3], regulates gene expression [4, 5], encodes protein, and plays other essential roles in biology. Therefore, RNA is an interesting and important target for developing drugs or probes of function [6, 7]. It is a vastly under-utilized target, however, mainly because of the limited information available on RNA ligand interactions that could facilitate rational design.

One advantage of using RNA as a drug target is that secondary structure information, which includes the motifs that comprise an RNA, can be easily obtained from sequence by free energy minimization [8, 9] or phylogenic comparison [10]. RNA tertiary structures are composites of the secondary structural motifs and the long-range contacts that form between them. Furthermore, RNA motifs can have similar properties both as isolated systems and as parts of larger RNAs. For example, aminoglycoside antibiotics affect the structure of the bacterial rRNA A-site similarly when they bind the entire ribosome or an oligonucleotide mimic of the bacterial rRNA A-site [11-16]. Studies on the binding of aminoglycosides and streptamine dimers to RNA hairpins [17-20] have facilitated the development of compounds to combat multidrug resistance by causing plasmid incompatibility [19, 20]. These results show that the identification of RNA motifs that bind small molecules can be useful for targeting the larger RNAs that contain them.

However, since RNA can adopt diverse structures, internal and hairpin loops for example, an understanding of how to target RNA with small molecules and other ligands has been elusive.

Illustrative methods to study and identify RNA ligand interactions include systematic evolution of ligands by exponential enrichment ("SELEX") [21, 22], structure-activity relationships ("SAR") by mass spectrometry ("MS") [23-26] and NMR [27], and chemical microarrays [28-30]. These methods probe RNA space (SELEX) or chemical space (SAR by MS and NMR and chemical microarrays) separately. However, these methods do not permit a systematic study of RNA-ligand interactions.

More recently, a method for systematically identifying RNA-ligand interactions has been developed. The method is described in, for example, Disney et al., "Using Selection to Identify and Chemical Microarray to Study the RNA Internal Loops Recognized by 6-N-Acylated Kanamycin A," *ChemBioChem*, 8:649-656 (2007); Childs-Disney et al., "A Small Molecule Microarray Platform to Select RNA Internal Loop-Ligand Interactions," *ACS Chem. Biol.*, 2(11):745-754 (2007) (and in the associated Supporting Information (available on the internet at http://pubs.acs.org/subscribe/journals/acbcct/suppinfo/cb700174r/cb700174r-File003.pdf)); U.S. patent application Ser. No. 11/998,466 of Disney et al., filed Nov. 29, 2007; and PCT Patent Application No. PCT/US07/024,546 of Disney et al., filed Nov. 29, 2007, each of which is hereby incorporated by reference.

While aforementioned methods identify RNA-ligand interactions, there continues to be a need for compounds and associated methods and materials that exploit such RNA-ligand interactions, and the present invention is directed, in part, to addressing this need.

SUMMARY OF THE INVENTION

The present invention relates to an RNA targeting compound having the formula:

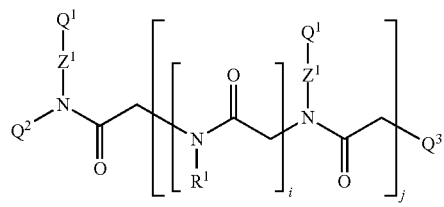

wherein j is an integer from 1 to 100; each i is the same or different and is zero or an integer from 1 to 100; each $Z^1$ represents the same or different linking moiety; each $R^1$ is the same or different and represents an alkyl group or an aryl group; each $Q^1$ represents the same or different RNA binding ligand; $Q^2$ is an alkyl group; $Q^3$ is a halogen, an alkyl group, an aryl group, or an amine.

The present invention also relates to an RNA targeting compound comprising a polymer backbone and two or more pendant RNA binding ligands, wherein said two or more pendant RNA binding ligands are bound to said polymer backbone.

BRIEF DESCRIPTION OF THE DRAWINGS

FIG. 3A is a reaction scheme for making peptoid backbones that can be used to prepare various compounds of the present invention.

DETAILED DESCRIPTION OF THE INVENTION

Figure 1A:
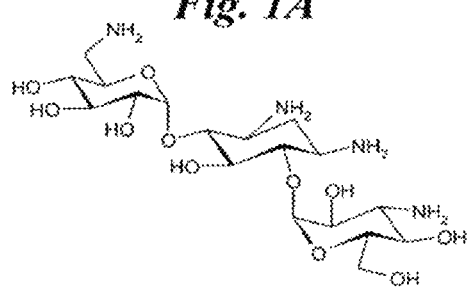
FIGS. 1A-1G are structural formulae of RNA binding ligands that can be used in the compounds of the present invention.

As used herein, "alkyl" is meant to include linear alkyls, branched alkyls, and cycloalkyls, each of which can be substituted or unsubstituted. "Alkyl" is also meant to include lower linear alkyls (e.g., C1-C6 linear alkyls), such as methyl, ethyl, n-propyl, n-butyl, n-pentyl, and n-hexyl; lower branched alkyls (e.g., C3-C8 branched alkyls), such as isopropyl, t-butyl, 1-methylpropyl, 2-methylpropyl, 1-methylbutyl, 2-methylbutyl, 3-methylbutyl, 1,2-dimethylpropyl, 1,1-dimethylpropyl, 2,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 2-methyl-2-ethylpropyl, 2-methyl-1-ethylpropyl, and the like; and lower cycloalkyls (e.g., C3-C8 cycloalkyls), such as cyclopropyl, cyclobutyl, cyclopentyl, cyclohexyl, and the like.

"Alkyl", as used herein, is meant to include unsubstituted alkyls, such as those set forth above, in which no atoms other than carbon and hydrogen are present. "Alkyl", as used herein, is also meant to include substituted alkyls. Suitable substituents include substituted or unsubstituted aryl groups (such as where the alkyl is a benzyl group or another aryl-substituted methyl group), heterocyclic rings (saturated or unsaturated and optionally substituted), alkoxy groups (which is meant to include aryloxy groups (e.g., phenoxy groups)), amine groups (e.g., unsubstituted, monosubstituted, or disubstituted with, for example, aryl or alkyl groups), guanidine and guanidinium groups (optionally substituted with, for example, one or more alkyl or aryl groups), carboxylic acid derivatives (e.g., carboxylic acid esters, amides, etc.), halogen atoms (e.g., Cl, Br, and I), and the like. Further, alkyl groups bearing one or more alkenyl or alkynyl substituents (e.g., a methyl group itself substituted with a prop-1-en-1-yl group to produce a but-2-en-1-yl substituent) is meant to be included in the meaning of "alkyl". Other suitable substituents include hydroxy groups and protected hydroxy groups (e.g., an acyloxy group, such at an acetoxy group; a silyl ether group, such as a trimethylsilyl ("TMS") ether group and a tert-butyldimethylsilyl ("TBS") ether group).

As used herein, "alkylene" refers to a bivalent alkyl group, where alkyl has the meaning given above. Linear, branched, and cyclic alkylenes, as well as examples thereof, are defined in similar fashion with reference to their corresponding alkyl group. Examples of alkylenes include eth-1,1-diyl (i.e., —CH(CH₃)—), eth-1,2-diyl (i.e., —CH₂CH₂—), prop-1,1-diyl (i.e., —CH(CH₂CH₃)—), prop-1,2-diyl (i.e., —CH₂—CH(CH₃)—), prop-1,3-diyl (i.e., —CH₂CH₂CH₂—), prop-2,2-diyl (e.g. —C(CH₃)₂—), cycloprop-1,1-diyl, cycloprop-1,2-diyl, cyclopent-1,1-diyl, cyclopent-1,2-diyl, cyclopent-1,3-diyl, cyclohex-1,1-diyl, cyclohex-1,2-diyl, cyclohex-1,3-diyl, cyclohex-1,4-diyl, but-2-en-1,1-diyl, cyclohex-1,3-diyl, but-2-en-1,4-diyl, but-2-en-1,2-diyl, but-2-en-1,3-diyl, but-2-en-2,3-diyl. Also included in the meaning of the term "alkylene" are compounds having the formula —R'—R"—, where —R' represents a linear or branched alkyl group and R"— represents a cycloalkyl group.

As used herein, "alkoxy" is meant to include groups having the formula —O—R, where R is an alkyl or aryl group. They include methoxy, ethoxy, propoxy, phenoxy, 4-methylphenoxy, and the like.

As used herein, "aryl" is meant to include aromatic rings, for example, aromatic rings having from 4 to 12 members, such as phenyl rings. These aromatic rings can optionally contain one or more heteroatoms (e.g., one or more of N, O, and S), and, thus, "aryl", as used herein, is meant to include heteroaryl moieties, such as pyridyl rings, pyridiminyl rings, and furanyl rings. The aromatic rings can be optionally substituted. "Aryl" is also meant to include aromatic rings to which are fused one or more other aryl rings or non-aryl rings. For example, naphthyl groups, indole groups, isoindole groups, and 5,6,7,8-tetrahydro-2-naphthyl groups (each of which can be optionally substituted) are aryl groups for the purposes of the present application. As indicated above, the aryl rings can be optionally substituted. Suitable substituents include alkyl groups (which can optionally be substituted), other aryl groups (which may themselves be substituted), heterocyclic rings (saturated or unsaturated), alkoxy groups (which is meant to include aryloxy groups (e.g., phenoxy groups)), amine groups (e.g., disubstituted with aryl or alkyl groups), carboxylic acid groups, carboxylic acid derivatives (e.g., carboxylic acid esters, amides, etc.), halogen atoms (e.g., Cl, Br, and I), and the like.

As used herein, "ring" is meant to include homocyclic or heterocyclic rings. The homocyclic or heterocyclic ring can be saturated or unsaturated, aromatic or nonaromatic. The ring can be unsubstituted, or it can be substituted with one or more substituents. The substituents can be saturated or unsaturated, aromatic or nonaromatic, and examples of suitable substituents include those recited above in the discussion relating to substituents on alkyl and aryl groups. Furthermore, two or more ring substituents can combine to form another ring, so that "ring", as used herein, is meant to include fused ring systems, and such fused ring systems can be saturated or unsaturated, aromatic or nonaromatic. In the case where the ring is saturated (i.e., in the case where each of the atoms making up the ring are joined by single bonds to other members of the ring), the ring may optionally include unsaturated (aromatic or nonaromatic) or saturated substituents. Illustratively, the ring or ring system can contain 3, 4, 5, 6, 7, 8, 9, 10, or more members.

The present invention relates to an RNA targeting compound having the following Formula I:

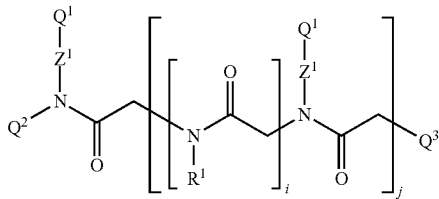

wherein j is an integer from 1 to 100; each i is the same or different and is zero or an integer from 1 to 100; each $Z^1$ represents the same or different linking moiety; each $R^1$ is the same or different and represents an alkyl group or an aryl group; each $Q^1$ represents the same or different RNA binding ligand; $Q^2$ is an alkyl group; $Q^3$ is a halogen, an alkyl group, an aryl group, or an amine.

As used herein RNA targeting compound is meant to refer to a compound that binds to RNA. By way of illustration, the RNA targeting compound can bind to one or more RNA motifs, such as RNA repeat motifs and/or RNA structural motifs. "RNA structural motif", as used herein, is meant to refer to a targetable RNA internal loop, hairpin loop, bulge, or other targetable RNA structural motifs, for example, as described in Batey et al., "Tertiary Motifs in RNA Structure and Folding," Angew. Chem. Int. Ed., 38:2326-2343 (1999), which is hereby incorporated by reference. Examples of RNA motifs include symmetric internal loops, asymmetric internal loops, 1×1 internal loops, 1×2 internal loops, 1×3 internal loops, 2×2 internal loops, 2×3 internal loops, 2×4 internal loops, 3×3 internal loops, 3×4 internal loops, 4×4 internal loops, 4×5 internal loops, 5×5 internal loops, 1 base bulges, 2 base bulges, 3 base bulges, 4 base bulges, 5 base bulges, 4 base hairpin loops, 5 base hairpin loops, 6 base hairpin loops, 7 base hairpin loops, 8 base hairpin loops, 9 base hairpin loops, 10 base hairpin loops, multibranch loops, pseudoknots, etc.

As noted above, j is an integer from 1 to 100. For example, j can be an integer from 1 to 50, from 1 to 20, from 1 to 10, from 2 to 100, from 2 to 50, from 2 to 20, from 2 to 10. Illustratively, j can be 1, 2, 3, 4, 5, 6, 7, 8, 9, 10, 11, 12, 13, 14, 15, 16, 17, 18, 19, or 20.

As noted above, each i is the same or different and is zero or an integer from 1 to 100, for example, zero or an integer from 1 to 50, zero or an integer from 1 to 20, zero or an integer from 1 to 10, an integer from 2 to 100, an integer from 2 to 50, an integer from 2 to 20, an integer from 2 to 10, 0, 1, 2, 3, 4, 5, 6, 7, 8, 9, 10, 11, 12, 13, 14, 15, 16, 17, 18, 19, or 20. For example, when j is 1, there is one i value; when j is 2, there are two i values, and these two i values can be the same or they can be different; when j is 3, there are three i values, and these three i values can all be the same, they can all be different, or two can be the same and the other can be different; etc.

In certain embodiments, j is an integer from 2 to 10, and each i is the same or different and is zero or an integer from 1 to 20. In certain embodiments, each i is the same and is zero or an integer from 1 to 20. In certain embodiments, j is an integer from 2 to 10, and each i is the same and is zero or an integer from 1 to 20.

As noted above, each $R^1$ is the same or different and represents an alkyl group or an aryl group. For example, when j is 1 and i is 1, there is one $R^1$; when j is 1 and i is 2, or when j is 2 and each i is 1, or when j is 2 and one i is 2 and the other is zero, etc., there are two $R^1$'s, and these two $R^1$'s can be the same or they can be different; when j is 1 and i is 3, or when j is 3 and each i is 1, or when j is 2 and one i is 1 and the other i is two, or when j is 3 and one i is 3 and the other two i's are zero, etc., there are three $R^1$'s, and these three $R^1$'s can all be the same, they can all be different, or two can be the same and the other can be different; etc.

In certain embodiments, each $R^1$ is the same, as in the case where each $R^1$ is an unsubstituted methyl, ethyl, or propyl group. In certain embodiments, at least one $R^1$ is different, as in the case where all but one of the $R^1$'s are the same, all but two of the $R^1$'s are the same, all but three of the $R^1$'s are the same, all but two of the $R^1$'s are different, all but three of the $R^1$'s are different, some of the $R^1$'s are the same and others are different, etc. By way of illustration, in certain embodiments, at least one $R^1$ is an alkyl group and at least one $R^1$ is an aryl group; in certain embodiments, each $R^1$ is the same or different and is an alkyl group; in certain embodiments, each $R^1$ is the same or different and is an aryl group; in certain embodiments, each $R^1$ is the same or different and is an unsubstituted alkyl; in certain embodiments, each $R^1$ is the same or different and is a C1-C12 alkyl, such as a substituted C1-C12 alkyl or an unsubstituted C1-C12 alkyl; in certain embodiments, each $R^1$ is the same or different and is a C1-C6 alkyl, such as a substituted C1-C6 alkyl or an unsubstituted C1-C6 alkyl; in certain embodiments, each $R^1$ is the same or different and is a linear alkyl, such as a substituted linear alkyl or an unsubstituted linear alkyl, such as a C1-C12 unsubstituted linear alkyl, a C1-C6 unsubstituted linear alkyl, a C1-C4 unsubstituted linear alkyl, or a C1-C3 unsubstituted linear alkyl.

As noted above, $Q^3$ can be a halogen, an alkyl group, an aryl group, or an amine. In certain embodiments, $Q^3$ is an amine, such as an unsubstituted amine, a monosubstituted amine, or a disubstituted amine.

For example, $Q^3$ can have the formula —$NR^2,R^3$, in which $R^2$ is a hydrogen atom or an alkyl group and in which $R^3$ is a hydrogen atom, an alkyl group or an alkylcarbonyl group, for example, as in the case where $R^2$ is a substituted alkyl and $R^3$ is a hydrogen atom, an alkyl group or an alkylcarbonyl group.

Illustratively, $Q^3$ can have the formula —$NR^2R^3$, in which $R^3$ is a hydrogen atom, an alkyl group or an alkylcarbonyl group and in which $R^2$ is a substituted alkyl having the formula —$Z^1$-$Q^1$, where in $Z^1$ and $Q^1$ are as described above and illustrated below. Thus, in certain embodiments, compounds of Formula I can have the following Formula II:

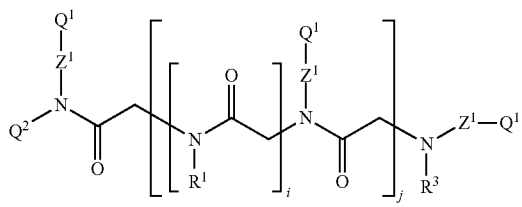

As yet further illustration, in certain embodiments, $Q^3$ can have the formula —$NR^2, R^3$, in which $R^2$ is a hydrogen atom or an alkyl group and in which $R^3$ is an alkylcarbonyl group, such as an unsubstituted alkylcarbonyl group or a substituted alkylcarbonyl group (e.g., an ω-aminoalkylcarbonyl group, such as one having the formula —C(O)—$(CH_2)_n$-$Q^6$, in which n is an integer from 1 to 20 (e.g., from 1 to 12, from 1 to 6, from 1 to 4, etc.) and in which $Q^6$ is an unsubstituted, monosubstituted, or disubstituted amino group). For example, $Q^3$ can have the formula —$NR^2, R^3$, in which $R^2$ is a hydrogen atom or an alkyl group and in which $R^3$ is an alkylcarbonyl group substituted with a dye, such as in the case where $Q^3$ can have the formula —$NR^2, R^3$, in which $R^2$ is a hydrogen atom or an alkyl group, in which $R^3$ has the formula —C(O)—$R^6$—$Z^4$-$Q^7$, and in which $R^6$ represents a bivalent alkyl moiety, $Z^4$ represents a linking moiety (e.g., an amide linkage, an ester linkage, a triazole ring linkage, etc.), and $Q^7$ represents a label, such as a dye (e.g., fluorescein dye or another fluorescent dye), a radioactive label, an enzymatic label, etc. As further examples of dyes that can be used, there can be mentioned Alexa dyes, Bodipy dyes, rhodamine dyes, pyrene dyes, dansyl dyes, cyanine dyes, PET (positron emission tomography) tracers, and the like. In an embodiment, $Q^7$ represents carboxyfluorescein dye (FAM dye) (e.g., 5-FAM, 6-FAM, etc.).

The compounds can include a molecular transporter. Examples of molecular transporters include small molecules and cell-penetrating peptides or proteins. The molecular transporter can be referred to as a cellular uptake tag. For example, $R^6$ can be a molecular transporter (e.g., a small molecule or cell-penetrating peptide or protein). Without intending to be bound by any particular theory, it is considered that the molecular transporters facilitate the uptake of a variety of molecular cargoes into cells such as, for example, a wide variety of covalently and noncovalently conjugated cargoes such as, for example, proteins, oligonucleotides, and liposomes. In an embodiment, $R^6$ is a nona-arginine molecular transporter.

As yet further illustration, in certain embodiments, $Q^3$ can have the formula —$NR^2, R^3$, in which $R^3$ is an alkylcarbonyl group substituted with a dye and in which $R^3$ has the formula —$Z^1$-$Q^1$.

As another example, $Q^3$ is an amine having the formula:

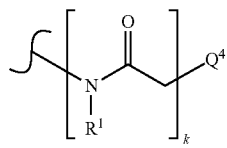

wherein k is an integer from 1 to 100 (e.g., as in the case where k is an integer from 1 to 50, from 1 to 20, from 1 to 10, from 2 to 100, from 2 to 50, from 2 to 20, from 2 to 10 and/or as in the case where k is 1, 2, 3, 4, 5, 6, 7, 8, 9, 10, 11, 12, 13, 14, 15, 16, 17, 18, 19, or 20) and wherein $Q^4$ is a halogen, an alkyl group, an aryl group, or an amine, examples of which include those discussed above with regard to $Q^3$. Thus, in certain embodiments, compounds of Formula I can have the following Formula III:

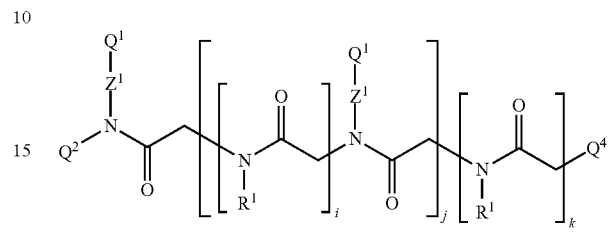

As noted above, $Q^2$ is an alkyl group, such as an unsubstituted alkyl group or a substituted alkyl group. In certain embodiments, $Q^2$ has the formula —$CH_2$—C(O)-$Q^5$, wherein $Q^5$ is an amine, such as an unsubstituted amine, a monosubstituted amine, or a disubstituted amine. Illustratively, $Q^2$ can have the formula —$CH_2$—C(O)—$NR^4R^5$, in which $R^4$ is a hydrogen atom or an alkyl group and in which $R^5$ is a hydrogen atom or an alkyl group. In certain embodiments, $Q^2$ has the formula —$CH_2$—C(O)—$NR^4R^5$, in which $R^4$ is an alkyl group substituted with a dye and in which $R^5$ is a hydrogen atom. In certain embodiments, $Q^2$ has the formula —$CH_2$—C(O)—$NR^4R^5$, in which $R^4$ is a hydrogen atom and in which $R^5$ is a hydrogen atom, for example, as in the case where a compound of Formula I has the following Formula IV:

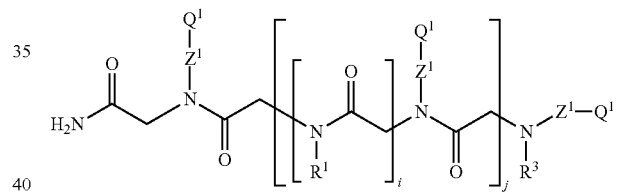

As another example, $Q^2$ can be a substituted alkyl in which $Q^2$ has the following formula:

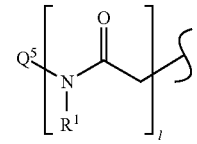

wherein l is an integer from 1 to 100 (e.g., as in the case where l is an integer from 1 to 50, from 1 to 20, from 1 to 10, from 2 to 100, from 2 to 50, from 2 to 20, from 2 to 10 and/or as in the case where l is 1, 2, 3, 4, 5, 6, 7, 8, 9, 10, 11, 12, 13, 14, 15, 16, 17, 18, 19, or 20), and wherein $Q^5$ is an alkyl group, examples of which include those discussed above with regard to $Q^2$. Thus, in certain embodiments, compounds of Formula I can have the following Formula V:

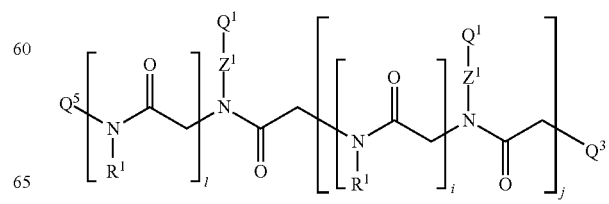

By way of still further illustration, compounds of Formula I can have the following Formula VI:

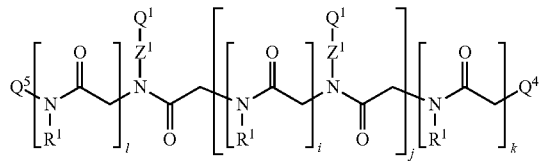

in which $Q^4$, $Q^5$, i, j, k, and l are as set forth above.

In the above Formulae I-VI, each $Z^1$ represents the same or different linking moiety; and each $Q^1$ represents the same or different RNA binding ligand.

For example, when j is 1, there are two $Q^1$'s and two $Z^1$'s in Formula I, the two $Q^1$'s can be the same or they can be different, and the two $Z^1$'s can be the same or they can be different; when j is 2, there are three $Q^1$'s and three $Z^1$'s in Formula I, the three $Q^1$'s can all be the same, they can all be different, or two can be the same and the other one can be different, and the three $Z^1$'s can all be the same, they can all be different, or two can be the same and the other one can be different; etc.

In certain embodiments, each $Q^1$ is the same. In certain embodiments, at least one $Q^1$ is different, as in the case where all but one of the $Q^1$'s are the same, all but two of the $Q^1$'s are the same, all but three of the $Q^1$'s are the same, all but two of the $Q^1$'s are different, all but three of the $Q^1$'s are different, some of the $Q^1$'s are the same and others are different, etc. In certain embodiments, each $Z^1$ is the same. In certain embodiments, at least one $Z^1$ is different, as in the case where all but one of the $Z^1$'s are the same, all but two of the $Z^1$'s are the same, all but three of the $Z^1$'s are the same, all but two of the $Z^1$'s are different, all but three of the $Z^1$'s are different, some of the $Z^1$'s are the same and others are different, etc. The $Z^1$'s and $Q^1$'s can be selected independently of one another. Thus, for example, in certain embodiments, all of the $Q^1$'s are the same, and all of the $Z^1$'s are the same; in certain embodiments, all of the $Q^1$'s are the same, but not all of the $Z^1$'s are the same; in certain embodiments, all of the $Z^1$'s are the same, but not all of the $Q^1$1's are the same; in certain embodiments, not all of the $Q^1$'s are the same, and not all of the $Z^1$'s are the same; etc.

As noted above, each $Z^1$ represents a linking moiety, such as a linking moiety that covalently links its corresponding RNA binding ligand (i.e., its corresponding $Q^1$) with the peptoid polymer backbone. By way of illustration, $Z^1$ can have the formula: $-Z^2-Z^3-Z^4-$ wherein $Z^2$ is an alkylene moiety, $Z^4$ is an alkylene moiety, and $Z^3$ is a linkage that serves to covalently connect the $Z^2$ and $Z^4$ alkylene moieties. Examples of suitable $Z^3$'s include amide linkages; ester linkages; ether linkages; and triazole ring linkages, e.g., triazole ring linkages having the formula:

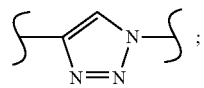

etc. In certain embodiments, $Z^1$ can have the formula $-Z^2-C(O)-NH-Z^4-$, e.g., the formula $-(CH_2)_y-C(O)-NH-(CH_2)_z-$; the formula $-Z^2-NH-C(O)-Z^4-$, e.g., the formula $-(CH_2)_y-NH-C(O)-(CH_2)_z-$; the formula $-Z^2-C(O)-O-Z^4-$, e.g., the formula $-(CH_2)_y-C(O)-O-(CH_2)_z-$; the formula $-Z^2-O-C(O)-Z^4-$, e.g., the formula $-(CH_2)_y-(O)-(CH_2)_z-$; the formula $-Z^2-O-Z^4-$, e.g., the formula $-(CH_2)_y-O-(CH_2)_z-$; the formula:

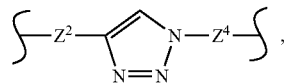

e.g., the formula:

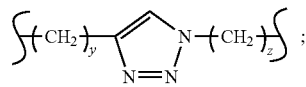

the formula:

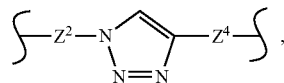

e.g., the formula:

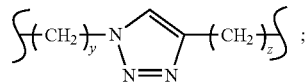

in which y is an integer from 1 to 6 and in which z is an integer from 1 to 6. $Z^1$ can also represent combinations of the above formulae, such as in the case where $Z^1$ has the formula $-Z^2-Z^6-Z^7-Z^8-Z^4$, in which $Z^2$, $Z^4$, and $Z^7$ are alkylene moieties, such as those discussed above; and $Z^6$ and $Z^8$ are independently selected from amide linkages, ester linkages, ether linkages, and triazole ring linkages.

As noted above, each $Q^1$ represents the same or different RNA binding ligand. As used herein, "RNA binding ligand" is meant to refer to non-nucleic acid compounds that may be capable of binding to or otherwise interacting with one or more RNAs or with one or more RNA motifs, such as the RNA motifs discussed above. In this regard, "interacting" is meant to refer to binding or other stabilized association between the ligand and the RNA or RNA motif. The association can be thermodynamically stabilized or kinetically stabilized or both, and the interaction can be the result of covalent bonding, hydrogen bonding, van der Waals interactions, electrostatic interactions, or combinations of these and/or other types of interactions. Examples of RNA binding ligands include proteins, polypeptides, carbohydrates, and other non-nucleic acid biopolymers; peptoids (which is meant to include polypeptoids); whole cells; and, small molecules. "Small molecules", as used herein, are meant to refer to non-biopolymer compounds having, for example, a molecular weight of less than 10,000 grams/mole, such as less than 9000 grams/mole, less than 8000 grams/mole, less than 7000 grams/mole, less than 6000 grams/mole, less than 5000 grams/mole, less than 4000 grams/mole, less than 3000 grams/mole, less than 2000 grams/mole, less than 1000 grams/mole, less than 900 grams/mole, less than 800 grams/mole, less than 700 grams/mole, less than 600 grams/mole, less than 500 grams/mole, less than 400 grams/mole, etc. that may be capable of binding to or otherwise interacting with one or more nucleic acids or nucleic acid motifs. Examples of small molecules that can be used in connection with the present invention include small molecule antibiotics, small molecule antiviral agents, small molecule antifungals, small molecule chemotherapeutics, small molecule heterocyclics, and other small molecule drugs. The small molecules can be biological compounds or mixtures of such compounds (e.g., derived from plant, fungal, bacterial, algal, or other extracts);

or they can be synthetic organic compounds; or they can be inorganic compounds (e.g., cisplatin).

Suitable RNA binding ligands (e.g., RNA binding ligands that bind to or otherwise interact with one or more target RNAs or with one or more target RNA motifs) can be identified, for example, using the methods described in Disney et al., "Using Selection to Identify and Chemical Microarray to Study the RNA Internal Loops Recognized by 6-N-Acylated Kanamycin A," *ChemBioChem*, 8:649-656 (2007); Childs-Disney et al., "A Small Molecule Microarray Platform to Select RNA Internal Loop-Ligand Interactions.," *ACS Chem. Biol.*, 2(11):745-754 (2007) (and in the associated Supporting Information (available on the internet at http://pubs.acs.org/subscribe/journals/acbcct/suppinfo/cb700174r/cb700174r-File003.pdf)); U.S. patent application Ser. No. 11/998,466 of Disney et al., filed Nov. 29, 2007; and/or PCT Patent Application No. PCT/US07/024,546 of Disney et al., filed Nov. 29, 2007, each of which is hereby incorporated by reference.

By way of illustration, two or more $Q^1$'s can be selected so as to bind to RNA structural motifs, such as RNA internal loop motifs, RNA hairpin loop motifs, RNA bulge motifs, RNA multibranch loop motifs, and/or RNA pseudoknot motifs.

For example, some (i.e., one or more) of the $Q^1$'s can be selected so as to bind to a first RNA structural motif and some (i.e., one or more) of the $Q^1$'s can be selected so as to bind to a second RNA structural motif, wherein the first RNA structural motif and the second RNA structural motif are different. Illustratively, some (i.e., one or more) of the $Q^1$'s can be selected so as to bind to an RNA internal loop motif and some (i.e., one or more) of the $Q^1$'s can be selected so as to bind to a second, different RNA internal loop motif; or, some (i.e., one or more) of the $Q^1$'s can be selected so as to bind to an RNA internal loop motif and some (i.e., one or more) of the $Q^1$'s can be selected so as to bind to an RNA hairpin loop motif; or some (i.e., one or more) of the $Q^1$'s can be selected so as to bind to an RNA internal loop motif and some (i.e., one or more) of the $Q^1$'s can be selected so as to bind to an RNA bulge motif; etc.

Alternatively, all of the $Q^1$'s can be selected so as to bind to the same RNA structural motif, for example, as where all of the $Q^1$'s are selected so as to bind to multiple copies of the same RNA structural motif. Illustratively, all of the $Q^1$'s are selected so as to bind to multiple copies of the same RNA internal loop motif, or the same RNA hairpin loop motif, or the same RNA bulge motif, etc.

By way of further illustration, two or more $Q^1$'s can be selected so as to bind to RNA repeat motifs, such as RNA triplet repeat motifs (e.g., CUG RNA triplet repeat motifs, CGG RNA triplet repeat motifs, GCC RNA triplet repeat motifs, GAA RNA triplet repeat motifs, CAG RNA triplet repeat motifs, etc.), RNA tetra repeat motifs (e.g., CCUG RNA tetra repeat motifs), or pentanucleotide repeats that cause spinocerebellar ataxia type 10 (AUUCU repeats) or Frontal temporal dementia and ALS (GGGGCC repeats).

For example, some (i.e., one or more) of the $Q^1$'s can be selected so as to bind to a first RNA repeat motif and some (i.e., one or more) of the $Q^1$'s can be selected so as to bind to a second RNA repeat motif, wherein the first RNA repeat motif and the second RNA repeat motif are different. Illustratively, some (i.e., one or more) of the $Q^1$'s can be selected so as to bind to a CUG RNA triplet repeat motif and some (i.e., one or more) of the $Q^1$'s can be selected so as to bind to a different RNA triplet repeat motif (e.g., a CAG RNA triplet repeat motif).

Alternatively, all of the $Q^1$'s can be selected so as to bind to the same RNA repeat motif, for example, as where all of the $Q^1$'s are selected so as to bind to a CUG RNA triplet repeat motif, a CGG RNA triplet repeat motif, a GCC RNA triplet repeat motif, a GAA RNA triplet repeat motif, a CAG RNA triplet repeat motif, a CUG RNA triplet repeat motif, a CCUG RNA tetra repeat motifs, or pentanucleotide repeats that cause spinocerebellar ataxia type 10 (AUUCU repeats) or Frontal temporal dementia and ALS (GGGGCC repeats).

By way of still further illustration, one or more of the $Q^1$'s can be selected so as to bind to an RNA structural motif, such as any of those described above (e.g., an RNA internal loop motif); and one or more of the $Q^1$'s can be selected so as to bind to an RNA repeat motif, such as any of those described above (e.g., a CUG RNA triplet repeat motif).

Figure 1B:
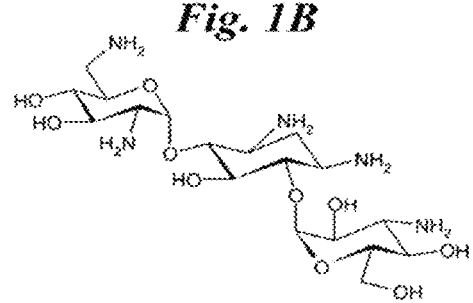
Figure 1C:
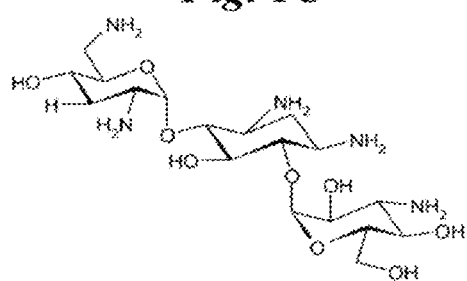
Figure 1D:
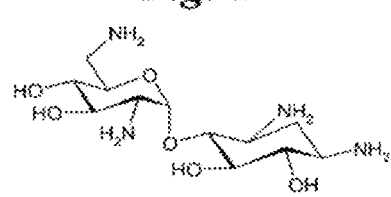
Figure 1E:
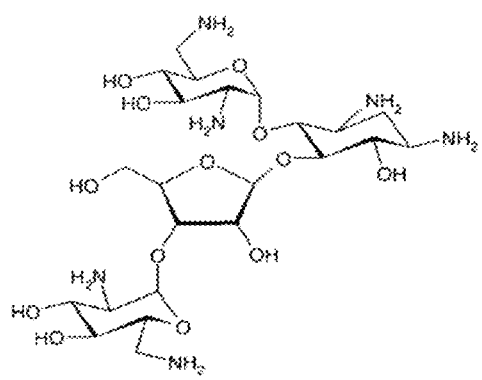
Figure 1F:
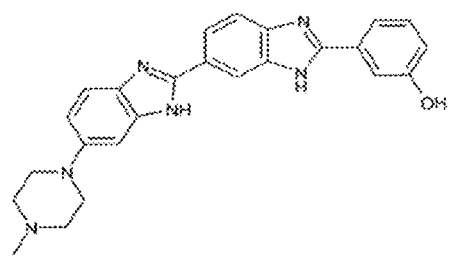
Figure 1G:
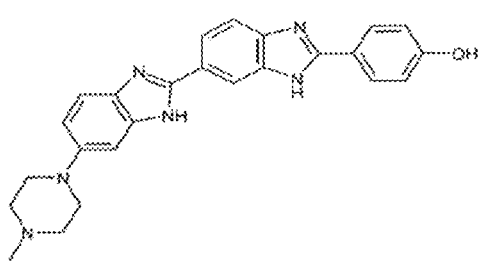

Examples of RNA binding ligands that can be used in the practice of the present invention include aminoglycoside sugars, such as kanamycins (e.g., kanamycin A's (e.g., having the structure shown in FIG. 1A), kanamycin B's (e.g., having the structure shown in FIG. 1B), etc.), tobramycins (e.g., having the structure shown in FIG. 1C), neamines (e.g., having the structure shown in FIG. 1D), neomycins (e.g., having the structure shown in FIG. 1E), and the like; and bisbenzimidazoles, such as pibenzimols (e.g., having the structures shown in FIGS. 1F and 1G, such as Hoechst 33258). Kanamycins, tobramycins, neamines, neomycins, and bisbenzimidazoles can be particularly useful in cases where the target RNA motifs are CUG RNA triplet repeat motifs and CCUG RNA tetranucleotide repeat motifs.

The manner in which the RNA binding ligands are coupled to the $Z^1$'s depends on the nature of the RNA binding ligand(s) being employed and the linkage(s) to be used. Illustratively, coupling can be affected via an RNA binding ligand's carbon atom that bears a hydroxyl group or amine group (e.g., via an RNA binding ligand's hydroxymethyl carbon atom, via an RNA binding ligand's aminomethyl carbon atom, via an RNA binding ligand's hydroxy-substituted ring carbon atom, via an RNA binding ligand's amine-substituted ring carbon atom, and the like). In cases where the RNA binding ligand is an aminoglycoside sugar, coupling can be effected, for example, via the aminoglycoside sugar's 6' position (e.g., via the 6' position of kanamycin A, kanamycin B, tobramycin, neamine, and neomycin); via the aminoglycoside sugar's 6" position (e.g., via the 6" position of kanamycin A, kanamycin B, and tobramycin); via the aminoglycoside sugar's 5 position (e.g., via the 5 position of neamine); in those cases where the aminoglycoside sugar includes a tetrahydrofuran ring, via the tetrahydrofuran ring's hydroxymethyl carbon atom (e.g., via the tetrahydrofuran ring's hydroxymethyl carbon atom in neomycin); etc.

In certain embodiments, each $Q^1$ is the same or different and is selected from aminoglycoside sugars and bisbenzimidazoles, such as in the case where each $Q^1$ is the same or different and is an aminoglycoside sugar. In certain embodiments, each $Q^1$ is a kanamycin A. In certain embodiments, each $Q^1$ is a neamine. In certain embodiments, each $Q^1$ is a bisbenzimidazole. In certain embodiments, some (i.e., one or more) of the $Q^1$'s are kanamycin A's and some of the $Q^1$'s are bisbenzimidazoles. In certain embodiments, some (i.e., one or more) of the $Q^1$'s are kanamycin A's and some of the $Q^1$'s are neamines. In certain embodiments, some (i.e., one or more) of the $Q^1$'s are neamines and some of the $Q^1$'s are bisbenzimidazoles.

For example, a $Q^1$ (or more than one $Q^1$) can be selected so as to bind to one or more RNA internal loop motifs that comprise a pyridimine across from a pyridimine (e.g., a uracil opposing a uracil, a cytosine across from a cytosine, a uracil across from a cytosine, etc.). Examples of such RNA internal loop motifs include 1×1, 2×2, 3×3, etc. internal loops, such as 5'C/3'C; 5'U/3'U; 5'AU/3'AU; 5'UA/3'UA; 5'UAU/3'UUU; 5'GUC/3'GCU; 5' GCU/3' GUC; 5' CUC/3' CGU; 5' CGU/3'CUC; 5'UGA/3'UGG; 5'UGG/3'UGA; etc. Such RNA internal loop motifs can be targeted with an aminoglycoside sugar, such as a kanamycin A (e.g., a kanamycin A coupled via its 6", position).

As a further example, a $Q^1$ (or more than one $Q^1$) can be selected so as to bind to one or more RNA internal loop motifs that comprise a guanine across from a guanine. Examples of such RNA internal loop motifs include 1×1, 2×2, 3×3, etc.

internal loops, such as 5'G/3'G; 5'CG/3'CG; 5'GA/3'GC; 5'GC/3'GA; 5'AG/3'GG; 5'GG/3'AG; 5'AG/3'CG; 5'CG/3'AG; 5'AGA/3'CGA; 5'CGA/3'AGA; etc. Such RNA internal loop motifs can be targeted with an aminoglycoside sugar, such as a tobramycin (e.g., a tobramycin coupled via its 6" position).

As a further example, a $Q^1$ (or more than one $Q^1$) can be selected so as to bind to one or more RNA internal loop motifs that comprise an adenine across from a guanine. Examples of such RNA internal loop motifs include 1×1, 2×2, 3×3, etc. internal loops, such as 5'A/3'G; 5'G/3'A; 5'CA/3'CG; 5'CG/3'CA; 5'AG/3'GG; 5'GG/3'AG; 5'UA/3'UG; 5'UG/3'UA; 5'GA/3'AA; 5'AA/3'GA; 5'GGA/3'AUG; 5'AUG/3'GGA; 5'AAC/3'GGU; 5'GGU/3'AAC; 5'AGA/3'CUG; 5'CUG/3'AGA; 5'AAG/3'CUA; 5'CUA/3'AAG; 5'AAC/3'GCU; 5'GCU/3'AAC; 5'AAC/3'GUA; 5'GUA/3'AAC; etc., and such RNA internal loop motifs can be targeted with an aminoglycoside sugar, such as a neamine (e.g., a neamine coupled via its 5 position). Other examples of such RNA internal loop motifs also include 1×1, 2×2, 3×3, etc. internal loops, such as 5'A/3'G; 5'G/3'A; 5'AA/3'GC; 5'GC/3'AA; 5'AA/3'CG; 5'CG/3'AA; 5'AA/3'GA; 5'AA/3'GA; 5'AU/3'GC; 5'GC/3'AU; 5'AA/3'GG; 5'GG/3'AA; 5'CAA/3'AUG; 5'AUG/3'CAA; 5'CAC/3'CGC; 5'CGC/3'CAC; 5'CUA/3'CCG; 5'CCG/3'CUA; 5'AGU/3'GGC; 5'GGC/3'AGU; 5'AAC/3'GGA; 5'GGA/3'AAC; 5'GUA/3'GAG; 5'GAG/3'GUA; 5'AGA/3'ACG; 5'ACG/3'AGA; 5'AGC/3'GCC; 5'GCC/3'AGC; etc., and such RNA internal loop motifs can be targeted with an aminoglycoside sugar, such as a neomycin (e.g., a neomycin coupled via the hydroxymethyl carbon atom of the neomycin's tetrahydrofuran ring).

The above-described RNA targeting compounds of Formula I in which j is 1 can have the following Formula VII:

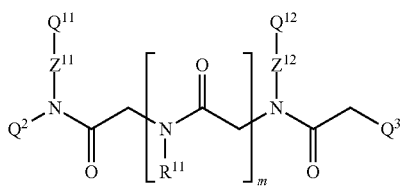

wherein m is zero or an integer from 1 to 100 (e.g., zero or an integer from 1 to 50, zero or an integer from 1 to 20, zero or an integer from 1 to 10, an integer from 2 to 100, an integer from 2 to 50, an integer from 2 to 20, an integer from 2 to 10, 0, 1, 2, 3, 4, 5, 6, 7, 8, 9, 10, 11, 12, 13, 14, 15, 16, 17, 18, 19, or 20); $Z^{11}$ and $Z^{12}$ represent the same or different linking moieties (examples of which include those described above with regard to $Z^1$); $R^{11}$ is an alkyl or aryl group (examples of which include those described above with regard to $R^1$); and $Q^{11}$ and $Q^{12}$ represent the same or different RNA binding ligands (examples of which include those described above with regard to $Q^1$).

The above-described RNA targeting compounds of Formula I in which j is 2 can have the following Formula VIII:

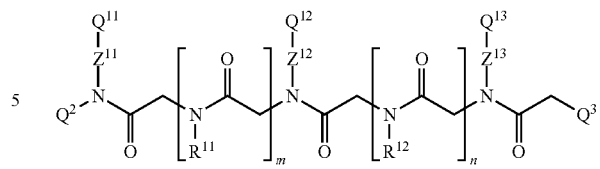

wherein m is zero or an integer from 1 to 100; n is zero or an integer from 1 to 100; $Z^{11}$, $Z^{12}$, and $Z^{13}$ represent the same or different linking moieties (examples of which include those described above with regard to $Z^1$); $R^{11}$ and $R^{12}$ represent the same or different alkyl or aryl groups (examples of which include those described above with regard to $R^1$); and $Q^{11}$, $Q^{12}$, and $Q^{13}$ represent the same or different RNA binding ligands (examples of which include those described above with regard to $Q^1$). Illustratively, m and n can be the same, or they can be different; and examples of suitable m and n include zero or an integer from 1 to 50, zero or an integer from 1 to 20, zero or an integer from 1 to 10, an integer from 2 to 100, an integer from 2 to 50, an integer from 2 to 20, an integer from 2 to 10, 0, 1, 2, 3, 4, 5, 6, 7, 8, 9, 10, 11, 12, 13, 14, 15, 16, 17, 18, 19, and 20).

The above-described RNA targeting compounds of Formula I in which j is 3 can have the following Formula IX:

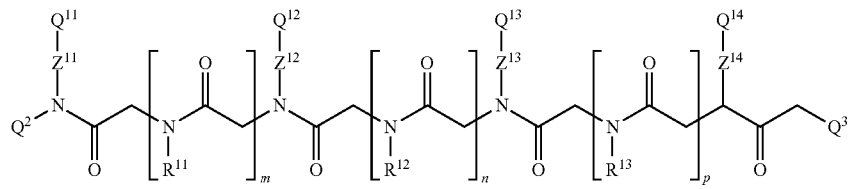

wherein m is zero or an integer from 1 to 100; n is zero or an integer from 1 to 100; p is zero or an integer from 1 to 100; $Z^{11}$, $Z^{12}$, $Z^{13}$, and $Z^{14}$ represent the same or different linking moieties (examples of which include those described above with regard to $Z^1$); $R^{11}$, $R^{12}$ and $R^{13}$, represent the same or different alkyl or aryl groups (examples of which include those described above with regard to $R^1$); and $Q^{11}$, $Q^{12}$, $Q^{13}$, and $Q^{14}$ represent the same or different RNA binding ligands (examples of which include those described above with regard to $Q^1$). Illustratively, m, n, and p can be the same, or they can be different; and examples of suitable m, n, and p include zero or an integer from 1 to 50, zero or an integer from 1 to 20, zero or an integer from 1 to 10, an integer from 2 to 100, an integer from 2 to 50, an integer from 2 to 20, an integer from 2 to 10, 0, 1, 2, 3, 4, 5, 6, 7, 8, 9, 10, 11, 12, 13, 14, 15, 16, 17, 18, 19, and 20).

In each of Formulae VII, VIII, and IX, $Q^2$ and $Q^3$ have the meanings described above with regard to Formula I. It will be appreciated that Formulae VII, VIII, and IX are intended to be illustrative of RNA targeting compounds of Formula I (specifically RNA targeting compounds of Formula I in which j is 1, 2, and 3, respectively). RNA targeting compounds of Formula I in which j is greater than 3 (e.g., 4, 5, 6, 7, 8, 9, 10, etc.) having structures that are analogous to Formulae VII, VIII, and IX can be readily envisioned are intended to be encompassed by Formula I.

The RNA targeting compounds of Formula I can be prepared by any suitable method, such as those described below and in the Examples that follow.

Illustratively, the compounds of the present invention can be prepared using a peptoid synthesis scheme in which the peptoid backbone is built in a step-wise manner by sequential reactions with (1) bromoacetic acid and (2) functionalized alkyl amines (i.e., alkyl amines in which the alkyl group bears a substituent to which an RNA binding ligand can be coupled) or non-functionalized alkyl amines (e.g., alkyl amines in which the alkyl group is unsubstituted or substituted with a group that is not involved in coupling the RNA binding ligand). The peptoid backbone can be built on a suitable substrate (e.g., a resin), and the resulting peptoid can be cleaved from the substrate after the reaction is complete. The step-wise process permits the introduction of functionalized alkyl groups at particular positions on the peptoid backbone and, consequently, permits one to control the spacing between RNA binding ligands (once the RNA binding ligands are coupled to the functionalized alkyl groups).

Figure 2:
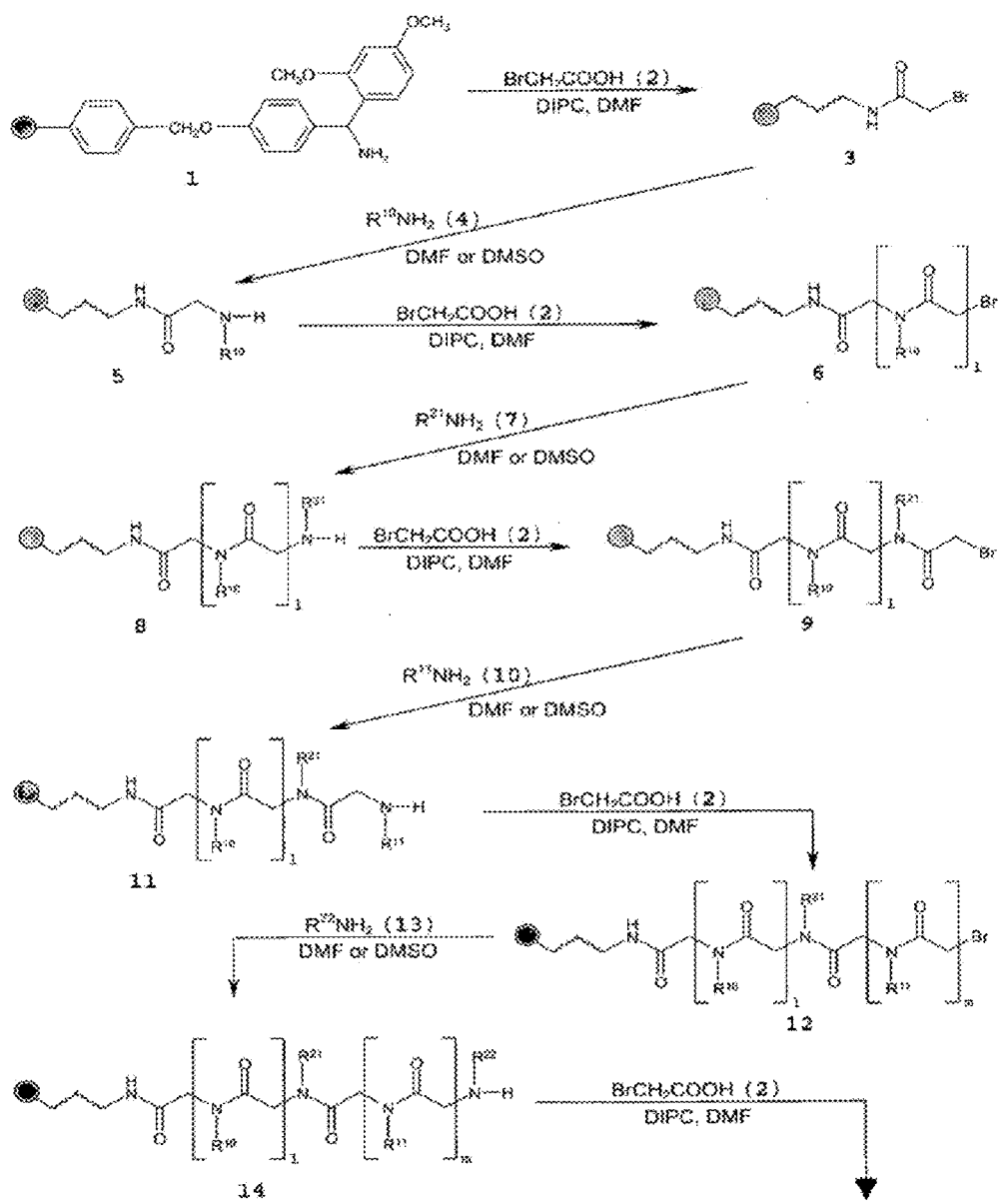
FIGS. 2 and 3A are reaction schemes for making peptoid backbones that can be used in the preparation of various compounds of the present invention.
Figure 2:
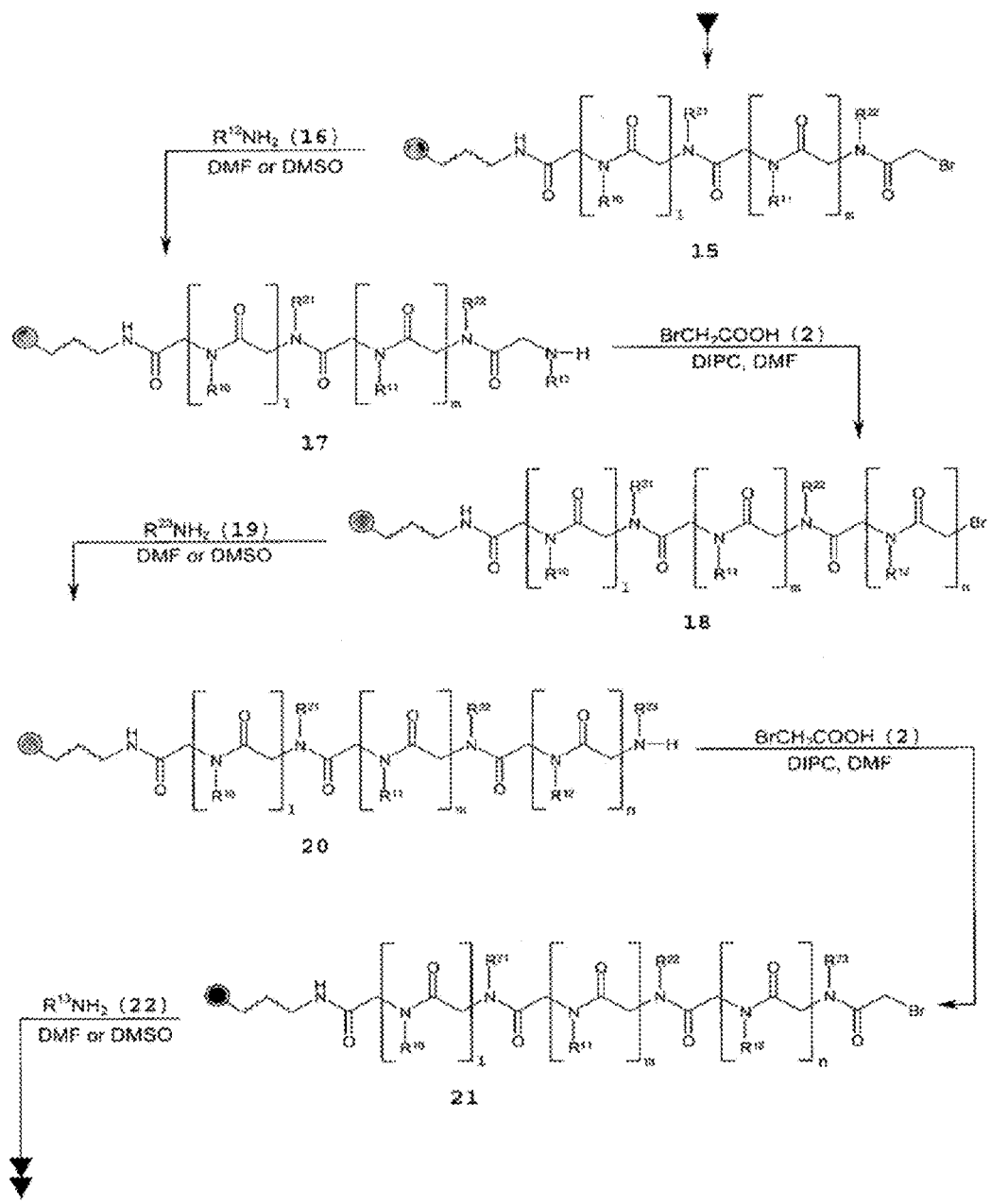
Figure 2:
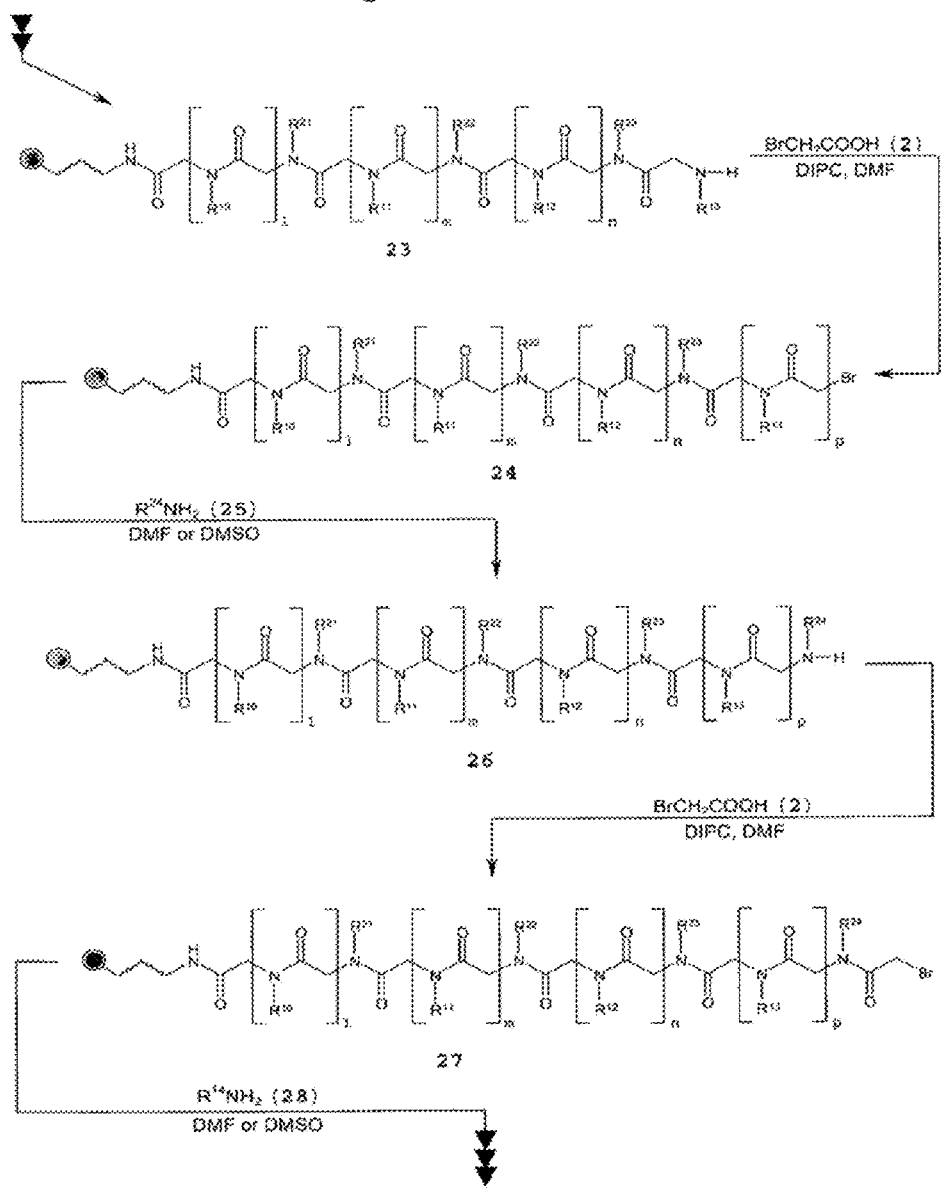
Figure 2:
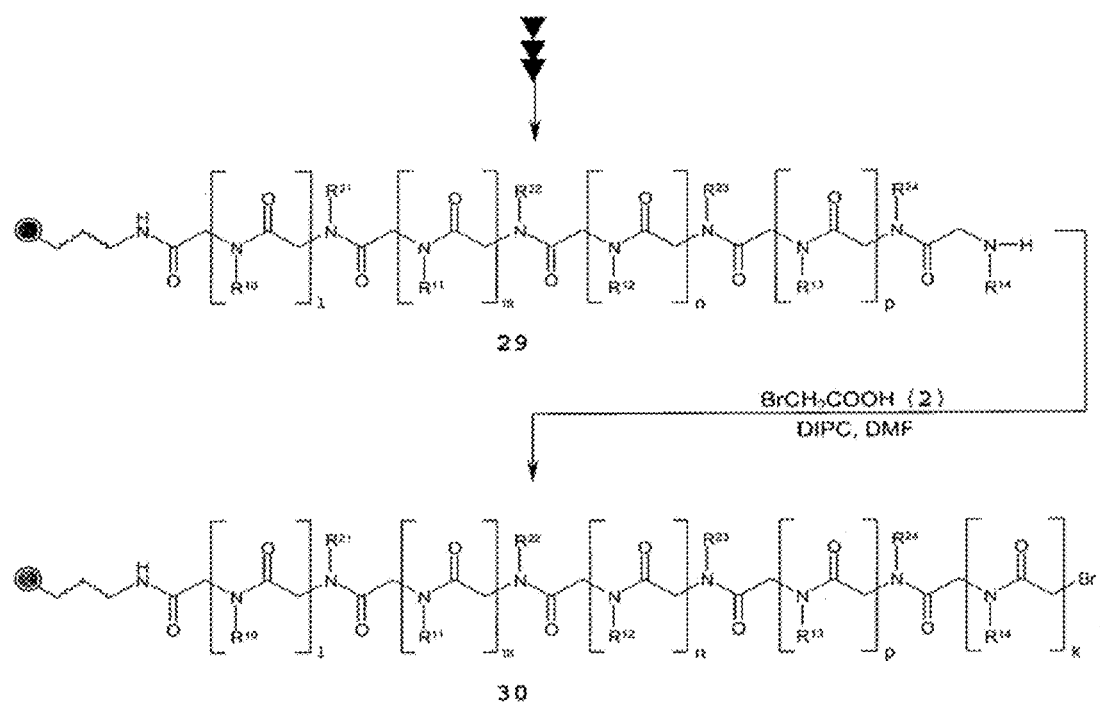

A step-wise synthetic scheme for the preparation of a compound of Formula I is presented in FIG. 2. More particularly, the scheme shown in FIG. 2 is designed to produce compounds of Formula I having the following Formula X:

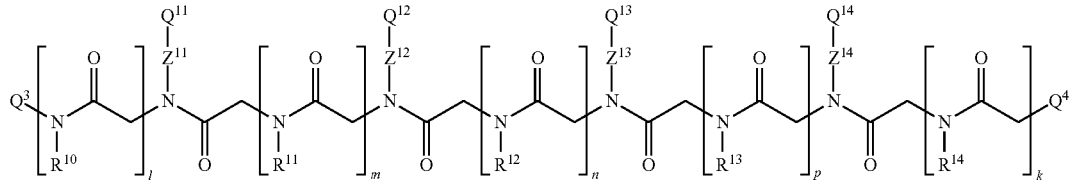

in which k, l, m, n, p, $R^{11}$, $R^{12}$, $R^{13}$, $Z^{11}$, $Z^{12}$, $Z^{13}$, $Z^{14}$, $Q^{11}$, $Q^{12}$, $Q^{13}$, $Q^{14}$, $Q^4$, and $Q^5$ are as described above and in which each $R^{10}$ and each $R^{14}$ are independently selected alkyl or aryl groups.

In an embodiment, the compounds of the present invention have the following structures:

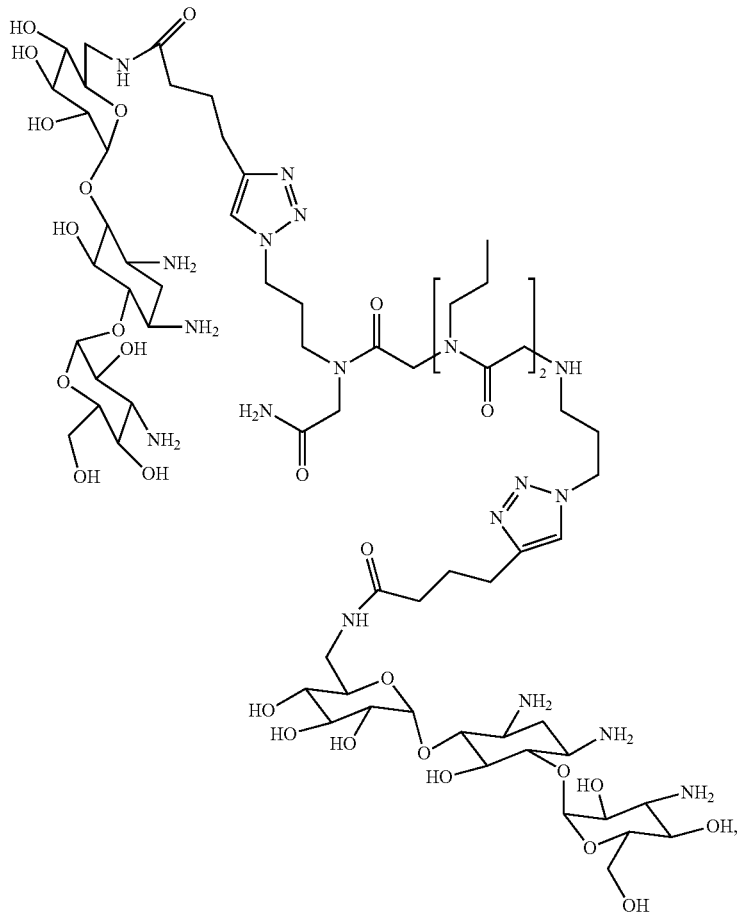

-continued
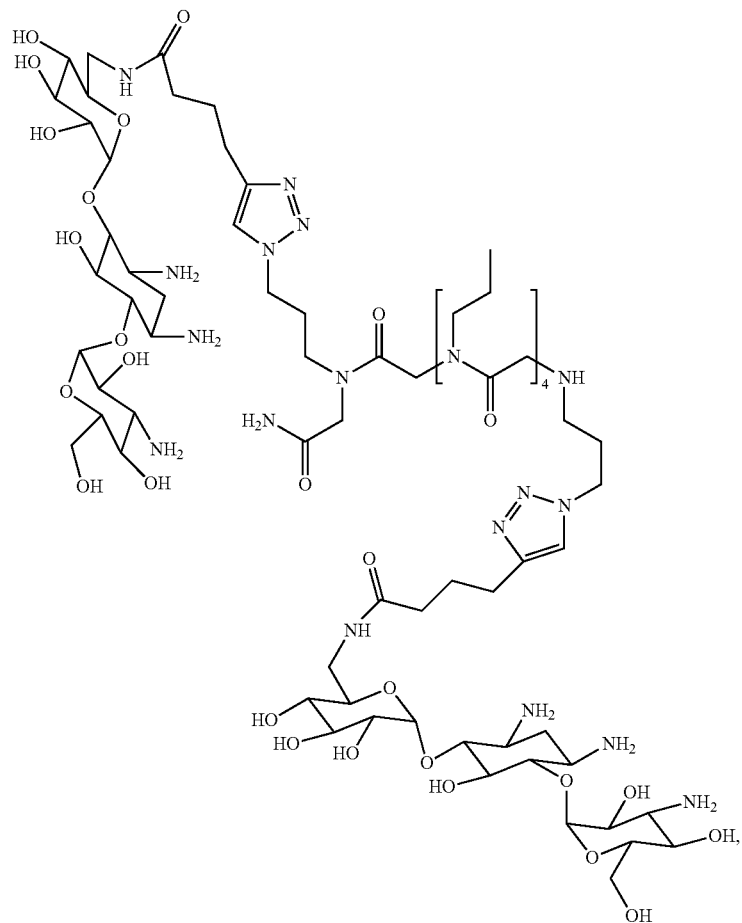

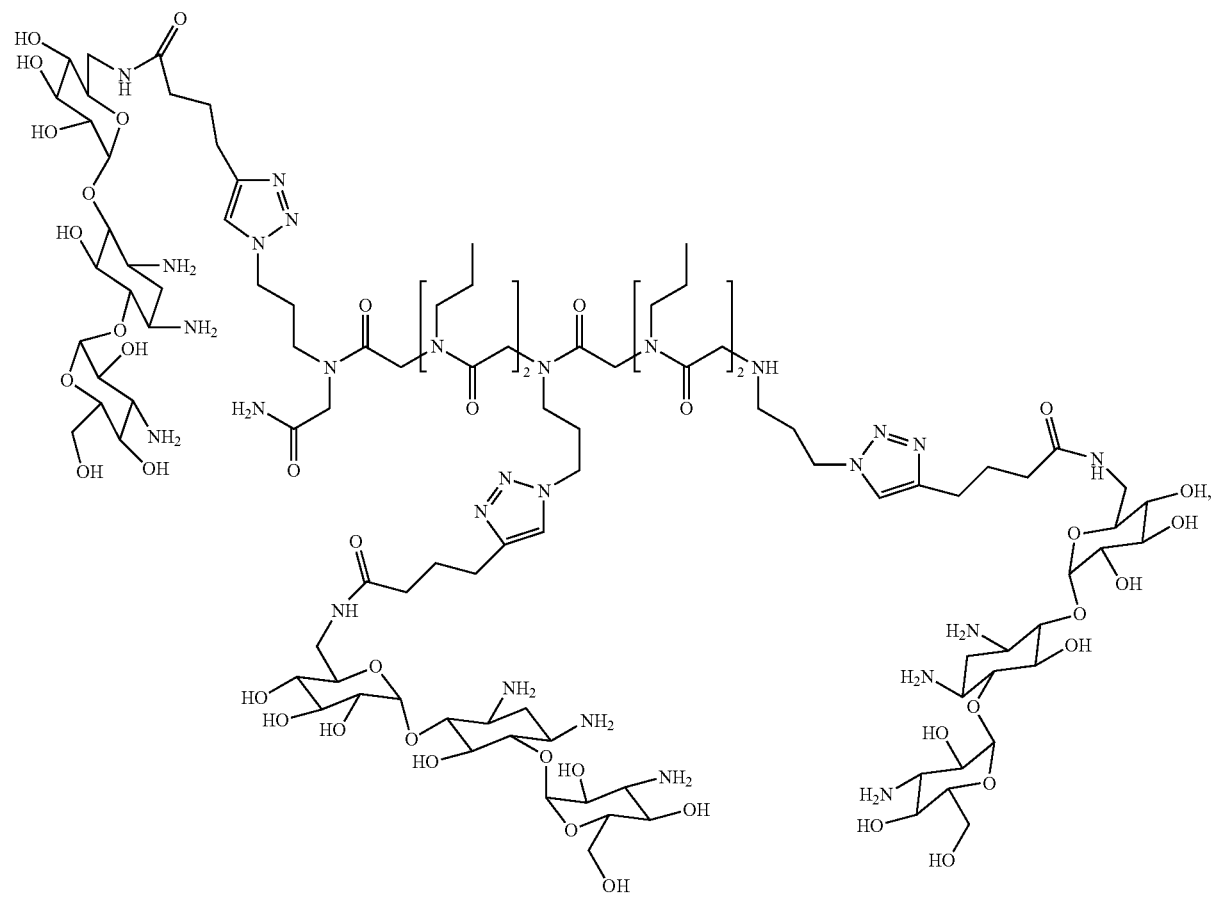

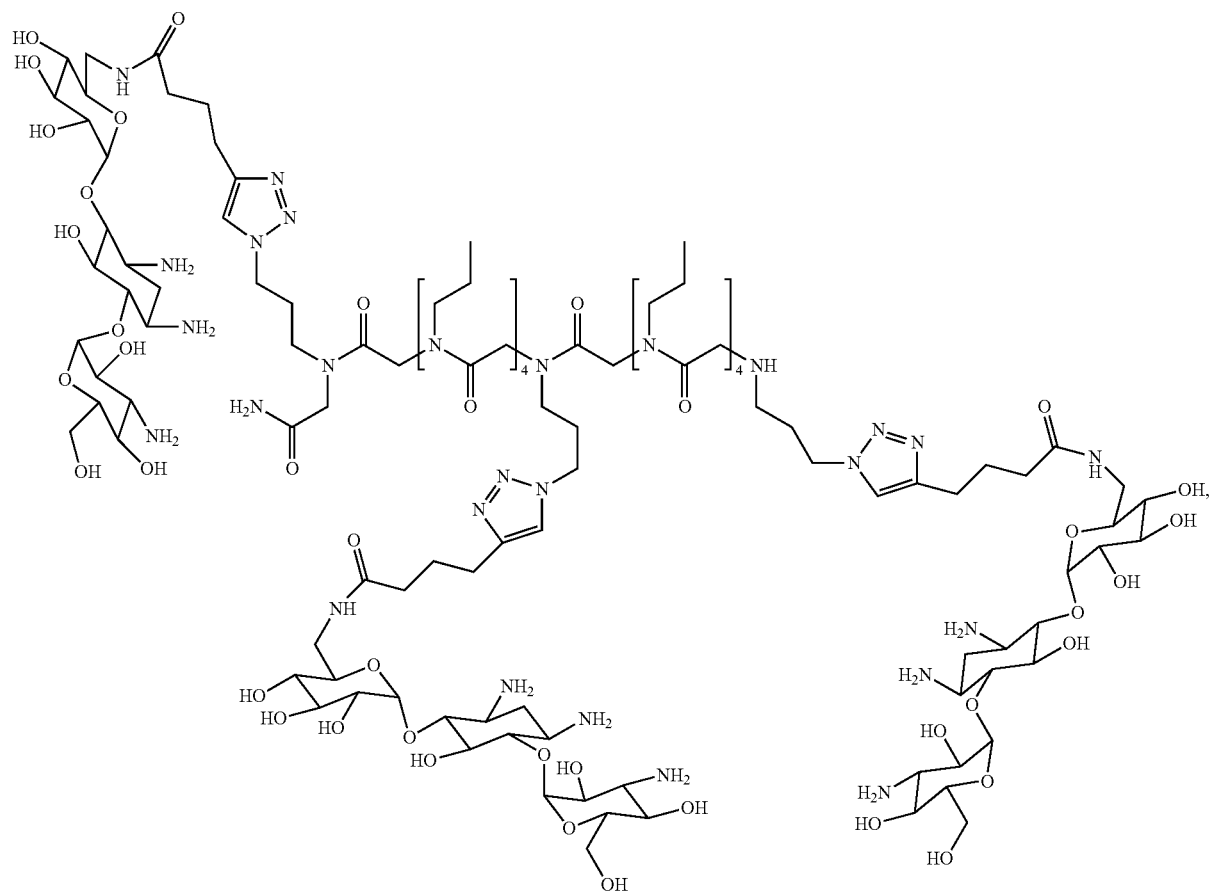
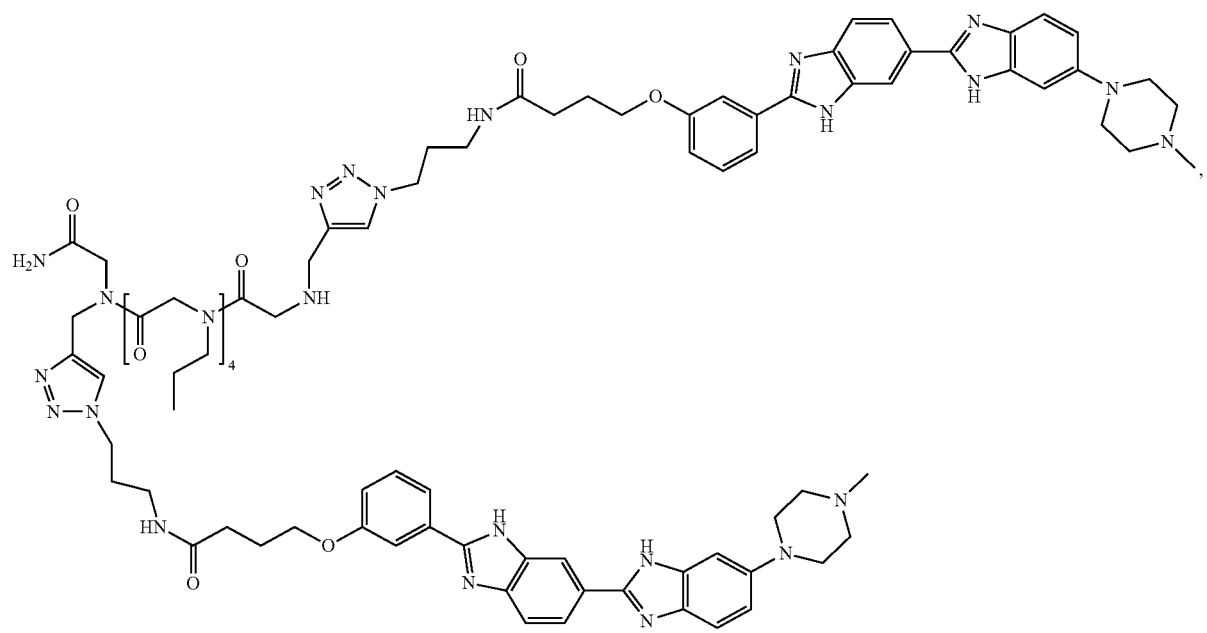

-continued
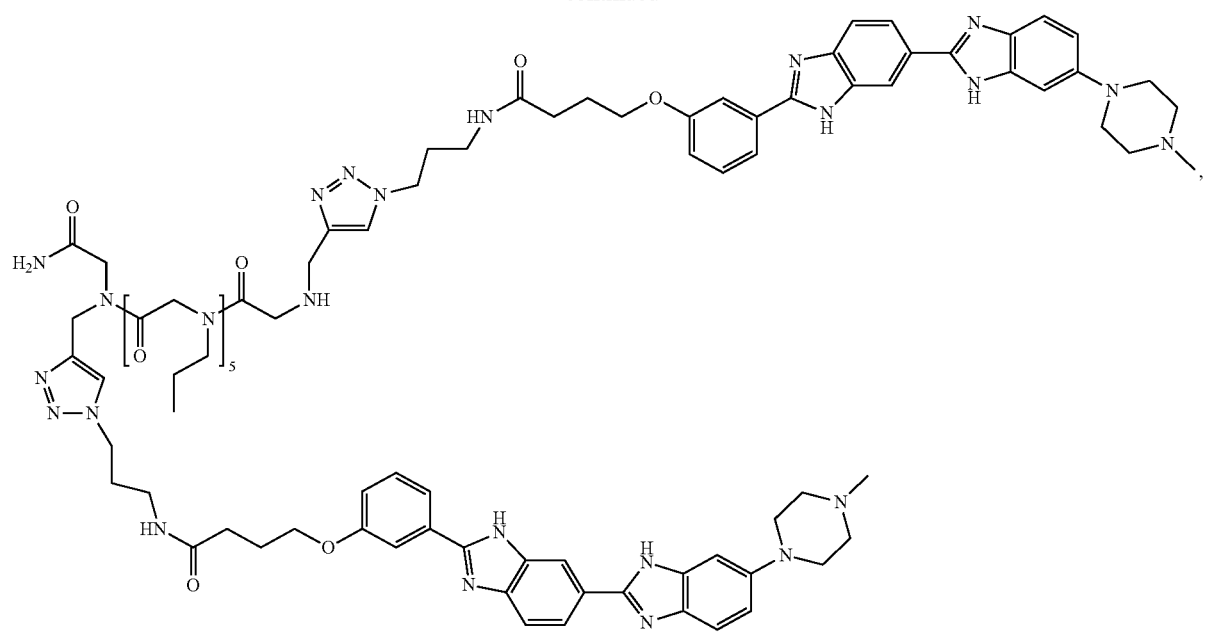
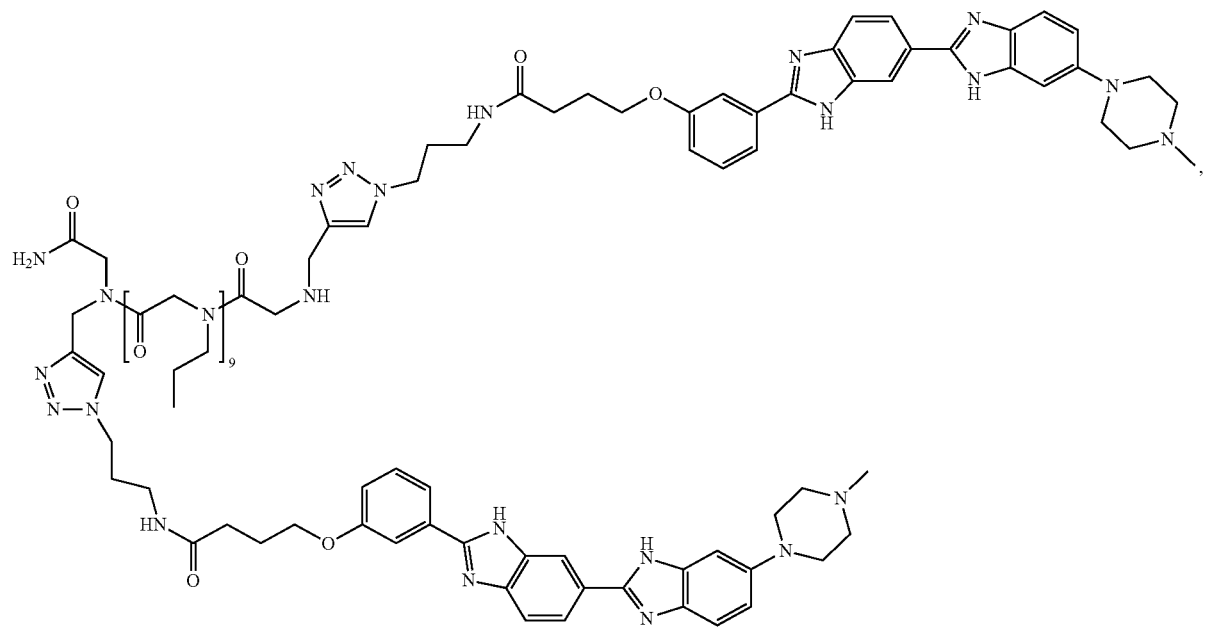

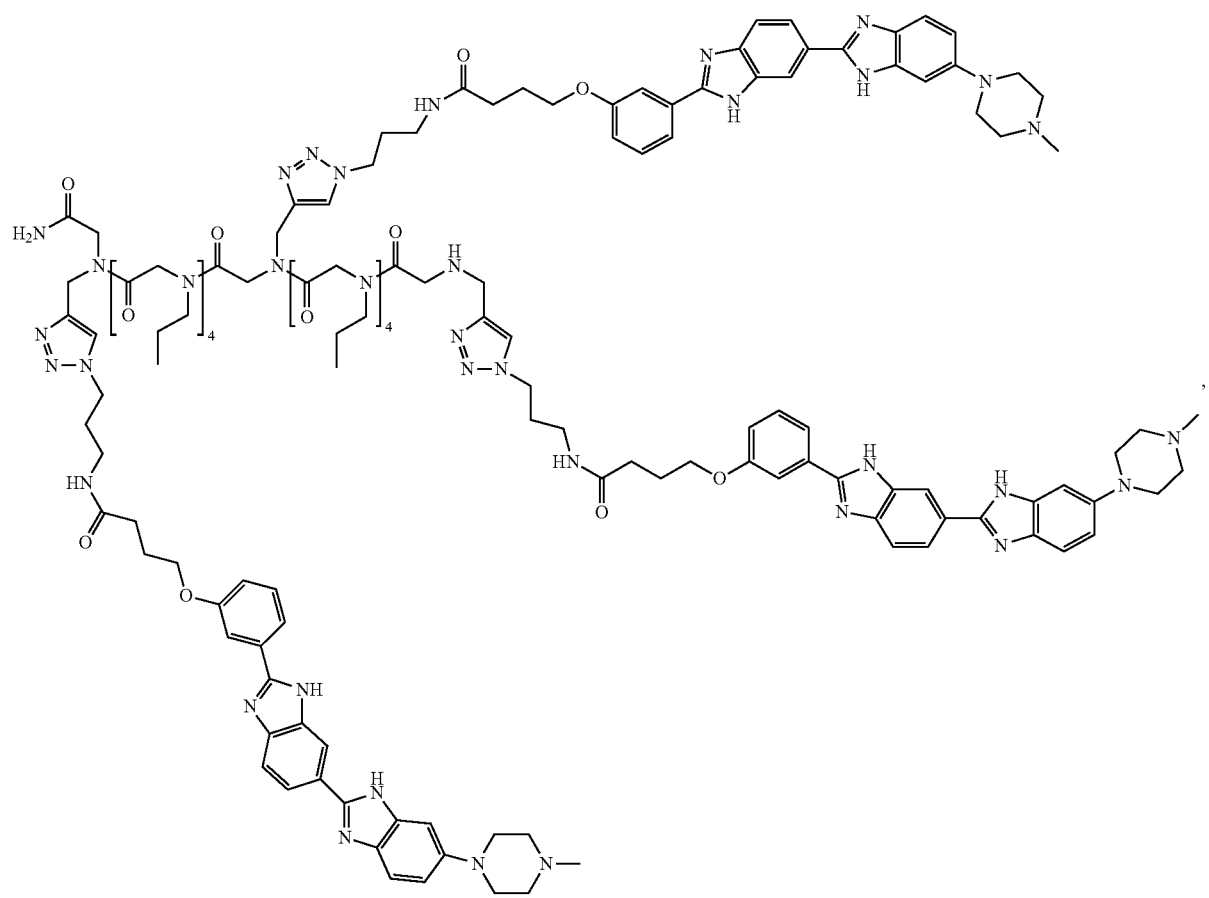

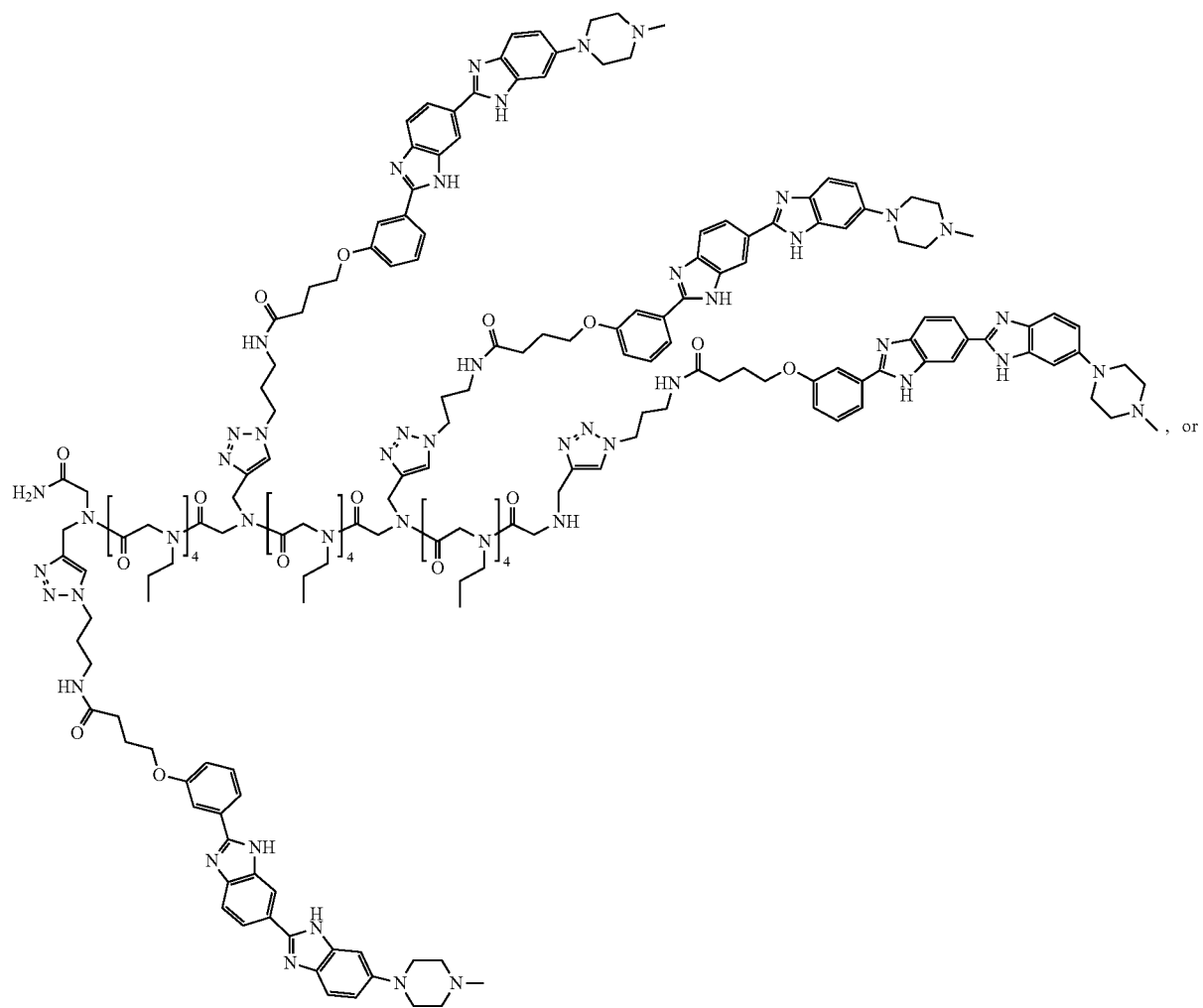, or

-continued
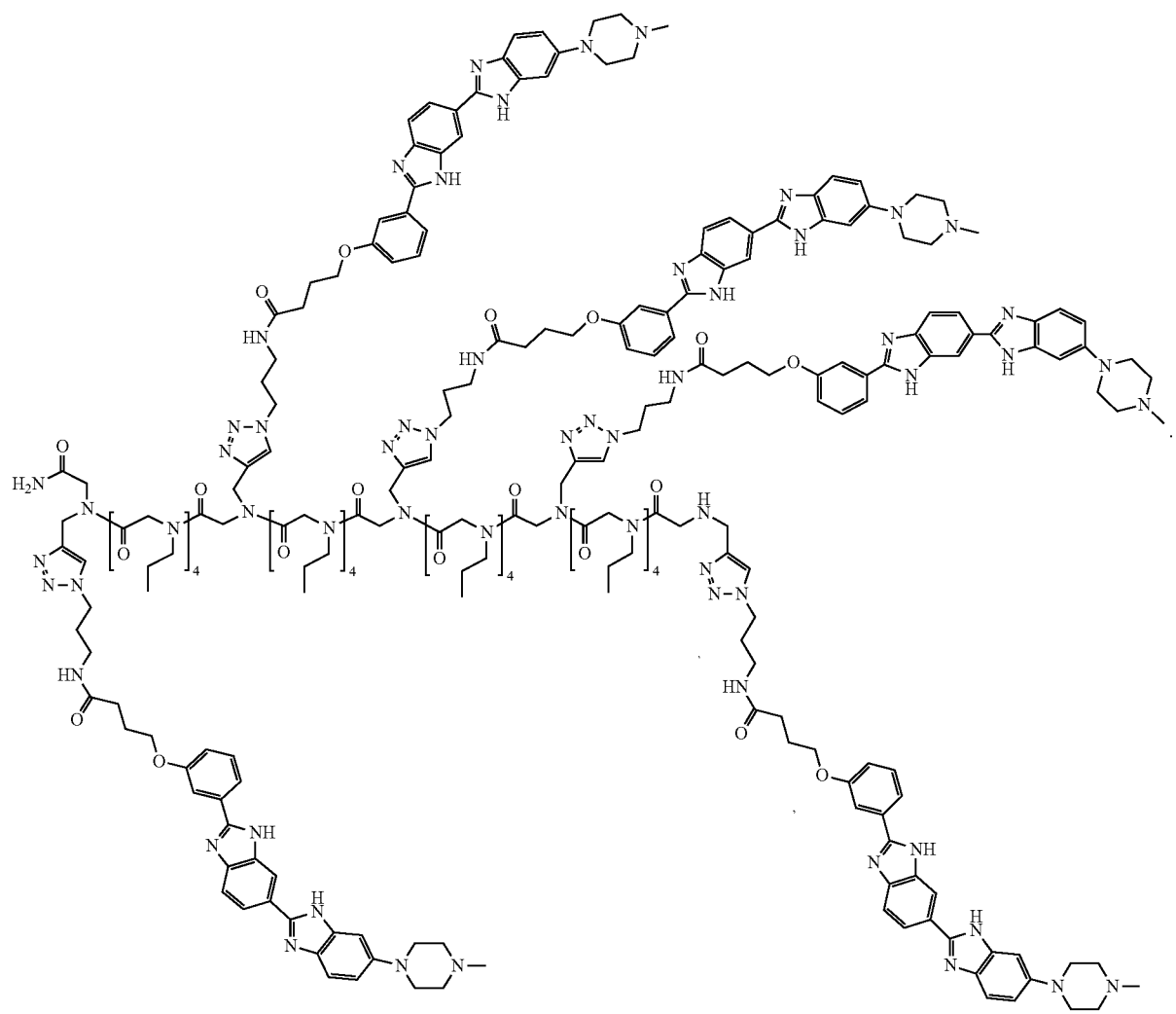

In an embodiment, the compounds of the present invention can have the following structures:
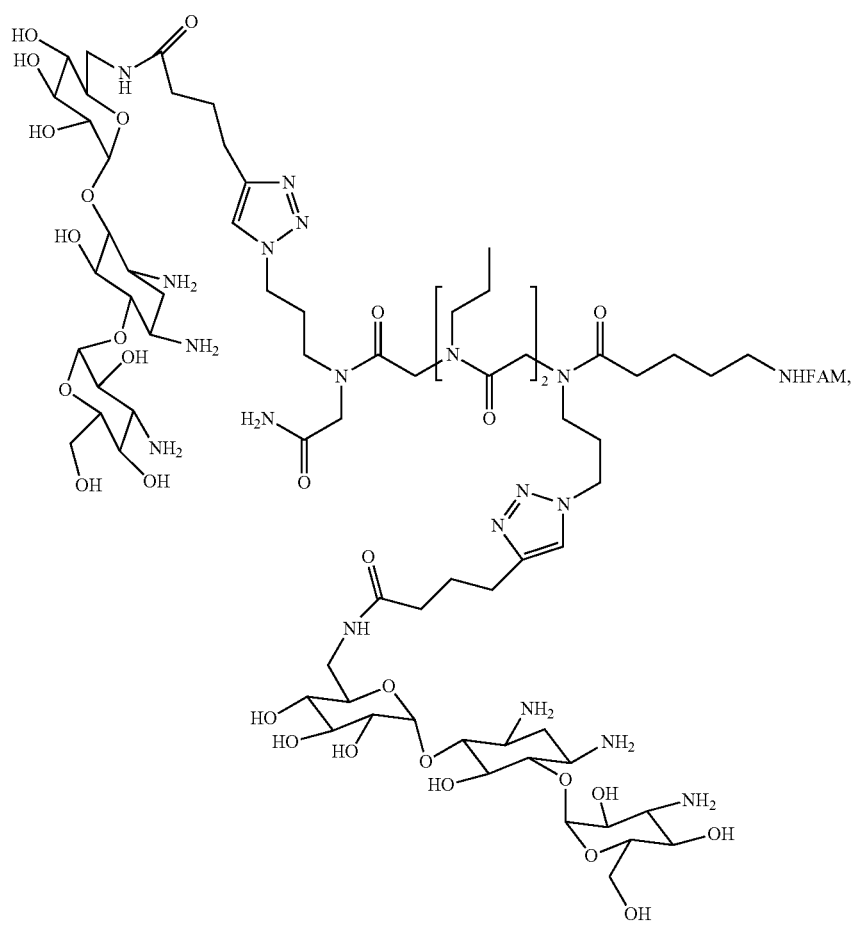

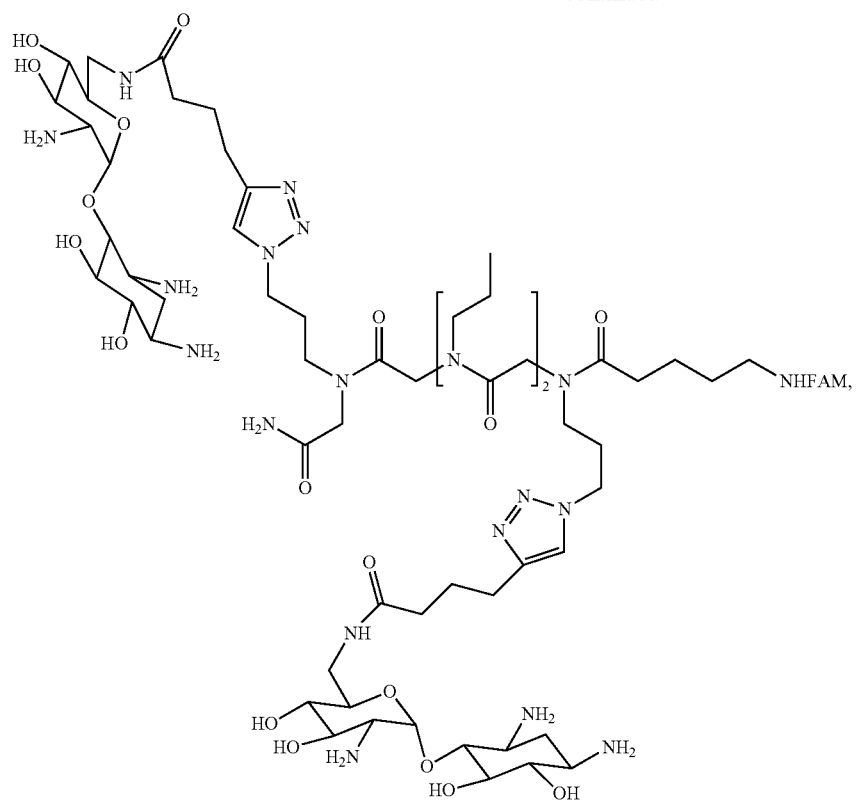
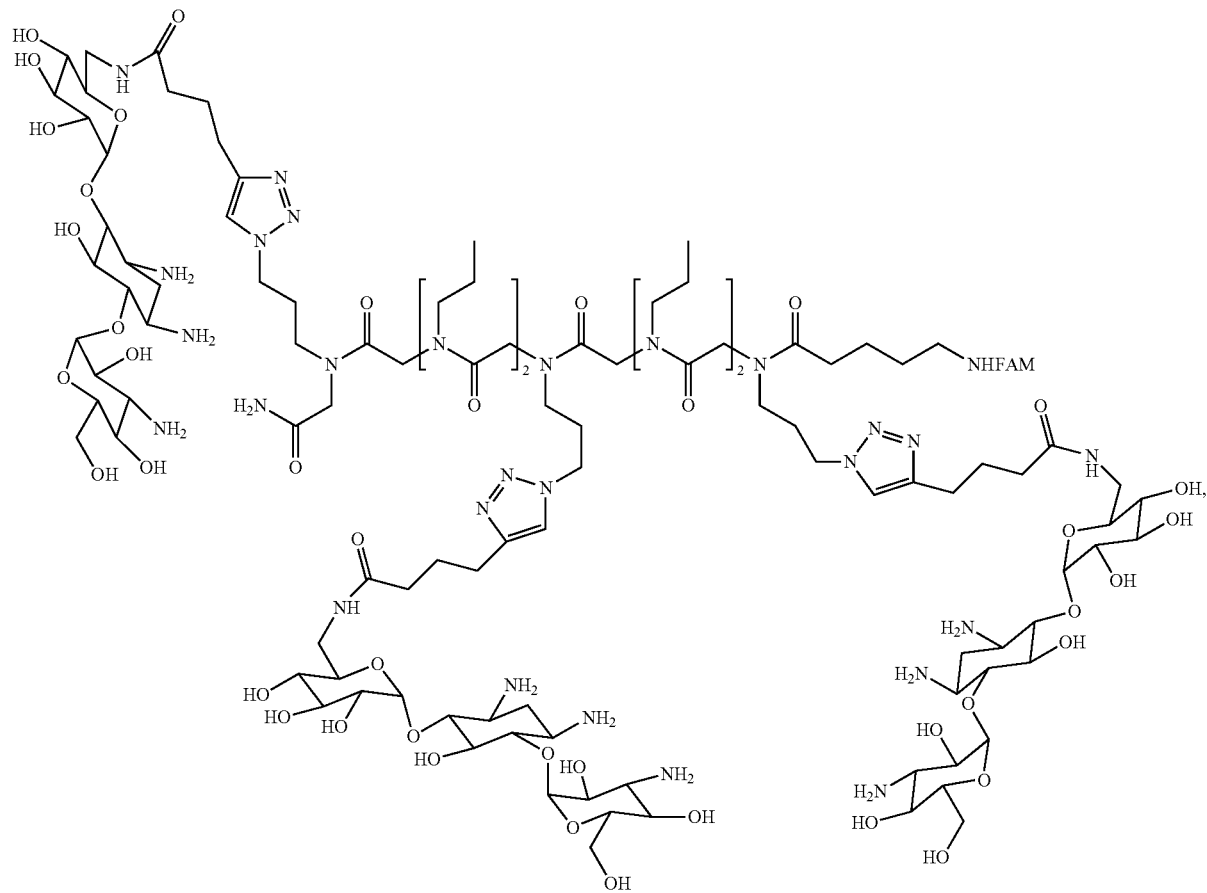

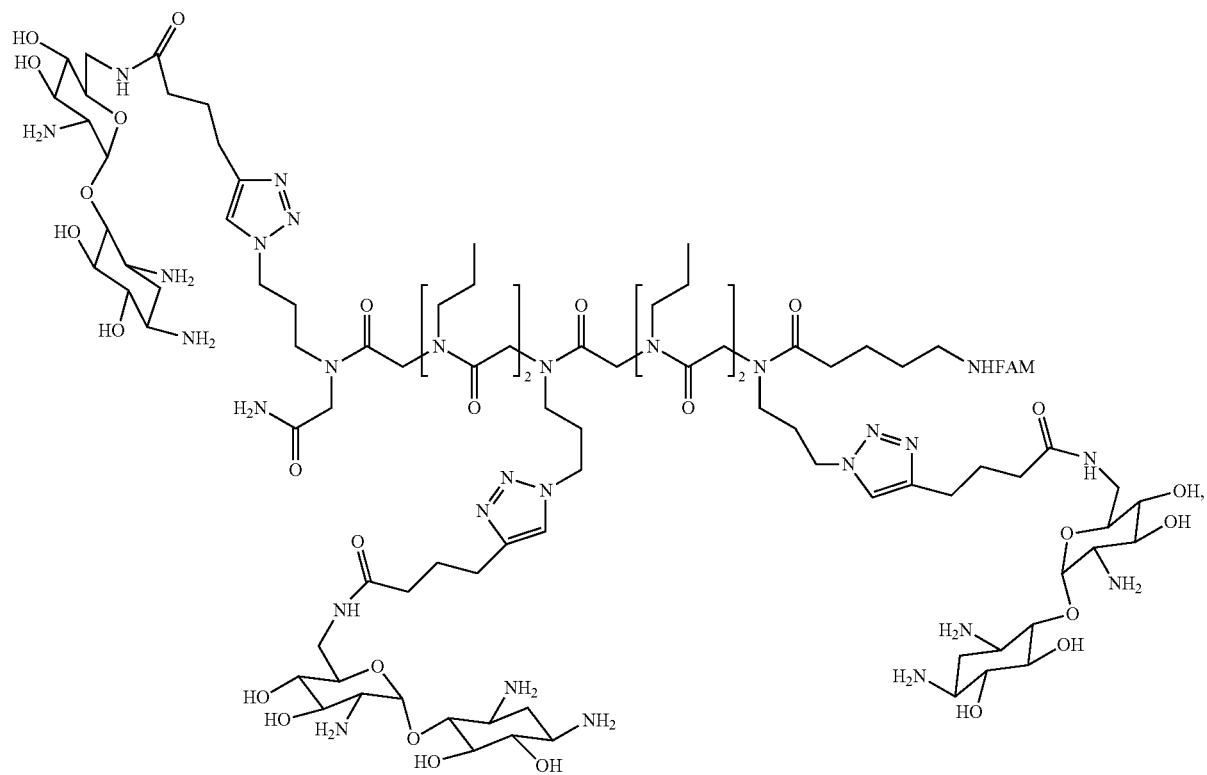
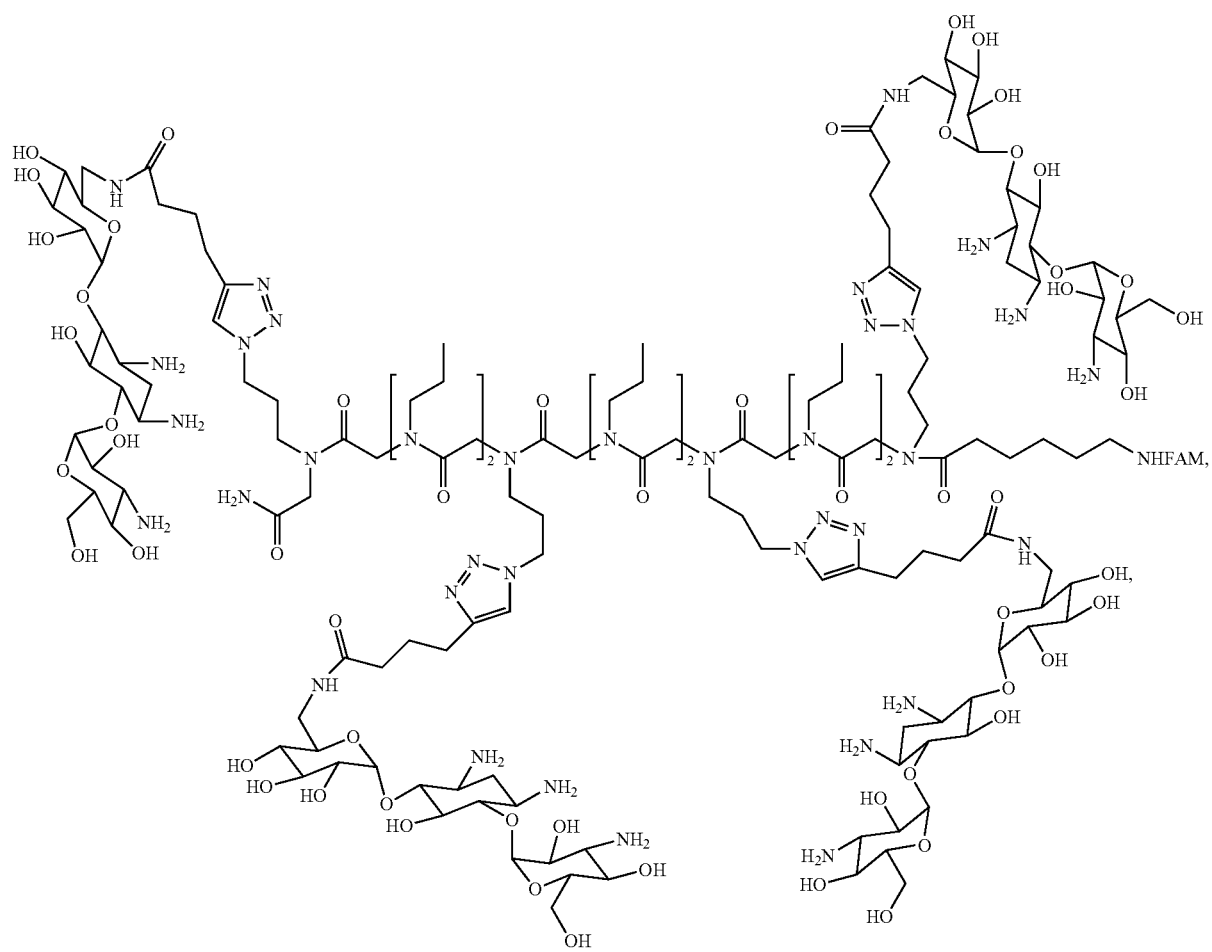

-continued
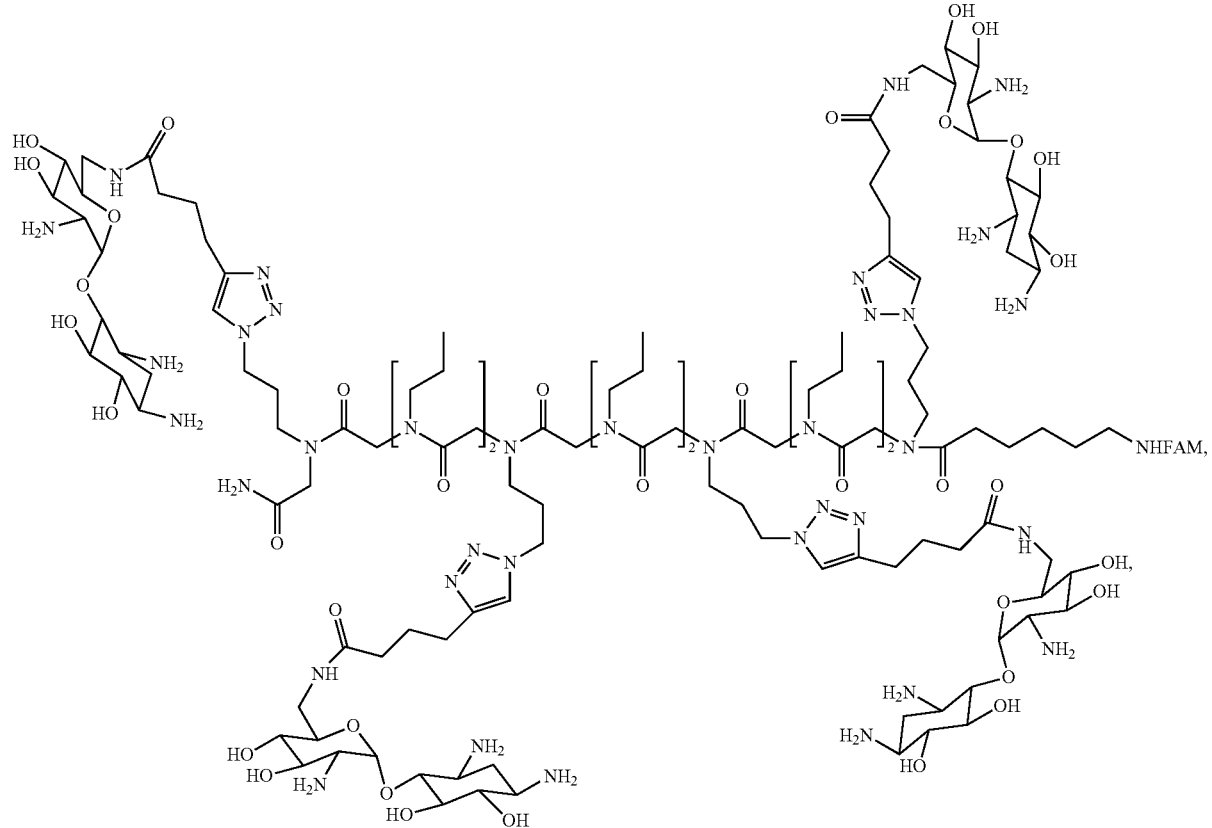

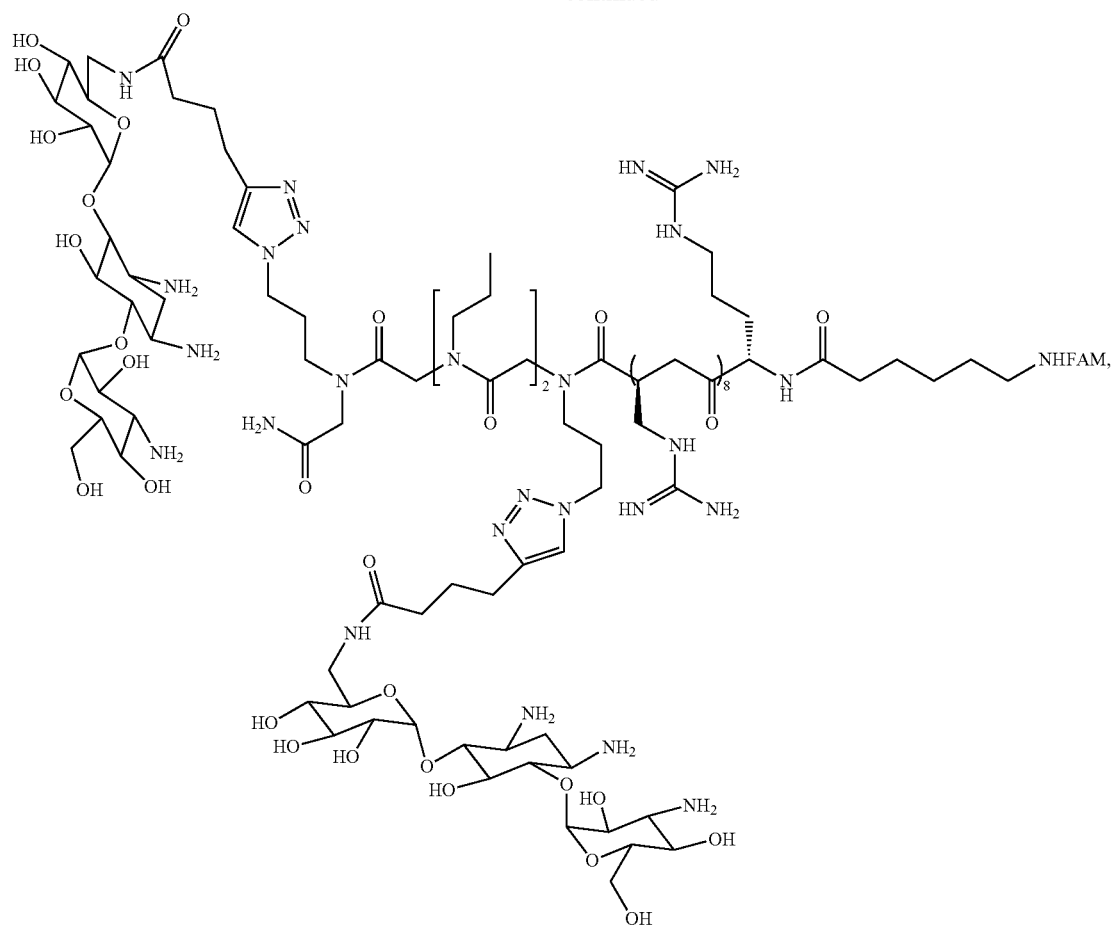
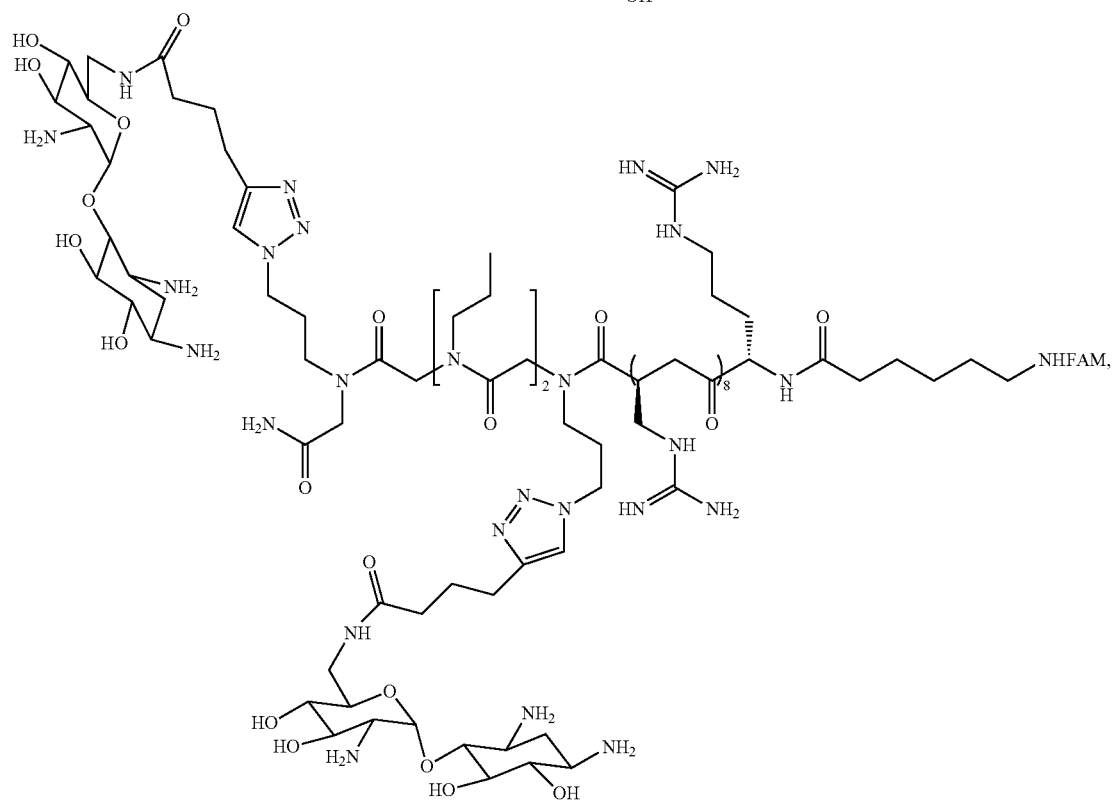

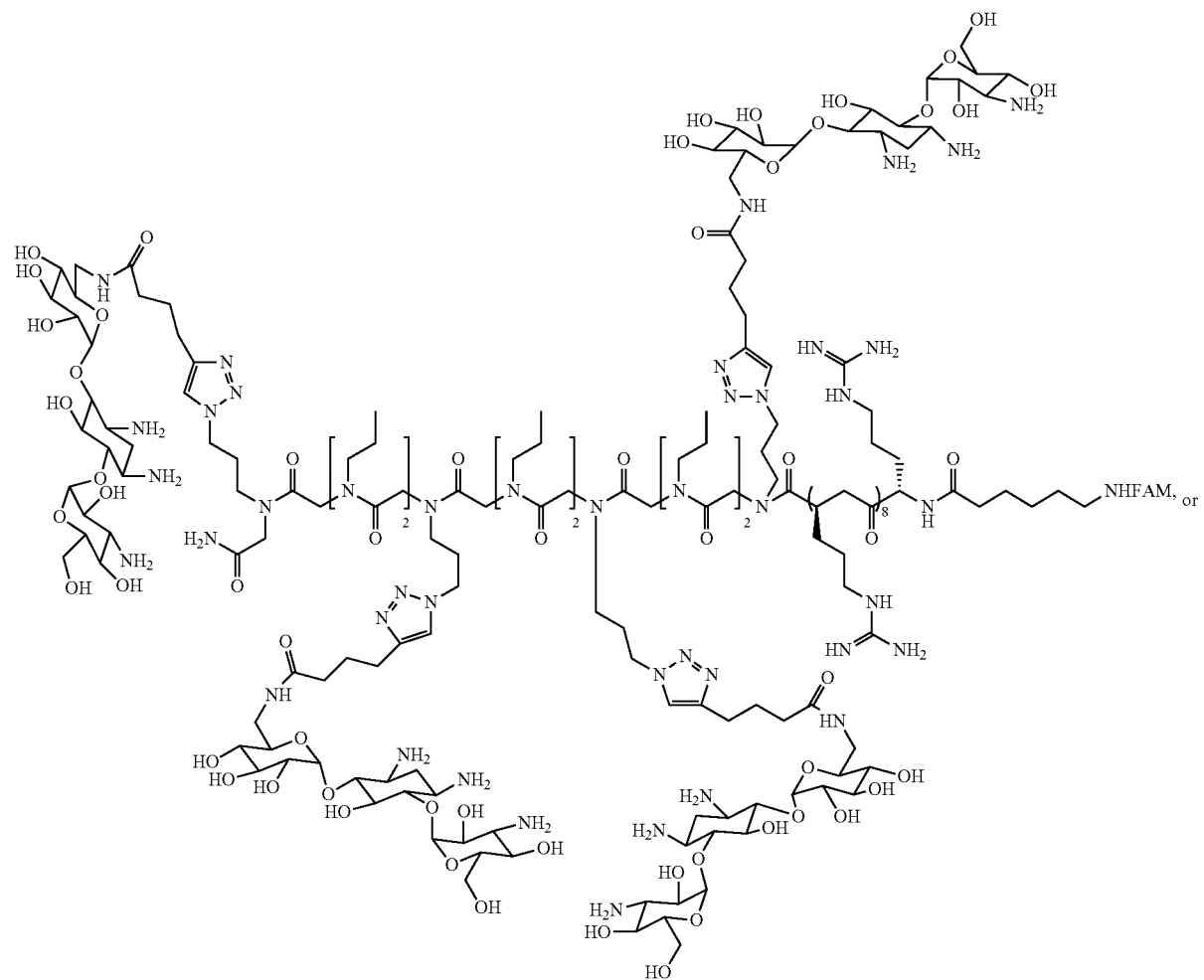

-continued

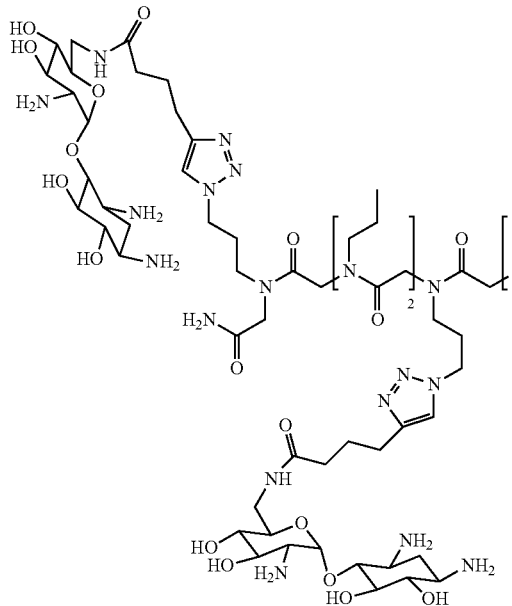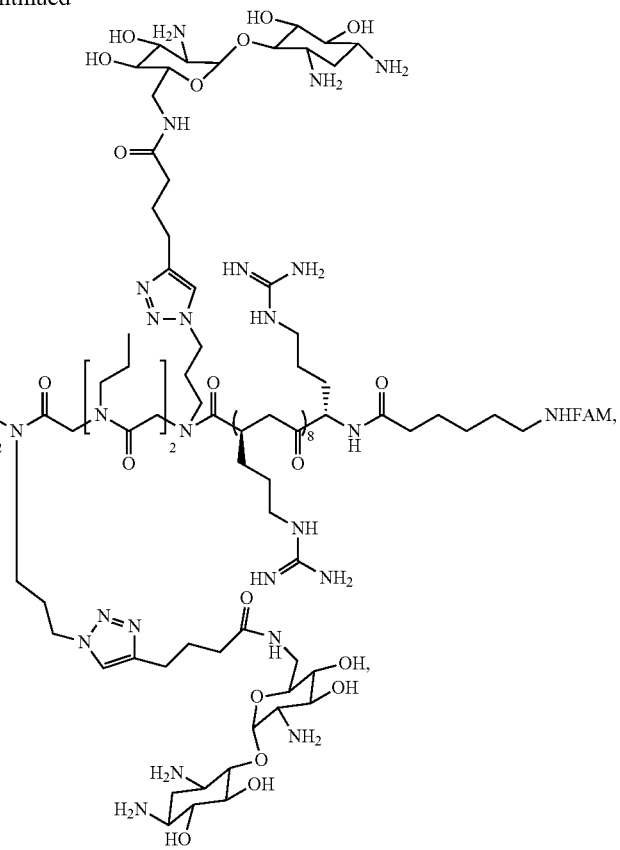

where FAM is a carboxyfluorescein.

Briefly, a resin bearing primary amine groups (such as deprotected Fmoc-Rink amide resin 1) is reacted with bromoacetic acid 2 in a suitable solvent (e.g., dimethylformamide ("DMF")) and in the presence of a dehydration agent, such as a dialkylcarbodiimide (e.g., diisopropylcarbodiimide ("DIPC")), for a suitable period of time (e.g., for from about 5 minutes to about 1 hour, such as for about 20 minutes) and at a suitable temperature (e.g., at from about room temperature to about 50° C., such as at about 37° C.) to produce bromoacetamide 3. After washing with a suitable solvent (e.g., dichloromethane ("DCM") or another suitable chlorinated hydrocarbon, DMF, or combinations thereof), bromoacetamide 3 is optionally (in those cases where 1 is not zero) reacted with non-functionalized amine 4 in a suitable solvent (e.g., DMF or tetrahydrofuran ("THF")) for a suitable period of time (e.g., for from about 5 minutes to about 1 hour, such as for about 20 minutes) and at a suitable temperature (e.g., at from about room temperature to about 50° C., such as at about 37° C.) to produce aminoacetamide 5; and, after washing with, for example, DCM and DMF, aminoacetamide 5 is then reacted with bromoacetic acid 2, as described above, to produce bromoacetamide 6 (1=1). In those cases where 1>1, the process (reaction with non-functionalized amine 4 followed by reaction with bromoacetic acid 2) is repeated 1-1 additional times. In each repetition, $R^{10}$ in non-functionalized amine 4 can be varied if desired.

Bromoacetamide 6 (1≠0) (or, in those cases where 1 is zero, bromoacetamide 3) is then reacted with functionalized amine 7 in a suitable solvent (e.g., DMF or THF) for a suitable period of time (e.g., for from about 5 minutes to about 1 hour, such as for about 20 minutes) and at a suitable temperature (e.g., at from about room temperature to about 50° C., such as at about 37° C.) to produce aminoacetamide 8. After washing with, for example, DCM and DMF, aminoacetamide 8 is then reacted with bromoacetic acid 2, as described above, to produce bromoacetamide 9.

Bromoacetamide 9 is optionally (in those cases where m is not zero) reacted with non-functionalized amine 10, as described above, to produce aminoacetamide 11; and, after washing with, for example, DCM and DMF, aminoacetamide 11 is then reacted with bromoacetic acid 2, as described above, to produce bromoacetamide 12 (m=1). In those cases where m>1, the process (reaction with non-functionalized amine 10 followed by reaction with bromoacetic acid 2) is repeated m−1 additional times. In each repetition, $R^{11}$ in non-functionalized amine 10 can be varied if desired.

Bromoacetamide 12 (m≠4) (or, in those cases where m is zero, bromoacetamide 9) is then reacted with functionalized amine 13 in a suitable solvent (e.g., DMF or THF), as described above, to produce aminoacetamide 14. After washing with, for example, DCM and DMF, aminoacetamide 14 is then reacted with bromoacetic acid 2, as described above, to produce bromoacetamide 15.

Bromoacetamide 15 is optionally (in those cases where n is not zero) reacted with non-functionalized amine 16, as described above, to produce aminoacetamide 17; and, after washing with, for example, DCM and DMF, aminoacetamide 17 is then reacted with bromoacetic acid 2, as described above, to produce bromoacetamide 18 (n=1). In those cases where m>1, the process (reaction with non-functionalized amine 16 followed by reaction with bromoacetic acid 2) is repeated n−1 additional times. In each repetition, $R^{12}$ in non-functionalized amine 16 can be varied if desired.

Bromoacetamide 18 (or, in those cases where n is zero, bromoacetamide 15) is then reacted with functionalized amine 19, as described above, to produce aminoacetamide 20. After washing with, for example, DCM and DMF, aminoacetamide 20 is then reacted with bromoacetic acid 2, as described above, to produce bromoacetamide 21.

Bromoacetamide 21 is optionally (in those cases where p is not zero) reacted with non-functionalized amine 22, as described above, to produce aminoacetamide 23; and, after washing with, for example, DCM and DMF, aminoacetamide 23 is then reacted with bromoacetic acid 2, as described above, to produce bromoacetamide 24 (p=1). In those cases where p>1, the process (reaction with non-functionalized amine 22 followed by reaction with bromoacetic acid 2) is repeated n−1 additional times. In each repetition, $R^{13}$ in non-functionalized amine 22 can be varied if desired.

Bromoacetamide 24 (or, in those cases where p is zero, bromoacetamide 21) is then reacted with functionalized amine 25, as described above, to produce aminoacetamide 26. Aminoacetamide 26 can then reacted with bromoacetic acid 2, as described above, to produce bromoacetamide 27.

In those cases where k is not 0, bromoacetamide 27 can then be reacted with non-functionalized amine 28, as described above, to produce aminoacetamide 29. In those cases where k>1, the process (reaction with non-functionalized amine 28 followed by reaction with bromoacetic acid 2) can be repeated k−1 more times. In each repetition, $R^{14}$ in non-functionalized amine 28 can be varied if desired. The resulting aminoacetamide 29 (k≠0) can then reacted with bromoacetic acid 2, as described above, to produce bromoacetamide 30 ($Q^4$=Br in Formula X).

As one skilled in the art will appreciate, the process described above can be repeated any number of times to extend the peptoid backbone and introduce additional functionalized alkyl groups.

The terminal bromine (e.g., the bromine on the right size of bromoacetamide 27 (in cases where k is zero) or the bromine on the right size of bromoacetamide 30 (in cases where k>0) provides a convenient place to perform additional chemistry. Illustratively, bromoacetamide 27 or bromoacetamide 30 can be alkylated or arylated to provide compounds in which $Q^4$ is an alkyl or aryl group. Alternatively, bromoacetamide 27 or bromoacetamide 30 can be reacted with a functionalized amine (e.g., $HNR^{25}$ in which $R^{21}$ is a functionalized alkyl), for example, to produce a compound in which $Q^4$ has the formula —$NHR^{25}$ (e.g., as a way of producing a compound of Formula X in which $Q^4$ has the formula —$NHZ^{15}$ $Q^{15}$ in which $Q^{15}$ is an RNA binding ligand (examples of which include those described above with regard to $Q^1$) and in which $Z^{15}$ is a linking moiety (examples of which include those described above with regard to $Z^1$)). Still alternatively, bromoacetamide 27 or bromoacetamide 30 can be reacted with a non-functionalized amine, for example, to produce a compound in which $Q^4$ has the formula —$NHR^{15}$ in which $R^{15}$ is an alkyl group or an aryl group (e.g., an unsubstituted alkyl group). In those cases where bromoacetamide 27 or bromoacetamide 30 are reacted with a functionalized or non-functionalized amine, the amine's nitrogen can provide a convenient site for further chemistry. For example, reaction of the terminal amine with an acid, such as a Fmoc-protected aminoalkanoic acid (e.g., a Fmoc-protected 6-aminohexanoic acid) provides a functionalized spacer, to which a dye (e.g., a fluorescent dye) or other labeling moiety can be coupled.

In FIG. 2 and in the above discussion, $R^{21}$, $R^{22}$, $R^{23}$, $R^{24}$, and $R^{25}$ represent functionalized alkyl groups (i.e., alkyl groups which bear a substituent to which an RNA binding ligand can be coupled via, for example, an amide linkage, an ester linkage, an ether linkage, or a triazole ring linkage. Suitable functional groups include, for example, carboxylic acids and protected carboxylic acids, amines and protected amines, hydroxyls and protected hydroxyls, alkynes, and azides. To produce compounds of Formula X, the functional groups on $R^2$, $R^{22}$, $R^{23}$, $R^{24}$, and $R^{25}$ are coupled to the desired RNA binding ligands to produce the —$Z^{11}$-$Q^{11}$, —$Z^{12}$-$Q^{12}$, $Z^{13}$-$Q^{13}$, $Z^{14}$-$Q^{14}$, and —$Z^{15}$-$Q^{15}$ moieties, respectively.

This can be done while the peptoid backbone is being constructed, for example, as in the case where $R^{21}$ of aminoacetamide 8 is coupled to the desired RNA binding ligand (to produce the —$Z^{11}$-$Q^{11}$ prior to reacting aminoacetamide 8 with bromoacetic acid 2 to produce bromoacetamide 9; and as in the case where $R^{21}$ of aminoacetamide 8 is coupled to the desired RNA binding ligand (to produce the —$Z^{11}$-$Q^{11}$ moiety) after reacting aminoacetamide 8 with bromoacetic acid 2 to produce bromoacetamide 9 but prior to optionally reacting bromoacetamide 9 with non-functionalized amine 10 to produce aminoacetamide 11 and/or prior to reacting bromoacetamide 12 with functionalized amine 13 to produce aminoacetamide 14. This step-wise coupling is particularly useful in those cases where different RNA binding ligands are to be coupled at different locations along the peptoid backbone.

In cases where some of the RNA binding ligands are the same and adjacent to one another (e.g., as in the case where $Q^{11}$ and $Q^{12}$ are the same but different from $Q^{13}$), $R^{21}$ and $R^{22}$ of aminoacetamide 14 can be coupled to the desired RNA binding ligand (to produce —Z-$Q^{11}$ and —$Z^{12}$-$Q^{12}$ moieties) in a single step prior to reacting bromoacetamide 18 with functionalized amine 19 to produce aminoacetamide 20.

In cases where all of the RNA binding ligands are the same, $R^{21}$, $R^{22}$, $R^{23}$, and $R^{24}$ of aminoacetamide 29 or bromoacetamide 30 or subsequent reaction products thereof (and any other functionalized alkyl groups that might be present, such as $R^{25}$) can be coupled to the desired RNA binding ligand in a single step. This single-step coupling can take place before or after the peptoids are cleaved from the resin or other substrate (described below).

After the peptoid backbone is prepared and after the RNA binding ligands are coupled (if such coupling is to be performed prior to cleavage from the resin or other substrate) and/or after any other desired chemistry is performed (e.g., any reactions involving the terminal bromine and/or terminal amine) (if such chemistry is to be performed prior to cleavage from the resin or other substrate), the peptoids are cleaved from the resin or other substrate. Methods for cleaving the peptoids from the substrate will depend on the nature of the substrate. Where a Fmoc-Rink amide resin is employed (as in FIG. 2 and the discussion above), cleavage can be effected using 95:5 trifluoroacetic acid:water.

The present invention, in another aspect thereof, relates to an RNA targeting compound that includes a polymer backbone and two or more pendant RNA binding ligands, wherein the two or more pendant RNA binding ligands are bound to the polymer backbone.

Illustratively, the RNA targeting compound can include 2 pendant RNA binding ligands, 3 or more pendant RNA binding ligands, 4 or more pendant RNA binding ligands, 5 or more pendant RNA binding ligands, from 2 to 100 pendant RNA binding ligands, from 2 to 50 pendant RNA binding ligands, from 2 to 20 pendant RNA binding ligands, and/or 2, 3, 4, 5, 6, 7, 8, 9, 10, 15, or 20 pendant RNA binding ligands.

The two or more pendant RNA binding ligands can bind to RNA structural motifs, such as in the case where each of the RNA structural motifs is independently selected from an RNA internal loop motif, an RNA hairpin loop motif, an RNA bulge motif, an RNA multibranch loop motif, and/or an RNA pseudoknot motif. Additionally, or alternatively, the two or more pendant RNA binding ligands can bind to RNA repeat motifs, such as RNA triplet repeat motifs (e.g., CUG RNA triplet repeat motifs, CUG RNA triplet repeat motifs, CGG RNA triplet repeat motifs, GCC RNA triplet repeat motifs, GAA RNA triplet repeat motifs, and/or CAG RNA triplet repeat motifs), RNA tetra repeat motifs (e.g., CCUG RNA tetra repeat motifs), or pentanucleotide repeats that cause spinocerebellar ataxia type 10 (AUUCU repeats) or Frontal temporal dementia and ALS (GGGGCC repeats).

In certain embodiments, each of the two or more pendant RNA binding ligands are the same. In certain embodiments, the two or more pendant RNA binding ligands are not the same (e.g., at least one is different from the others, at least two are different from the others; etc.).

Examples of suitable pendant RNA binding ligands include those described above (e.g., with regard to $Q^1$). Illustratively, the two or more pendant RNA binding ligands can be the same or different and are selected from aminoglycoside sugars and bisbenzimidazoles. In certain embodiments, the two or more pendant RNA binding ligands are aminoglycoside sugars, such as kanamycins (e.g., kanamycin A's, kanamycin B's), tobramycins, neamines, neomycins, and the like. In certain embodiments, the two or more pendant RNA binding ligands are kanamycin A's. In certain embodiments, the two or more pendant RNA binding ligands are neamines. In certain embodiments, the two or more pendant RNA binding ligands are tobramycins. In certain embodiments, the two or more pendant RNA binding ligands are neomycins. In certain embodiments, the two or more pendant RNA binding ligands are bisbenzimidazoles, such as in the case where the two or more pendant RNA binding ligands are pibenzimols, examples of which include Hoechst 33258.

As used herein in this context, "polymer backbone" is meant to refer to a repeating, substantially linear collection of 3 or more (e.g., 4 or more, 5 or more, etc.) atoms that are covalently bonded to one another. The polymer backbone can be, for example, a peptoid polymer backbone (e.g., as in the case where the polymer backbone has a repeating —C(O)—N-alkylene-structure (e.g., a repeating —C(O)—N—CH$_2$— structure, such as where the polymer backbone can be represented by the formula: [C(O)—N—CH$_2$]$_z$ where z is an integer greater than or equal to 2, such as from 2 to 1000, from 3 to 1000, from 4 to 1000, from 5 to 1000, from 2 to 200, from 3 to 200, from 4 to 200, from 5 to 200, from 2 to 100, from 3 to 100, from 4 to 100, from 5 to 100, and/or 2, 3, 4, 5, 6, 7, 8, 9, 10, 20, 30, 40, 50, and the like. Other suitable polymer backbones include those based on biological monomers, such as peptides (e.g., alpha amino acids, beta amino acids, etc.) as well as those based on non-biological monomers (e.g., polyethers; polyurethanes; polyamides; polyacrylates; polyethylenes, polypropylenes, and other polyolefins; polyethylene glycols; and the like).

As noted above, the two or more pendant RNA binding ligands are bound (e.g., covalently) to the polymer backbone, for example, via a linking moiety, examples of which include those discussed above in the context of Formula I. Illustratively, in the case where the polymer backbone is a peptoid polymer backbone, the two or more pendant RNA binding ligands can be bound (e.g., via an optional linker) to some or all of the peptoid polymer backbone's nitrogen atom. Those nitrogen atoms in the peptoid polymer backbone that are not bound to pendant RNA binding ligands can be substituted with the same or different substituents, such as alkyl or aryl groups (some or all of which alkyl or aryl groups can be substituted or not).

Methods for making the subject RNA targeting compounds that utilize a peptoid polymer backbone include those described hereinabove in relation to the preparation of RNA targeting compounds of Formula I. In those cases where non-peptoid polymer backbones are employed, one skilled in the art can readily identify suitable methods of preparation, taking into account the functional groups that may be present on the polymer backbone to be used, the functional groups that may be present on the RNA binding ligands to be used, the preparative methods described above with regard to the synthesis of compounds of Formula I, and conventional synthetic methodologies.

The compounds of the present invention can be used in a variety of ways.

Illustratively, the compounds can be used, for example in a competitive binding assay, to determine the ability of other compounds to bind to particular RNA or particular RNA motifs.

By way of further illustration, compounds of the present invention that include a dye (e.g., a fluorescent dye), a label, a marker, or other probe can be used to detect the presence of a particular RNA or particular RNA motifs in a sample. Such assays can be carried out in vivo, ex vivo, or in vitro. Illustratively, compounds of the present invention that include a dye (e.g., a fluorescent dye) or other probe can be used to detect the presence, quantify the amount, and/or determine the location of the particular RNA or particular RNA motifs that may be present in a sample, such as a biological sample, a tissue sample, a blood sample, a urine sample, a cell sample, or in an organism.

By way of still further illustration, compounds of the present invention can be used to treat RNA-mediated diseases or conditions, such as diseases or conditions that are caused by triplet repeats, for example, triplet repeats in non-coding regions (examples of which include myotonic dystrophy (CUG repeat), spinocerebellar ataxia type 8 (CUG repeat), Fragile X syndrome (CGG repeat), Fragile XE syndrome (GCC repeat), Friedreich ataxia (GAA repeat), and spinocerebellar ataxia type 12 (CAG repeat)) and triplet repeats in coding regions (examples of which include spinocerebellar ataxia type 1 (CAG repeat), spinocerebellar ataxia type 2 (CAG repeat), spinocerebellar ataxia type 3 (CAG repeat), spinobulbar muscular atrophy (Kennedy's Disease) (CAG repeat), Huntington's Disease (CAG repeat), dentatorubral-pallidoluysian atrophy (CAG repeat), spinocerebellar ataxia type 6 (CAG repeat), and spinocerebellar ataxia type 7 (CAG repeat)); or that are caused by RNA tetra repeats, such as myotonic dystrophy type 2 (CCUG repeats), or pentanucleotide repeats that cause spinocerebellar ataxia type 10 (AUUCU repeats) or Frontal temporal dementia and ALS (GGGGCC repeats).

For example, the present invention relates to a method for treating a disease caused by RNA triplet or tetra repeats in a subject, and the method includes administering, to the subject, an RNA targeting compound of the present invention in which at least some of the RNA binding ligands (e.g., each of the RNA binding ligands) bind to a RNA triplet or tetra repeat motif. In certain embodiments, the disease is myotonic dystrophy, and some or all of the RNA binding ligands bind to a CUG RNA triplet repeat motif. In certain embodiments, the disease is myotonic dystrophy, and the RNA binding ligands are the same or different and are selected from aminoglycoside sugars and bisbenzimidazoles. In certain embodiments, the disease is spinocerebellar ataxia type 8, and some or all of the RNA binding ligands bind to a CUG RNA triplet repeat motif. In certain embodiments, the disease is spinocerebellar ataxia type 8, and the RNA binding ligands are the same or different and are selected from aminoglycoside sugars and bisbenzimidazoles. In certain embodiments, the disease is Fragile X syndrome, and some or all of the RNA binding ligands bind to a CGG RNA triplet repeat motif. In certain embodiments, the disease is Fragile XE syndrome, and some or all of the RNA binding ligands bind to a GCC RNA triplet repeat motif. In certain embodiments, the disease is Friedreich ataxia, and some or all of the RNA binding ligands bind to a GAA RNA triplet repeat motif. In certain embodiments, the disease is selected from spinocerebellar ataxia type 1, type 2, type 3, type 6, type 7, or type 12, spinobulbar muscular atrophy, Huntington's Disease, and dentatorubral-pallidoluysian atrophy; and some or all of the RNA binding ligands bind to a CAG RNA triplet repeat motif. In certain embodiments, the disease is myotonic dystrophy type 2, and some or all of the RNA binding ligands bind to a CCUG RNA tetra repeat motif, or pentanucleotide repeats that cause spinocerebellar ataxia type 10 (AUUCU repeats) or Frontal temporal dementia and ALS (GGGGCC repeats).

The aforementioned RNA targeting compound of the present invention can be administered to the subject by any conventional route. The compositions herein may be made up in any suitable form appropriate for the desired use. Examples of suitable dosage forms include oral, parenteral, or topical dosage forms.

Illustratively, suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers that may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, such as ethyl-p-hydroxybenzoate.

Dosage forms suitable for parenteral administration include solutions, suspensions, dispersions, emulsions, and the like. They may also be manufactured in the form of solid compositions that can be dissolved or suspended in sterile injectable medium immediately before use. They may contain suspending or dispersing agents known in the art. Examples of parenteral administration are intraventricular, intracerebral, intramuscular, intravenous, intraperitoneal, rectal, and subcutaneous administration.

In addition to the above, generally non-active components of the above-described formulations, these formulations can include other active materials, for example, actives that have been identified as useful in the treatment of autoimmune disorders or conditions or in the alleviation of symptoms associated therewith. These actives can be broad-based actives, such as those that are useful in the treatment of a variety of autoimmune disorders or conditions or in the alleviation of symptoms associated with a variety of autoimmune disorders or conditions; or they may be more specific, for example, as in the case where the other active is specific for the treatment of the particular autoimmune disorder or condition with which the subject is afflicted or in the alleviation of symptoms associated with the particular autoimmune disorder or condition. As further illustration of the actives that can be additionally included in the above-described formulations (i.e., in addition to the RNA targeting compounds and in addition to non-active components), there can be mentioned actives which are conventionally employed to treat or otherwise alleviate the symptoms of myotonic dystrophy and/or related complications.

It will be appreciated that the actual preferred amount of RNA targeting compound to be administered according to the present invention will vary according to the particular RNA targeting compound being employed, the particular composition formulated, and the mode of administration. Many factors that may modify the action of the RNA targeting compound (e.g., body weight, sex, diet, time of administration, route of administration, rate of excretion, condition of the subject, drug combinations, and reaction sensitivities and severities) can be taken into account by those skilled in the art. Administration can be carried out continuously or periodically within the maximum tolerated dose. Optimal administration rates for a given set of conditions can be ascertained by those skilled in the art using conventional dosage administration tests.

By way of still further illustration, RNA targeting compounds of the present invention can be used to interfere with the interaction of muscleblind protein with RNA molecules that comprise CUG repeats. The method includes contacting the RNA molecules with an RNA targeting compound of the present invention in which some or all of the RNA binding ligands bind to a CUG RNA triplet repeat motif. Illustratively, the RNA binding ligands can be the same or different and can be selected from aminoglycoside sugars and bisbenzimidazoles, examples of which include those discussed above. Contacting can be carried out in vivo, ex vivo, or in vitro. In those cases where contacting is carried out in vivo, for example, in a subject suffering from myotonic dystrophy and/or other diseases or conditions involving the interaction of muscleblind protein with RNA molecules that comprise CUG repeats, the RNA targeting compound can be administered by any of the routes and in any of the compositions described above.

The present invention is further illustrated by the following non-limiting examples.

Example 1

Preparation Of Multivalent RNA-Targeting Compounds Displaying Kanamycin a RNA Binding Ligands This Example 1 and in the following Examples 2-4 describe methods to prepare multivalent oligomers that target RNA. These oligomers are decorated with multiple copies of a single ligand or several different ligands that bind to an RNA motif. Ligands are multivalently displayed on peptoid polymers [31] that are functionalized with azides suitable for conjugation to ligands that display an alkyne via a 1,3 dipolar Huisgen cycloaddition reaction [32-34]. Also described are the design and synthesis of peptoids that vary the spacing between the ligands by coupling methylamine into a growing peptoid chain.

To illustrate the present invention, these examples describe the synthesis of peptoids that display 6'-N-5-hexynoate kanamycin A with varying spacing is described. We have identified this kanamycin derivative as a lead compound for binding to the 5'CUG/3'GUC motif that is present in multiple copies in a RNA that causes a form of muscular dystrophy called myotonic dystrophy ("DM") [35-41]. The presence of an expanded 5'CUG/3'GUC repeat ($CUG_n$) binds to muscleblind protein, preventing normal muscle function and causing DM. Disruption of muscleblind-$CUG_n$ by multivalently displayed kanamycin A could be the first treatment of the cause of DM.

Example 2

Preparation of RNA Binding Ligands

N-Succinimidyl-5-hexynoate was prepared using the procedure described below:

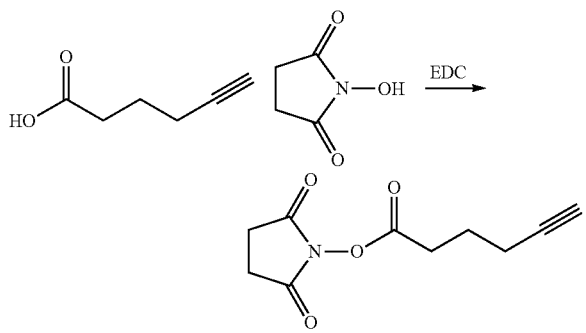

5-hexynoic acid (1 g, 8.3 mmole) was dissolved in 4 mL of a mixture of chloroform and DMF (9:1) and stirred. To this solution was added N-hydroxyl succinimide (0.95 g, 8.3 mmole) and N-(3-dimethylaminopropyl)-N'-ethylcarbodimide ("EDC") (1.58 g, 8.3 mmole), and the reaction was stirred overnight. The reaction was then diluted to 100 mL with methylene chloride and extracted with 0.1 N HCl (3×50 mL) and 5% NaHCO$_3$ (3×50 mL), dried over MgSO$_4$, and concentrated. The crude reaction mixture was used for all subsequent experiments (1.1 g, yield 60%). TLC analysis (3:7 EtOAc:CH$_2$Cl$_2$) showed a single product (R$_f$ 0.70).

N-benzyloxycarbonyloxy-5-norebornene-endo-2,3 dicarboximide was prepared using the procedure described below:

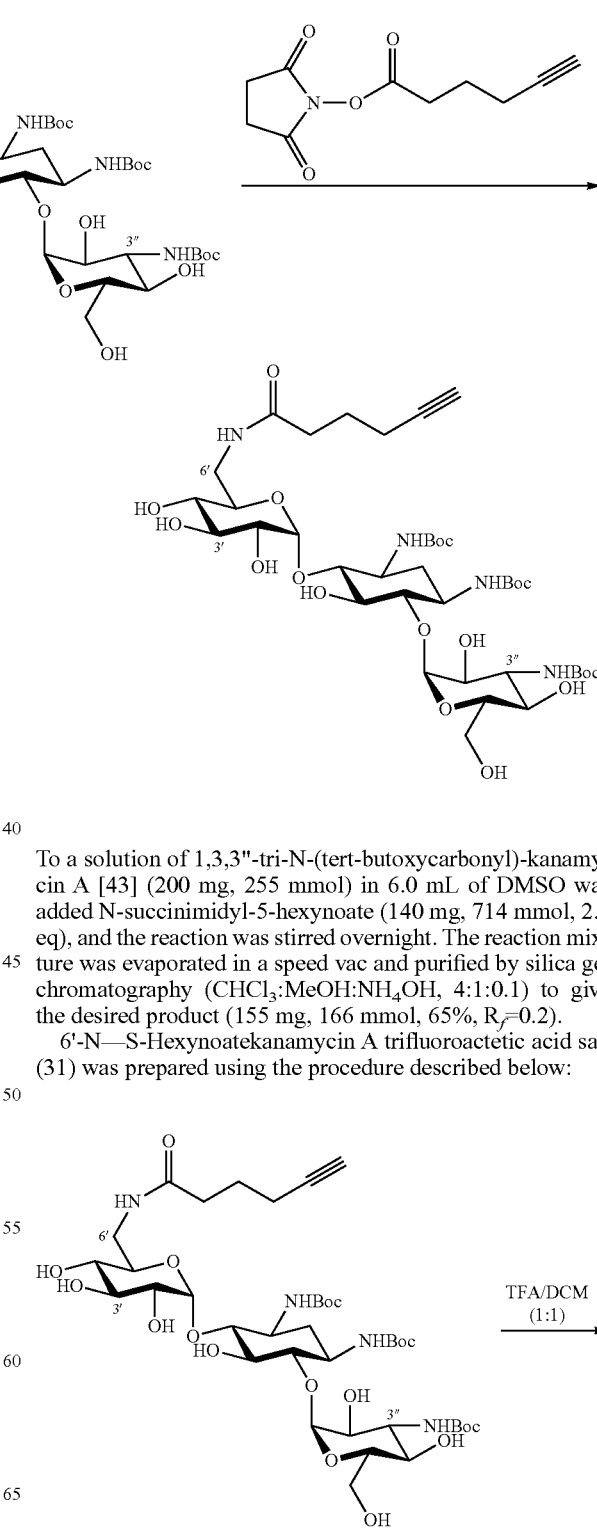

A synthesis of this compound using phosgene has been reported [42]. To eliminate the use of phosgene, a new and safer synthesis was developed. This compound was used in the synthesis of 1,3,3"-tri-N-(tert-butoxycarbon-yl)-kanamycin A and 1,3,3"-tri-N-(tert-butoxycarbon-yl)-neamine, as described [43]. Endo-N-hydroxy-5-norbornene-2,3-dicarboximide (10 g, 56 mmole) was dissolved in 100 mL of CH$_2$Cl$_2$ and 5 mL of pyridine and stirred in an ice bath. Bezylchloroformate was added, and the solution was stirred overnight and warmed to room temperature. The next morning, the solution was heated at 48° C. for 3 h. Solvent was removed via rotovap, and the solid was recrystallized from 90% aqueous MeOH to afford clear needles (10.1 g, 31 mmole, 57% yield). The spectrum $^1$H NMR spectrum was identical to that reported [42].

1,3,3'-Tri-N-(tert-butoxycarbonyl)-6'-N-5-hexyno-ate-kanamycin A was prepared using the procedure described below:

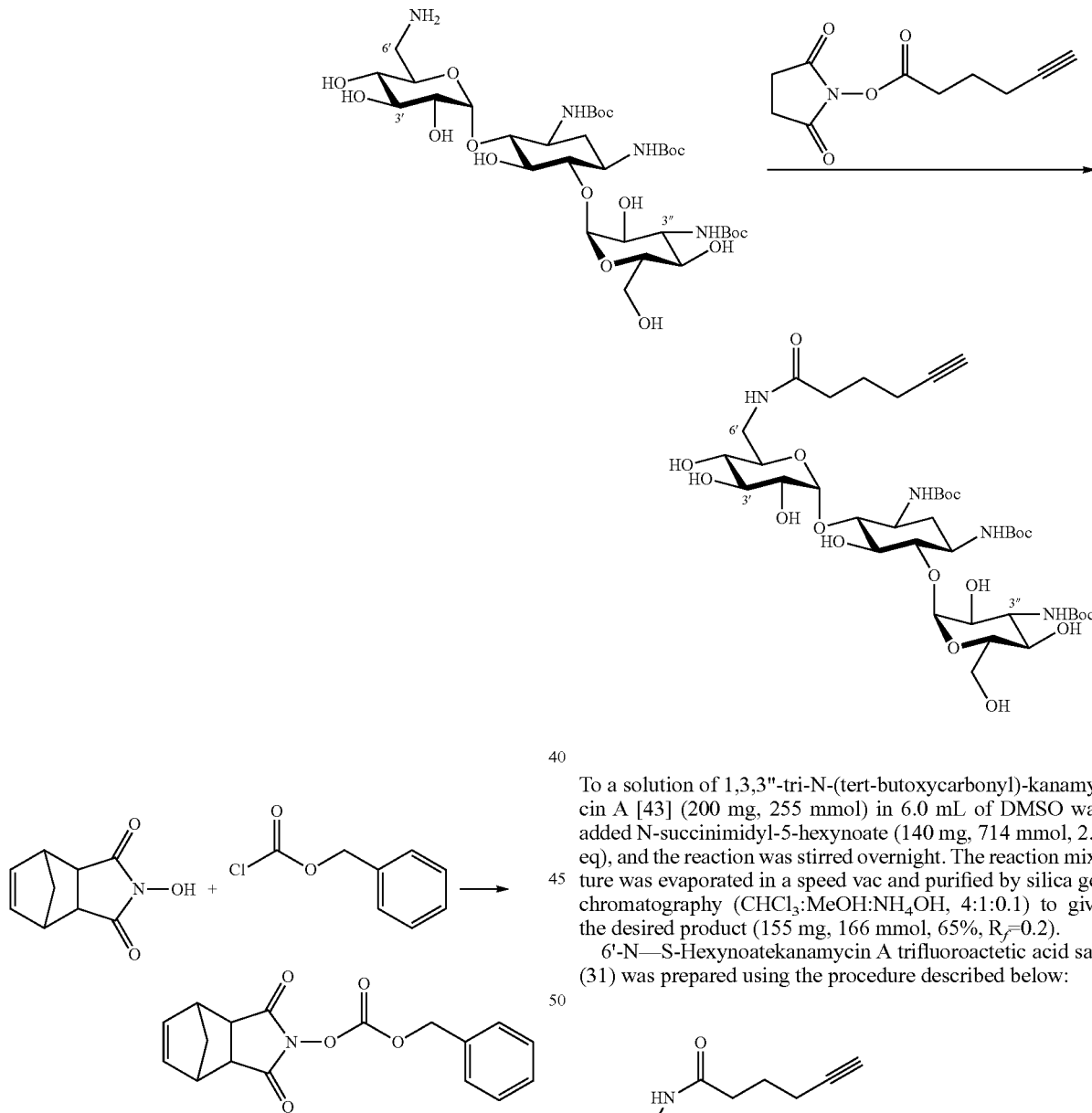

To a solution of 1,3,3"-tri-N-(tert-butoxycarbonyl)-kanamycin A [43] (200 mg, 255 mmol) in 6.0 mL of DMSO was added N-succinimidyl-5-hexynoate (140 mg, 714 mmol, 2.8 eq), and the reaction was stirred overnight. The reaction mixture was evaporated in a speed vac and purified by silica gel chromatography (CHCl$_3$:MeOH:NH$_4$OH, 4:1:0.1) to give the desired product (155 mg, 166 mmol, 65%, R$_f$=0.2).

6'-N—S-Hexynoatekanamycin A trifluoroactetic acid salt (31) was prepared using the procedure described below:

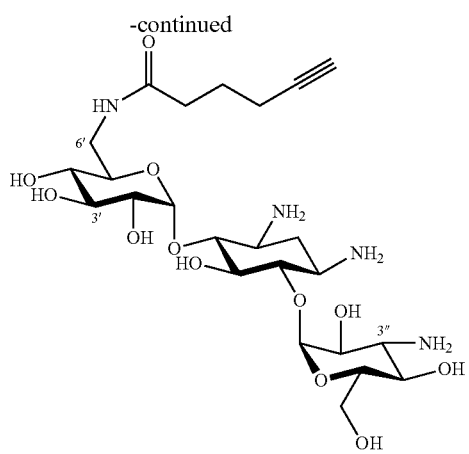

1,3,3''-Tri-N-(tert-butoxycarbonyl)-6'-N-5-hexynoate-kanamycin A (95 mg, 105 μmol) was dissolved in 10 mL of a mixture of CH$_2$Cl$_2$ and trifluoroactetic acid ("TFA") (1:1) and stirred for 1 h at room temperature. The reaction was diluted with 10 mL of toluene and concentrated. Then an additional portion of toluene was added, and the reaction was concentrated again. A yellow oil was obtained that was dissolved in 10 mL of nanopure water and lyophilized. A tan solid was isolated, and the solid was placed into Eppendorf tubes into which 4 mL of diethyl ether was added. The tubes were tumbled for 2 h. The tubes were centrifuged to pellet the solid, and the ether was decanted. Residual solvent was removed via vacuum concentration, and a white solid was obtained (45 mg, 80 mmole, 76%).

1,3,2'-Tri-N-(tert-butoxycarbonyl)-6'-N-5-hexynoateneamine was prepared using the procedure described below:

chromatography (CHCl$_3$:MeOH:NH$_4$OH, 4:1:0.1) to give the desired product (408 mg, 560 mmol, 74%, R$_f$=0.2).

6'-N-5-Hexynoateneamine trifluoroactetic acid salt was prepared using the procedure described below:

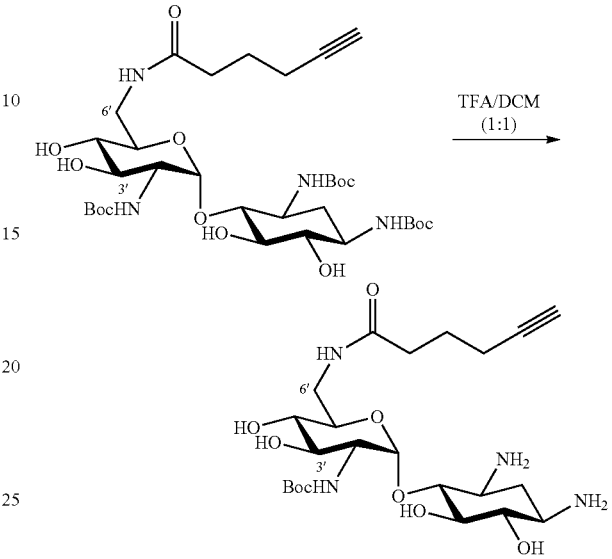

1,3,2'-Tri-N-(tert-butoxycarbonyl)-6'-N-5-hexynoate-neamine (320 mg, 447 μmole) was added to 10 mL of 1:1 TFA:DCM, and the reaction was stirred at room temperature for 1 h. A 10 mL aliquot of toluene was added to the solution, and it was concentrated in vacuo. An additional 10 mL of toluene

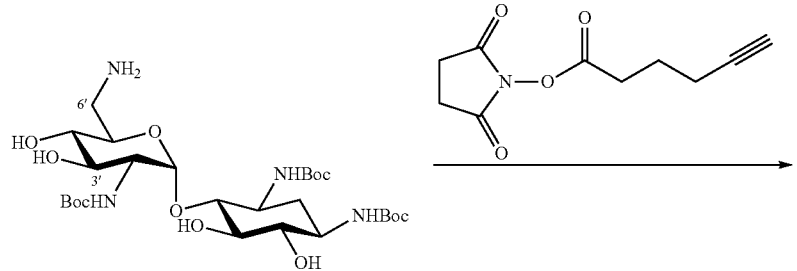

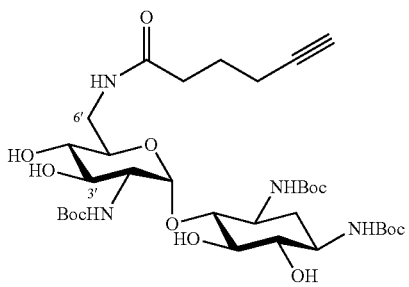

To a solution of 1,3,3''-tri-N-(tert-butoxycarbonyl)-neamine [43] (480 mg, 770 mmol) in 25.0 mL of MeOH with 200 μl of triethylamine was added N-succinimidyl-5-hexynoate (150 mg, 730 mmol), and the reaction was stirred overnight. The reaction was evaporated in vacuo and purified via column was added and evaporated. The sample was then dissolved in 4 mL of water and evaporated in a vacuum concentrator to obtain a tan solid. To the solids was added 10 mL of diethyl ether, and the solution was stirred for an hour. The solids were filtered, and the remaining ether removed via vacuum concentration to afford a white solid (180 mg, 432 μmol, 97%).

Example 3

Figure 3A:
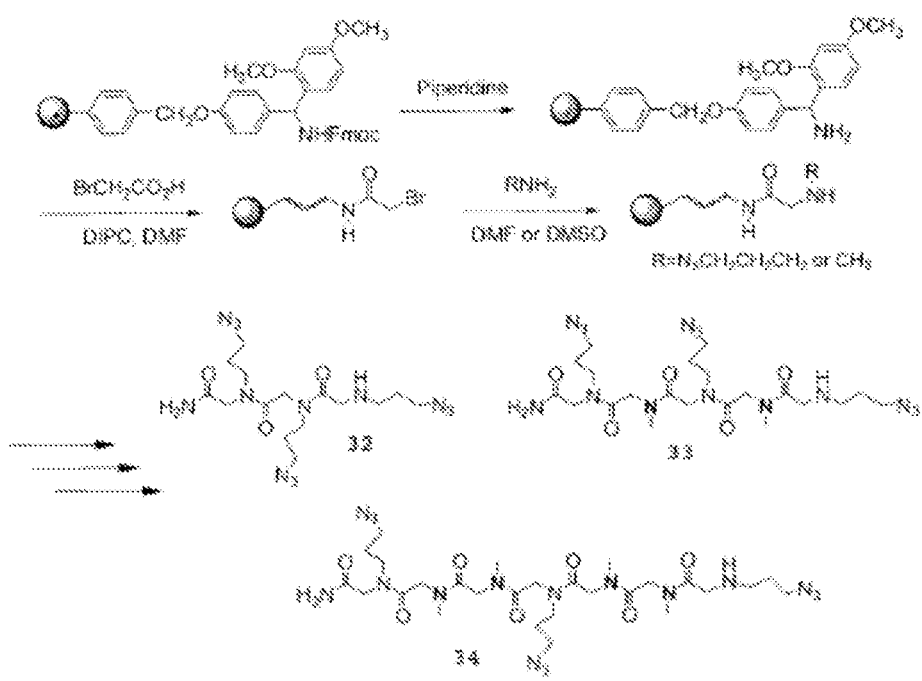
Figure 3B:
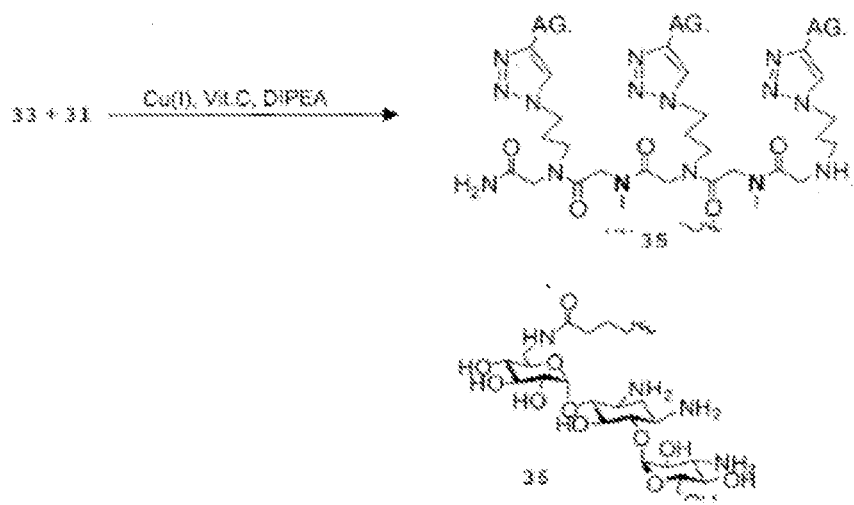
FIG. 3B is a reaction scheme for making a compound of the present invention.

Synthesis of Peptoid Oligomers Displaying Azides for Multivalent Display of RNA-Targeting Ligands FIG. 3A shows a schematic of the synthesis of multivalent peptoid oligomers to display multiple copies of 6'-N—S-hexynoate kanamycin A. Use of methylamine as a reactant in the synthesis allowed variation in the spacing of the 6'-N—S-hexynoate kanamycin A RNA-targeting ligand along the peptoid backbone, as can be seen in the azide-displaying peptoids 32, 33, and 34 (FIG. 3A). The azide-displaying peptoids are then conjugated to 6'-N-5-hexynoate kanamycin A using Cu(I) catalyst conditions to produce RNA targeting compound 35, as shown in FIG. 3B. In FIG. 3B, the group identified as "AG" has structure 36.

A description of the peptoid synthesis procedure (illustrated in FIG. 3A) is set forth below.

A 100 mg portion of Fmoc-Rink amide resin (0.67 mmol/g loading) was prepared for the first coupling step in a 10 mL solid-phase reaction flask (Chem Glass) by swelling for 20 min in DMF followed by washing with methanol and then dichloromethane. A 2 mL solution of 20% piperidine in DMF was added to the resin, and the resin was shaken at room temperature for 20 min. The solvent was removed, and the step was repeated. The solution was then washed with DMF and DCM (2×4 mL each) and then with anhydrous DMF (3×4 mL).

The first coupling of bromoacetic acid was accomplished by adding 2 mL of 1 M bromoacetic acid in DMF to the resin along with 400 mL of diisopropylcarbodiimide ("DIPC"). The solution was then placed into a conventional microwave oven and heated 3×10 s on the defrost setting. The flask was removed and manually shaken to mix the resin between each microwave irradiation. The flask was then shaken at 37° C. for 20 min. The reagents were drained, and the coupling steps were repeated. After the second coupling, the resin was washed with DCM and DMF (2×4 mL each) and finally with anhydrous DMF (3×4 mL).

The resin was then coupled to 3-azidopropyl-amine (200 μL, 3 mmol) in 2 mL of DMF, and the reaction flask was heated in a microwave, incubated at 37° C., and washed as described above. For peptoid 32, all subsequent couplings used 3-azidopropylamine. For peptoids 33 and 34, methylamine was used at different steps to vary the spacing of the azide on the peptoid chain. Methylamine was coupled by incubating the resin with 2 mL of a 2 M solution of methylamine in tetrahydro-furan ("THF"), as described for the bromoacetic acid coupling; and each methylamine coupling was repeated 3 times. Each of these steps was alternated until a peptoid of the desired composition was obtained (33 and 34).

After all coupling steps, the resin was washed with methanol and DCM (4×3 mL each), and the peptoids were cleaved from the resin by adding 2 mL of a deprotection cocktail composed of 95:5 trifluoroacetic acid ("TFA"):$H_2O$. The reaction flask was shaken at room temperature for 30 min. The solvent containing the crude peptoid was removed from the resin, and the resin was deprotected again with 3×2 mL of deprotection cocktail. The solutions containing crude peptoid were combined and dried in a speed vac concentrator. A yellow/tan viscous oil was obtained. The peptoids were then purified by using a Waters HPLC equipped with 3 μm 19×150 mm C8 column at 10 mL/min and UV detection at 218 nm. A gradient of 95% Water/5% acetonitrile (MeCN) with 0.1% TFA to 30% water/70% acetonitrile with 0.1% TFA over 30 min was applied to the system. The retention times for the peptoids were: 14.5 min for 32; 16.0 min for 33, and 24 min for 34. The samples were then subjected to analysis by mass spectrometry ("MS") to confirm the identity of the products. ESI-MS: 32, observed 438 ($M+H^+$); 33, observed 602 ($M+Na^+$); 34 observed 722 ($M+H^+$).

A description of the procedure used to couple the peptoids to 31 via click chemistry (illustrated in FIG. 3B) is set forth below.

Peptoids 32-34 were reacted with 31 using 2 equivalents of 31 relative to the loading of the azide on the peptoids. Typical reactions were completed with 5.7 μmole of pure peptoid and 34.2 μmole of 31. These reactions were completed in 4:1 dimethylsulfoxide ("DMSO"):$H_2O$ with 2 mM ascorbic acid, 200 μM of TBTA [32] (a Cu+ ligand that accelerates Huigsen 1,3 dipolar cycloaddition reactions), and 1 mM $CuSO_4$. After all of the reagents were added, the reaction vessel (a 2 mL Eppendorf tube) was sonicated to dissolve all reagents. The tube was then tumbled at room temperature overnight. Crude reactions were then purified by HPLC using the same conditions as described for peptoid purification above. Compounds had a typical retention time of 18 min for each compound. MALDI MS was used to confirm the identity of the products. The click product of 32+31: observed 2172 ($M+H^+$); click product (35) of 33+31: observed 2337 ($M+Na^+$); click product of 34+31: observed 2457 ($M+H^+$).

Example 4

Binding of 31 to an Oligonucleotide that Displays a Single Copy of 5'CUG/3'CUG Motif that, when Present in Multiple Copies of the DMPK Gene, Causes Myotonic Dystrophy A fluorescence-based assay was used to study the binding of 31 to several RNAs and DNAs. In order to complete these studies, we conjugated a fluorescein tag onto 31 by reacting fluorescein isothiocyanate with 3-azidopropylamine. The azide-labeled fluoresceine was conjugated to 31.

The synthesis of 5-(3-(3-azidopropyl)thio-ureido)-2-(3-hydroxy-6-oxo-6H-xanthen-9-yl)benzoic acid was carried out using the following procedure:

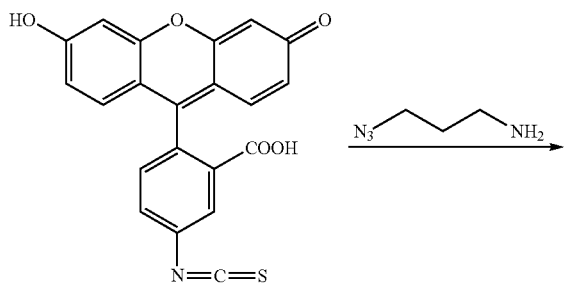

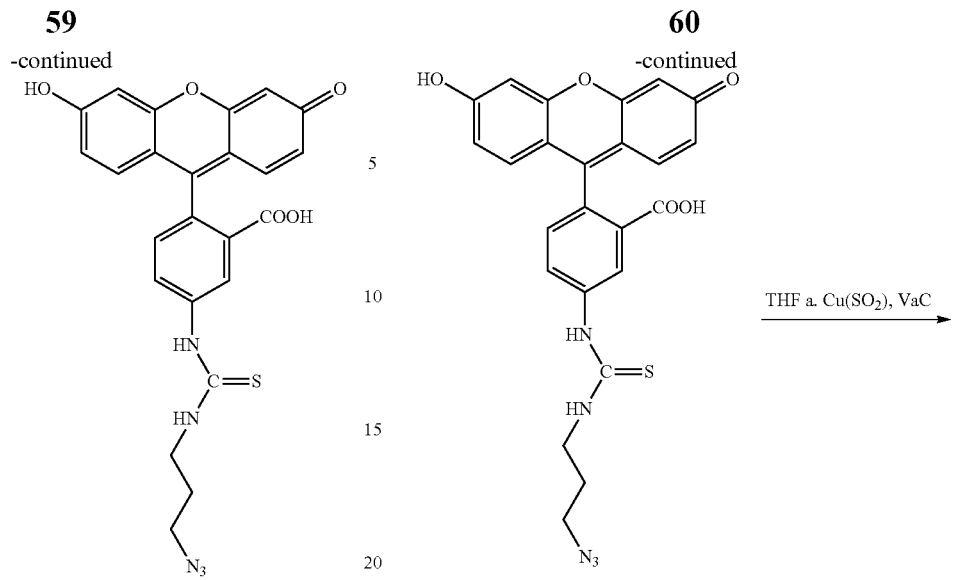

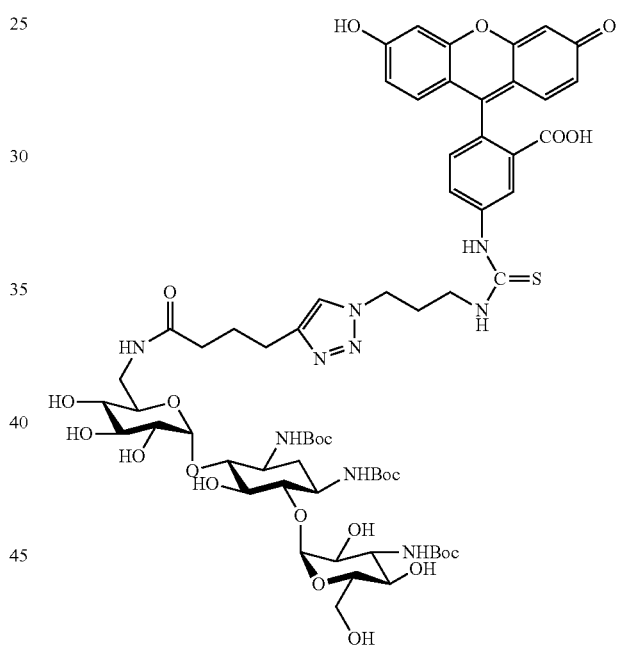

Fluorescein isothiocyanate (34 mg, 87 mmole) was dissolved in 500 μL of DMF with 15 μL, of Hünig's base. Then 3-azidoproplyamine (1.3 eq, 10.5 mg, 12 μL) was added. The reaction was sonicated to dissolve all reagents and tumbled at room temperature overnight. An aliquot of the reaction was then subjected to mass spectrometry to confirm formation of the product and consumption of the starting material. (ESI+) found: 490.1 (M+H$^+$). The reaction was then placed into a speed vac overnight to remove the solvent and uncoupled 3-azidopropylamine A quantitative yield was obtained.

Boc-protected fluorescein-labeled 6'-N-5-hexynoate kanamycin A was prepared using the procedure described below:

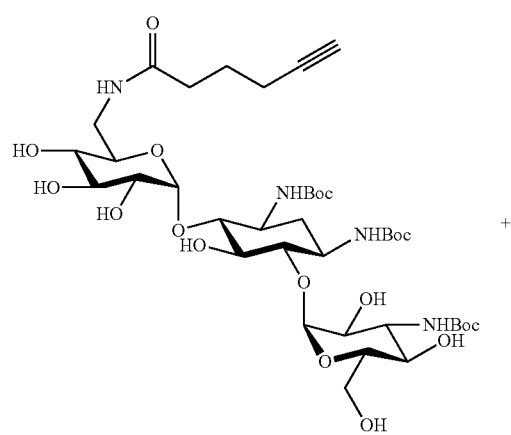

To a solution containing 1,3,3"-tri-N-(tert-butoxycarbon-yl)-6'-N-5-hexynoate kanamycin A (21.6 mg, 24 μmoles) in a 7:3 mixture of DMSO:H$_2$O was added 5-(3-(3-azidopropyl)-thioureido)-2-(3-hydroxy-6-oxo-6H-xanthen-9-yl)benzoic acid (15 mg, 30 μmoles), 1 mM CuSO$_4$, 1 mM Vitamin C, and 100 μM of TBTA [32], and the reaction was tumbled overnight in an Eppendorf tube at 37° C. The reaction was analyzed by mass spectrometry to confirm formation of the product and consumption of the 6'-N—S-hexynoate kanamycin A starting material. (ESI+) found: 1368 (M+H$^+$). The product was then purified via HPLC equipped with a Waters Symmetry C8 preparative column (7 μm, 19×150 mm). A flow rate of 10 mL/min and a gradient of methanol from 0 to 100% over 30 min was applied (I, product, 24.4 min). Isolated yield: 12 mg, 40%.

Fluorescein-labeled 6'-N-5-hexynoate kanamycin A was prepared using the procedure described below:

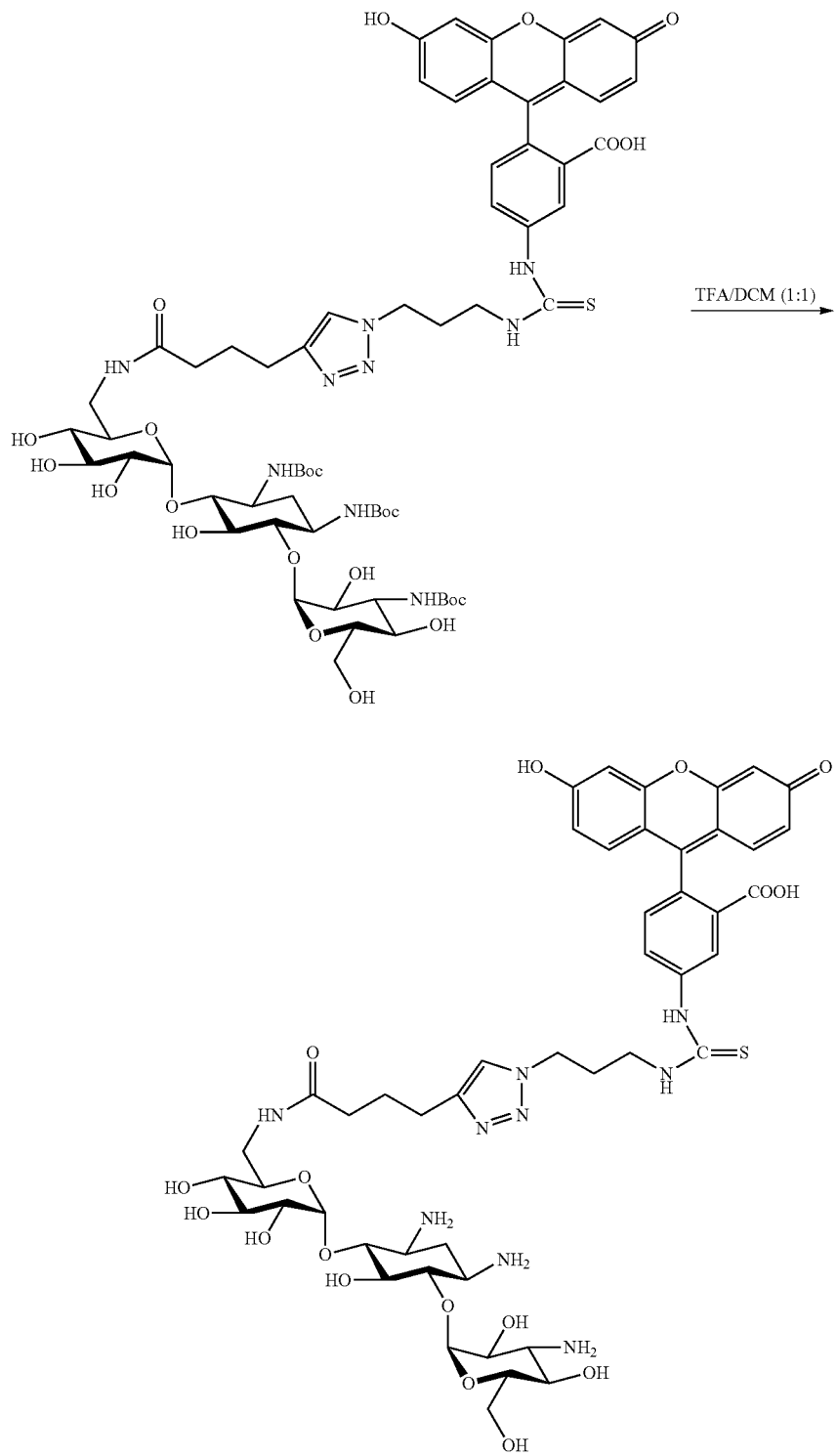

To a 500 μL solution containing 12 mg of Boc-protected fluorescein-labeled 6'-N-5-hexynoate kanamycin A was added 500 μL of trifluoroacetic acid, and the reaction was stirred for 30 min. The reaction was then diluted to 10 mL with toluene and evaporated to dryness. The product was then dissolved in water and concentrated in a speed vac overnight. The residue was tumbled twice in 1 mL of diethyl ether with the ether being removed between washes. The product was obtained as a fluorescent yellow/green solid. MS (ESI+): 1068 (100%, M+H$^+$) and 1090 (45%, M+Na$^+$). A quantitative yield was obtained.

Figure 4A:
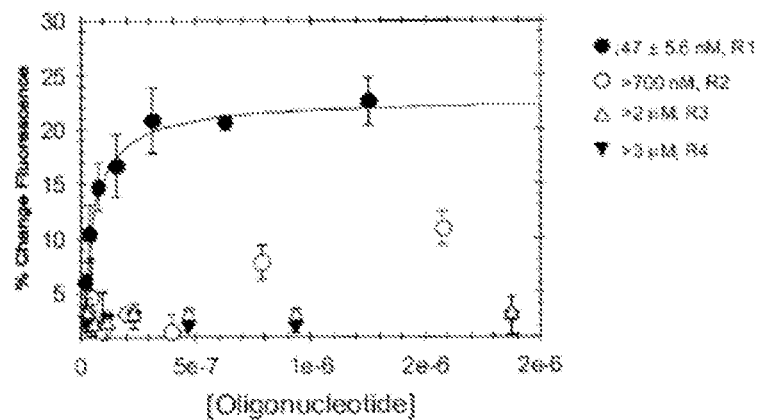
FIG. 4A is a graph showing the effect of various oligonucleotides on the fluorescence of a fluorescently-labeled RNA binding ligand that can be used in the compounds of the present invention.
Figure 4B:
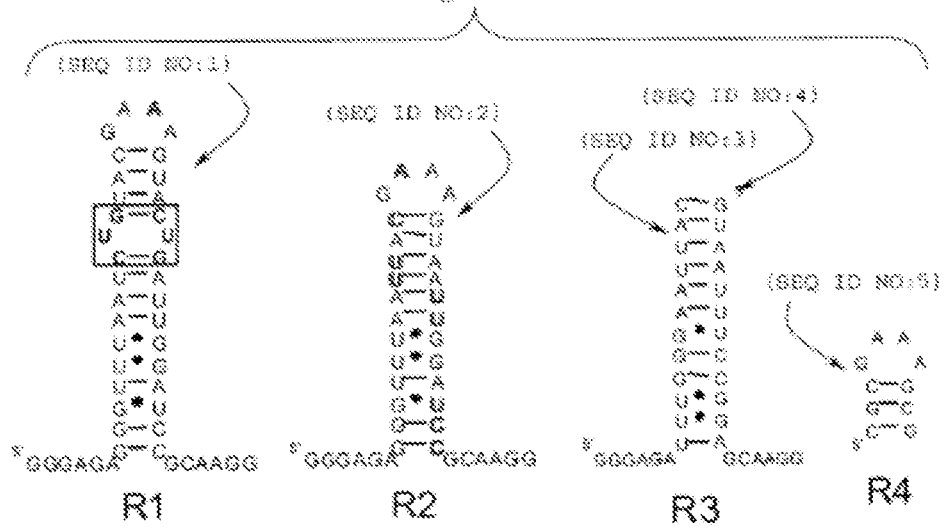
FIG. 4B are structures of the RNAs on which the assays were performed.

A fluorescence-based assay was used to determine the dissociation constants and the number of interacting sites of small molecule-internal loop interactions. More particularly, for the in solution affinity assays, serially diluted concentrations of RNA were annealed in 1×HB+40 μg/mL BSA at 60° C. for 5 min and allowed to slow cool on the benchtop. FITC-labeled 31 in 1×HB+40 μg/mL BSA was added to the solution of RNA at a final concentration of 10 nM. Samples were then placed into a well of a black 96-well plate. Samples were allowed to incubate for at least 30 min before reading the fluorescence on a Bio-Tek Synergy HT fluorescence plate reader set to FITC filters and a sensitivity between 38-40. Several different times were sampled to ensure that the fluorescence intensity was taken after these interactions reached equilibrium. Control experiments included incubation of a selected internal loop (concentration of 3 μM) with 10 nM FITC. No change in fluorescence was observed. The data were fit to one-site saturation curve in Sigma plot. When data was fit to a two-site saturation equation, the curve fit did not converge to the data. The binding data are shown in FIG. 4, along with the structures of the RNAs on which the assays were performed. The data show that 31 binds specifically to RNAs that have a single copy of the 5'CUG/3'GUC motif that causes myotonic dystrophy.

Figure 5:
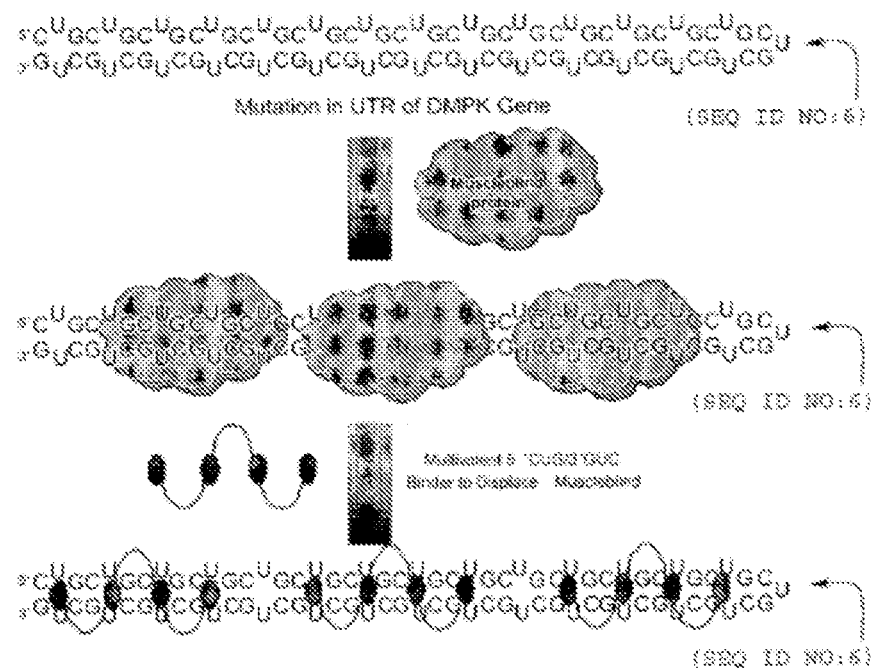
FIG. 5 is a schematic illustrating a strategy for using compounds of the present invention to inhibit muscleblind-CUG$_n$ interactions.

FIG. 5 is a schematic that outlines a strategy to use multivalent peptoids displaying 31 to inhibit muscleblind-$CUG_n$ interactions. As shown, the expanded triplet repeat folds into a hairpin structure that sequesters muscleblind and causes myotonic dystrophy. Experiments have been performed which show that multivalent peptoids displaying 31, prepared as described herein, binds unexpectedly well to RNAs that contain multiple CUG oligomers (e.g., $r(CUG)_{110}$), and it is believed that this binding will disrupt the muscleblind-$CUG_n$ interactions and can be used to treat myotonic dystrophy.

Example 5

Preparation of Multivalent RNA-Targeting Compounds Displaying Bisimidazole RNA Binding Ligands This Example 5 describes the synthesis of a multivalent RNA-targeting compound displaying a bisimidazole RNA binding ligand, Hoechst 33258 azide to target $CUG_{140}$.

Figure 6A:
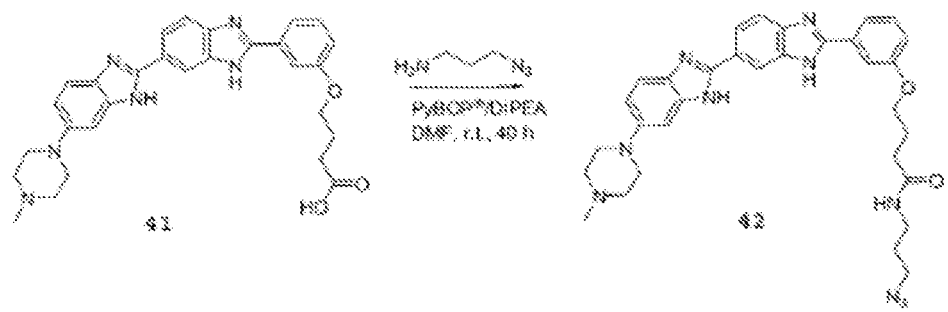
FIG. 6A is a reaction scheme showing structural formulae of RNA binding ligands that can be used to prepare compounds of the present invention and a way to convert one to the other.

Hoechst-azide derivative 42 was synthesized by a modified procedure [44] from Hoechst derivative 41 and 3-azidopropylamine as shown in FIG. 6A.

Figure 6B:
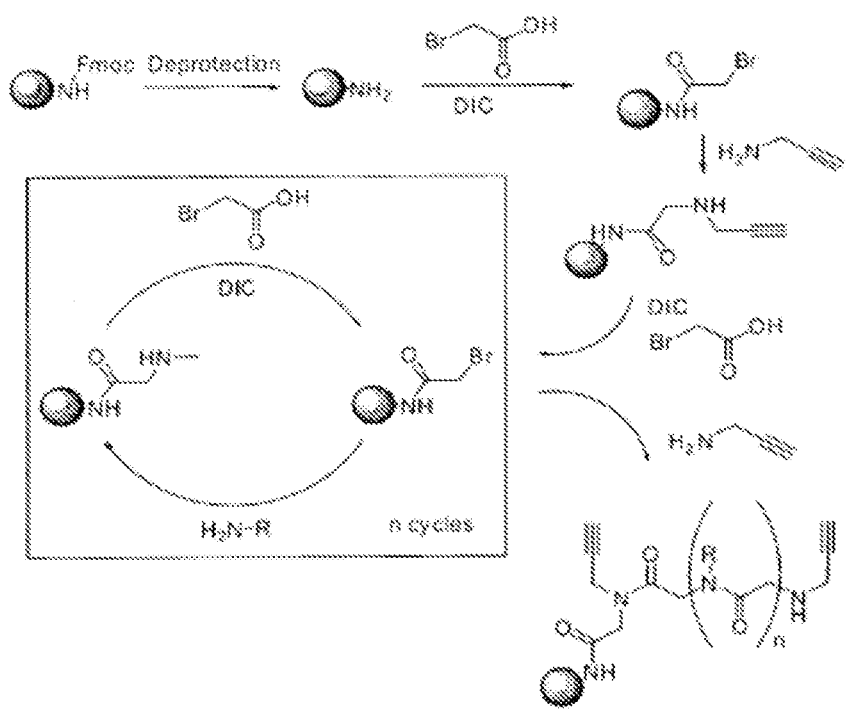
FIG. 6B is a reaction scheme for making peptoid backbones that can be used in the preparation of various compounds of the present invention.

Peptoid backbones were synthesized on a Rink amide resin solid support via standard protocol, as shown in FIG. 6B, using the methods analogous to those discussed in Example 3.

Figure 6C:
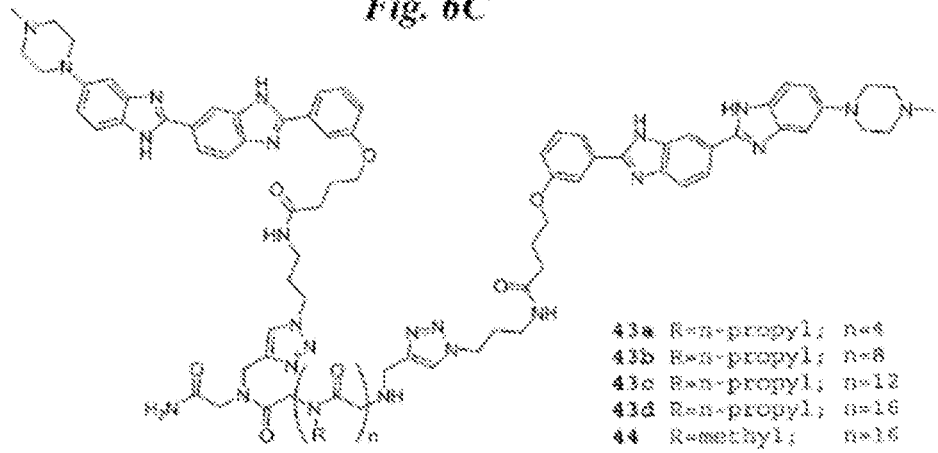
FIG. 6C is structural formulae of several compounds of the present invention.

Conjugation of Hoechst-azide 42 to the peptoid backbone was achieved via modified post-oligomerization click chemistry protocol [45] followed by cleavage. Following that procedure, five bivalent RNA-targeting compounds (43a, 43b, 43c, 43d, and 44) were isolated after HPLC purification. The products have the structure shown in FIG. 6C. In compounds 43a, 43b, 43c, and 43d, R is n-propyl, and n is 4, 8, 12, and 16, respectively. In compound 44, R is methyl, and n is 16.

The following method was used to prepare meta-(4-Hydroxybutyric acid)-Hoechst (41). A mixture of ethyl 4-(3-formylphenoxy)butanoate [46] (0.37 g, 2.1 mmol) and 4-(5-(4-methylpiperazin-1-yl)-1H-benzo[d]imidazol-2-yl)benzene-1,2-diamine [44], acetate salt (0.8 g, 2.1 mmol) in 45 mL of nitrobenzene was stirred at 140° C. for 36 h under argon. Then the solution was concentrated to dryness in vacuo, and the residue was triturated with ethyl ether (50 mL), filtered, and washed on the filter with ethyl ether (4×20 mL). The crude product was dried and dissolved in ethanol (15 mL) and then, to the solution, potassium hydroxide (0.47 g, 8 mmol) was added, and the mixture was refluxed for 4 h. The reaction was cooled down to room temperature, diluted with water (15 mL), and saturated with $CO_2$. In about 1 h, crystals of the product started to precipitate. The product was filtered, washed on the filter with ethyl ether (4×20 mL), and dried. Yield 0.9 g (84%). MS-ESI(+) 511 (M+H$^+$).

The following method was used to prepare meta-(N-(3-azidopropyl)-4-hydroxybutanamide)-Hoechst, hexafluorophosphate mono salt (42). A mixture of meta-(4-hydroxybutyric acid)-Hoechst (41) (0.9 g, 1.76 mmol), PyBOP™ (1.4 g, 2.64 mmol), and diisopropylethylamine (0.68 g, 5.28 mmol) in DMF (15 mL) was stirred under argon at room temperature for 30 min, and then 3-azidopropylamine (0.27 g, 2.64 mmol) was added. The reaction was stirred at room temperature for 40 h while monitoring the reaction progress by TLC (ethyl acetate/methanol/triethylamine, 16:8:1). Then the solution was concentrated in vacuo to a thick, gummy residue. The residue was washed with water (3×20 mL) and crystallized from ethanol (10 mL), providing off-white crystals of the product. Yield 0.7 g (54%). MS-ESI(+) 593 (M+H$^+$), MS-ESI (−) 145 (60%, PF6$^-$), 591 (30%, M$^-$), 637 (100%, M+HCO$_2^-$).

Example 6

Figure 7A:
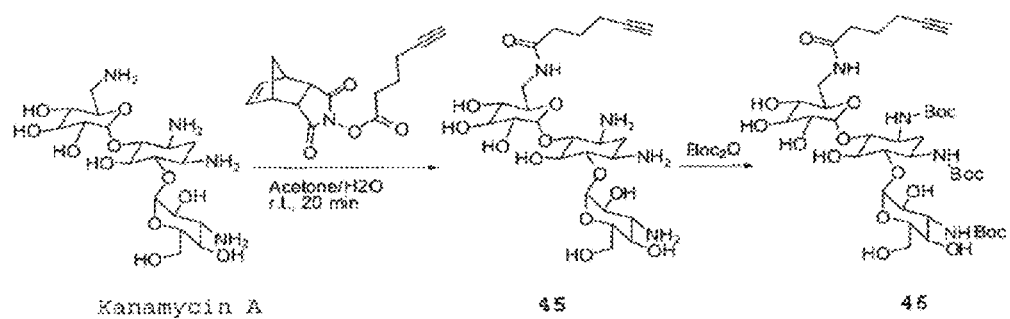
FIGS. 7A, 7B, and 7E are reaction schemes showing structural formulae of various RNA binding ligands that can be used in the preparation of compounds of the present invention and ways to convert one to another.
Figure 7B:
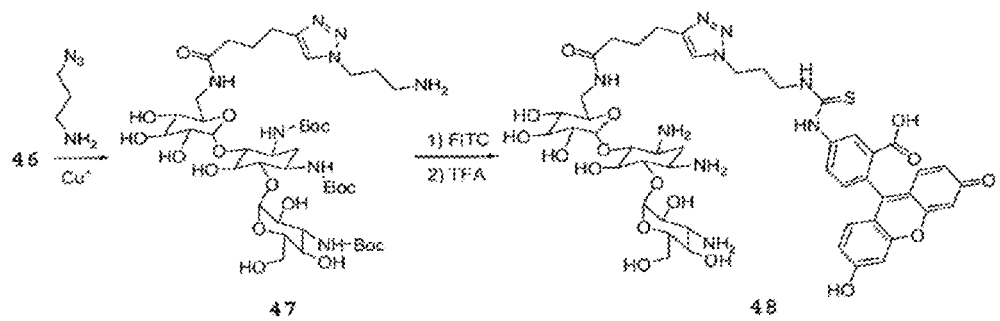

Preparation of Kanamycin-6'-N-Hexynoate and Use Thereof in the Preparation of RNA-Targeting Compounds Kanamycin-6'-N-hexynoate (45) was synthesized by analogy to the reported regio- and chemo-selective 6'-N-derivatization procedure [46] followed by one-pot Boc-protection to yield the kanamycin-alkyne derivative 46. The synthetic scheme is set forth in FIG. 7A.

Click chemistry modification of kanamycin-alkyne derivative 46 with 1-amino-3-azidopro-pane followed by treatment with FITC and deprotection led to a monovalent fluorescein-labeled ligand 48.

Figure 7C:
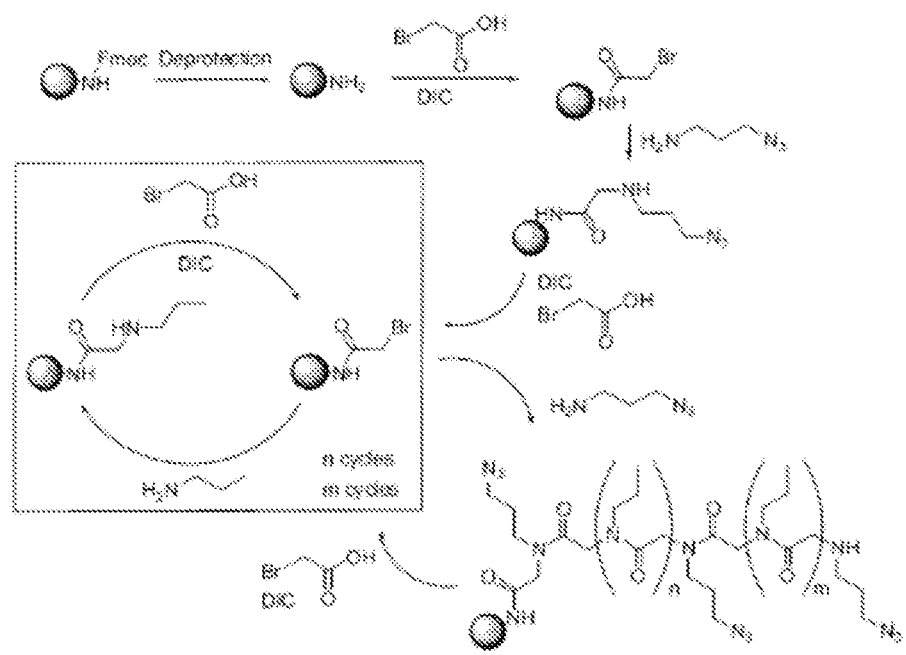
FIG. 7C is a reaction scheme for making peptoid backbones that can be used in the preparation of various compounds of the present invention.

Preparation of Peptoid Backbones was Carried out using the scheme set forth in FIG. 7C. Briefly, peptoid backbones were synthesized similarly to the scheme utilized for the Hoechst-based ligands except, here, the peptoid backbones have an azide display instead of alkyne one.

Figure 7D:
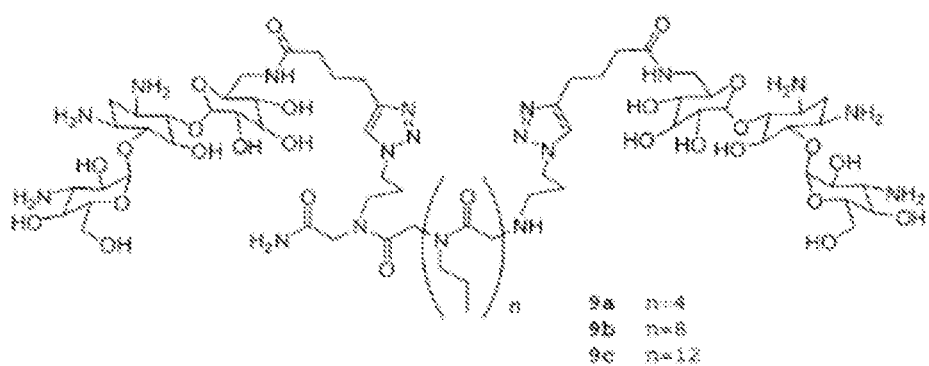
FIGS. 7D and 7F are structural formulae of several compounds of the present invention.

Conjugation of kanamycin-alkyne derivative 46 to the peptoid backbone was carried out similarly to the Hoechst click protocol followed by cleavage with simultaneous Boc-protective group removal. Following that procedure, three bivalent RNA-targeting compounds (49a, 49b, and 49c) were isolated after HPLC purification. The products have the structure shown in FIG. 7D. In compounds 49a, 49b, and 49c, n is 4, 8, and 12, respectively.

Figure 7E:
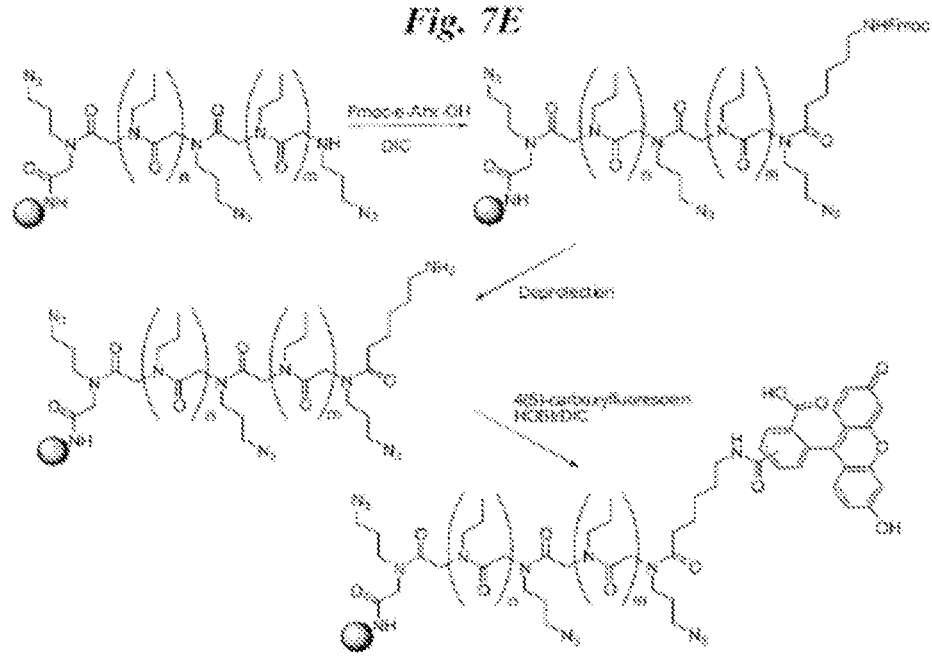

For easier quantification and binding assays, peptoids with terminal fluorescein marker attached through a 6-aminohexanoic (a 6-aminopentylcarbonyl) linker [47] were synthesized using the preparative scheme set forth in FIG. 7E.

Figure 7F:
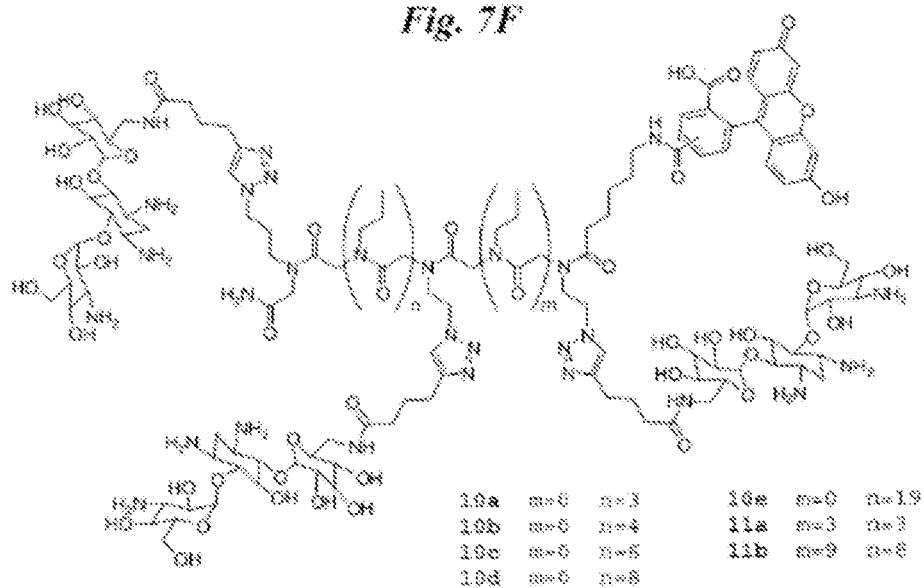

After conjugation with kanamycin-alkyne derivative 46 and subsequent cleavage from the resin and HPLC purification, five bivalent and two trivalent ligands were isolated. The products have the structure shown in FIG. 7F. In compounds 10a, 10b, 10c, 10d, 10e, m is 0, and n is 3, 4, 6, 8, and 19, respectively. In compound 11a, m is 3, and n is 3; and in compound 11a, m is 9, and n is 8.

Example 7

Experimental Procedures and Details Used in the Preparation of Multivalent RNA-Targeting Compounds Displaying Bisimidazole and Kanamycin RNA Binding Ligands This Example 7 further describes the experimental procedures and details used in Examples 5 and 6.

The following HPLC procedures were used.

Synthetic purity was evaluated by analytical HPLC on a Waters SYMMETRY™ C8.5 μm 4.6×150 mm column at room temperature on a Waters 1525 Binary HPLC Pump equipped with Waters 2487 Dual λ Absorbance Detector system at 1 mL/min flow rate and 218/254 nm wavelength. Linear gradient 5% to 95% B in A over 35 min (A: water+ 0.1% TFA, B: methanol+0.1% TFA, v/v).

Purification of the peptoid ligands was performed by preparative HPLC on a SYMMETRYPREP™ C8.7 μm 19×150 mm column at room temperature on a Waters 1525 Binary HPLC Pump equipped with Waters 2487 Dual Absorbance Detector system at 10 mL/min flow rate and 218/254 nm wavelength.

The following method was used to prepare meta-(4-Hydroxybutyric acid)-Hoechst (41). A mixture of ethyl 4-(3-formylphenoxy)butanoate [48] (0.37 g, 2.1 mmol) and 4-(5-(4-methylpiperazin-1-yl)-1H-benzo[d]imidazol-2-yl) benzene-1,2-diamine [44], acetate salt (0.8 g, 2.1 mmol) in 45 mL of nitrobenzene was stirred at 140° C. for 36 h under argon. Then the solution was concentrated to dryness in vacuo, and the residue was triturated with ethyl ether (50 mL), filtered, and washed on the filter with ethyl ether (4×20 mL). The crude product was dried and dissolved in ethanol (15 mL) and then, to the solution, potassium hydroxide (0.47 g, 8 mmol) was added, and the mixture was refluxed for 4 h. The reaction was cooled down to room temperature, diluted with water (15 mL), and saturated with $CO_2$. In about 1 h, crystals of the product started to precipitate. The product was filtered, washed on the filter with ethyl ether (4×20 mL), and dried. Yield 0.9 g (84%). MS-ESI(+) 511 (M+H$^+$).

The following method was used to prepare meta-(N-(3-azidopropyl)-4-hydroxybutanamide)-Hoechst, hexafluorophosphate mono salt (42). A mixture of meta-(4-hydroxybutyric acid)-Hoechst (41) (0.9 g, 1.76 mmol), PyBOP™ (1.4 g, 2.64 mmol), and diisopropylethylamine (0.68 g, 5.28 mmol) in DMF (15 mL) was stirred under argon at room temperature for 30 min, and then 3-azidopropylamine (0.27 g, 2.64 mmol) was added. The reaction was stirred at room temperature for 40 h while monitoring the reaction progress by TLC (ethyl acetate/methanol/triethylamine, 16:8:1). Then the solution was concentrated in vacuo to a thick, gummy residue. The residue was washed with water (3×20 mL) and crystallized from ethanol (10 mL), providing off-white crystals of the product. Yield 0.7 g (54%). MS-ESI(+) 593 (M+H$^+$), MS-ESI (−) 145 (60%, PF6$^-$), 591 (30%, M$^-$), 637 (100%, M+HCO$_2^-$).

The following method was used to prepare 1,3,3"-tri-N-(tert-butoxycarbonyl)-kanamycin-6'-N-hexynoate (46). To a solution of kanamycin A free base (0.2 g, 0.4 mmol) in an acetone-water mixture (1:1, 10 mL), N-(6-hexynoyloxy)-5-norbornene-2,3-dicarboximide (0.1 g, 0.36 mmol) was added, and the reaction was stirred at room temperature for 20 min. Then, to the mixture, Boc anhydride (0.53 g, 2.4 mmol) was added, and the reaction was stirred 24 h at room temperature. White precipitate was filtered, washed with ethyl ether (6×5 mL), and dried, providing pure product identical to the reference sample obtained via a different synthetic scheme. Yield 0.17 g (47%). MS-ESI(+) 879 (M+H$^+$).

The following method was used to prepare 6'-N-fluorescein labeled kanamycin (48). To a solution of 1,3,3"-tri-N-(tert-butoxycarbonyl)-kanamycin-6'-N-hexynoate (46) (9 mg, 10 μmol) in DMSO (81 μL), 3-azidopropylamine (6 μL, 50 μmol) and solutions of TRIS.HCl (1 μL, 1M in water), CuSO$_4$ (10 μL, 0.01M in water), ascorbic acid (1 μL, 0.1M in water), and TBTA (1 μL, 0.01 M in DMSO/tert-butanol, 1:4) were added. The mixture was incubated at 60° C. overnight and concentrated to dryness. The residue was dissolved in DMSO (0.2 mL), and, to the solution, fluoresceinisothiocyanate ("FITC") (8 mg, 20 μmol) and triethylamine (7 μL, 50 μmol) were added. The reaction was incubated at 40° C. for 1 h and then concentrated to dryness. The residue was dissolved in methanol and purified by preparative HPLC. Combined fractions were concentrated to dryness, and, to the residue, a mixture of TFA/DCM/water (60:40:2, 0.5 mL) was added. The solution was gently shaken at room temperature for 1 h and concentrated to dryness. After lyophilization from water, 7.3 mg (5.2 μmol) of the product (tris-trifluoroacetate salt) were obtained. MS-ESI(+) 1068 (100%, M+H$^+$), 535 (50%, M+2H$^+$).

The general protocol for the peptoid synthesis is described below. The peptoid oligomers were synthesized at room temperature (22° C.) in BioRad POLY-PREP™ chromatography columns (0.8×4 cm) orthogonally installed on a plate of Thermolyne MAXI-MIX III™ shaker. Fmoc-protected Rink amide polystyrene resin (AnaSpec) with a substitution level 0.45 mmol/g (23 mg, 10 μmol) was swollen in DCM (1 mL) for 20 min, drained, and deprotected with 1 mL of 20% piperidine in DMF for 40 min with shaking at 800 rpm, followed by draining and then rinsing with DMF (6×3/6×3 mL).

The coupling step was carried out as follows. To the resin-bound amine bromoacetic acid (0.2 mL, 1M in DMF) and diisopropylcarbodiimide ("DIC") (0.2 mL, 1M in DMF) were added. The resin was shaken for 20 min at 1000 rpm, drained, and then rinsed with DMF (5×2/5×2 mL).

The displacement step involved a two step process. In one step, a click counterpart was introduced by sequentially adding, into a column, DMF (0.2 mL) and corresponding amine (20 μL of either 3-azidopropylamine or propargylamine). The resin was shaken for 3 h at 1000 rpm, drained, and then rinsed with DMF (5×2/5×2 mL). In the other step, the chain was extended with a spacer by sequentially adding, into a column, DMF (0.2 mL) and propyl amine (50 μL). The resin was shaken for 20 min at 1000 rpm, drained, and then rinsed with DMF (5×2/5×2 mL).

The following general protocol was followed for the peptoid post-oligomerization ligand introduction, click chemistry. The resin-bound oligomer was washed with methanol (3×2 mL) and dichloromethane (3×2 mL) and dried under stream of air, and a small portion of the resin was cleaved and analyzed by HPLC and MS-ESI prior to a conjugation step. Then, into a resin-bound oligomer containing column, a click counterpart (4 equivalents per conjugation site) was added. The column was sealed with a rubber septum and purged with argon for 20 min. Then the column was capped from another side, and 2 mL of the pre-prepared catalyst solution (0.1M copper acetate, 1M diisopropylethylamine, 0.1M ascorbic acid, and 0.01M TBTA in pyridine/DMF, 3:7) were loaded into the column under argon. The reaction was sonicated (Branson BRANSONIC™ 5210, 140 watts, 47 kHz) in darkness at 40° C. with periodic vortexing for 36 h. The click solution was drained; and the resin was rinsed with DMF (5×2 mL), 2% ascorbic acid in pyridine (5×2 mL), and DMF (5×2/

5×2 mL) and washed with methanol (3×2 mL) and dichloromethane (3×2 mL). The product was cleaved from the resin in a mixture of TFA/DCM/water (60:40:2, 2×1 mL) with shaking (600 rpm) at room temperature for 1 h. The filtrate was concentrated under a stream of air, the residue was dissolved in water, and product was isolated by preparative HPLC. Fractions were analyzed by MS-ESI. Combined fractions of the product were concentrated to dryness, and the product was lyophilized from water.

The following general protocol was followed for peptoid post-oligomerization fluorescein labeling. The resin-bound oligomer was washed with methanol (3×2 mL) and DCM (3×2 mL) and dried under a stream of air; and Fmoc-6-aminohexanoic acid ("Fmoc-e-Ahx-OH") (18 mg, 50 mmol) and DIC (0.2 mL, 1M in DMF) were added. The resin was shaken at room temperature for 2 h at 800 rpm, drained, rinsed with DMF (5×2/5×2 mL), and deprotected with 1 mL of 20% piperidine in DMF for 50 min with shaking at 800 rpm, followed by draining and then rinsing with DMF (6×3/6×3 mL). Then, into a column, 4(5)-carboxy-fluorescein (19 mg, 50 mmol), N-hydroxybenzotriazole (11 mg, 80 mmol), DMF (0.1 mL), and DIC (0.2 mL, 1M in DMF) were added. The resin was shaken at room temperature for 2 h at 800 rpm, drained, washed with DMF (6×3 mL), and rinsed with DMF (5×2/5×2 mL). The resulting resin-bound oligomer with fluorescein marker was then conjugated with the corresponding ligand.

Although the invention has been described in detail for the purpose of illustration, it is understood that such detail is solely for that purpose, and variations can be made therein by those skilled in the art without departing from the spirit and scope of the invention which is defined by the claims that are set forth below after the section entitled "References".

REFERENCES

1. Doudna, J. A. (2000) Structural genomics of RNA, Nat. Struct. Biol. 7 Suppl., 954-956.
2. Batey, R. T., et al. (1999) Tertiary motifs in RNA structure and folding, Angew. Chem., Int. Ed. Engl. 38, 2326-2343.
3. Zaug, A. J., et al. (1986) The intervening sequence RNA of tetrahymena is an enzyme, Science 231, 470-475.
4. Lagos-Quintana, M., et al. (2001) Identification of novel genes coding for small expressed RNAs, Science 294, 853-858.
5. Winkler, W., et al. (2002) Thiamine derivatives bind messenger RNAs directly to regulate bacterial gene expression, Nature 419, 952-956.
6. Gallego, J., et al. (2001) Targeting RNA with small molecule drugs: therapeutic promise and chemical challenges, Acc. Chem. Res. 34, 836-843.
7. Hamy, F., et al. (1997) An inhibitor of the Tat/TAR RNA interaction that effectively suppresses HIV-1 replication, Proc. Natl. Acad. Sci. U.S.A. 94, 3548-3553.
8. Mathews, D. H., et al. (2004) Incorporating chemical modification constraints into a dynamic programming algorithm for prediction of RNA secondary structure, Proc. Natl. Acad. Sci. U.S.A. 101, 7287-7292.
9. Mathews, D. H., et al. (1999) Expanded sequence dependence of thermodynamic parameters improves prediction of RNA secondary structure, J. Mol. Biol. 288, 911-940.
10. Woese, C. R., et al. (1980) Secondary structure model for bacterial 16S ribosomal RNA: phylogenetic, enzymatic and chemical evidence, Nucleic Acids Res. 8, 2275-2293.
11. Fourmy, D., et al. (1996) Structure of the A site of *Escherichia coli* 16S ribosomal RNA complexed with an aminoglycoside antibiotic, Science 274, 1367-1371.
12. Lynch, S. R., et al. (2003) Comparison of X-ray crystal structure of the 30S subunit-antibiotic complex with NMR structure of decoding site oligonucleotide-paromomycin complex, Structure (Cambridge, Mass., US) 11, 43-53.
13. Carter, A. P., et al. (2000) Functional insights from the structure of the 30S ribosomal subunit and its interactions with antibiotics, Nature 407, 340-348.
14. Kaul, M., et al. (2006) Aminoglycoside induced reduction in nucleotide mobility at the ribosomal RNA a-site as a potentially key determinant of antibacterial activity, J. Am. Chem. Soc. 128, 1261-1271.
15. Kaul, M., et al. (2004) Fluorescence based approach for detecting and characterizing antibiotic-induced conformational changes in ribosomal RNA: comparing aminoglycoside binding to prokaryotic and eukaryotic ribosomal RNA sequences, J. Am. Chem. Soc. 126, 3447-3453.
16. Shandrick, S., et al. (2004) Monitoring molecular recognition of the ribosomal decoding site, Angew. Chem., Int. Ed. Engl. 43, 3177-3182.
17. Thomas, J. R., et al. (2006) Biochemical and thermodynamic characterization of compounds that bind to RNA hairpin loops: toward an understanding of selectivity, Biochemistry 45, 10928-10938.
18. Thomas, J. R., et al. (2005) Size-specific ligands for RNA hairpin loops, J. Am. Chem. Soc. 127, 12434-12435.
19. Thomas, J. R., et al. (2005) The relationship between aminoglycosides' RNA binding proclivity and their antiplasmid effect on an IncB plasmid combating drug-resistant bacteria: small molecule mimics of plasmid incompatibility as antiplasmid compounds, Biochemistry 44, 6800-6808.
20. Denap, J. C., et al. (2004) Combating drug-resistant bacteria: small molecule mimics of plasmid incompatibility as antiplasmid compounds, J. Am. Chem. Soc. 126, 15402-15404.
21. Klug, S. J., et al. (1994) All you wanted to know about SELEX, Mol. Biol. Rep. 20, 97-107.
22. Joyce, G. F. (1994) In vitro evolution of nucleic acids, Curr. Opin. Struct. Biol. 4, 331-336.
23. Griffey, R. H., et al. (1999) Determinants of aminoglycoside-binding specificity for rRNA by using mass spectrometry, Proc. Natl. Acad. Sci. U.S.A. 96, 10129-10133.
24. Swayze, E. E., et al. (2002) SAR by MS: a ligand based technique for drug lead discovery against structured RNA targets, J. Med. Chem. 45, 3816-3819.
25. He, Y., et al. (2004) Synthesis and evaluation of novel bacterial rRNA-binding benzimidazoles by mass spectrometry, Bioorg. Med. Chem. Lett. 14, 695-699.
26. Seth, P. P., et al. (2005) SAR by MS: discovery of a new class of RNA-binding small molecules for the hepatitis C virus: internal ribosome entry site IIA subdomain, J. Med. Chem. 48, 7099-7102.
27. Johnson, E. C., et al. (2003) Application of NMR SHAPES screening to an RNA target, J. Am. Chem. Soc. 125, 15724-15725.
28. MacBeath, G., et al. (1999) Printing small molecules as microarrays and detecting protein-ligand interactions en masse, J. Am. Chem. Soc. 121, 7967-7968.
29. Disney, M. D., et al. (2004) Aminoglycoside microarrays to explore interactions of antibiotics with RNAs and proteins, Chemistry 10, 3308-3314.
30. Ratner, D. M., et al. (2004) Tools for glycomics: mapping interactions of carbohydrates in biological systems, Chem Bio Chem 5, 1375-1383.
31. R. N. Zuckermann, J. M. Kerr, S. B. H. Kent, W. H. Moos, J Am Chem Soc 1992, 114, 10646.

32. T. R. Chan, R. Hilgraf, K. B. Sharpless, V. V. Fokin, Org Lett 2004, 6, 2853.
33. H. C. Kolb, K. B. Sharpless, Drug Discov Today 2003, 8, 1128.
34. H. C. Kolb, M. G. Finn, K. B. Sharpless, Angew Chem Int Ed Engl 2001, 40, 2004.
35. B. Tian, R. J. White, T. Xia, S. Welle, D. H. Turner, M. B. Mathews, C. A. Thornton, RNA 2000, 6, 79.
36. R. N. Kanadia, K. A. Johnstone, A. Mankodi, C. Lungu, C. A. Thornton, D. Esson, A. M. Timmers, W. W. Hauswirth, M. S. Swanson, Science 2003, 302, 1978.
37. A. Mankodi, E. Logigian, L. Callahan, C. McClain, R. White, D. Henderson, M. Krym, C. A. Thornton, Science 2000, 289, 1769.
38. A. Mankodi, C. A. Thornton, Curr Opin Neurol 2002, 15, 545.
39. X. Lin, J. W. Miller, A. Mankodi, R. N. Kanadia, Y. Yuan, R. T. Moxley, M. S. Swanson, C. A. Thornton, Hum Mol Genet. 2006, 15, 2087.
40. A. Mankodi, C. R. Urbinati, Q. P. Yuan, R. T. Moxley, V. Sansone, M. Krym, D. Henderson, M. Schalling, M. S. Swanson, C. A. Thornton, Hum Mol Genet. 2001, 10, 2165.
41. J. W. Miller, C. R. Urbinati, P. Teng-Umnuay, M. G. Stenberg, B. J. Byrne, C. A. Thornton, M. S. Swanson, Embo J 2000, 19, 4439.
42. P. Henklein, H. U. Heyne, W. R. Halatsch, H. Niedrich, Synthesis-Stuttgart 1987, 166.
43. J. Roestamadji, I. Grapsas, S. Mobashery, J Am Chem Soc 1995, 117, 11060.
44. Satz, A. L.; Bruice, T. C. Biorg. Med. Chem. 2000, 8, 1871-1880.
45. Jong, H.; Fafarman, A.; Holub, J. M.; Kirshenbaum, K. Org. Lett. 2005, 7, 1951-1954.
46. Gao, F.; Yan, X.; Baetting, O. M.; Berghuis, A. M.; Auclair, K. Angew. Chem. Int. Ed. 2005, 44, 6859-6862.
47. Weber, P. J. A.; Bader, J. E.; Folkers, G.; Beck-Sickinger, A. G. Biorg. Med. Chem. Lett. 1998, 8, 597-600.

Example 8

Myotonic dystrophy type 1 (DM1) is caused when an expanded r(CUG) repeat (r(CUG)$^{exp}$) binds the RNA splicing regulator muscleblind-like 1 protein (MBNL1) as well as other proteins. The modularly assembled small molecules displaying a 6'-N-5-hexynoate kanamycin A RNA-binding module (K) on a peptoid backbone potently inhibit the binding of MBNL1 to r(CUG)$^{exp}$. To improve the cellular permeability and localization properties of modularly assembled small molecules displaying a 6'-N-5-hexynoate kanamycin A RNA-binding module (K) on a peptoid backbone, second-generation compounds that are conjugated to a D-Arg9 molecular transporter were synthesized. These modified compounds enter cells in higher concentrations than parent compounds without such transporters and are efficacious in cell-based DM1 model systems at low micromolar concentrations. In particular, they improve three defects that are the hallmarks of DM1: a translational defect due to nuclear retention of transcripts containing r(CUG)$^{exp}$; pre-mRNA splicing defects due to inactivation of MBNL1; and the formation of nuclear foci. A compound having desirable properties in cell-based studies was tested in a mouse model of DM1. Modest improvement of pre-mRNA splicing defects was observed. These studies show that a modular assembly approach can afford bioactive compounds that target RNA.

Potential RNA drug targets are plentiful in the transcriptome; however, only the bacterial rRNA, and hence the ribosome, are tried and true targets for small molecules.(1) Ideally, both coding and non-coding RNAs that have important biological functions could be targeted with small molecules. (2) There are significant challenges for the development of small molecules that modulate RNA function, either by screening or rational design. These issues are mainly centered on the identification of selective small molecule ligands that target specific RNAs and parallel efforts to identify the RNA motifs that selectively bind small molecule ligands.(3)

The current state of the art in developing compounds that target RNA is the use of antisense nucleic acids or interfering RNA.(4-6) Although both of these strategies are powerful, oligonucleotide-based therapeutics can have undesirable properties such as non-specific stimulation of the immune system and off-target effects.(7, 8) In addition, the compounds have poor cellular permeability and are more expensive to manufacture than small molecules. The advantage of oligonucleotides is their unparalleled simplicity of design based on base-pairing rules.

In an effort to develop methods to target RNA with small molecules, a program was developed to define a database of RNA motif-ligand interactions by using multidimensional combinatorial screening.(9-12) In this approach, a library of small molecules is probed for binding to a library of discrete RNA motifs that are commonly found in the repertoire human RNA structures (hairpins or internal loops, for example). By selecting RNA motif-ligand binding partners, the optimal RNA motifs that bind small molecules are defined and deposited into the database. This database can be mined against transcriptomic data and secondary structure predictions to determine if a particular RNA has ligand-targetable motifs. The small molecules that bind to these motifs serve as lead compounds to target the RNA of interest.(13-16)

It was determined that 6'-N—S-hexynoate kanamycin A (K), binds a 2×2 nucleotide pyrimidine-rich internal loop that is present in the RNA that causes myotonic dystrophy type 2 (DM2).(9, 12, 13) DM2 is caused by an expanded r(CCUG) repeat in intron 1 of the zinc finger 9 protein (ZNF9). The expanded repeat folds into a hairpin with an array of 5'CCUG/3'GUCC motifs. These loops serve as a high affinity-binding site for Muscleblind-like 1 (MBNL1) protein, a regulator of pre-mRNA splicing.(17) DM2 is associated with the inactivation of MBNL1, which leads to a variety of pre-mRNA splicing defects.(18, 19) By using the information that K binds to RNA motifs like those present multiple times in r(CCUG)$^{exp}$, a potent in vitro inhibitor of the r(CCUG)$^{exp}$-MBNL1 interaction was designed. Specifically, the optimal multivalent compound displays the K module with the same periodicity as the array of 5'CCUG/3'GUCC motifs present in r(CCUG)$^{exp}$.(13)

During the course of studies to understand the RNA targets of 6'-N-5-hexynoate kanamycin A, it was determined that a suboptimal motif for ligand binding is 5'CUG/3'GUC, the motif that is highly reiterated in the expanded r(CUG) repeat (r(CUG)$^{exp}$) that causes myotonic dystrophy type 1 (DM1). DM1 and DM2 share a similar molecular basis of disease as both expanded repeats bind and inactivate MBNL1. The r(CUG) expansion is also located in a non-coding sequence, the 3' untranslated region (UTR) of the dystrophia myotonica protein kinase (DMPK) mRNA.(20, 21)

Figure 8:
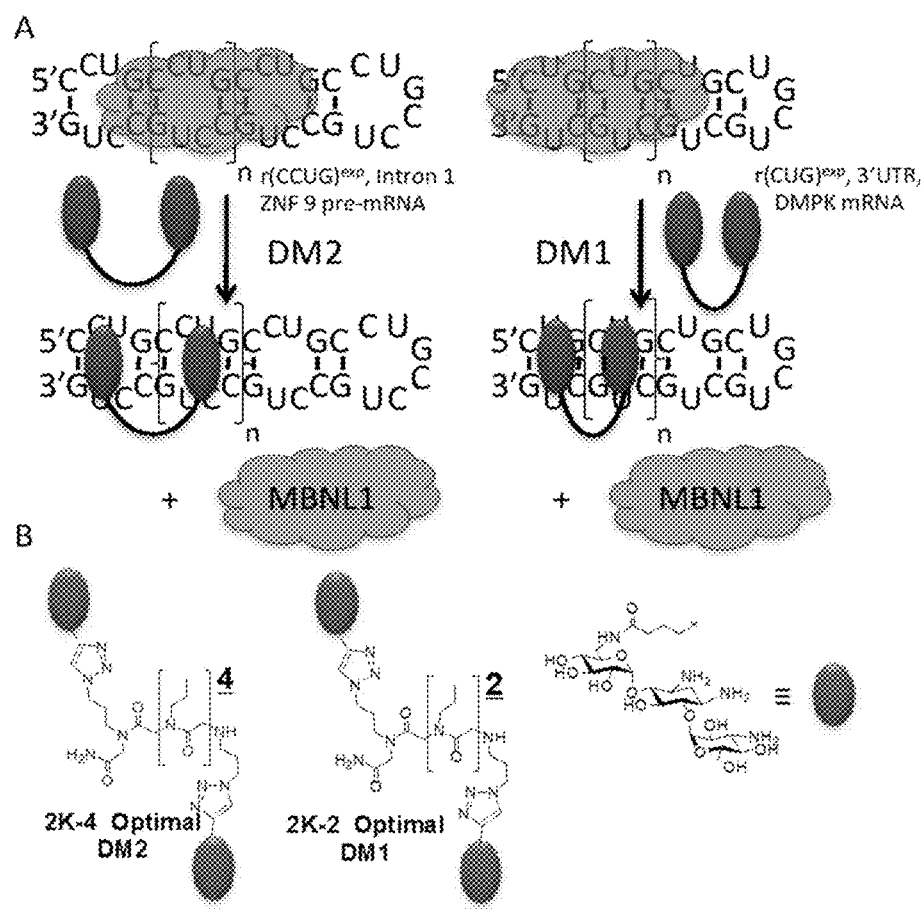
FIG. 8 is an example of the disease mechanism for DM1 and DM2 and the strategy employed to design modularly assembled small molecules that target the RNAs that cause disease. A, the secondary structures of r(CCUG)$^{exp}$ and r(CUG)$^{exp}$, the causative agents of DM2 and DM1, respectively. The expansions bind MBNL1 protein and cause pre-mRNA splicing defects. By using modularly assembled small molecules, the repeats can be effectively targeted to inhibit or displace MBNL1. B, the structures of the optimal modularly assembled compounds that target DM2- and DM1-causing RNAs by using a 6' acylated kanamycin A derivative as the RNA-binding module. Previous studies have shown that binding affinity and selectivity can be controlled such that the compounds are specific for DM1 or DM2 RNAs by altering the spacing between the RNA-binding modules. 2K-2 is selective for DM1 while 2K-4 is selective for DM2.

It was hypothesized that the optimal distance between K modules would be shorter for the DM1 RNA than the DM2 RNA due to the smaller size of the internal loop (FIG. 8). Indeed, by decreasing the distance between K modules, a modularly assembled compound that was selective for r(CUG) repeats and potently inhibitory for the r(CUG)$^{exp}$-MBNL1 interaction in vitro was identified.(15) These studies established that both the nature of the RNA-binding module and the spacing between modules are independent determinants of RNA-binding properties of modularly assembled ligands.

In this example, it is disclosed that second generation modularly assembled compounds that target r(CUG)$^{exp}$ were effective in cell culture and animal models of DM1. These compounds were engineered for enhanced cellular permeability and nuclear localization via conjugation to a D-Arg$_9$ (DR$_9$) molecular transporter.(22-25) Specifically, the designer compounds improve pre-mRNA splicing defects in cell culture and animal models, improve translational defects in a cell-based model system, and disrupt the formation of nuclear foci.

Results & Discussion

We previously reported that modularly assembled small molecules displaying 6'-N-5-hexynoate kanamycin A (K) inhibit the formation of the r(CUG)$^{exp}$-MBNL1 complex in vitro.(13, 15, 16) The optimal compounds consist of a peptoid backbone in which the K ligand modules are separated by two propylamine spacers. The nomenclature for these structures is nK-2, where n is the number of RNA-binding modules displayed on a single chain (or valency), K indicates the RNA-binding module (a conjugated version of 6'-N-5-hexynoate kanamycin A), and the number after the dash indicates the number of propylamine spacers between K modules. The structures of these and related control compounds are shown in FIG. 8.

The Bioactivity of nK-2 Compounds in DM1 Cell-Based Model Systems.

The presence of r(CUG)$^{exp}$ causes various defects in vivo, including (i) dysregulation of pre-mRNA splicing controlled by MBNL1; (19, 26) (ii) nuclear retention and hence decreased translation of r(CUG)$^{exp}$-containing transcripts; (27, 28) and, (iii) formation of nuclear foci, which consist of r(CUG)$^{exp}$-protein aggregates. (29, 30)

Two cell-based models were used to determine if the optimal compound from in vitro studies, 4K-2, could improve DM1-associated defects. These assays were completed as described previously.(31) First, the effect of 4K-2 on pre-mRNA splicing was assayed in HeLa cells.(32) Briefly, cells were co-transfected with a DM mini-gene that expresses 960 interrupted r(CUG) repeats and a cardiac troponin T (cTNT) pre-mRNA mini-gene.(31, 32) After transfection, the cells were treated with compound in growth medium. cTNT alternative splicing (FIG. 10) was then analyzed by RT-PCR and denaturing gel electrophoresis as previously described.(31)

Figure 11:
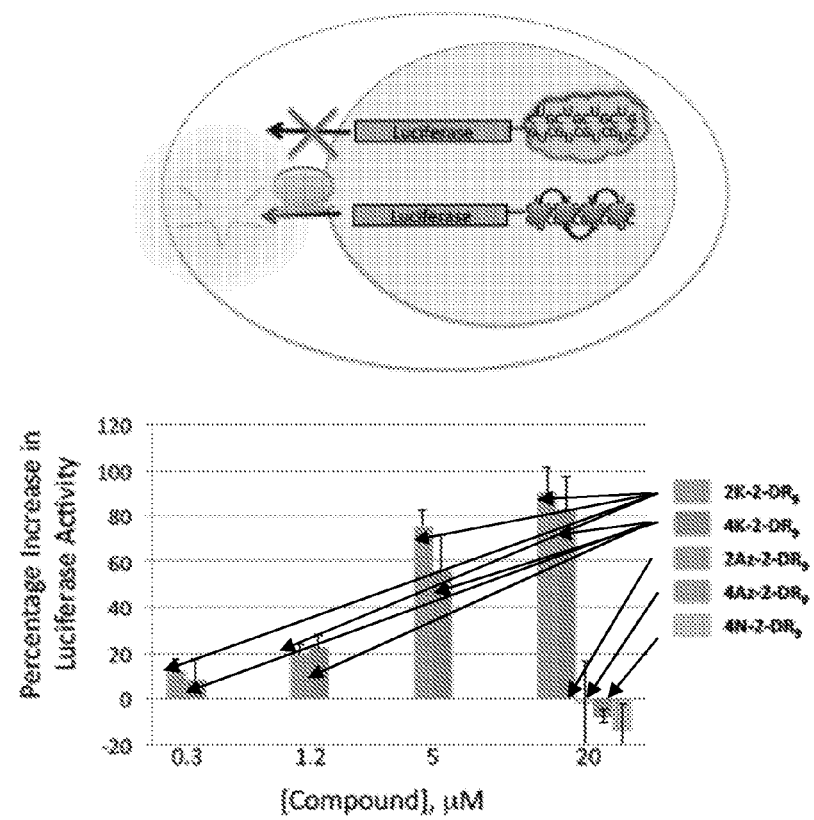
FIG. 11 is an example for assessing the bioactivity of modularly assembled small molecules targeting r(CUG)$^{exp}$ in a translational assay. Top, a schematic of the translational assay used to assess the effect of compounds on the DM1 translation defect. Bottom, 2K-2-DR9 and 4K-2-DR9 improve the DM1 translation defect as determined by an increase in luciferase activity. Please note that untreated cells have a "Percentage Increase of Luciferase Activity" value of 0.

The second model system mimics the DMPK translation defect (FIG. 11). The C2C12 cell line was stably transfected with the firefly luciferase gene in which r(CTG)$_{800}$ was placed in the 3'UTR.(31) Expression of luciferase is low in this cell line due to the binding of r(CUG)$_{800}$ to MBNL1 and other proteins, resulting in nuclear retention of the luciferase mRNA. If a compound is efficacious, then an increase in luciferase activity in cell lysates is observed.

Figure 10:
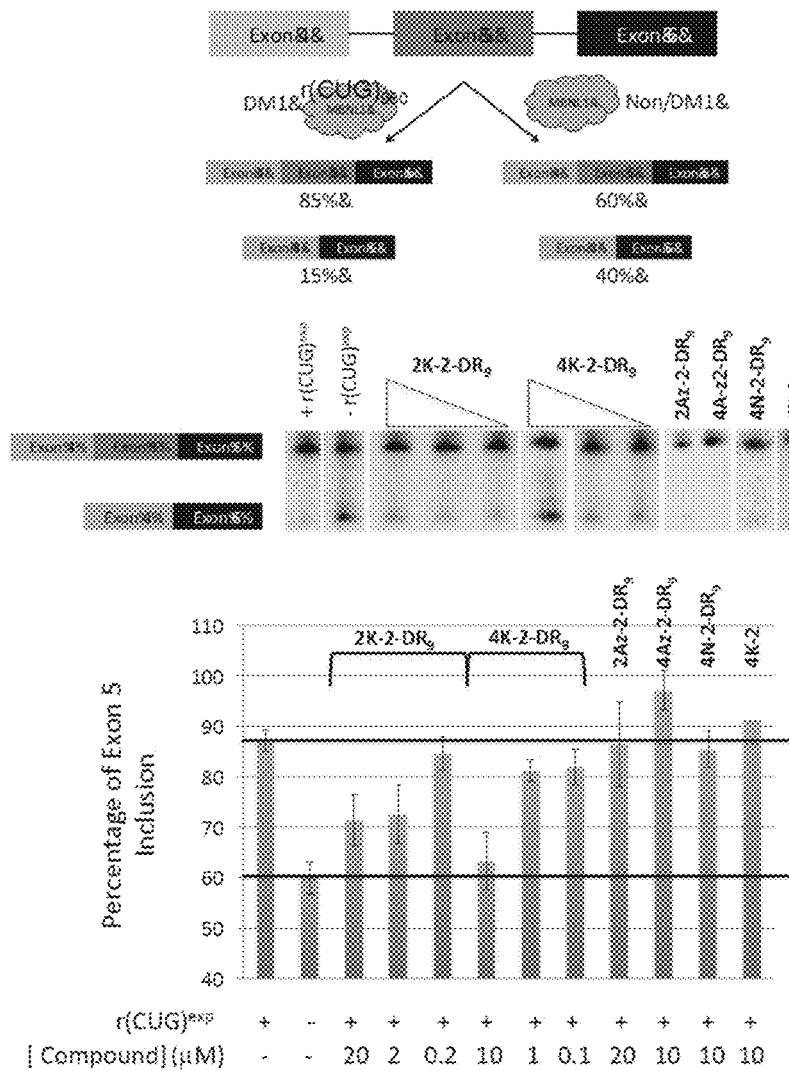
FIG. 10 is an example for assessing the bioactivity of modularly assembled small molecules targeting r(CUG)$^{exp}$ in a pre-mRNA splicing defect assay. A, top, a schematic of the cTNT mini-gene that was used in this assay. Middle, representative gel autoradiogram assaying improvement of cTNT pre-mRNA splicing when a cellular model system of DM1 is treated with various compounds. Concentrations of compounds correspond to the plot shown below. Bottom, plot of the data for cTNT mini-gene splicing in the presence and absence of modularly assembled compounds. 4K-2-DR$_9$ restores pre-mRNA splicing patterns to levels observed in the absence of r(CUG)$^{exp}$ when cells are treated with 10 µM compound. Modest improvement in splicing defects is observed when cells are treated with lower concentrations of 4K-2-DR$_9$ or with 2K-2-DR$_9$. B, top, 2K-2-DR$_9$ and 4K-2-DR$_9$ do not affect the splicing of the cTNT mini-gene in the absence of r(CUG)$^{exp}$. B, bottom, 2K-2-DR$_9$ and 4K-2-DR$_9$ do not affect the splicing of the PLEKHH2 mini-gene in the presence or absence of r(CUG)$^{exp}$. The alternative splicing of PLEKHH2 is not regulated by MBNL1.
Figure 10:
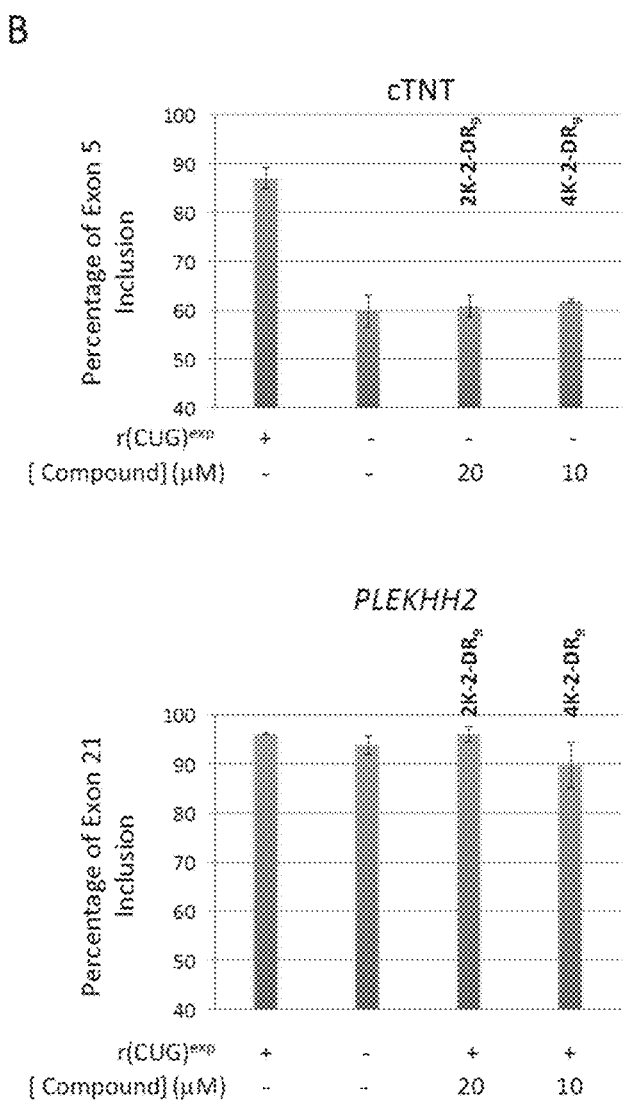

In both model systems, 4K-2 was not active, or only very slightly active at 10 µM (FIG. 10). Previous studies of the cellular permeability of 2K-2 and 4K-2 showed that, although the compounds are cell permeable, they localize mainly to the perinuclear region.(13, 15, 16, 33) We hypothesized that if the cellular permeability and nuclear localization of the compounds could be improved, then the compounds might be efficacious.

Cellular Permeability of nK-2-DR$_9$ Compounds.

Figure 9:
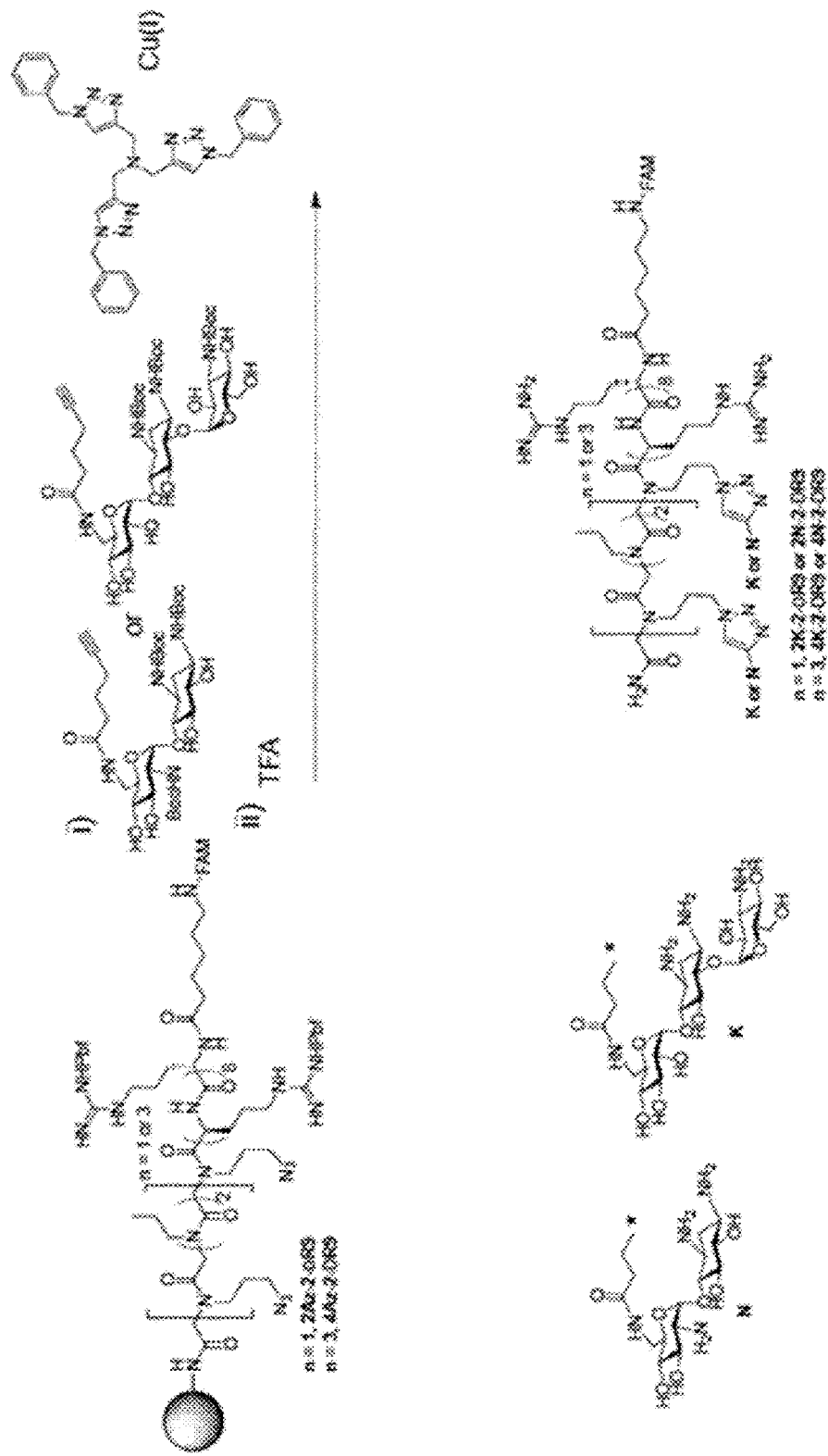
FIG. 9 is an example of the synthetic scheme used to provide modularly assembled small molecules that target r(CUG)$^{exp}$. The modularly assembled small molecules were synthesized to contain a D-Arg$_9$ tag to facilitate cellular permeability. Bioactive peptoids contain K modules while control peptoids that have no biological activity contain N modules.

To develop compounds with increased cellular permeability and nuclear localization, the molecular transporter D-R$_9$ (DR$_9$) (23, 24) was conjugated onto 4K-2 to yield 4K-2-DR$_9$ (FIG. 9). Previous studies have shown that multiple guanidinium units facilitate cellular uptake of cargo ranging from small molecules to peptides and proteins. (23, 34) Furthermore, mechanistic studies have shown that poly arginines enter mammalian cells through a variety of pathways that include binding to cell surface heparin sulfate and endocytotic uptake.(35) Since many cell and tissue types present heparin sulfate,(36) we envisioned that DR$_9$ conjugation could engender compounds with the ability to more efficiently enter a variety of cell lines and mouse tissues.

To study if the nK-2-DR$_9$ compounds have enhanced cellular uptake relative to the parent molecules, flow cytometry experiments were complete using the HeLa cell line since it was also used to assay pre-mRNA splicing defects. Compounds were added in growth medium to the cells and incubated for 1.5 h. The cells were trypsinized from the surface and stained with propidium iodide (detects dead or damaged cells with compromised cell membranes). Since the compounds are labeled with fluorescein, it was used to quantify cellular permeability. Compound 4K-2 was only taken up by ca. 1% of the cells in these conditions, while 4K-2-DR$_9$ was taken up by 13-fold higher number of cells. Two related compounds were also studied, 4N-2-DR$_9$ and 4Az-2-DR$_9$ where N indicates the conjugation of 6'-N—S-hexyonate neamine to the peptoid backbone and Az indicates the unconjugated (azide-displaying backbone). 4N-2-DR$_9$ and 4K-2-DR$_9$ have similar cellular permeabilities while 4Az-2-DR$_9$ is taken up by 75-fold more cells than 4K-2. It is likely that the decreased cellular permeability of 4N-2-DR$_9$ and 4K-2-DR$_9$ relative to 4Az-2-DR$_9$ is due to the highly cationic aminoglycoside cargo. Confocal microscopy images confirm that 4K-2-DR$_9$ is permeable to almost all cells after longer incubation times (16 h, FIG. 13). In all cases there is no change in the number of cells that are stained by propidium iodide, which indicates cell death relative to cells that are not treated with compound (Table 4). Thus, addition of a DR$_9$ tag enhances cell uptake by greater than 10-fold while not at the expense of cell toxicity. Furthermore, addition of cargo (K or N modules) onto a peptoid with DR$_9$ decreases uptake.

In Vitro Potency and Affinity of nK-2-DR$_9$ Compounds.

The potency of the second-generation compounds for disruption of the r(CUG)$_{10}$-MBNL1 complex are summarized in Table 1. 2K-2-DR$_9$ and 4K-2-DR$_9$ disrupt the r(CUG)$_{10}$-MBNL1 complex in vitro with IC$_{50}$'s of 1430±160 nM and 240±5 nM while the corresponding monomer, FITC-K has an IC$_{50}$>250 µM. Once normalized for the number of K units, the multivalent effect (37) for 4K-2-DR$_9$ is >250-fold. Control peptoids in which the backbone in unconjugated (4Az-2-DR$_9$) or conjugated to a neamine derivative (4N-2-DR$_9$) have IC$_{50}$'s of 5400±510 and 1030±90 nM, respectively. Thus display of the appropriate module, K, imparts improved potency (by at least 5-fold) for the disruption of the pre-formed r(CUG)$_{10}$-MBNL1 complex. The observation that both 4Az-2-DR$_9$ and 4N-2-DR$_9$ inhibit the r(CUG)$_{10}$-MBNL1 complex suggests that addition of the DR$_9$ tag causes some level of non-specific binding of the compounds to RNA, which is not unexpected. This is further verified by the IC$_{50}$ for 4K-2, which is 16300 µM in this assay. The large difference in IC$_{50}$ between 4K-2 and 4K-2-DR$_9$ is likely because the DR$_9$-conjugate occupies a larger amount of the RNA's surface area. A larger difference in potency was previously observed for 4K-2 and 4N-2 (>33-fold) than for 4K-2-DR$_9$ and 4N-2-DR$_9$, although these experiments were completed using a different assay.(15)

We previously reported that the distance between K modules also affects potency and affinity.(15) As shown in FIG. 8, the optimal distance for r(CUG)$^{exp}$ is afforded by two propylamine spacing modules while the optimal distance for r(CCUG)$^{exp}$ is four propylamines. In order to determine if conjugation of DR$_9$ affects the optimal distance between K modules for r(CUG)$^{exp}$, the potencies of 2K-4-DR$_9$, 3K-4-DR$_9$, and 2N-4-DR$_9$ were determined (Table 1). As expected, 2K-4-DR$_9$ is a 38-fold weaker inhibitor of the r(CUG)-MBNL1 complex (IC$_{50}$=55 µM) than 2K-2-DR$_9$. Increasing the valency to 3K-4-DR$_9$ improves potency by ~2-fold (26 µM) but it is still a less potent inhibitor by ~18-fold than 2K-2-DR$_9$ and ~100-fold weaker inhibitor than 4K-2-DR$_9$. Interestingly, 2N-4-DR$_9$ is a better inhibitor than 2K-4-DR$_9$ (IC$_{50}$=9 µM; ~6-fold worse than 2K-2-DR$_9$), suggesting that the optimal distance between RNA-binding modules is ligand-dependent.

To further understand the nature of inhibition of the complex and the effect of affinity of the RNA-ligand complex, binding measurements were completed with 4K-2-DR$_9$ and the control compounds (Table 1). The RNA used in these studies contains 12 5'CUG/3'GUC motifs or 24 r(CUG) repeats (r(CUG)$_{12\times2}$) embedded in a hairpin cassette (15). This construct was used so that comparisons could be made to binding affinities reported previously.(15) The data are summarized in Table 1.

The RNA-binding module, FITC-K, a fluorescently labeled derivative of 6'-N-5-hexynoate kanamycin A has a previously reported K$_d$ of 1 µM.(13) The affinities of the modularly assembled compounds, however, are much higher. For example, 4K-2 has a binding affinity of 4 nM and 4K-2-DR$_9$ has a K$_d$ of 3.5 nM. 4K-2-DR$_9$ binds to r(CUG)$_{12\times2}$ with a stoichiometry of 3.7±1.2. Since the RNA target contains 12 copies of the 5'CUG/3'GUC motif, the stoichiometry indicates that the designed ligand is approximately interacting with each 5'CUG/3'GUC motif. This was expected based on previous experiments with 4K-2 and other related compounds.(13)

Additionally, 4K-2-DR$_9$ was tested for binding to potential cellular bystander RNA, using bulk yeast. The compound interacts with tRNAs very weakly with a K$_d$ of greater than 2 µM. The control compounds, 4Az-2-DR$_9$ and 4N-2-DR$_9$, bind tRNA and r(CUG)$_{12\times2}$ very weakly; binding curves indicate that the K$_d$'s are greater than 2 µM. The addition of the uptake tag does induce some non-specific RNA binding, as expected and as evidenced by the protein displacement data (Table 1).

Biological Efficacy of nK-2-DR$_9$ Compounds in Cell-Based Model Systems of DM1.

Next, the compounds and their appropriate controls were studied for modulating the toxicity of r(CUG)$^{exp}$ in cell-based models of DM1. Three models were used that probe (i) r(CUG)$^{exp}$ toxicity derived from pre-mRNA splicing defects due to sequestration of MBNL1;(19, 26) (ii) r(CUG)$^{exp}$ toxicity derived from nuclear retention, and thus reduced translation, of the DMPK mRNA;(27, 28) and, (iii) formation of nuclear foci due to r(CUG)$^{exp}$-protein complexes.(29, 30)

Improvement of Pre-mRNA Splicing Defects.

Pre-mRNA alternative splicing was assayed in HeLa cells as described above.(32) Briefly, cells were transfected with a DM1 mini-gene that expresses 960 interrupted r(CUG) repeats and a pre-mRNA splicing reporter mini-gene of interest.(31, 32) We first investigated the effect of the compounds on the alternative splicing of the cTNT mini-gene, (21) the parent gene of which is mis-spliced in DM patients.(21, 38, 39) In healthy cells, MBNL1 binds upstream of exon 5 in the cTNT pre-mRNA and represses its inclusion.(38, 40) In the DM1 model system, approximately 65% of exon 5 is included in cTNT mRNA in the absence of r(CUG)$^{exp}$ while approximately 90% of exon 5 is included in the presence of r(CUG)$^{exp}$ (FIG. 10).

As shown in FIG. 10, 2K-2-DR$_9$ and 4K-2-DR$_9$ improve the pre-mRNA splicing defect observed in the cTNT mini-gene towards healthy/wild type levels (no r(CUG)$^{exp}$ expression) at micromolar concentrations. For 2K-2-DR$_9$, pre-mRNA splicing defects improve ~50% when cells are treated with 2 and 20 µM (two-tailed p value=0.0418) while no effect is observed at lower concentrations. For 4K-2-DR$_9$, pre-mRNA splicing defects are only modestly affected at 1 and 0.1 µM; however, pre-mRNA splicing is restored to levels observed in the absence of r(CUG)$^{exp}$ when cells are treated with 10 M compound (two-tailed p value=0.0309). Thus, designed compounds improve pre-mRNA alternative splicing towards a non-DM1-like state to varying extents, with 4K-2-DR$_9$ being more efficacious in vitro and in vivo.

A series of control experiments were also completed. First, 4Az-2-DR$_9$ and 4N-2-DR$_9$ were also studied for affecting pre-mRNA splicing. The control compounds were chosen to investigate the role of the RNA-binding module. The compounds are weak in vitro inhibitors (Table 1). As shown in FIG. 10, neither compound improves cTNT pre-mRNA splicing. Additional control experiments demonstrated that neither 2K-2-DR$_9$ nor 4K-2-DR$_9$ affect (i) the alternative splicing of the cTNT mini-gene in the absence of r(CUG)$^{exp}$ (FIG. 3B); (ii) the alternative splicing of a PLEKHH2 mini-gene, the alternative splicing of which is not regulated by MBNL1 (FIG. 10B); and (iii) the alternative splicing of endogenous genes (CAMKK2 and TTC8) which are also not regulated by MBNL1.

Improvement of Translational Defects.

In order to determine if 2K-2-DR$_9$ or 4K-2-DR$_9$ can improve DM1-associated translational defects, a stably transfected cell line in which r(CUG)$_{800}$ was placed in the 3' UTR of firefly luciferase mRNA was used (FIG. 11).(31) As mentioned above, expression of luciferase is low due to the binding of r(CUG)$_{800}$ to MBNL1 and other proteins, resulting in nuclear retention of the luciferase mRNA. In good agreement with the results of the pre-mRNA splicing assays described above, 2K-2-DR$_9$ and 4K-2-DR$_9$ increase the nuclear export and translation of the luciferase mRNA as determined by an increase in luciferase activity. For example, 0.3 and 1.2 µM of each compound stimulates luciferase production by at best 20%. However, both compounds stimulate luciferase production by over 50% and by as much as 90% when cells are dosed with 5 or 20 µM compound. In contrast, no effect on luciferase activity was observed when the cells were treated with as much as 20 µM of the two control compounds, 4Az-2-DR$_9$ and 4N-2-DR$_9$.

Control assays were completed in which 2K-2-DR$_9$ and 4K-2-DR$_9$ were tested for non-specific production of luciferase by using a luciferase mRNA without r(CUG)$^{exp}$ in the 3' UTR. No change in luciferase production was observed when the cells were treated with as much as 20 µM 2K-2-DR$_9$ or 4K-2-DR$_9$.

Disruption of Nuclear Foci.

Figure 12:
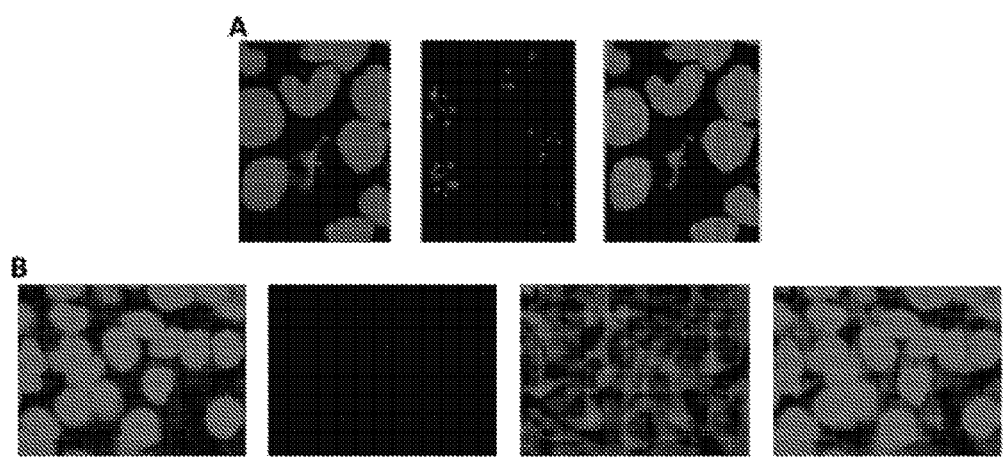
FIG. 12 is an example of how K-2-DR$_9$ disrupts the formation of nuclear foci in a DM1 model system as assayed by fluorescence in situ hybridization. A, confocal microscopy images of untreated cells that express r(CUG)$^{exp}$. From left to right: DAPI fluorescence (nuclear stain), Cy3 fluorescence (probe for r(CUG)$^{exp}$), and an overlay of these images. B, confocal microscopy images of cells that express r(CUG)$^{exp}$ after treatment with 4K-2-DR$_9$ for 16 h. From right to left: DAPI fluorescence (nuclear stain), Cy3 fluorescence (probe for r(CUG)$^{exp}$), fluorescein fluorescence (uptake of 4K-2-DR$_9$), and an overlay of these images. The 4K-2-DR$_9$ compound markedly reduces the number of nuclear foci, as expected since the compound improves pre-mRNA splicing and translation defects.

Another hallmark of DM1-affected cells is the presence of nuclear foci that consist of r(CUG)$^{exp}$-protein complexes (26). Therefore, a fluorescence in situ hybridization assay (FISH) was used to probe if 4K-2-DR$_9$ can decrease the occurrence of nuclear foci. HeLa cells were transfected with the DM1 mini-gene and treated with 4K-2-DR$_9$. The cells were then probed with a 2'-O-methyl oligonucleotide labeled with Cy3 that is complementary to r(CUG)$^{exp}$. The cells were then imaged via confocal microscopy (FIG. 12). In the absence of 4K-2-DR$_9$, multiple nuclear foci are observed in each cell, which correspond to r(CUG)$^{exp}$-protein complexes (FIG. 12a). Upon addition of 4K-2-DR$_9$, however, there is a marked reduction in the number of the nuclear foci and the small number of foci that remain are much smaller in size compared to those observed in untreated cells. Since 4K-2-DR$_9$ is labeled with fluorescein, cellular permeability and localization can also be imaged. Fluorescence from the compound is observed in almost every cell and is highly abundant in the cytoplasm with some nuclear localization.

The microscopy data support the results obtained from the luciferase reporter system used to assay the DM1 translational defect. For example, if 4K-2-DR$_9$ was completely localized to the nucleus, then it could cause a further decrease in the production of luciferase by increasing the transcript's nuclear retention. The observation that 4K-2-DR$_9$, however, enhances luciferase production and is mainly cytoplasmic with some nuclear localization lends some support to a mechanism in which 4K-2-DR$_9$ binding to r(CUG)$^{exp}$, displaces MBNL1 and enables cytoplasmic transport.

4K-2-DR$_9$ Improves Pre-mRNA Splicing Defects in a Mouse Model of DM1.

Figure 13:
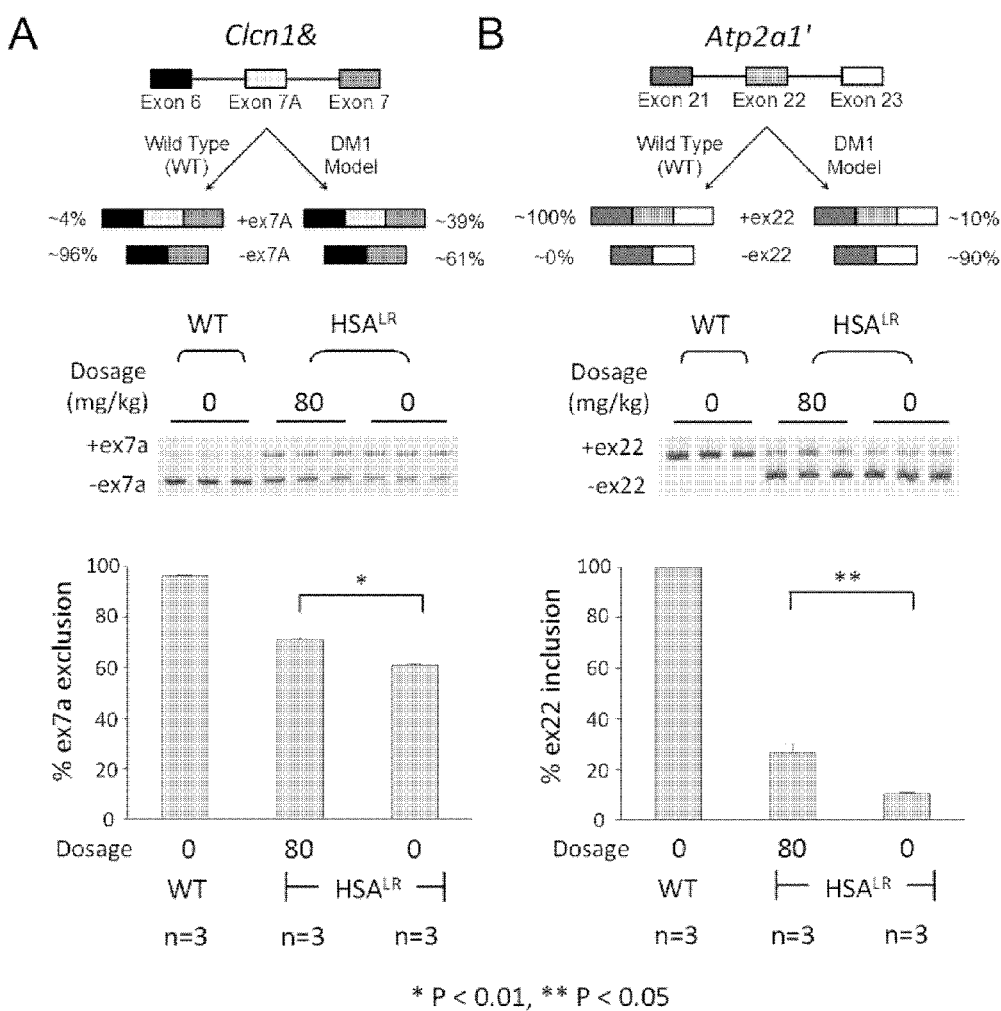
FIG. 13 is an example of how K-2-DR$_9$ improves pre-mRNA splicing defects in the muscle-specific chloride ion channel (Clcn1) and sarco(endo)plasmic reticulum Ca$^{2+}$ ATPase 1 (Serca1/Atp2a1) pre-mRNAs in a DM1 mouse model. The DM1 mouse model expresses the human skeletal actin (HSA) transgene containing 250 CTG repeats (HSA$^{LR}$; where LR indicates "long repeats"). Wild type mice (WT) are FVB mice. All dosages are in mg/kg. A, top: schematic of Clcn1 alternative splicing in wild type and DM1 mice. A, bottom: analysis of Clcn1 alternative splicing by RT-PCR when mice are treated with 4K-2-DR$_9$ including a representative gel image and a plot of the corresponding data (p=0.0022). The three lanes under each dosage in the gel image correspond to the results from treatment of three different mice. B, top: schematic of Atp2a1 alternative splicing in wild type and DM1 mice. B, bottom: analysis of Atp2a1 alternative splicing by RT-PCR when mice are treated with 4K-2-DR$_9$ including a representative gel image and a plot of the corresponding data (p=0.0491). The three lanes under each dosage in the gel image correspond to the results from treatment of three different mice.
Figure 14:
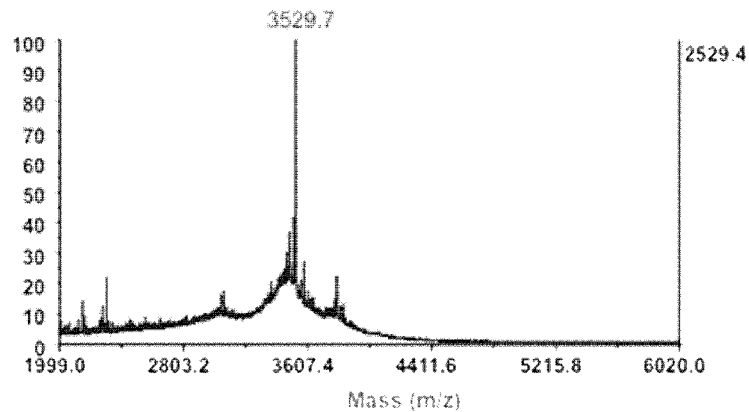
FIG. 14 is a representative Maldi-TOF mass spectrum of 2K-2-DR9.
Figure 15:
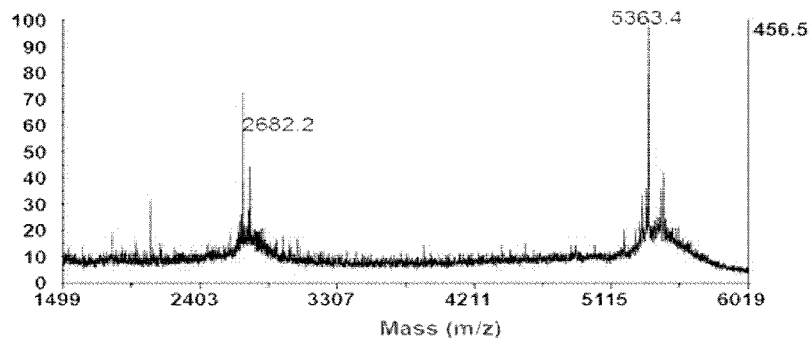
FIG. 15 is a representative Maldi-TOF mass spectrum of 4K-2-DR9.
Figure 16:
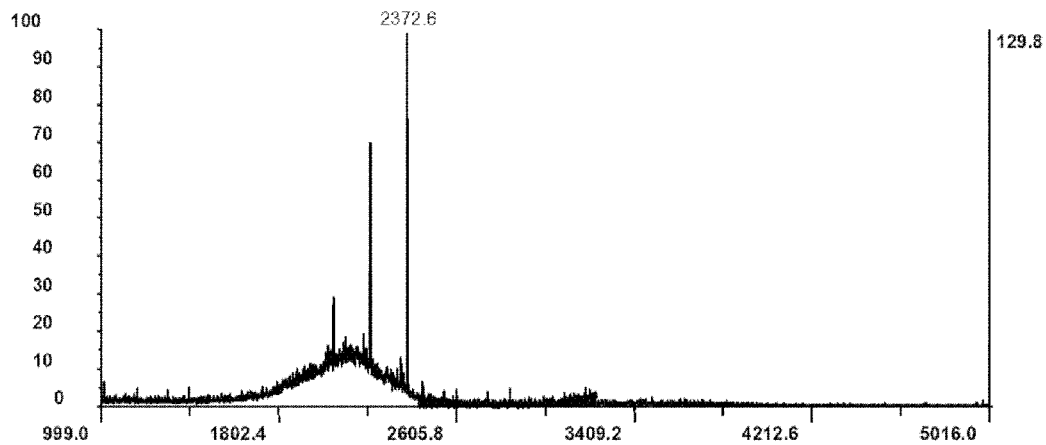
FIG. 16 is a representative Maldi-TOF mass spectrum of 2Az-2-DR9.
Figure 17:
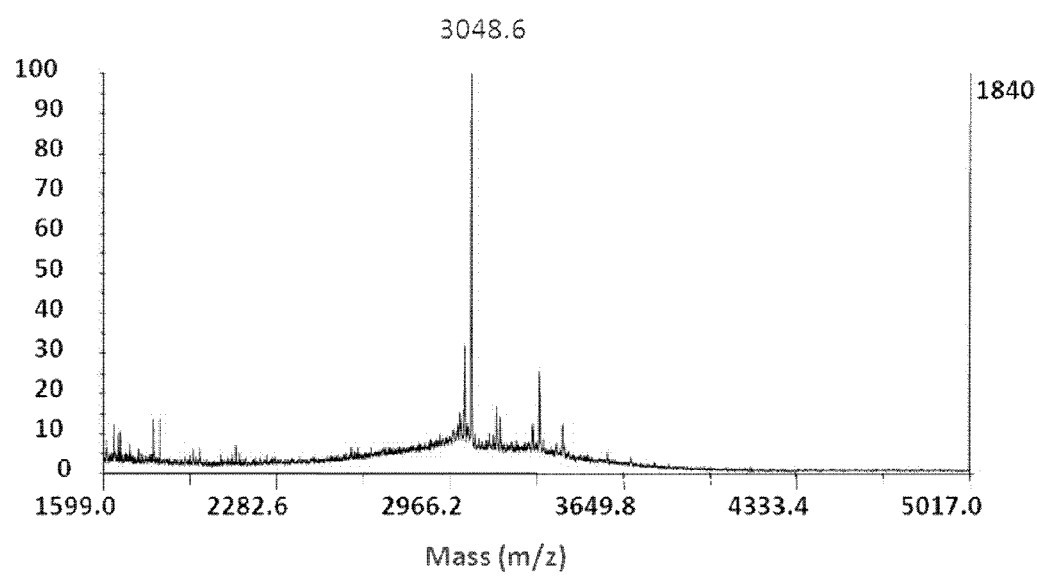
FIG. 17 is a representative Maldi-TOF mass spectrum of 4Az-2-DR9.
Figure 18:
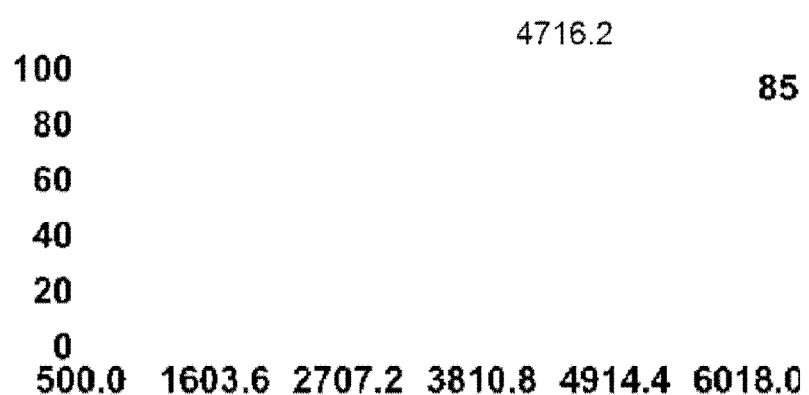
FIG. 18 is a representative Maldi-TOF mass spectrum of 4N-2-DR9.
Figure 19:
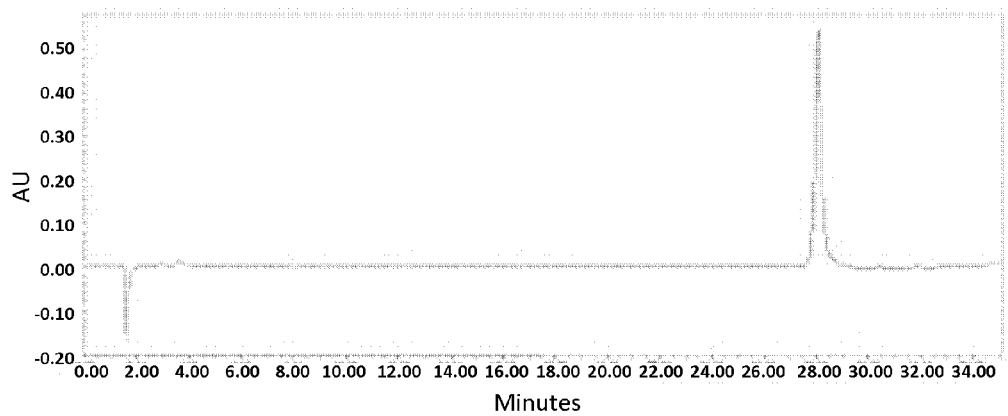
FIG. 19 is a representative analytical HPLC trace of 2K-2-DR9.
Figure 20:
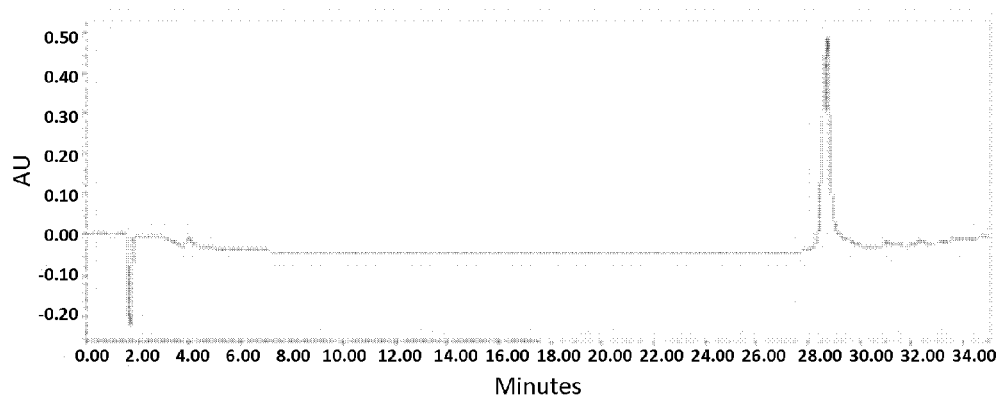
FIG. 20 is a representative analytical HPLC trace of 4K-2-DR9.
Figure 21:
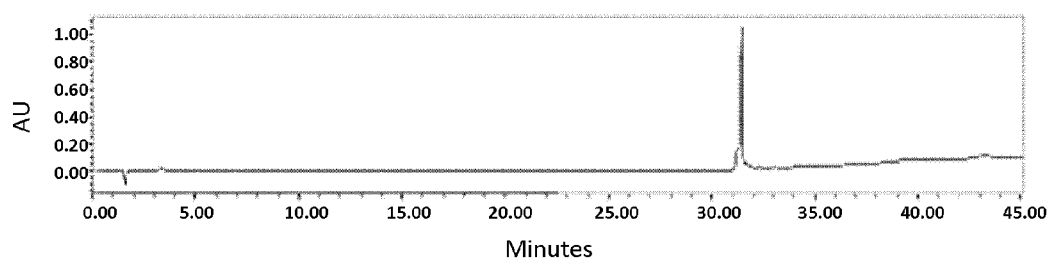
FIG. 21 is a representative analytical HPLC trace of 2Az-2-DR9.
Figure 22:
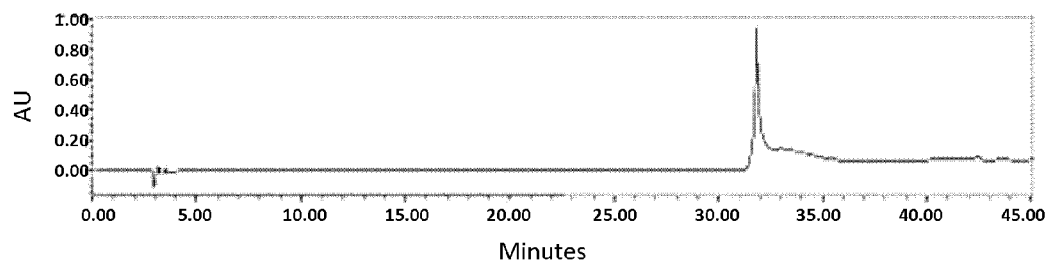
FIG. 22 is a representative analytical HPLC trace of 4Az-2-DR9.
Figure 23:
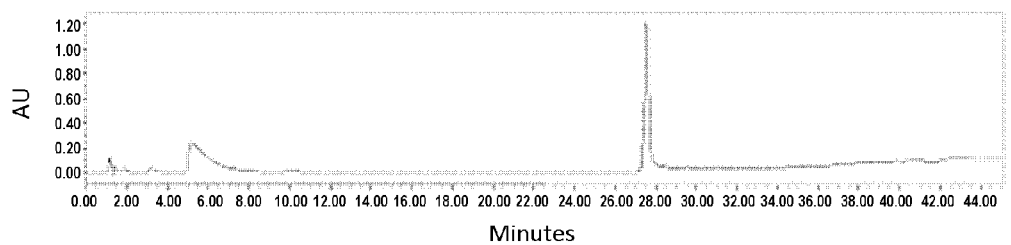
FIG. 23 is a representative analytical HPLC trace of 4N-2-DR9.
Figure 24:
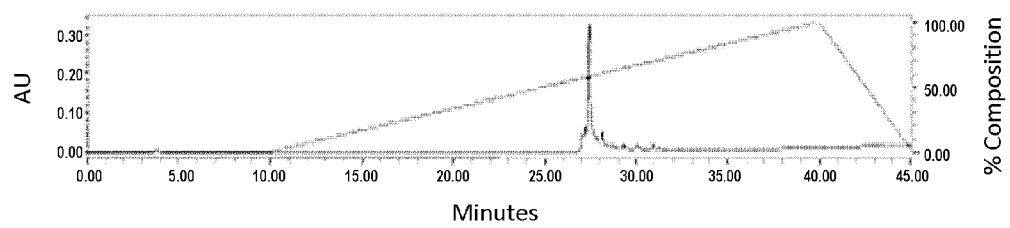
FIG. 24 is a representative analytical HPLC trace of 2K-4-DR9.
Figure 25:
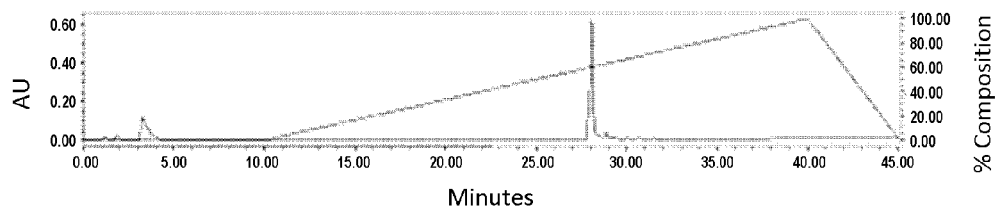
FIG. 25 is a representative analytical HPLC trace of 3K-4-DR9.
Figure 26:
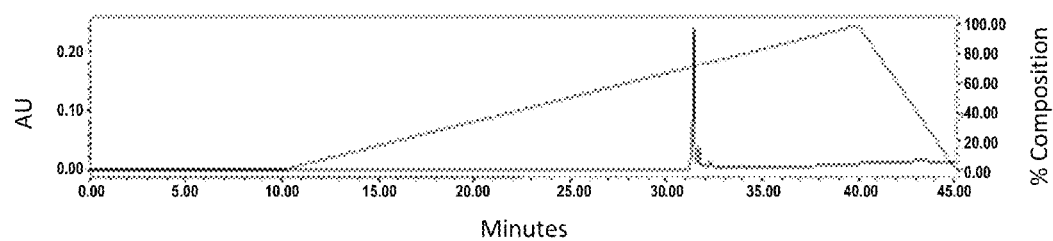
FIG. 26 is a representative analytical HPLC trace of 2Az-4-DR9.
Figure 27:
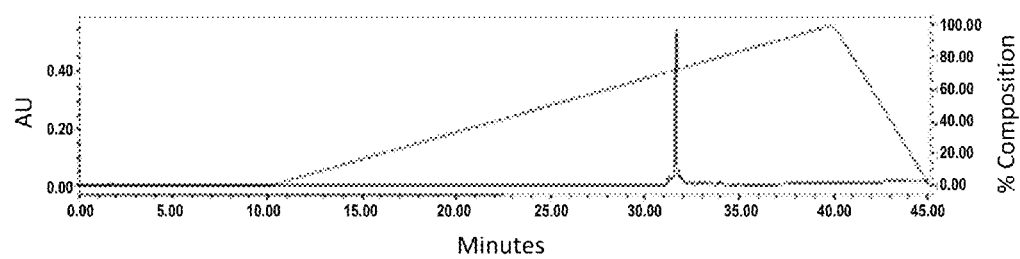
FIG. 27 is a representative analytical HPLC trace of 3Az-4-DR9.
Figure 28:
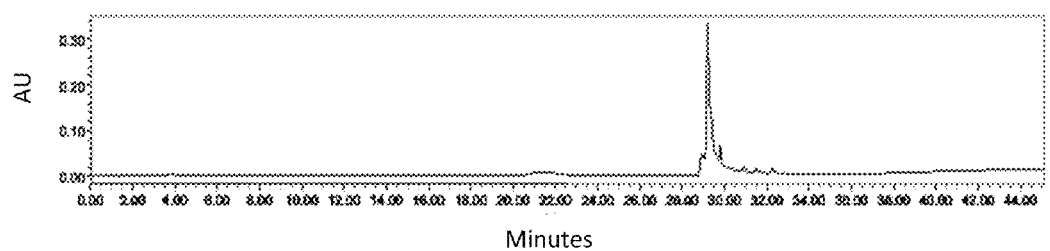
FIG. 28 is a representative analytical HPLC trace of 2N-4-DR9.
Figure 29:
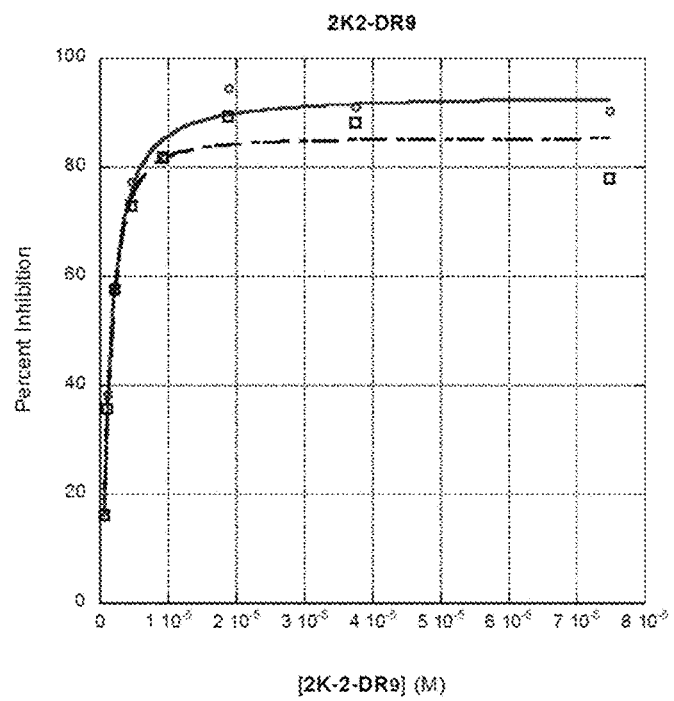
FIG. 29 is a representative IC$_{50}$ Plot for 2K-2-DR9.
Figure 30:
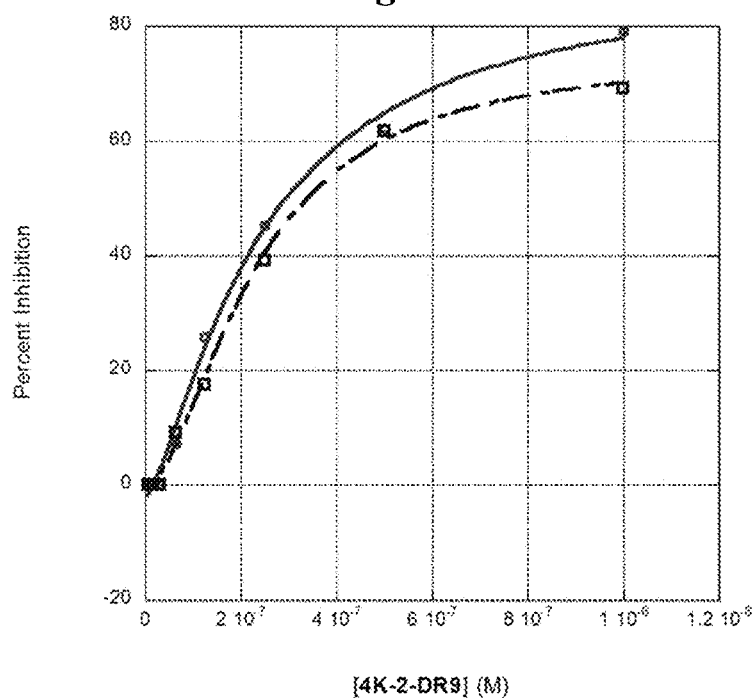
FIG. 30 is a representative $IC_{50}$ Plot for 4K-2-DR9.
Figure 31:
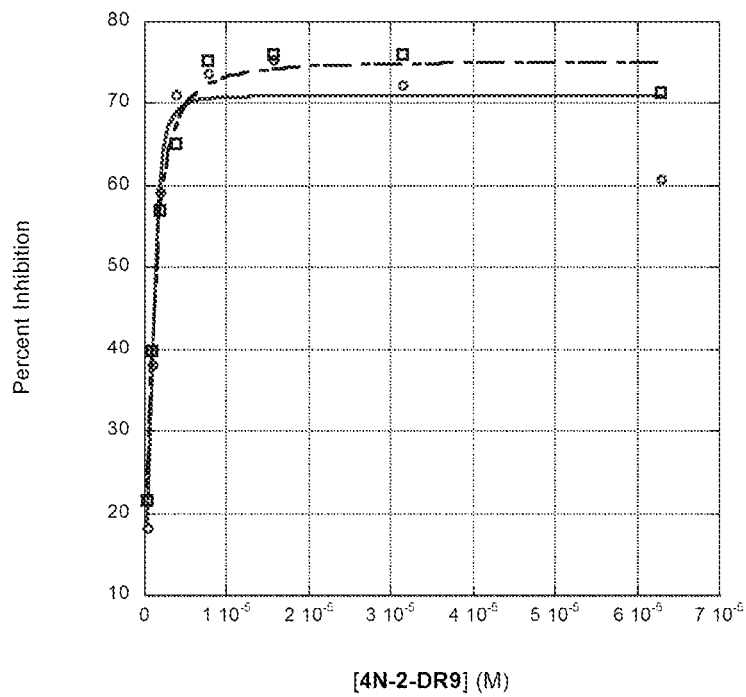
FIG. 31 is a representative $IC_{50}$ Plot for 4N-2-DR9.
Figure 32:
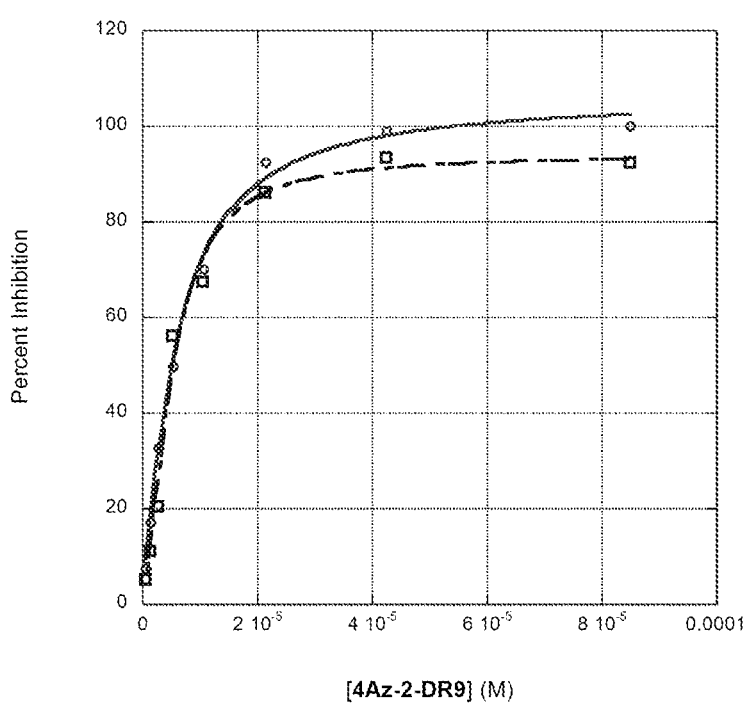
FIG. 32 is a representative $IC_{50}$ Plot for 4Az-2-DR9.
Figure 33:
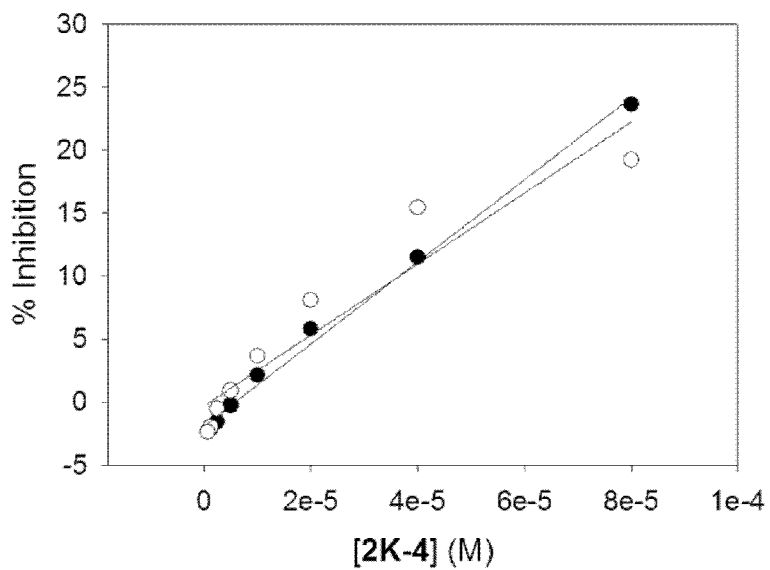
FIG. 33 is a representative $IC_{50}$ Plot for 2K-4.
Figure 34:
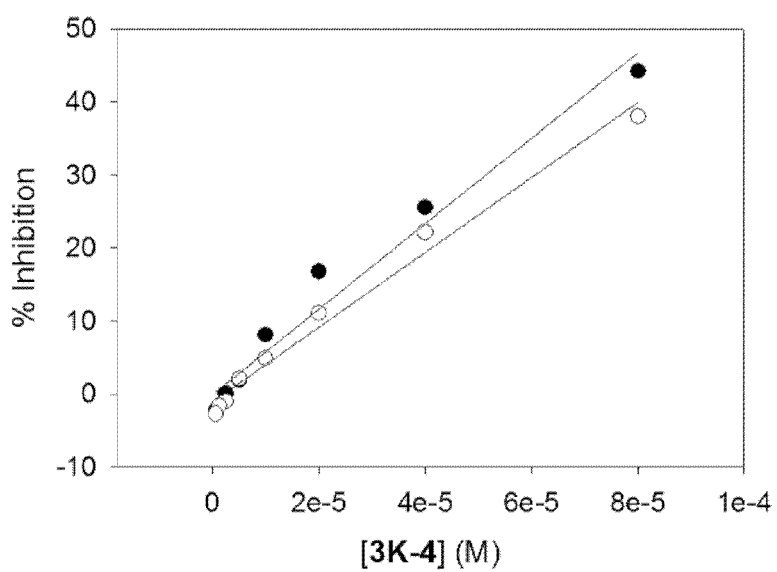
FIG. 34 is a representative $IC_{50}$ Plot for 3K-4.
Figure 35:
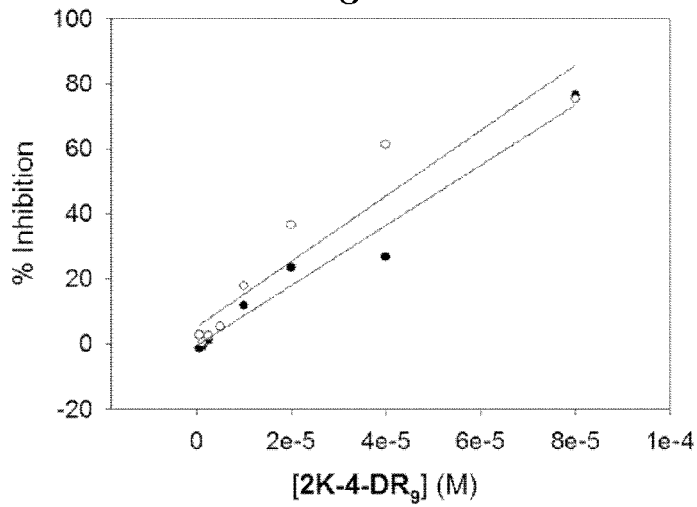
FIG. 35 is a representative $IC_{50}$ Plot for 2K-4-DR9.
Figure 36:
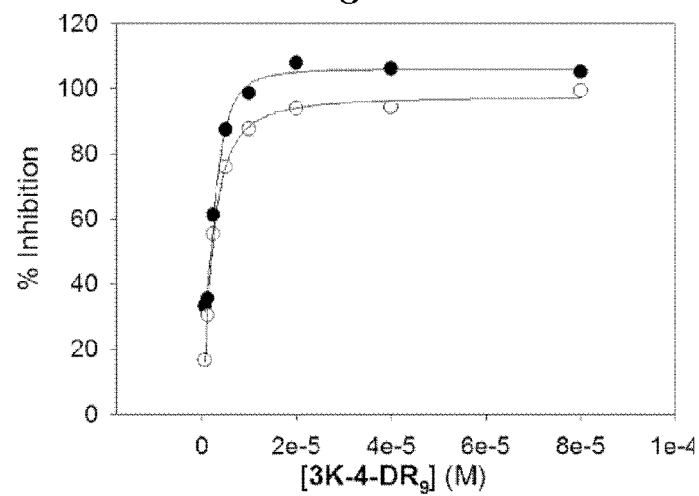
FIG. 36 is a representative $IC_{50}$ Plot for 3K-4-DR9.
Figure 37:
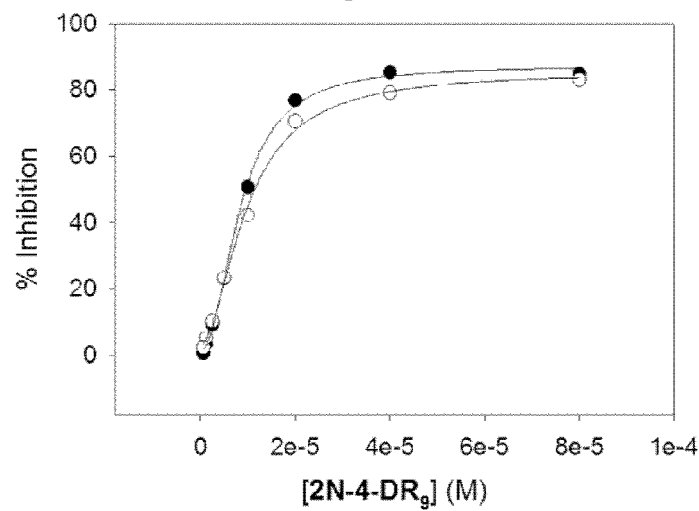
FIG. 37 is a representative $IC_{50}$ Plot for 2N-4-DR9.

A mouse model of DM1 has been reported in which expanded r(CUG) repeat are expressed using a skeletal actin promoter (HSA$^{LR}$).(20) The presence of the repeats causes the mis-splicing of the muscle-specific chloride ion channel (Clcn1) and the sarco(endo)plasmic reticulum Ca$^{2+}$ ATPase 1 (Serca1/Atp2a1) pre-mRNAs.(41-44) Normal adult mice have a Clcn1 exon 7a exclusion rate of 96%; DM1 mice have an exclusion rate of 61% (FIG. 13). When DM1 mice are dosed with 80 mg/kg of 4K-2-DR$_9$, the exclusion rate is partially rescued to 71% (FIG. 13). These improvements in splicing are statistically significant as determined by at t test (p=0.0022). Atp2a1 mis-splicing is also partially rescued. In normal adult mice, the inclusion rate for exon 22 is 100% while the inclusion rate in the HSA$^{LR}$ line is only 10% (FIG. 13). When mice are dosed with 80 mg/kg of 4K-2-DR$_9$, splicing is partially rescued with an inclusion rate of 26% (FIG. 13). Again, the improvement in splicing is statistically significant (p=0.0491).

Comparison to Other Studies.

Previous studies have reported three other compounds that improve DM1-associated defects in cell culture. They include pentamidine, (32) a bis-benzimidazole (H1), (45) and modularly assembled compounds displaying a derivative of Hoechst 33258 as the RNA-binding module (2H-4, 3H-4, and 4H-4).(31) The concentrations required to afford bioactivity is much greater with the lower molecular weight and thus more "drug-like" small molecules (pentamidine and H1) than with the modularly assembled structures. For example, the IC$_{50}$'s of H1 and pentamidine that improve pre-mRNA splicing defects are 500 and 50 μM, respectively.(32, 45) The modularly assembled structure 2H-4, 3H-4, and 4H-4 restore splicing patterns to levels that are observed in the absence of r(CUG)$^{exp}$ at low micromolar concentrations (10, 50, or 50 μM, respectively).(31) Thus, 2K-2-DR$_9$ and 4K-2-DR$_9$ are as effective in these cell-based assays as other modularly assembled compounds targeting r(CUG)$^{exp}$ but are much more effective than bioactive monomeric ligands.

Improvement of the translational defect was also probed with the modularly assembled Hoechst 33258 compounds. (31) 2H-4, 3H-4, and 4H-4 increased translation by 100% at 6, 3, and 3 μM, respectively. 2K-2-DR$_9$ and 4K-2-DR$_9$ also stimulate translation; dosing of 20 μM of either compound increases translation by 80-90%. Thus, 2K-2-DR$_9$ and 4K-2-DR$_9$ are slightly less effective than the nH-4 compounds that were previously described.

METHODS. Quantitative Time-Resolved Fluorescence Resonance Energy Transfer (qTR-FRET) Assay.

The qTR-FRET assay used to identify lead inhibitors of the r(CUG)$_{10}$-MBNL1 complex is based on previously published report.(46) Briefly, 5'-biotinylated r(CUG)$_{10}$ was folded in 1× Folding Buffer (20 mM HEPES, pH 7.5, 110 mM KCl, and 10 mM NaCl) by heating at 60° C. followed by slowly cooling to room temperature on the bench top. The buffer for r(CUG)$_{10}$ was adjusted to 1× Assay Buffer (20 mM HEPES, pH 7.5, 110 mM KCl, 10 mM NaCl, 2 mM MgCl$_2$, 2 mM CaCl$_2$, 5 mM DTT, 0.1% BSA, and 0.5% Tween-20) and MBNL1-His$_6$ was added. The final concentrations of RNA and MBNL1 were 80 nM and 60 nM, respectively. The sample was allowed to equilibrate at room temperature for 5 min, and then the compound of interest was added. After 15 min, strepatividin-XL665 (cisbio Bioassays) and anti-His$_6$-Tb (cisbio Bioassays) were added to final concentrations of 40 nM and 0.44 ng μL$^{-1}$, respectively, in a total volume of 10 μL. The samples were incubated for 1 h at room temperature and then transferred to a well of a white 384-well plate.

Time-resolved fluorescence was measured on a Molecular Devices SpectraMax M5 plate reader. Fluorescence was first measured using an excitation wavelength of 345 nm and an emission wavelength of 545 nm (fluorescence due to Tb). TR-FRET was then measured by using an excitation wavelength of 345 nm, an emission wavelength of 665 nm, a 200 μs evolution time, and a 1500 μs integration time.

The ratio of fluorescence intensity of 545 nm and 665 nm as compared to the ratios in the absence of ligand and in the absence of RNA were used to determine IC$_{50}$'s. The percentage of MBNL1 binding that was inhibited was plotted versus ligand concentration and the resulting curve was fit to Sigma-Plot's 4-parameter logistic function in order to determine the IC$_{50}$ (Equation 1):

$$y = D + \frac{A - D}{1 + \left(\frac{x}{IC_{50}}\right)^{Hill\,slope}} \qquad \text{Equation 1}$$

where y is the percentage of MBNL1 bound, D is the minimum response plateau, A is the maximum response plateau, and x is the concentration of ligand. A and D are typically 100% and 0%, respectively. In cases of weak inhibition, IC$_{50}$'s were determined by fitting the curves to a straight line.

RNA Binding Assays.

The affinities of RNA-ligand complexes were determined as described using a fluorescence emission-based assay. Briefly, RNA was annealed in 1×MBNL Buffer (50 mM Tris HCl, pH 8.0, 50 mM NaCl, 50 mM KCl, 1 mM MgCl$_2$) without MgCl$_2$ by incubating at 60° C. for 5 min followed by slowly cooling to room temperature. Then, MgCl$_2$, BSA, and ligand of interest were added to final concentrations of 1 mM, 40 μg mL$^{-1}$, and 100 nM, respectively. The RNA was serially diluted in 1×MBNL buffer containing 40 μg mL$^{-1}$ BSA and 100 nM ligand and incubated for 1 h at room temperature. Fluorescence intensity was determined using a BioTek FLX-800 plate reader. Scatchard analyses were completed to determine stoichiometry and dissociation constants, accounting for statistical effects by using a functional form of the Scatchard equation for large ligands binding to a lattice (Equation 2) (47, 48):

$$\frac{v}{[L]} = \frac{N(1 - lv/N)}{k}\left(\frac{1 - lv/N}{1 - (l-1)v/N}\right)^{l-1} \quad \text{Equation 2}$$

where v is the moles of ligand per moles of RNA lattice, [L] is the concentration of ligand, N is the number of repeating units on the RNA, l is the number of consecutive lattice units occupied by the ligand, and k is the microscopic dissociation constant. This equation simplifies to the commonly used form of the Scatchard equation for simple systems.(47, 48) Experiments were completed in triplicate and the reported errors are the standard deviations in those measurements.

Improvement of Splicing Defects in a Cell Culture Model Using RT-PCR.

In order to determine if the compounds improve splicing defects in vivo, a previously reported method was employed. (32) Briefly, HeLa cells were grown as monolayers in 96-well plates in growth medium (1×DMEM, 10% FBS, and 1× GlutaMax (Invitrogen)). After the cells reached 90-95% confluency, they were transfected with 200 ng of total plasmid using Lipofectamine 2000 reagent (Invitrogen) per the manufacturer's standard protocol. Equal amounts of a plasmid expressing a DM1 mini-gene with 960 CTG repeats (21) and a mini-gene of interest (cTNT (21) or PLEKHH2 (40)) were used. Approximately 5 h post-transfection, the transfection cocktail was removed and replaced with growth medium containing the compound of interest. After 16-24 h, the cells were lysed in the well, and total RNA was harvested with a Qiagen RNAEasy kit. An on-column DNA digestion was completed per the manufacturer's recommended protocol.

A sample of RNA was subjected to reverse transcription-polymerase chain reaction (RT-PCR) as previously described (40) except 5 units of AMV Reverse Transcriptase from Life Sciences were used. Approximately 300 ng were reverse transcribed, and 150 ng were subjected to PCR using a radioactively labeled forward primer. RT-PCR products were observed after 25-30 cycles of: 95° C. for 1 min; 55° C. for 1 min; 72° C. for 2 min and a final extension at 72° C. for 10 min. The products were separated on a denaturing 5% polyacrylamide gel and imaged using a Typhoon phosphorimager.

Control experiments were also completed in which HeLa cells were transfected with a plasmid encoding a mini-gene with five CTG repeats in the 3' UTR or with a mini-gene that encodes a pre-mRNA whose splicing is not controlled by MBNL1 (PLEKHH2; (40)). The effect of the compound on the splicing of endogenous mRNAs not regulated by MBNL1 (TTC8 and CAMKK2) was also determined as previously described.(32) Differences in alternative splicing were evaluated by at t test. Please see the Supporting Information for a list of the primers used for each gene.

Disruption of Nuclear Foci Using Fluorescence In Situ Hybridization (FISH) (32).

HeLa cells were grown as monolayers in Mat-Tak glass-bottomed, 96-well plates. After the cells reached 90-95% confluency, they were transfected with 200 ng of a plasmid encoding a DM1 mini-gene (21) using Lipofectamine 2000 per the manufacturer's standard protocol. The transfection cocktail was removed 5 h post-transfection, and the compound of interest was added in growth medium.

After 16-24 h, the cells were washed with 1×DPBS and fixed with 4% paraformaldehyde in 1×DPBS for 10 min at 37° C./5% $CO_2$. After washing with 1×DPBS, the cells were permeabilized with 1×DPBS+0.1% Triton X-100 for 10 min at room temperature. The cells were washed with 1×DPBS+ 0.1% Triton X-100 and then with 30% formamide in 2×SSC Buffer (30 mM sodium citrate, pH 7.0, 300 mM NaCl) for 10 min at room temperature.

The cells were incubated in 1×FISH Buffer (30% formamide, 2×SSC Buffer, 66 μg mL$^{-1}$ bulk yeast tRNA, 2 μg mL$^{-1}$ BSA, 2 mM vanadyl complex (New England Bio Labs) and 1 ng μL$^{-1}$ DY547-2'OMe-(CAGCAGCAGCAGCAGCAGC)) for 2 h at 37° C. They were then washed with 30% formamide in 2×SSC for 30 min at 42° C., 1×SSC for 30 min at 37° C., and 1×DPBS+0.1% Triton X-100 for 5 min at room temperature. Finally, nuclei were stained by incubating the cells with 1 μg mL$^{-1}$ DAPI for 5 min at room temperature. The cells were washed with 1×DPBS+0.1% Triton X-100, and 100 μL of 1× DPBS were added to each well. The cells were imaged using an Olympus FluoView 1000 Confocal Microscope at 60× magnification.

Treatment in Mice.

All experimental procedures, mouse handling, and husbandry were completed in accordance with the Association for Assessment and Accreditation of Laboratory Animal Care. A mouse model for DM1, HSA$^{LR}$ in line 20b, (20) was used to investigate if 4K-2-DR$_9$ improves splicing defects in animals. HSA$^{LR}$ mice express human skeletal actin RNA with r(CUG)$^{exp}$ in the 3' UTR. Age- and gender-matched HSA$^{LR}$ mice were injected intraperitoneally with 80 mg/kg 4K-2-DR$_9$ in saline or saline alone once per day for 7 days. Mice were sacrificed one day after the last injection. The vastus muscle was removed, and the RNA was extracted. cDNA was synthesized as previously described.(44) PCR amplification was carried out for 22-24 cycles with the following primer pairs: Clcn1 forward: 5'-TGAAGGAATACCTCACACT-CAAGG and reverse: 5'-CACGGAACACAAAGGCACTG; Atp2a1 forward: 5'-GCTCATGGTCCTCAAGATCTCAC and reverse: 5'-GGGTCAGTGCCTCAGCTTTG. The PCR products were separated by polyacrylamide gel electrophoresis, and the gel was stained with SYBR Green I (Invitrogen). The gel was imaged with a laser fluorimager (Typhoon, GE Healthcare) and the products quantified using ImageQuant. At t test was used to determine the statistical significance of differences between two groups.

REFERENCES

1. Poehlsgaard, J., and Douthwaite, S. (2005) The bacterial ribosome as a target for antibiotics, Nat. Rev. Microbial. 3, 870-881.
2. Thomas, J. R., and Hergenrother, P. J. (2008) Targeting RNA with small molecules, Chem. Rev. 108, 1171-1224.
3. Guan, L., and Disney, M. D. (2012) Recent Advances in Developing Small Molecules Targeting RNA, ACS Chem. Biol. 7, 73-86.
4. Alvarez-Salas, L. M. (2008) Nucleic acids as therapeutic agents, Curr. Top. Med. Chem. 8, 1379-1404.
5. Iorns, E., Lord, C. J., Turner, N., and Ashworth, A. (2007) Utilizing RNA interference to enhance cancer drug discovery, Nat. Rev. Drug Discov. 6, 556-568.
6. Nesterova, M., and Cho-Chung, Y. S. (2004) Killing the messenger: antisense DNA and siRNA, Curr. Drug Targets 5, 683-689.
7. Boggs, R. T., McGraw, K., Condon, T., Flournoy, S., Villiet, P., Bennett, C. F., and Monia, B. P. (1997) Characterization and modulation of immune stimulation by modified oligonucleotides, Antisense Nucleic Acid Drug Dev. 7, 461-471.
8. Farman, C. A., and Kornbrust, D. J. (2003) Oligodeoxynucleotide studies in primates: antisense and immune stimulatory indications, Toxicol. Pathol. 31 Suppl., 119-122.

9. Childs-Disney, J. L., Wu, M., Pushechnikov, A., Aminova, O., and Disney, M. D. (2007) A small molecule microarray platform to select RNA internal loop-ligand interactions, *ACS Chem. Biol.* 2, 745-754.

10. Disney, M. D., Labuda, L. P., Paul, D. J., Poplawski, S. G., Pushechnikov, A., Tran, T., Velagapudi, S. P., Wu, M., and Childs-Disney, J. L. (2008) Two-dimensional combinatorial screening identifies specific aminoglycoside-RNA internal loop partners, *J. Am. Chem. Soc.* 130, 11185-11194.

11. Velagapudi, S. P., Seedhouse, S. J., French, J., and Disney, M. D. (2011) Defining the RNA internal loops preferred by benzimidazole derivatives via 2D combinatorial screening and computational analysis, *J. Am. Chem. Soc* 133, 10111-10118.

12. Disney, M. D., and Childs-Disney, J. L. (2007) Using selection to identify and chemical microarray to study the RNA internal loops recognized by 6'-N-acylated kanamycin A, *Chembiochem* 8, 649-656.

13. Lee, M. M., Pushechnikov, A., and Disney, M. D. (2009) Rational and modular design of potent ligands targeting the RNA that causes myotonic dystrophy 2, *ACS Chem. Biol.* 4, 345-355.

14. Pushechnikov, A., Lee, M. M., Childs-Disney, J. L., Sobczak, K., French, J. M., Thornton, C. A., and Disney, M. D. (2009) Rational design of ligands targeting triplet repeating transcripts that cause RNA dominant disease: application to myotonic muscular dystrophy type 1 and spinocerebellar ataxia type 3, *J. Am. Chem. Soc.* 131, 9767-9779.

15. Lee, M. M., Childs-Disney, J. L., Pushechnikov, A., French, J. M., Sobczak, K., Thornton, C. A., and Disney, M. D. (2009) Controlling the specificity of modularly assembled small molecules for RNA via ligand module spacing: targeting the RNAs that cause myotonic muscular dystrophy, *J. Am. Chem. Soc.* 131, 17464-17472.

16. Disney, M. D., Lee, M. M., Pushechnikov, A., and Childs-Disney, J. L. (2010) The role of flexibility in the rational design of modularly assembled ligands targeting the RNAs that cause the myotonic dystrophies, *Chembiochem* 11, 375-382.

17. Liquori, C. L., Ricker, K., Moseley, M. L., Jacobsen, J. F., Kress, W., Naylor, S. L., Day, J. W., and Ranum, L. P. (2001) Myotonic dystrophy type 2 caused by a CCTG expansion in intron 1 of ZNF9, *Science* 293, 864-867.

18. Savkur, R. S., Philips, A. V., Cooper, T. A., Dalton, J. C., Moseley, M. L., Ranum, L. P., and Day, J. W. (2004) Insulin receptor splicing alteration in myotonic dystrophy type 2, *Am. J. Hum. Genet.* 74, 1309-1313.

19. Faustino, N. A., and Cooper, T. A. (2003) Pre-mRNA splicing and human disease, *Genes Dev.* 17, 419-437.

20. Mankodi, A., Logigian, E., Callahan, L., McClain, C., White, R., Henderson, D., Krym, M., and Thornton, C. A. (2000) Myotonic dystrophy in transgenic mice expressing an expanded CUG repeat, *Science* 289, 1769-1773.

21. Philips, A. V., Timchenko, L. T., and Cooper, T. A. (1998) Disruption of splicing regulated by a CUG-binding protein in myotonic dystrophy, *Science* 280, 737-741.

22. Goun, E. A., Shinde, R., Dehnert, K. W., Adams-Bond, A., Wender, P. A., Contag, C. H., and Franc, B. L. (2006) Intracellular cargo delivery by an octaarginine transporter adapted to target prostate cancer cells through cell surface protease activation, *Bioconjug. Chem.* 17, 787-796.

23. Goun, E. A., Pillow, T. H., Jones, L. R., Rothbard, J. B., and Wender, P. A. (2006) Molecular transporters: synthesis of oligoguanidinium transporters and their application to drug delivery and real-time imaging, *Chembiochem* 7, 1497-1515.

24. Luedtke, N. W., Carmichael, P., and Tor, Y. (2003) Cellular uptake of aminoglycosides, guanidinoglycosides, and poly-arginine, *J. Am. Chem. Soc.* 125, 12374-12375.

25. Frankel, A. D., and Pabo, C. O. (1988) Cellular uptake of the tat protein from human immunodeficiency virus, *Cell* 55, 1189-1193.

26. Cardani, R., Mancinelli, E., Rotondo, G., Sansone, V., and Meola, G. (2006) Muscleblind-like protein 1 nuclear sequestration is a molecular pathology marker of DM1 and DM2, *Eur. J. Histochem.* 50, 177-182.

27. Mastroyiannopoulos, N. P., Feldman, M. L., Uney, J. B., Mahadevan, M. S., and Phylactou, L. A. (2005) Woodchuck post-transcriptional element induces nuclear export of myotonic dystrophy 3' untranslated region transcripts, *EMBO Rep.* 6, 458-463.

28. Amack, J. D., Paguio, A. P., and Mahadevan, M. S. (1999) Cis and trans effects of the myotonic dystrophy (DM) mutation in a cell culture model, *Hum. Mol. Genet.* 8, 1975-1984.

29. Jiang, H., Mankodi, A., Swanson, M. S., Moxley, R. T., and Thornton, C. A. (2004) Myotonic dystrophy type 1 is associated with nuclear foci of mutant RNA, sequestration of muscleblind proteins and deregulated alternative splicing in neurons, *Hum. Mol. Genet.* 13, 3079-3088.

30. Wojciechowska, M., and Krzyzosiak, W. J. (2011) Cellular toxicity of expanded RNA repeats: focus on RNA foci, *Hum. Mol. Genet.* 20, 3811-3821.

31. Childs-Disney, J. L., Hoskins, J., Rzuczek, S., Thornton, C., and Disney, M. D. (2012) Rationally designed small molecules targeting the RNA that causes myotonic dystrophy type 1 are potently bioactive, *ACS Chem Biol. in press*

32. Warf, M. B., Nakamori, M., Matthys, C. M., Thornton, C. A., and Berglund, J. A. (2009) Pentamidine reverses the splicing defects associated with myotonic dystrophy, *Proc. Natl. Acad. Sci. U.S.A.* 106, 18551-18556.

33. Lee, M. M., French, J. M., and Disney, M. D. (2011) Influencing uptake and localization of aminoglycoside-functionalized peptoids, *Mol. Biosyst.* 7, 2441-2451.

34. Koepsell, H., Lips, K., and Volk, C. (2007) Polyspecific organic cation transporters: structure, function, physiological roles, and biopharmaceutical implications, *Pharm. Res.* 24, 1227-1251.

35. Fuchs, S. M., and Raines, R. T. (2004) Pathway for polyarginine entry into mammalian cells, *Biochemistry* 43, 2438-2444.

36. Iozzo, R. V. (1998) Matrix proteoglycans: from molecular design to cellular function, *Annu. Rev. Biochem.* 67, 609-652.

37. Mammen, M., Choi, S. K., and Whitesides, G. M. (1998) Polyvalent interactions in biological systems: Implications for design and use of multivalent ligands and inhibitors, *Angew. Chem. Int. Ed. Engl.* 37, 2755-2794.

38. Ho, T. H., Charlet, B. N., Poulos, M. G., Singh, G., Swanson, M. S., and Cooper, T. A. (2004) Muscleblind proteins regulate alternative splicing, *EMBO J.* 23, 3103-3112.

39. Nezu, Y., Kino, Y., Sasagawa, N., Nishino, I., and Ishiura, S. (2007) Expression of MBNL and CELF mRNA transcripts in muscles with myotonic dystrophy, *Neuromuscul. Disord.* 17, 306-312.

40. Warf, M. B., and Berglund, J. A. (2007) MBNL binds similar RNA structures in the CUG repeats of myotonic dystrophy and its pre-mRNA substrate cardiac troponin T, *RNA* 13, 2238-2251.

41. Mankodi, A., Takahashi, M. P., Jiang, H., Beck, C. L., Bowers, W. J., Moxley, R. T., Cannon, S. C., and Thornton, C. A. (2002) Expanded CUG repeats trigger aberrant splicing of ClC-1 chloride channel pre-mRNA and hyperexcitability of skeletal muscle in myotonic dystrophy, *Mol. Cell.* 10, 35-44.

42. Charlet, B. N., Savkur, R. S., Singh, G., Philips, A. V., Grice, E. A., and Cooper, T. A. (2002) Loss of the muscle-specific chloride channel in type 1 myotonic dystrophy due to misregulated alternative splicing, *Mol. Cell.* 10, 45-53.

43. Kimura, T., Nakamori, M., Lueck, J. D., Pouliquin, P., Aoike, F., Fujimura, H., Dirksen, R. T., Takahashi, M. P., Dulhunty, A. F., and Sakoda, S. (2005) Altered mRNA splicing of the skeletal muscle ryanodine receptor and sarcoplasmic/endoplasmic reticulum Ca2+-ATPase in myotonic dystrophy type 1, *Hum. Mol. Genet.* 14, 2189-2200.

44. Lin, X., Miller, J. W., Mankodi, A., Kanadia, R. N., Yuan, Y., Moxley, R. T., Swanson, M. S., and Thornton, C. A. (2006) Failure of MBNL1-dependent post-natal splicing transitions in myotonic dystrophy, *Hum. Mol. Genet.* 15, 2087-2097.

45. Parkesh, R., Childs-Disney, J. L., Nakamori, M., Kumar, A., Wang, E., Wang, T., Hoskins, J., Housman, D. E., Thornton, C. A., Disney, M. D., and Tran, T. (2012) Design of a bioactive small molecule that targets the myotonic dystrophy type 1 RNA via an RNA motif-ligand database & chemical similarity searching, *J. Am. Chem. Soc.* 134, 4731-4742.

46. Chen, C. Z., Sobczak, K., Hoskins, J., Southall, N., Marugan, J. J., Zheng, W., Thornton, C. A., and Austin, C. P. (2012) Two high-throughput screening assays for aberrant RNA-protein interactions in myotonic dystrophy type 1, *Anal. Bioanal. Chem.* 402, 1889-1898.

47. Cantor, C. R., and Schimmel, P. R. (1980) Biophysical Chemistry, W. H. Freeman and Company, San Francisco.

48. McGhee, J. D., and Hippel, P. H. v. (1974) Theoretical aspects of DNA-protein interactions: co-operative and non-co-operative binding of large ligands to a one-dimensional homogeneous lattice, *J. Mol. Biol.* 86, 469-489.

Methods for the Chemical Synthesis of nY-X-DR$_9$ Compounds

Instrumentation.

Mass spectra were recorded on an ABI 4800 MALDI-TOF spectrometer. Preparative HPLC purifications and analytical HPLC were completed on a Waters 1525 Binary HPLC Pump equipped with a Waters 2487 Dual Absorbance Detector system. Sonication was performed using a Branson Bransonic® 5210 sonicator (140 watts, 47 kHz). Resin was agitated by shaking on a Thermolyne Maxi-Mix III™ shaker.

Chemicals.

Fmoc-protected Rink amide resin and diisopropylcarbodiimide (DIC) were from Anaspec; N—N-dimethylformamide (DMF) was from VWR and was used without further purification; bromoacetic acid and HPLC grade acetonitrile were from Sigma Aldrich; 3-bromopropylamine hydrobromide was from TCI or Fluka; all other reagents were from Acros or Alfa Aesar and were used without further purification except piperidine, which was distilled prior to use.

HPLC.

Component A is water+0.1% trifluoroacetic acid (TFA) (v/v). Component B is acetonitrile+0.1% TFA (v/v). Absorbance was monitored at 254 nm.

Peptoid Synthesis.

Fmoc-protected Rink amide (AnaSpec) polystyrene resin (115 mg, 100 µmol) was placed in a solid phase reaction vessel and swollen in DCM (5 mL) for 30 min. The DCM was drained and the resin was swollen in DMF (5 mL) for 30 min. The DMF was drained, and the resin was deprotected with 4 mL of 20% piperidine in DMF for 40 min with shaking at 800 rpm. The deprotection step was repeated twice. The DMF was drained, and the resin was washed with rDMF (5×3 mL) and dDMF (5×3 mL); rDMF refers to ACS certified DMF whereas dDMF refers to anhydrous DMF.

Bromoacetic Acid Coupling Step:

The deprotected resin was coupled with bromoacetic acid (1 mL, 2 M in DMF) and DIC (1 mL, 1 M in DMF), using a conventional microwave for 3×15 s. This process was repeated twice.

TABLE 1

The binding affinity and stoichiometry for RNA and the potency for inhibition of the r(CUG)-MBNL1 complex.

| Compounds | r(CUG)$_{12\times2}$ | | tRNA | | IC$_{50}$ for r(CUG)-MBNL1 | M.V.[b] |
|---|---|---|---|---|---|---|
| | K$_d$ (nM) | Stoichiometry | K$_d$ (nM) | Stoichiometry | (µM)[a] | |
| FITC-K | 1000 ± 250[c] | 11[c] | >10000 | ND | >250 | — |
| 4K-2 | 4 ± 1[c] | 2.6[c] | >2000 | <1:10 | 16 ± 1 | >4 |
| 2K-4 | NM | NM | NM | NM | 170 ± 14 | >0.7 |
| 3K-4 | NM | NM | NM | NM | 93 ± 10 | >0.9 |
| 2K-2-DR$_9$ | NM | NM | NM | NM | 1.43 ± 0.16 | >87 |
| 2K-4-DR$_9$ | NM | NM | NM | NM | 55 ± 0.7 | >2 |
| 2N-4-DR$_9$ | NM | NM | NM | NM | 9 ± 1 | >13 |
| 3K-4-DR$_9$ | NM | NM | NM | NM | 26 ± 6 | >3 |
| 4K-2-DR$_9$ | 3.5 ± 1.8 | 3.7 ± 1.2 | >2000 | <1:10 | 0.240 ± 0.005 | >260 |
| 4Az-2-DR$_9$ | >2000 | <1:5 | >2000 | <1:10 | 5.4 ± 0.51 | >11 |
| 4N-2-DR$_9$ | >2000 | <1:5 | >2000 | <1:10 | 1.03 ± 0.09 | >60 |
| MBNL1 | 250[c] | — | NM | NM | NM | — |

[a]These experiments were completed by using the qTR-FRET assay described in the Methods section. The r(CUG)$_{10}$-MBNL1 complex was pre-formed followed by addition of MBNL1; thus, the IC$_{50}$'s are for displacement.
[b]Values for multivalent effects. These values are calculated by normalizing the IC$_{50}$ for the number of RNA-binding modules displayed on a peptoid backbone by the IC$_{50}$ for the K module, or FITC-K.(15)
[c]Data were taken from a previous report.(15)

Amine Displacement:

After the bromoacetic acid step, the bromide group was displaced with appropriate amine (3-azidopropylamine or proplyamine) DMF (2 mL) and the amine (1 mL) were added to the resin, and the resin was agitated in a conventional microwave for 3×15 s. This process was repeated twice.

Addition of Fmoc-Arg (PbJ)-OH:

To the resin-bound peptoid (50 µmol) was added DMF (1 mL) containing D-Fmoc-Arg (Pbf)-OH (0.162 mg, 250 µmol), HOAt (0.034 mg, 250 µmol) and DIC (250 µmol, 0.48 mL). The mixture was stirred overnight. The solution was drained, and the resin was washed with rDMF (4×3 mL) and dDMF (4×3 mL). The Fmoc group was then deprotected with 20% piperidine. This deprotection was repeated twice. Eight additional couplings and deprotections of D-Fmoc-Arg (Pbf) were completed to afford the desired nAz-2-$DR_9$ conjugate. The coupling of the last eight D-Fmoc-Arg (Pbf)-OH's was performed for at least 3 h.

Fluorescein Labelling of 2Az-X-$DR_9$, 3Az-X-$DR_9$ and 4Az-X-$DR_9$ Peptoid conjugate:

The resin-bound $DR_9$ conjugate (10 µmol) was washed with methanol (3×5 mL) and DCM (3×5 mL). To this was added 2 mL of N-methyl-2-pyrrolidone (NMP) containing Fmoc-6-aminohexanoic acid (30 µmol, 3 equivalents for nAz-2-$DR_9$ conjugates and 50 µmol for nAz-4-$DR_9$ conjugates), 8.0 mg of PyBOP (30 µmol, 3 equivalents), 50 µL of N,N-diisopropylethylamine (DIPEA), and 50 µmol of 0.5 M HBTU (in NMP). The resin was shaken at 800 rpm at room temperature overnight. The solution was drained and resin washed with rDMF (3×5 mL) and dDMF (3×5 mL). The Fmoc group was deprotected by shaking the resin with 1 mL of 20% piperidine in DMF for 50 min. The solution was drained and resin washed extensively with rDMF (6×5 mL) followed by dDMF (6×5 mL). Then to the reaction vessel was added 4(5)-carboxyfluorescein (50 µmol, 19 mg), HOBt (80 µmol, 11 mg), DMF (0.1 mL) and DIC (0.2 mL, 1 M in DMF). The resin was then stirred at room temperature overnight.

Conjugation of 1,3,3"-Tri-N(tert-butoxycarbonyl)-6'-N-5-hexynoate kanamycin A to the nAz-X-$DR_9$ peptoid conjugates:

The resin-bound $DR_9$ conjugate (5 µmol for nAz-2-$DR_9$ conjugates and 10 µmol for nAz-4-$DR_9$ conjugates) was washed with methanol (3×5 mL) and DCM (3×5 mL) and air-dried. The samples were transferred to a glass vial to which Boc-protected 6'-N-5-hexynoate kanamycin A was added (10 equivalents per click site: 44 mg for 2Az-2-$DR_9$ and 90 mg for 4Az-2-$DR_9$ conjugate; 88 mg for 2Az-4-$DR_9$; 130 mg for 3Az-4-$DR_9$). The glass vial was sealed with a rubber septum and purged with argon for 20 min. Then, 2 mL of the prepared catalyst solution (0.1 M copper acetate, 1 M DIPEA, 0.1 M ascorbic acid and 0.01 M TBTA in pyridine/DMF, 3:7) were added via syringe. The reaction vial was sonicated for 10 min and then heated at 50° C. in sand bath for 4 days for nAz-2-$DR_9$ conjugates and 3 days for nAz-4-$DR_9$ conjugates. After this, the solution was drained. The resin was transferred to a solid-phase reaction vessel and washed with DMF (5×5 mL), 2% ascorbic acid in pyridine (5×5 mL), DMF (5×5 mL), methanol (5×5 mL) and finally with DCM (5×5 mL).

The peptoid conjugate was then cleaved from the resin using 60% TFA in DCM by shaking for 2 h at room temperature. The solution was lyophilized and the residue dissolved in water for nAz-2-$DR_9$ conjugates and 10:90 methanol:water for nAz-4-$DR_9$ conjugates. The product was purified by preparative HPLC using a gradient of 5 mL/min, 10% to 100% B in A over 45 min. Fractions were analyzed by MALDI-TOF. Fractions containing product were concentrated to dryness, lyophilized from water, and washed with cold ether.

Neamine conjugates were synthesized analogously using Boc-protected 6'-N-5 hexynoate neamine.

Characterization of New Compounds Including Mass Spectra and Analytical HPLC Traces

TABLE 2

Summary of HPLC retention times ($t_R$) and masses of nY-X-$DR_9$ compounds

| | Ligand Formula | Exact Mass | Observed Mass $(+H^+)$ m/z | prep. HPLC $t_R$ (min) | isolated yield (%) |
|---|---|---|---|---|---|
| 2K-2-$DR_9$ | $C_{149}H_{252}N_{56}O_{44}$ | 3529 | 3529 | 8.2 | 22 |
| 4K-2-$DR_9$ | $C_{131}H_{220}N_{60}O_{26}$ | 5362 | 5363 | 9 | 20 |
| 2Az-2-$DR_9$ | $C_{101}H_{168}N_{48}O_{20}$ | 2373 | 2373 | 22 | 26 |
| 4Az-2-$DR_9$ | $C_{119}H_{207}N_{59}O_{21}$ | 3049 | 3049 | 23 | 24 |
| 4N-2-$DR_9$ | $C_{119}H_{207}N_{59}O_{21}$ | 4714 | 4716 | 10 | 21 |
| 2K-4-$DR_9$ | $C_{161}H_{278}N_{58}O_{46}$ | 3760 | 3760 | 10 | |
| 3K-4-$DR_9$ | $C_{211}H_{230}N_{70}O_{63}$ | 4890 | 2446 (M + 2H/2) | 9 | |
| 2Az-4-$DR_9$ | $C_{111}H_{186}N_{50}O_{22}$ | 2751 | 2751 | 20 | |
| 3Az-4-$DR_9$ | $C_{136}H_{230}N_{58}O_{27}$ | 3108 | 3108 | 22 | |
| 2N-4-$DR_9$ | $C_{147}H_{250}N_{58}O_{36}+K^+$ | 3443 | 3443 | 29 | |

List of Primers Used for RT-PCR Analysis

TABLE 3

Primer sets used for RT-PCR analysis of alternative splicing.

| Gene | Forward Primer | Reverse Primer |
|---|---|---|
| cTNT mini-gene | 5' GTT CAC AAC CAT CTA AAG CAA GAT G | 5' GTT GCA TGG CTG GTG CAG G |
| PLEKHH2 mini-gene | 5' CGG GGT ACC AAA TGC TGC AGT TGA CTC TCC | 5' CCG CTC GAG CCA TTC ATG AAG TGC ACA GG |
| TTC8 | 5' AGC TAT TTT AGG CGC AGG AAG T | 5' TTT TCA TCC AGC ATC ATT TCT G |
| CAMKK2 | 5' CCT GGT GAA GAC CAT GAT ACG | 5' GGC CCA GCA ACT TTC CAC |

Summary of Flow Cytometry Data

TABLE 4

Cellular permeability and toxicity of 4K-2 and 4X-2-$DR_9$ compounds.

| | Percentage of Cells With Compound (FITC) | Percentage of Cells Stained with Propidium Iodide |
|---|---|---|
| Untreated | — | 10 |
| 4K-2 | <1 | 10 |
| 4K-2-DR9 | 13 | 10 |
| 4N-2-DR9 | 12 | 14 |
| 4Az-2-DR9 | 75 | 11 |

Example 9

RNA is an important drug target, but it is difficult to design or discover small molecules that modulate RNA function. In this example, we describe that rationally designed, modularly assembled small molecules that bind the RNA that causes myotonic dystrophy type 1 (DM1) are potently bioactive in cell culture models. DM1 is caused when an expansion of r(CUG) repeats, or r(CUG)$^{exp}$, is present in the 3' untranslated region (UTR) of the dystrophia myotonica protein kinase (DMPK) mRNA. r(CUG)$^{exp}$ folds into a hairpin with regularly repeating 5'CUG/3'GUC motifs and sequester muscleblind-like 1 protein (MBNL1). A variety of defects are associated with DM1 including: (i) formation of nuclear foci, (ii) decreased translation of DMPK mRNA due to its nuclear retention, and (iii) pre-mRNA splicing defects due to inactivation of MBNL1, which controls the alternative splicing of various pre-mRNAs. Modularly assembled ligands targeting r(CUG)$^{exp}$ were designed using information in an RNA motif-ligand database. It was shown that a bis-benzimidazole (H) binds the 5'CUG/3'GUC motif in r(CUG)$^{exp}$. Therefore, multivalent ligands were designed to bind multiple copies of this motif simultaneously in r(CUG)$^{exp}$. The designed compounds improved DM1-associated defects including improvement of translational and pre-mRNA splicing defects and the disruption of nuclear foci. These studies establish a foundation to exploit other RNA targets in genomic sequence.

Genome sequencing studies have deposited a wealth of information in public databases.(1, 2) The ultimate use of such information is the development of pharmaceutical agents to treat diseases. Various approaches have validated many targets for small molecule drugs in genomic sequence. (3, 4) Genomic sequencing and functional genomics efforts have provided information on RNA as potential drug target. For example, non-coding RNAs have been shown to regulate cellular pathways and their disregulation can cause disease. (5, 6) Despite the great potential of RNA as a drug target for small molecules, the vast majority of RNA targets remain unexploited. This is mainly due to the difficulty in identifying lead ligands that target RNA with high affinity and specificity using standard high throughput screening approaches. In an effort to expedite the identification and design of selective and potent small molecules targeting RNA, a database of RNA motif-ligand interactions identified using a variety of methods (7-10) is being constructed. The database can serve as a rich source of lead small molecules that bind RNA.

Figure 38:
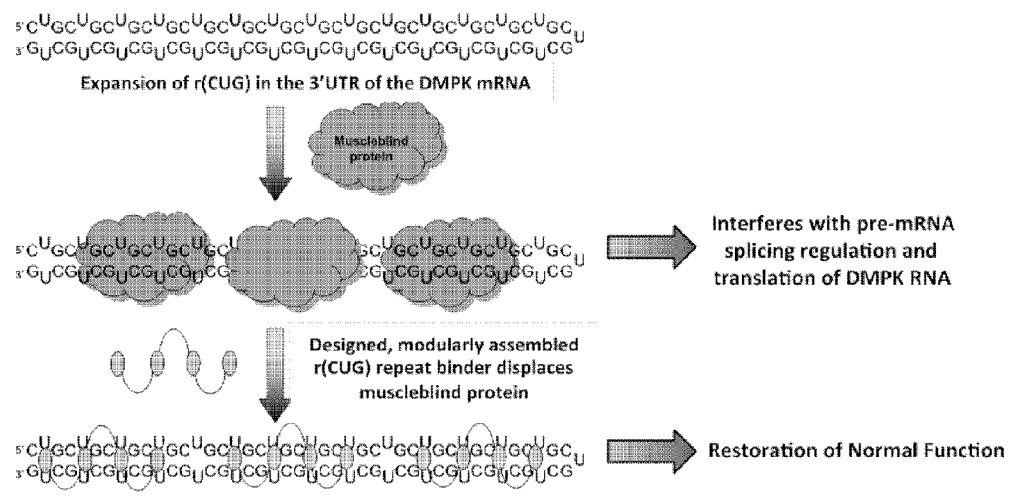
FIG. 38 is a representative schematic for the molecular mechanism of DM1. An expanded r(CUG) repeat $(r(CUG)^{exp})$ in the 3'UTR of the DMPK mRNA folds into a hairpin that binds to muscleblind-like 1 protein (MBNL1), a pre-mRNA splicing regulator. Sequestration of MBNL1 by $r(CUG)^{exp}$ causes disregulation of alternative splicing of genes controlled by MBNL1, decreased translation of the DMPK pre-mRNA, and formation of nuclear foci. Designed, modularly assembled ligands targeting the repeating transcript have potential to improve these defects.
Figure 39:
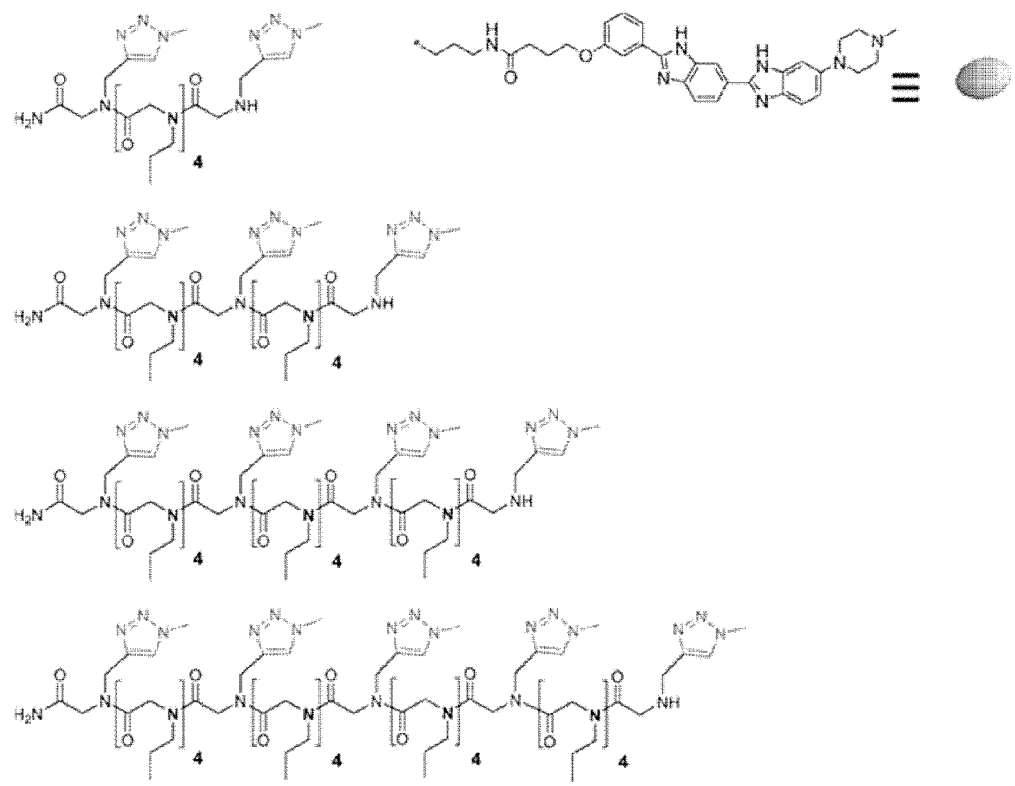
FIG. 39 is an example of the structures of the optimal modularly assembled, nH-4 (13) compounds that inhibit formation of the $r(CUG)^{exp}$-MBNL1 interaction in vivo.

During the course of studies aimed at populating the RNA motif-ligand database, it was determined that small molecules bind RNA internal loops that are present in repeat-containing transcripts that cause neurological diseases. These include the 5'CUG/3'GUC (FIG. 38) and 5'CCUG/3'GUCC motifs present in myotonic dystrophy types 1 and 2 (DM1 and DM2), respectively.(11-13) Since each transcript with expanded repeats contains regularly repeating copies of the targetable motifs, modular assembly strategies were developed to bind multiple motifs simultaneously (FIG. 38). (11, 13, 14) In order to target the 5'CUG/3'GUC motifs found in r(CUG)$^{exp}$, a series of compounds with different valenices (numbers) of a bis-benzamidazole using a peptoid backbone were synthesized (FIG. 39). The compounds bind r(CUG)$^{exp}$ with nanomolar affinities and inhibit the r(CUG)$^{exp}$-MBNL1 complex in vitro with nanomolar IC$_{50}$'s (Table 5).(13)

In DM1, the expanded r(CUG) repeat, or r(CUG)$^{exp}$, resides in the 3' untranslated region (UTR) of the dystrophia myotonica protein kinase (DMPK) mRNA. The expanded repeats cause disease by binding to muscleblind-like 1 protein (MBNL1). Sequestration of MBNL1 by the repeats causes defects in the alternative splicing of the cardiac troponin T (cTNT), the muscle-specific chloride ion channel, and the insulin receptor pre-mRNAs, among others.(15-17) In addition, a translational defect in DMPK is observed because the complex formed between r(CUG)$^{exp}$ with various proteins including MBNL1 leads to formation of nuclear foci and thus reduced nucleocytoplasmic transport of the DMPK mRNA. (18, 19)

This example describes that the designed compounds displaying multiple copies of a bis-benzimidazole (FIG. 39) improved DM1-associated defects in cell culture models. In particular, they improve alternative splicing defects observed for the cTNT pre-mRNA, improved nucleocytoplasmic transport and hence translational levels, and disrupted nuclear foci to varying extents.

Modularly assembled compounds containing multiple copies of a ligand that binds the 5'CUG/3'GUC bind r(CUG)$^{exp}$ and inhibit the r(CUG)$^{exp}$-MBNL1 interaction in vitro (Table 5).(13) The compounds consist of a peptoid backbone that displays multiple copies of a bis-benzimidazole (H) separated by spacing modules (FIG. 39).(13) The number of spacing modules has been optimized to span the two GC pairs that separate each of the 1×1 nucleotide UU internal loops in the DM1 RNA (FIG. 38). The compounds have the general format nH-4 where n is the number of ligand modules, or valency, H indicates the RNA-binding ligand module (Hoechst-like, FIG. 39), and 4 indicates the number of spacing modules between H's (FIG. 39). These compounds bind to r(CUG)$^{exp}$ with greater affinity and specificity than MBNL1. (13) They inhibit MBNL1 binding and displace MBNL1 from r(CUG)$^{exp}$ in vitro with nanomolar potencies (Table 5).(13)

nH-4 Compounds Improve Alternative Splicing Defects in a DM1 Cell Culture Model.

To assess the biological activity of the designer compounds, we determined whether they could improve pre-mRNA splicing defects that are associated with DM1 in a cell culture model. HeLa cells were co-transfected with plasmids encoding a DM1 mini-gene that contains 960 interrupted CTG repeats and a cTNT mini-gene.(20, 21) cTNT pre-mRNA is mis-spliced in DM1 patients.(21-23) In normal cells, MBNL1 binds upstream of exon 5 in the cTNT pre-mRNA and represses its inclusion.(22, 24) After transfection, cells were treated with 2.5-25 µM of 2H-4 or 5-50 µM of 3H-4, 4H-4, or 5H-4. Their effects on splicing defects, indicative of the ability to displace MBNL1 from r(CUG)$^{exp}$, was determined was determined by reverse transcription polymerase chain reaction (RT-PCR) as previously described (20).

Figure 40:
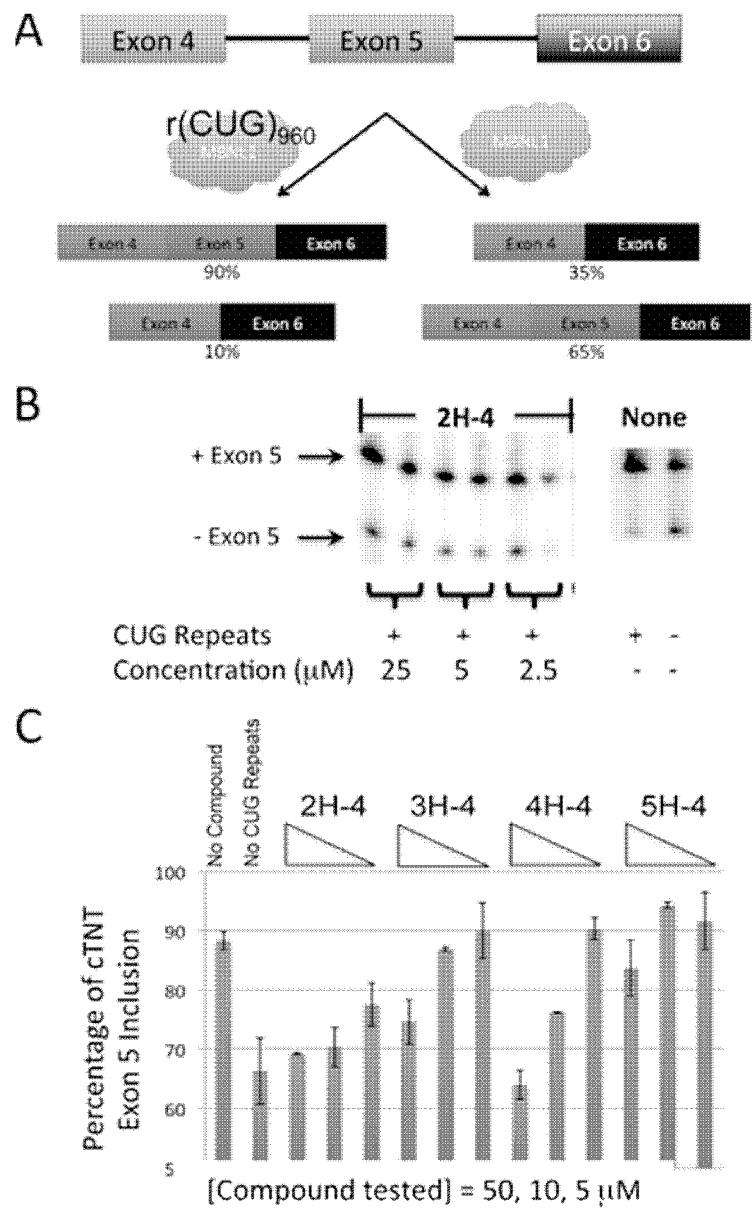
FIG. 40 is an example of how nH-4 ligands improve DM1-associated pre-mRNA splicing defects. A, schematic of the pre-mRNA splicing pattern observed for the cTNT mini-gene (21) in the presence and absence of the DM1 mini-gene (21). B, representative gel autoradiogram to assess the effect of nH-4 compounds on the alternative splicing of the cTNT mini-gene. HeLa cells were transfected with either a DM1 mini-gene containing 960 interrupted CTG repeats and the cTNT mini-gene or a wild type (WT) mini-gene containing five CTG repeats and the cTNT mini-gene. After transfection, nH-4 compounds or water were added in growth medium to the cells. Total RNA was harvested 16-24 h later, and alternative splicing was assessed by RT-PCR using a radioactively labeled forward primer. The RT-PCR products were separated using a denaturing 5% polyacrylamide gel. The size of the RT-PCR products was confirmed using a radioactively labeled 100 bp DNA ladder. C, plot of data obtained from RT-PCR analysis. Statistically significant improvement of splicing is observed when cells are treated with 2H-4, 3H-4, and 4H-4 while only modest improvement is observed for 5H-4. Each experiment was completed in at least duplicate and the errors are the standard deviations from replicate measurements.

As shown in FIG. 40, statistically significant improvement of splicing defects was observed for 2H-4, 3H-4, and 4H-4 while only modest improvement was observed for 5H-4. That is, splicing is improved to approximately wild type levels when cells are treated with 25 and 5 µM 2H-4 (with two-tailed p-values of 0.0014 and 0.0083, respectively), 50 µM 3H-4 (with a two-tailed p-value of 0.0412), and 50 and 10 µM 4H-4 (with two-tailed p-values of 0.0061 and 0.0035, respectively). Based on the corresponding in vitro potencies (Table 5), it was expected that the higher valency oligomers would be more effective at improving splicing defects. However, both 4H-4 and 5H-4 were not completely soluble in cell culture medium, with 5H-4 being less soluble than 4H-4. The H monomer was also tested in order to determine if it could restore splicing patterns in the DM1 cell culture model. No effect on splicing was observed when cells were treated with up to 100 µM H. Thus, modular assembly affords bioactive compounds even when the RNA-binding modules are not bioactive. It should be noted that no toxicity is observed in cell culture at concentrations of the ligands that are bioactive, as assessed by changes in cell morphology and cell death.

Control experiments were also completed in which HeLa cells were co-transfected with a mini-gene containing only five CTG repeats (21) and the cTNT mini-gene.(21) The compounds do not affect cTNT splicing in the absence of r(CUG) repeats. Moreover, the nH-4 compounds have no effect on the alternative splicing of PLEKHH2 pre-mRNA, which is not controlled by MBNL1. (The PLEKHH2 mini-gene is described in reference (20).)

Previously, the small molecule pentamidine was found to improve DM1-associated pre-mRNA splicing defects. The $IC_{50}$ of pentamidine for improving cTNT splicing defects is ~50 μM, (20) which is 5-fold higher than the concentration of 2H-4 that improves splicing defects to approximately wild type levels (FIG. 40). Thus, modular assembly provides designed compounds that are more bioactive than lower molecular weight compounds that are classically more "drug-like."

nH-4 Compounds Improve DM1 Translation Defects in a Cell Culture Model.

Next, compounds that improved splicing defects were tested for their ability to improve the DMPK translational defect observed in DM1-affected cells. A C2C12 cell line that stably expresses the firefly luciferase gene containing a $(CTG)_{800}$ expansion in the 3' UTR was employed for these studies. As in DM1-affected cells, the presence of $r(CUG)_{800}$ causes nuclear retention of the luciferase mRNA and thus decreased expression of luciferase. If our compounds disrupt the $r(CUG)_{800}$-MBNL1 interaction, then the luciferase mRNA will be more efficiently exported into the cytoplasm and translated, which is correlated to the luciferase activity in cell extracts (FIG. 41).

Figure 41:
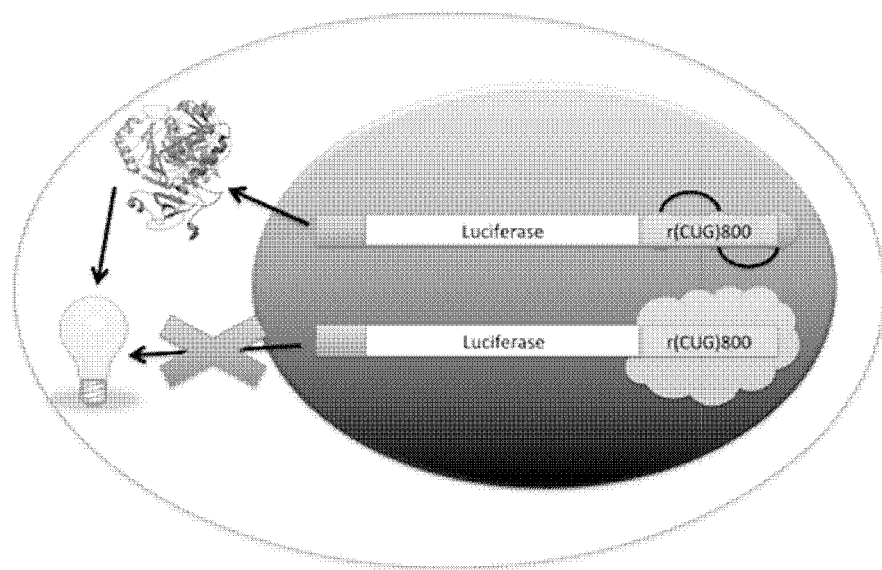
FIG. 41 is an example of designed small molecules targeting $r(CUG)^{exp}$ improve DM1-associated translational defects in a cell culture model. Top, a schematic of the model cell-based system that was used to study the efficacy of the compounds. Briefly, a stably transfected C2C12 line was created that expresses firefly luciferase mRNA with $r(CUG)_{800}$ in the 3' UTR. In the absence of a small molecule that targets $r(CUG)_{800}$, the transcript is mostly retained in the nucleus and thus it is not efficiently translated. If, however, a small molecule binds to the $r(CUG)_{800}$ and displaces or inhibits MBNL1 binding, then the transcript is more efficiently exported from the nucleus and translated in the cytoplasm. Bottom, 2H-4, 3H-4, and 4H-4 improve translational defects associated with DM1. No effect on translation of firefly luciferase is observed when 50 µM of each compound is tested in a model system lacking r(CUG) repeats. Each experiment was completed in at least triplicate and the errors are the standard errors from replicate measurements.
Figure 41:
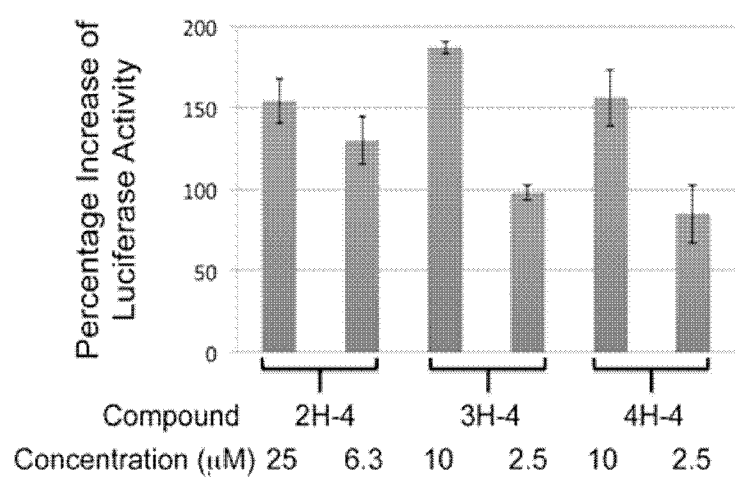

Each of the three compounds, 2H-4, 3H-4, and 4H-4, stimulate production of luciferase when the transcript's 3'UTR contains $r(CUG)_{800}$ (FIG. 41). There is at least a 150% increase in luciferase activity when cells are treated with 25 μM of 2H-4, or with 10 μM of 3H-4 or 4H-4. An ≈100% increase is observed when cells are treated with 2.5 μM of 3H-4 or 4H-4. Increased luciferase activity is not observed when a stably transfected cell line expressing a luciferase construct that does not contain $(CTG)_{800}$ is treated with 50 μM of 2H-4, 3H-4, or 4H-4. Thus, the effect of the compounds is specific to the presence of $r(CUG)^{exp}$. That is, the compounds do not generally upregulate translation or specifically upregulate translation of the luciferase mRNA.

Of the four compounds tested, 2H-4 most effectively improves pre-mRNA splicing defects while 3H-4 most effectively improves the DMPK mRNA translational defect. These differences may be traced to the synergistic ability of compounds to bind $r(CUG)^{exp}$ in vivo while simultaneously enabling the ligand-bound expanded repeat to be transported to the cytoplasm for translation. It could be that 2H-4 shows improved cellular permeability and nuclear localization, leading to disruption of the RNA-MBNL1 complex and restoration of MBNL1 activity. The extent of cytoplasmic transport may be greater with 3H-4 due to its ability to sequester a larger amount of the RNA's surface area and prevent the binding of other proteins such as CUGBP1, MBNL2, and MBNL3.(25, 26)

nH-4 Compounds Disrupt Nuclear Foci.

Figure 42:
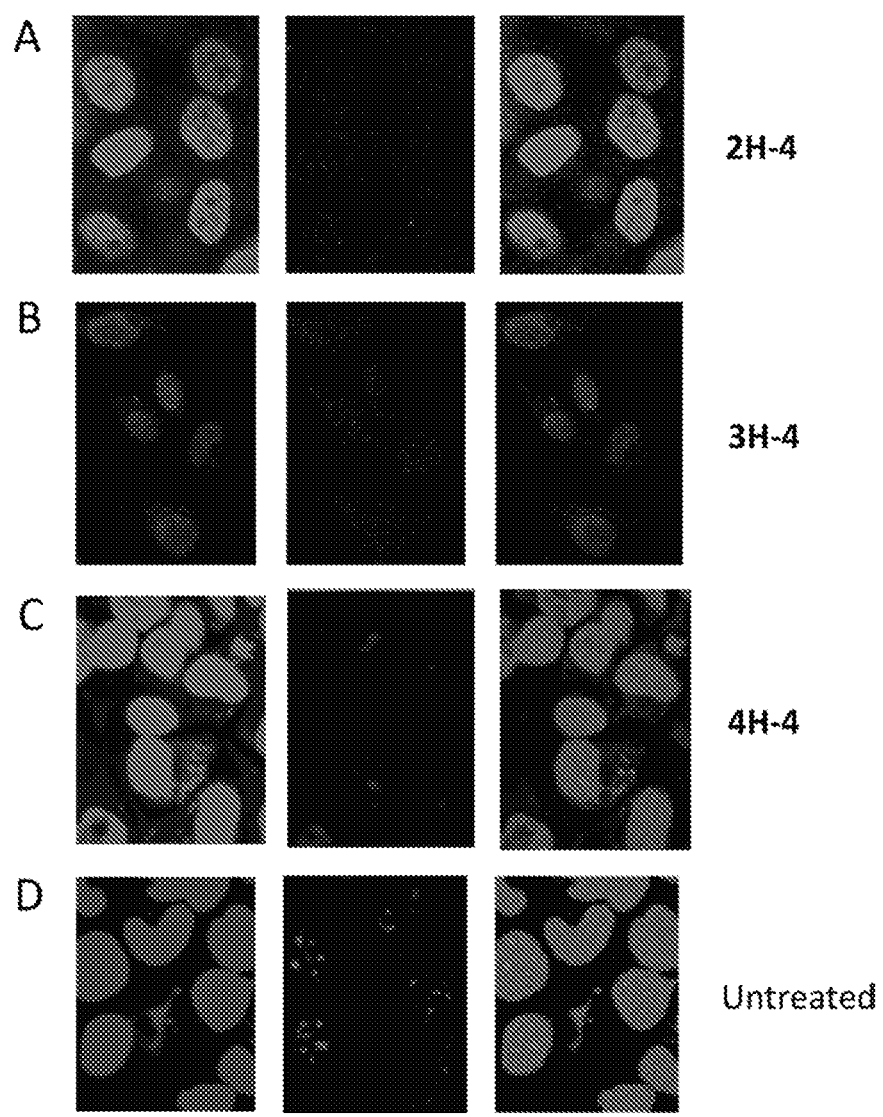
FIG. 42 is an example of disruption of nuclear foci by 2H-4 and 3H-4 as determined by fluorescence in situ hybridization (FISH). HeLa cells were transfected with a DM1 mini-gene containing 960 interrupted CTG repeats and then treated with the nH-4 compound.(21) After 16-24 h, the cells were fixed and the rCUG repeats were detected by FISH using DY547-2'OMe-(CAGCAGCAGCAGCAGCAGC). The cells were imaged by confocal microscopy. A, cells treated with 25 µM of 2H-4. B, cells treated with 25 µM of 3H-4. C, untreated cells. For all panels: left, fluorescence in the DAPI channel indicating nuclei or nH-4 compound (nH-4 compounds have similar spectral properties as DAPI); middle, DY547 fluorescence indicating the presence of rCUG repeats; C, overlay of DY547 and DAPI/nH-4 images.

Another hallmark of DM1 is the presence of nuclear foci caused by aggregates of $r(CUG)^{exp}$ and various proteins including MBNL1.(26-31) Thus, it was determined if nH-4 compounds can disrupt formation of nuclear foci. HeLa cells were transiently transfected with the DM1 mini-gene (21) and treated with an nH-4 modularly assembled compound. Fluorescence in situ hybridization (FISH) was then used to visualize the $r(CUG)^{exp}$. As shown in FIG. 42, the number of foci is decreased and the foci are more diffuse when cells are treated with 25 μM of 2H-4 or 3H-4.

METHODS. Improvement of Splicing Defects in a Cell Culture Model Using RT-PCR.

In order to determine if nH-4 compounds improve splicing defects in vivo, a previously reported method was employed. (20) Briefly, HeLa cells were grown as monolayers in 96-well plates in growth medium (1×DMEM, 10% FBS, and 1× GlutaMax (Invitrogen)). After the cells reached 90-95% confluency, they were transfected with 200 ng of total plasmid using Lipofectamine 2000 reagent (Invitrogen) per the manufacturer's standard protocol. Equal amounts of a plasmid expressing a DM1 mini-gene with 960 CTG repeats (21) and a mini-gene of interest (cTNT (21) or PLEKHH2 (24)) were used. Approximately 5 h post-transfection, the transfection cocktail was removed and replaced with growth medium containing the compound of interest. After 16-24 h, the cells were lysed in the well, and total RNA was harvested with a Qiagen RNAEasy kit. An on-column DNA digestion was completed per the manufacturer's recommended protocol.

A sample of RNA was subjected to reverse transcription-polymerase chain reaction (RT-PCR) as previously described (24) except 5 units of AMV Reverse Transcriptase from Life Sciences were used. Approximately 300 ng were reverse transcribed, and 150 ng were subjected to PCR using a radioactively labeled forward primer. RT-PCR products were observed after 25-30 cycles of: 95° C. for 1 min; 55° C. for 1 min; 72° C. for 2 min and a final extension at 72° C. for 10 min. The products were separated on a denaturing 5% polyacrylamide gel and imaged using a Typhoon phosphorimager. The length of the RT-PCR products was confirmed by comparison to a $5'$-$^{32}$P end labeled 100 bp ladder. Differences in alternative splicing were evaluated by a t-test.

The RT-PCR primers for the cTNT mini-gene were: 5'GTTCACAACCATCTAAAGCAAGATG (forward) and 5'GTTGCATGGCTGGTGCAGG (reverse). The RT-PCR primers for the PLEKHH2 mini-gene were: 5'CGGGGTAC-CAAATGCTGCAGTTGACTCTCC (forward) and 5'CCGCTCGAGCCATTCATGAAGTGCACAGG (reverse).

Control experiments were also completed in which HeLa cells were transfected with a plasmid encoding a mini-gene with five CTG repeats in the 3' UTR or with a mini-gene that encodes a pre-mRNA whose splicing is not controlled by MBNL1 (PLEKHH2).(24)

Generation of C1-S and C5-14 Cell Lines to Assess Improvement of Translational Defects.

The pLLC14 gpab plasmid contains a CMV/chicken beta-actin enhancer/promoter (a gift from Dr. J. Miyazaki) followed by a floxed EGFP-Puromycin gene fusion with a triple-stop SV40 transcription terminator followed by a firefly luciferase gene with the human DMPK (hDMPK) 3' UTR. This design allows for conditional expression of the firefly transcript after Cre recombination by removal of the floxed EGFP-Puromycin-SV40 triple-stop. The hDMPK 3' UTR contains a modified restriction site for the inclusion of CTG repeats. An uninterrupted CTG tract of ~500 repeats was generated by rolling circle amplification (RCA) of the repeat donor plasmid pDWD by Phi29 polymerase as previously described, (32) and then ligated into the hDMPK 3' UTR of the pLLC14 gpab plasmid. The ligation was used directly for transfection into C2C12 cells to prevent the inevitable CTG repeat truncation that occurs in the bacterial cloning process. (33)

C2C12 cells were co-transfected with ~100 ng pLLC14 gpab (with or without 500 CTG repeats) and 5 μg of a pPhiC31o (34) expressing PhiC31 integrase, which yields efficient, site-specific, single copy integration of pLLC14gpab at its attB element. (35) Transfected cells were grown in DMEM (Gibco) supplemented with 10% FBS+1% Penicillin/Streptomic+3 µg/ml puromycin for ~10 days to select for clones with successful pLLC14gpab integration, and colonies were picked and expanded. Clones were then transfected with pHSVCre$^{WT}$ expressing Cre recombinase (a gift from Dr. W. Bowers) for the removal of the EGFP-Puromycin-SV40 triple stop, thus activating expression of the firefly luciferase transgene. A Cre-recombined no-CTG clone was identified by fluorescence-activated cell sorting (FACS) by sorting for GFP negative cells. The Cre-recombined (CTG)$_{500}$ clones were screened for CUG repeat RNA nuclear foci by fluorescence in situ hybridization (FISH) as previously described (36), and foci-positive cells were cloned by limiting dilution. The no-repeat, FACS sorted cells were designated C1-S and the CTG repeat-containing clone with bright, consistent CUG RNA foci was designated C5-14. Cre recombination for both cell lines was confirmed by PCR across the floxed region of the integrated pLLC$_{14}$ gpab construct, and both semi-quantitative RT-PCR and TaqMan real-time qRT-PCR analyses of the firefly luciferase transgene indicated strong and comparable expression in both C1-S and C5-14 cells. PCR analysis across the CTG repeat region of the C5-14 clone revealed an expansion of the CTG tract to ~800 CTG repeats, which was stable over the course of several passages.

Improvement of Translational Defects Using a Luciferase Assay.

C2C12 cell lines expressing 800 (C5-14) or 0 (C1-S) CTG repeats in the 3' UTR of luciferase were maintained as monolayers in growth medium (1×DMEM (Invitrogen) supplemented with 10% FBS (Invitrogen), 1× Glutamax (Invitrogen), and 1× Penicillin/Streptomycin (MP Biomedicals, LLC)). The cells were plated in 96-well plates and allowed to grow for 24 h. The compound of interest was then added in 50 µL, and the cells were treated for 24 h.

The growth medium containing the compound of interest was removed and replaced with 100 µL of medium and 10 µL of WST-1 reagent (Roche). After 30 min, 60 µL aliquots were removed and placed into clear 96-well plates. The absorbance of the medium was measured at 450 nm and 690 nm. The corrected absorbance (Abs$_{450}$-Abs$_{690}$) was used to normalize each well for cell count.

The remaining medium containing WST-1 reagent was removed, and 20 µL of 1× Passive Lysis Buffer (Promega) was added to each well. The cells were placed at −20° C. for 15 min. After the buffer thawed, 100 µL of Luciferase Assay Substrate (Promega) were added to each well. Luminescence was immediately read on a SpectraMax M5 plate reader using an integration time of 5000 ms. The luminescence signal was normalized to the number of cells in the corresponding well using the results of the WST-1/cell proliferation assay.

Disruption of Nuclear Foci Using Fluorescence In Situ Hybridization (FISH).(20)

HeLa cells were grown as monolayers in Mat-Tek glass-bottomed, 96-well plates. After the cells reached 90-95% confluency, they were transfected with 200 ng of a plasmid encoding a DM1 mini-gene (21) using Lipfoectamine 2000 per the manufacturer's standard protocol. The transfection cocktail was removed 5 h post-transfection, and the compound of interest was added in growth medium. Growth medium was added to untreated cells.

After 16-24 h, the cells were washed with 1×DPBS and fixed with 4% paraformaldehyde in 1×DPBS for 10 min at 37° C. After washing with 1×DPBS, the cells were permeabilized with 1×DPBS+0.1% Triton X-100 for 5 min at 37° C. The cells were washed with 1×DPBS+0.1% Triton X-100 three times and then with 30% formamide in 2×SSC Buffer (30 mM sodium citrate, pH 7.0, 300 mM NaCl).

The cells were incubated in 1×FISH Buffer (30% formamide, 2×SSC Buffer, 66 µg/mL bulk yeast tRNA, 2 µg/mL BSA, 2 mM vanadyl complex (New England Bio Labs) and 1 ng/µL DY547-2'OMe-(CAGCAGCAGCAGCAGCAGC)) for 1.5 h at 37° C. They were then washed with 30% formamide in 2×SSC for 30 min at 42° C., 1×SSC for 30 min at 37° C., and 1×DPBS+0.1% Triton X-100 for 5 min at room temperature. The cells were washed with 1×DPBS+0.1% Triton X-100, and 100 µL of 1×DPBS were added to each well. Untreated cells were stained with 1 µg mL$^{-1}$ DAPI for 5 min at room temperature, and then washed with 1×DPBS+0.1% Triton X-100. The cells were imaged using an Olympus Fluo-View 1000 Confocal Microscope at 100× magnification.

ABBREVIATIONS cTNT, cardiac troponin T pre-mRNA; CUGBP1, CUG binding protein 1; DM1, myotonic dystrophy type 1; DM2, myotonic dystrophy type 2; DMPK, dystrophia myotonica protein kinase; MBNL1, muscleblind-like 1 protein; MBNL2, muscleblind-like 2 protein; MBNL3, muscleblind-like 3 protein; PLEKHH2, Pleckstrin-2; UTR, untranslated region.

REFERENCES

1. Venter, J. C., et al. (2001) The sequence of the human genome, *Science* 291, 1304-1351.
2. Lander, E. S., et al. (2001) Initial sequencing and analysis of the human genome, *Nature* 409, 860-921.
3. Iorns, E., Lord, C. J., Turner, N., and Ashworth, A. (2007) Utilizing RNA interference to enhance cancer drug discovery, *Nat. Rev. Drug Discov.* 6, 556-568.
4. De Backer, M. D., Nelissen, B., Logghe, M., Viaene, J., Loonen, I., Vandoninck, S., de Hoogt, R., Dewaele, S., Simons, F. A., Verhasselt, P., Vanhoof, G., Contreras, R., and Luyten, W. H. (2001) An antisense-based functional genomics approach for identification of genes critical for growth of *Candida albicans, Nat. Biotechnol.* 19, 235-241.
5. Calin, G. A., and Croce, C. M. (2006) MicroRNAs and chromosomal abnormalities in cancer cells, *Oncogene* 25, 6202-6210.
6. St Laurent, G., 3rd, Faghihi, M. A., and Wahlestedt, C. (2009) Non-coding RNA transcripts: sensors of neuronal stress, modulators of synaptic plasticity, and agents of change in the onset of Alzheimer's disease, *Neurosci. Lett.* 466, 81-88.
7. Childs-Disney, J. L., Wu, M., Pushechnikov, A., Aminova, O., and Disney, M. D. (2007) A small molecule microarray platform to select RNA internal loop-ligand interactions, *ACS Chem. Biol.* 2, 745-754.
8. Velagapudi, S. P., Seedhouse, S. J., and Disney, M. D. (2010) Structure-activity relationships through sequencing (StARTS) defines optimal and suboptimal RNA motif targets for small molecules, *Angew. Chem. Int. Ed. Engl.* 49, 3816-3818.
9. Velagapudi, S. P., Seedhouse, S. J., French, J., and Disney, M. D. (2011) Defining the RNA internal loops preferred by benzimidazole derivatives via 2D combinatorial screening and computational analysis, *J. Am. Chem. Soc.* 133, 10111-10118.
10. Disney, M. D., Labuda, L. P., Paul, D. J., Poplawski, S. G., Pushechnikov, A., Tran, T., Velagapudi, S. P., Wu, M., and Childs-Disney, J. L. (2008) Two-dimensional combinatorial screening identifies specific aminoglycoside-RNA internal loop partners, *J. Am. Chem. Soc.* 130, 11185-11194.
11. Lee, M. M., Childs-Disney, J. L., Pushechnikov, A., French, J. M., Sobczak, K., Thornton, C. A., and Disney, M. D. (2009) Controlling the specificity of modularly assembled small molecules for RNA via ligand module spacing: targeting the RNAs that cause myotonic muscular dystrophy, *J. Am. Chem. Soc.* 131, 17464-17472.
12. Disney, M. D., Lee, M. M., Pushechnikov, A., and Childs-Disney, J. L. (2010) The role of flexibility in the rational design of modularly assembled ligands targeting the RNAs that cause the myotonic dystrophies, *ChemBioChem* 11, 375-382.
13. Pushechnikov, A., Lee, M. M., Childs-Disney, J. L., Sobczak, K., French, J. M., Thornton, C. A., and Disney, M. D. (2009) Rational design of ligands targeting triplet repeating transcripts that cause RNA dominant disease: application to myotonic muscular dystrophy type 1 and spinocerebellar ataxia type 3, *J. Am. Chem. Soc.* 131, 9767-9779.
14. Lee, M. M., Pushechnikov, A., and Disney, M. D. (2009) Rational and modular design of potent ligands targeting the RNA that causes myotonic dystrophy 2, *ACS Chem. Biol.* 4, 345-355.
15. Day, J. W., and Ranum, L. P. (2005) RNA pathogenesis of the myotonic dystrophies, *Neuromuscul. Disord.* 15, 5-16.
16. Kanadia, R. N., Johnstone, K. A., Mankodi, A., Lungu, C., Thornton, C. A., Esson, D., Timmers, A. M., Hauswirth, W. W., and Swanson, M. S. (2003) A muscleblind knockout model for myotonic dystrophy, *Science* 302, 1978-1980.
17. Kanadia, R. N., Shin, J., Yuan, Y., Beattie, S. G., Wheeler, T. M., Thornton, C. A., and Swanson, M. S. (2006) Reversal of RNA missplicing and myotonia after muscleblind overexpression in a mouse poly(CUG) model for myotonic dystrophy, *Proc. Natl. Acad. Sci. U.S.A.* 103, 11748-11753.
18. Mastroyiannopoulos, N. P., Feldman, M. L., Uney, J. B., Mahadevan, M. S., and Phylactou, L. A. (2005) Woodchuck post-transcriptional element induces nuclear export of myotonic dystrophy 3' untranslated region transcripts, *EMBO Rep.* 6, 458-463.
19. Sarkar, P. S., Han, J., and Reddy, S. (2004) In situ hybridization analysis of DMPK mRNA in adult mouse tissues, *Neuromuscul. Disord.* 14, 497-506.
20. Warf, M. B., Nakamori, M., Matthys, C. M., Thornton, C. A., and Berglund, J. A. (2009) Pentamidine reverses the splicing defects associated with myotonic dystrophy, *Proc. Natl. Acad. Sci. U.S.A.* 106, 18551-18556.
21. Philips, A. V., Timchenko, L. T., and Cooper, T. A. (1998) Disruption of splicing regulated by a CUG-binding protein in myotonic dystrophy, *Science* 280, 737-741.
22. Ho, T. H., Charlet, B. N., Poulos, M. G., Singh, G., Swanson, M. S., and Cooper, T. A. (2004) Muscleblind proteins regulate alternative splicing, *EMBO J.* 23, 3103-3112.
23. Nezu, Y., Kino, Y., Sasagawa, N., Nishino, I., and Ishiura, S. (2007) Expression of MBNL and CELF mRNA transcripts in muscles with myotonic dystrophy, *Neuromuscul. Disord.* 17, 306-312.
24. Warf, M. B., and Berglund, J. A. (2007) MBNL binds similar RNA structures in the CUG repeats of myotonic dystrophy and its pre-mRNA substrate cardiac troponin T, *RNA* 13, 2238-2251.
25. Timchenko, N. A., Cai, Z. J., Welm, A. L., Reddy, S., Ashizawa, T., and Timchenko, L. T. (2001) RNA CUG repeats sequester CUGBP1 and alter protein levels and activity of CUGBP1, *J. Biol. Chem.* 276, 7820-7826.
26. Fardaei, M., Rogers, M. T., Thorpe, H. M., Larkin, K., Hamshere, M. G., Harper, P. S., and Brook, J. D. (2002) Three proteins, MBNL, MBLL and MBXL, co-localize in vivo with nuclear foci of expanded-repeat transcripts in DM1 and DM2 cells, *Hum. Mol. Genet.* 11, 805-814.
27. Cardani, R., Mancinelli, E., Rotondo, G., Sansone, V., and Meola, G. (2006) Muscleblind-like protein 1 nuclear sequestration is a molecular pathology marker of DM1 and DM2, *Eur. J. Histochem.* 50, 177-182.
28. Fardaei, M., Larkin, K., Brook, J. D., and Hamshere, M. G. (2001) In vivo co-localisation of MBNL protein with DMPK expanded-repeat transcripts, *Nucleic Acids Res.* 29, 2766-2771.
29. Ho, T. H., Savkur, R. S., Poulos, M. G., Mancini, M. A., Swanson, M. S., and Cooper, T. A. (2005) Colocalization of muscleblind with RNA foci is separable from mis-regulation of alternative splicing in myotonic dystrophy, *J. Cell. Sci.* 118, 2923-2933.
30. Mankodi, A., Urbinati, C. R., Yuan, Q. P., Moxley, R. T., Sansone, V., Krym, M., Henderson, D., Schalling, M., Swanson, M. S., and Thornton, C. A. (2001) Muscleblind localizes to nuclear foci of aberrant RNA in myotonic dystrophy types 1 and 2, *Hum. Mol. Genet.* 10, 2165-2170.
31. Taneja, K. L., McCurrach, M., Schalling, M., Housman, D., and Singer, R. H. (1995) Foci of trinucleotide repeat transcripts in nuclei of myotonic dystrophy cells and tissues, *J. Cell. Biol.* 128, 995-1002.
32. Osborne, R. J., and Thornton, C. A. (2008) Cell-free cloning of highly expanded CTG repeats by amplification of dimerized expanded repeats, *Nucleic Acids Res.* 36, e24.
33. Kang, S., Jaworski, A., Ohshima, K., and Wells, R. D. (1995) Expansion and deletion of CTG repeats from human disease genes are determined by the direction of replication in *E. coli, Nat. Genet.* 10, 213-218.
34. Raymond, C. S., and Soriano, P. (2007) High-efficiency FLP and PhiC31 site-specific recombination in mammalian cells, *PLoS One* 2, e162.
35. Thyagarajan, B., Olivares, E. C., Hollis, R. P., Ginsburg, D. S., and Calos, M. P. (2001) Site-specific genomic integration in mammalian cells mediated by phage phiC31 integrase, *Mol. Cell. Biol.* 21, 3926-3934.
36. Nakamori, M., Pearson, C. E., and Thornton, C. A. (2011) Bidirectional transcription stimulates expansion and contraction of expanded (CTG)*(CAG) repeats, *Hum. Mol. Genet.* 20, 580-588.

TABLE 5

The binding affinities and potencies of rationally designed, modularly assembled small molecules targeting r(CUG)$^{exp}$. The data were previously reported. (13)

| Compound | $K_d$ (nM) | $IC_{50}$ (nM) |
|---|---|---|
| MBNL1 | 250 | — |
| H | 150 | 110,000 |
| 2H-4 | 100 | 11,000 |
| 3H-4 | 65 | 410 |
| 4H-5 | 35 | 210 |
| 5H-4 | 13 | 77 |

What is claimed is:

1. A compound having the formula:

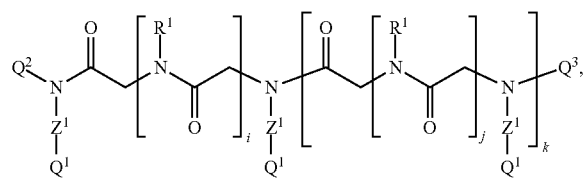

wherein i is an integer from 2 to 9; j is an integer from 0-4; k is an integer from 0-3; each $Z^1$ represents the same or different linking moiety; each $R^1$ is the same or different and represents an alkyl group or an aryl group; each $Q^1$ is the same or different and is selected from aminoglycoside sugars and bis-benzimidazoles; $Q^2$ is an unsubstituted or substituted alkyl group; and $Q^3$ is H or a substituted carbonyl group.

2. A compound according to claim 1, wherein the compound has the following structure:

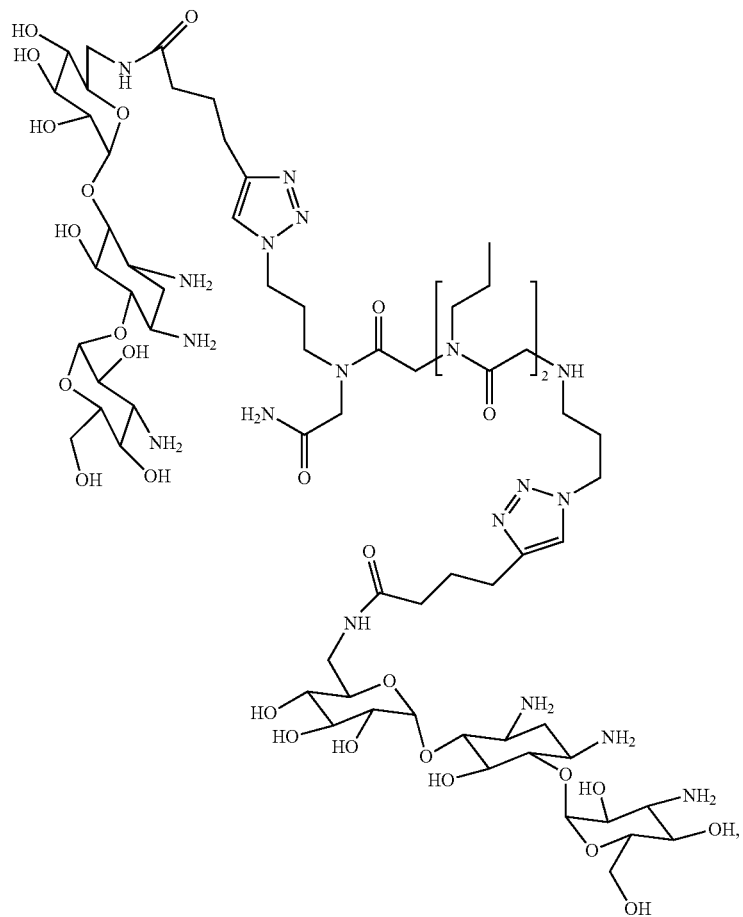

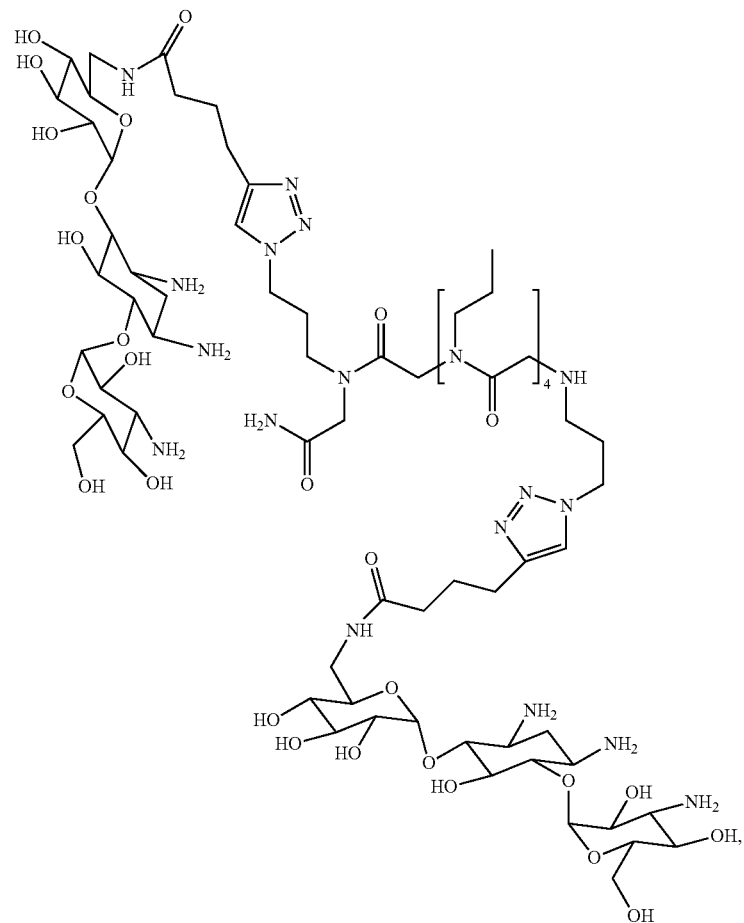

-continued
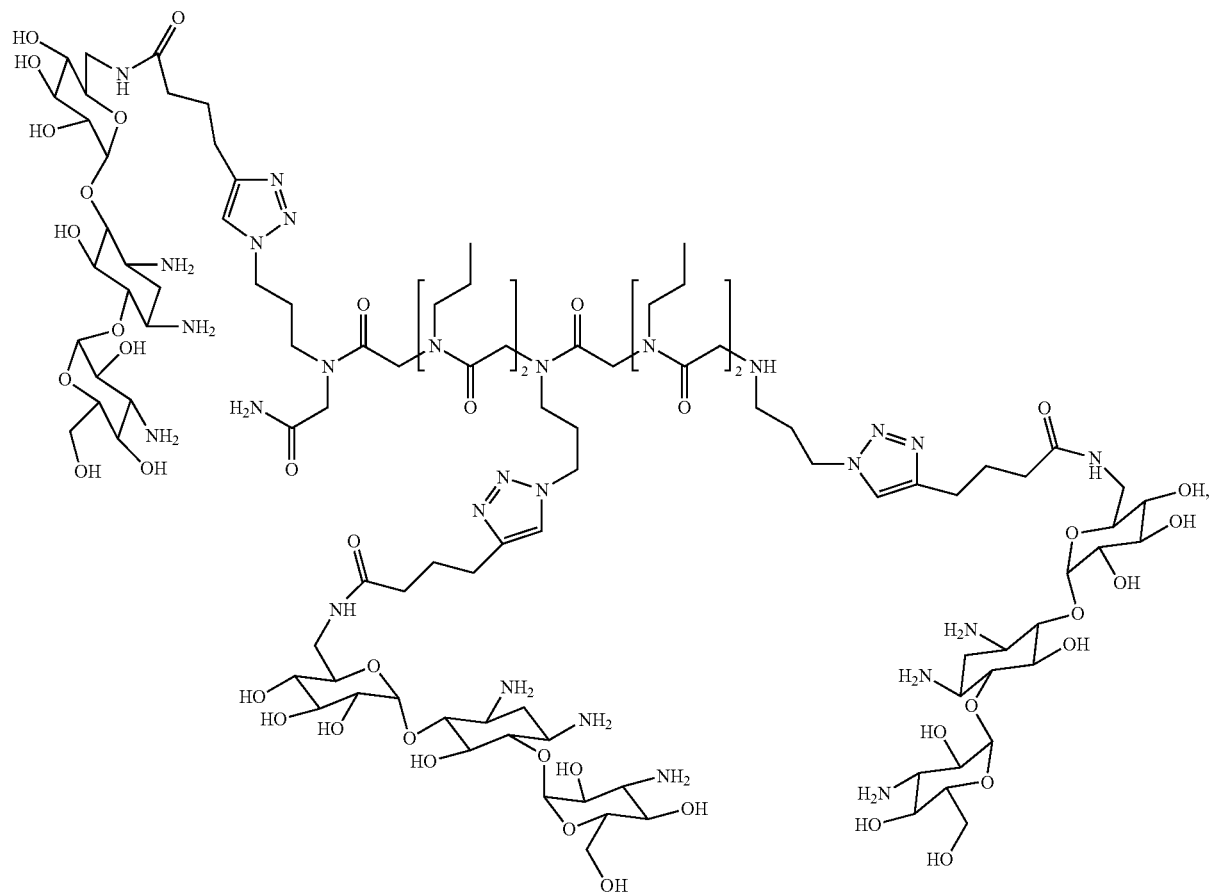

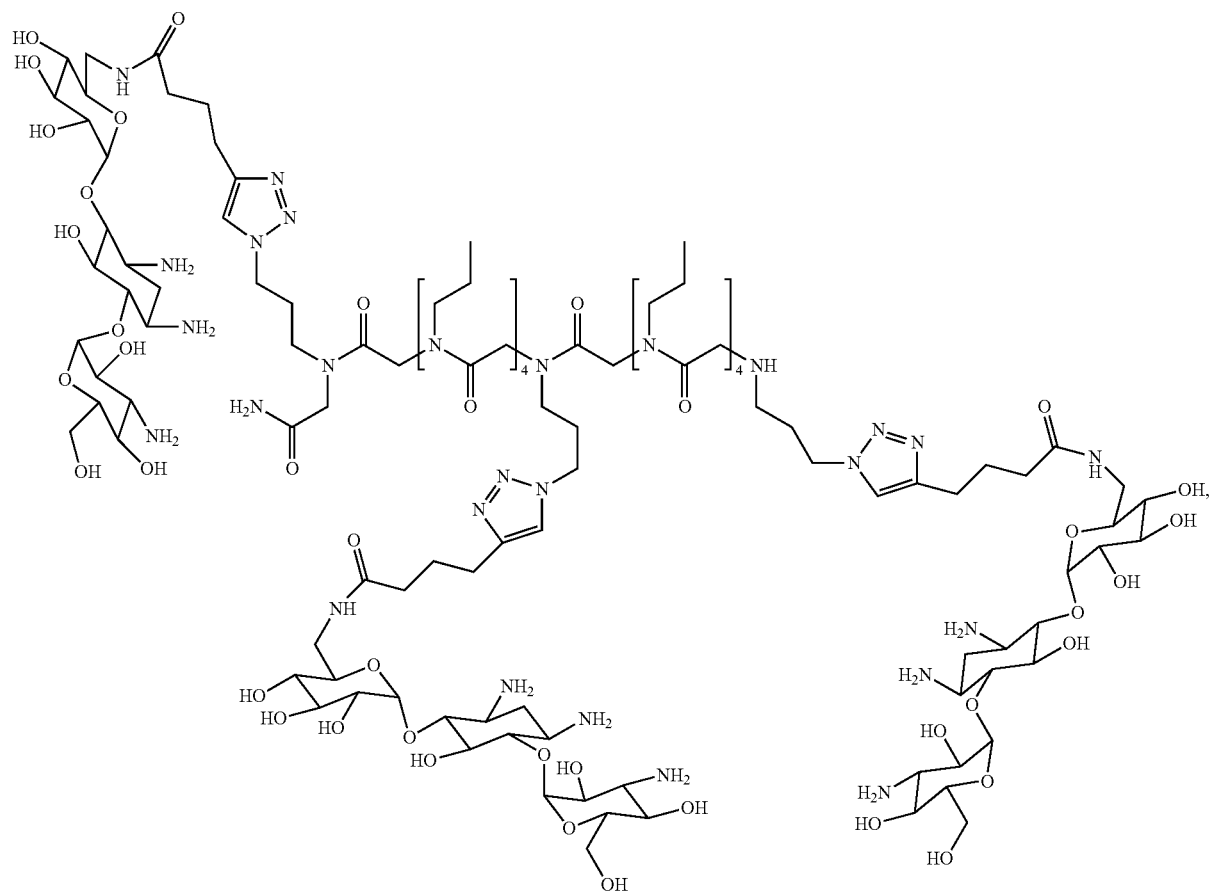
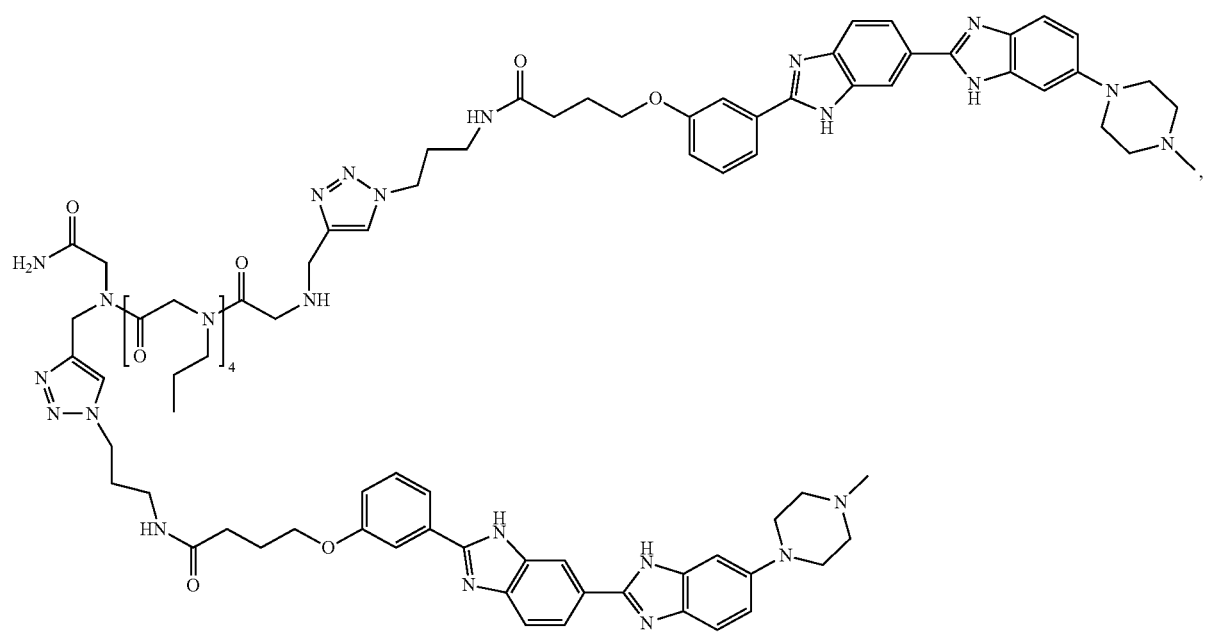

107
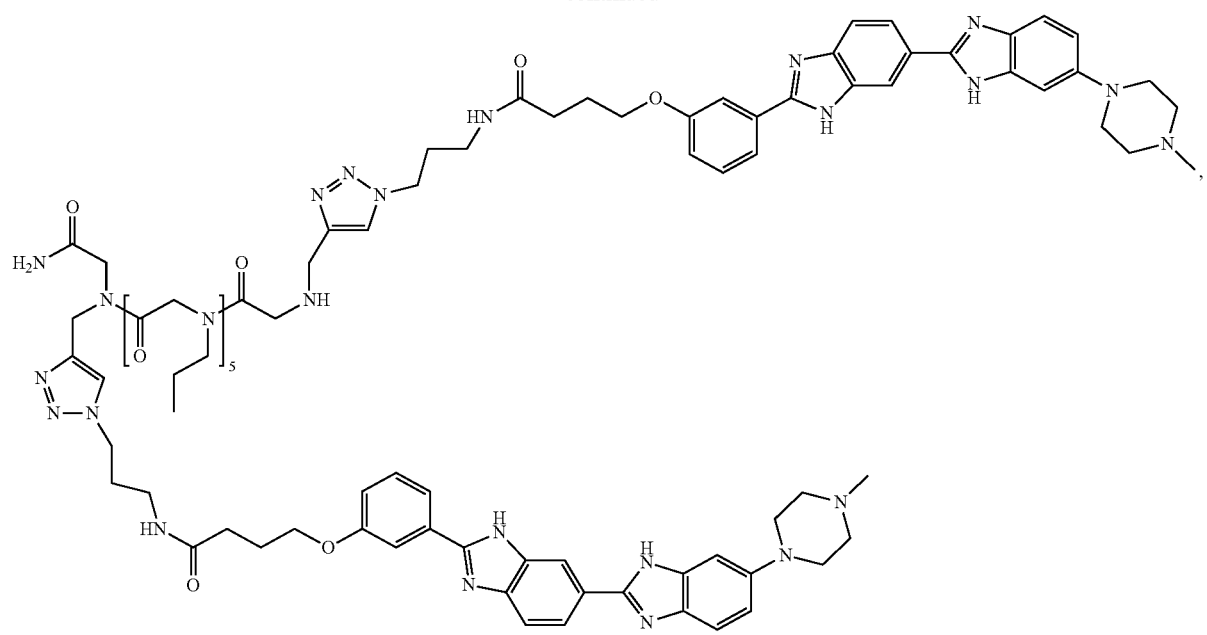
108
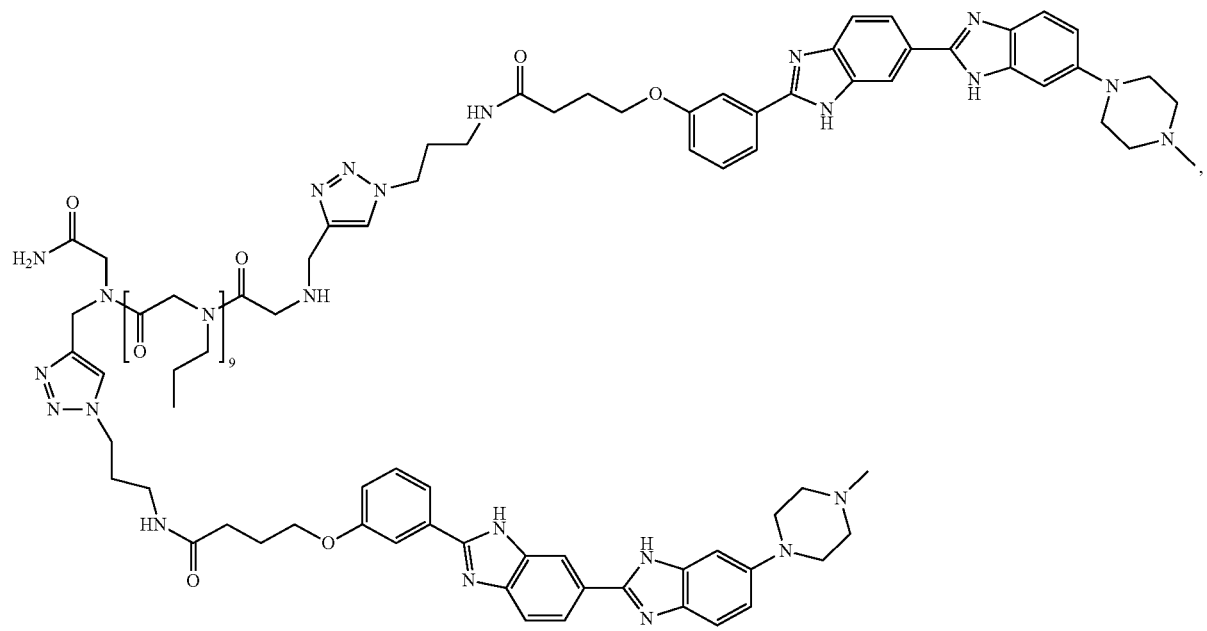

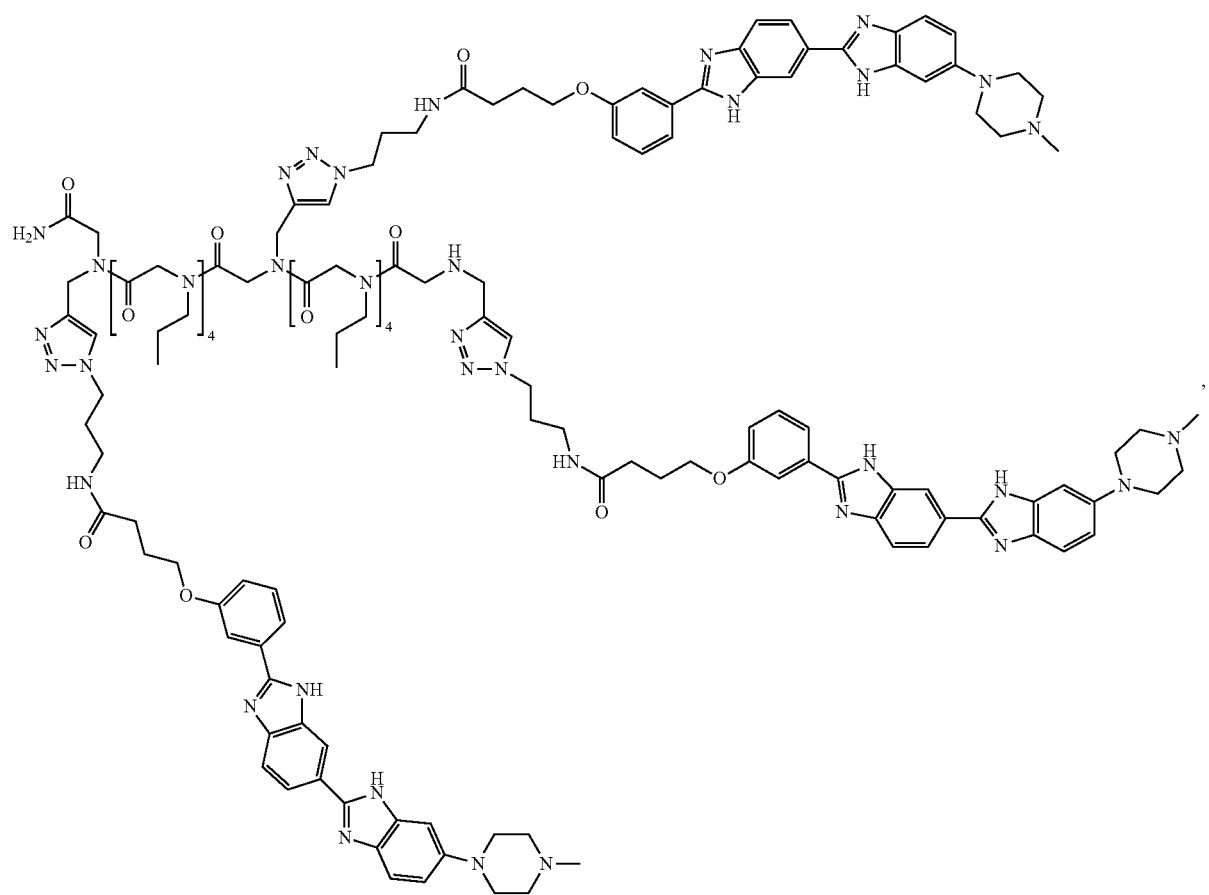

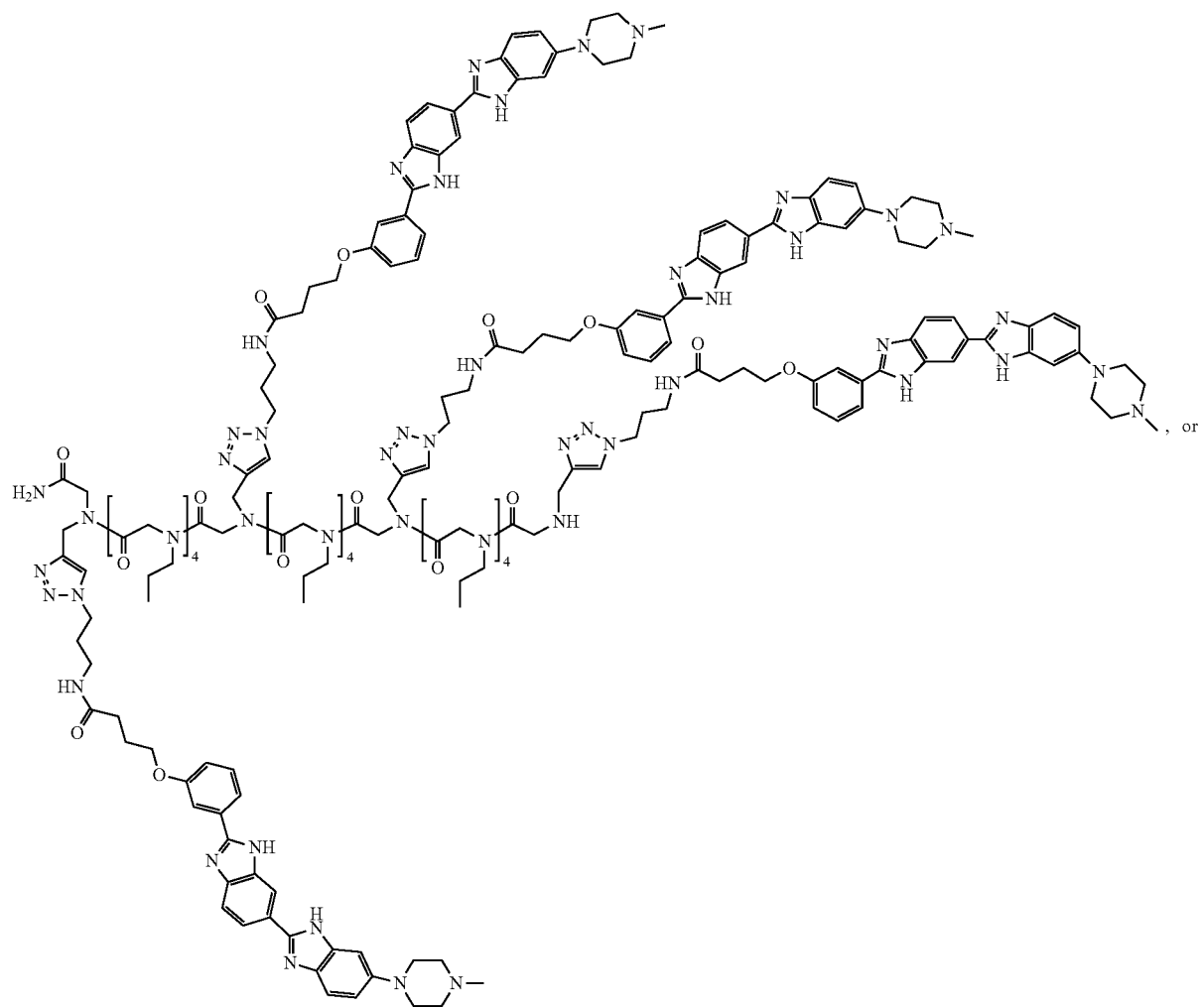

-continued
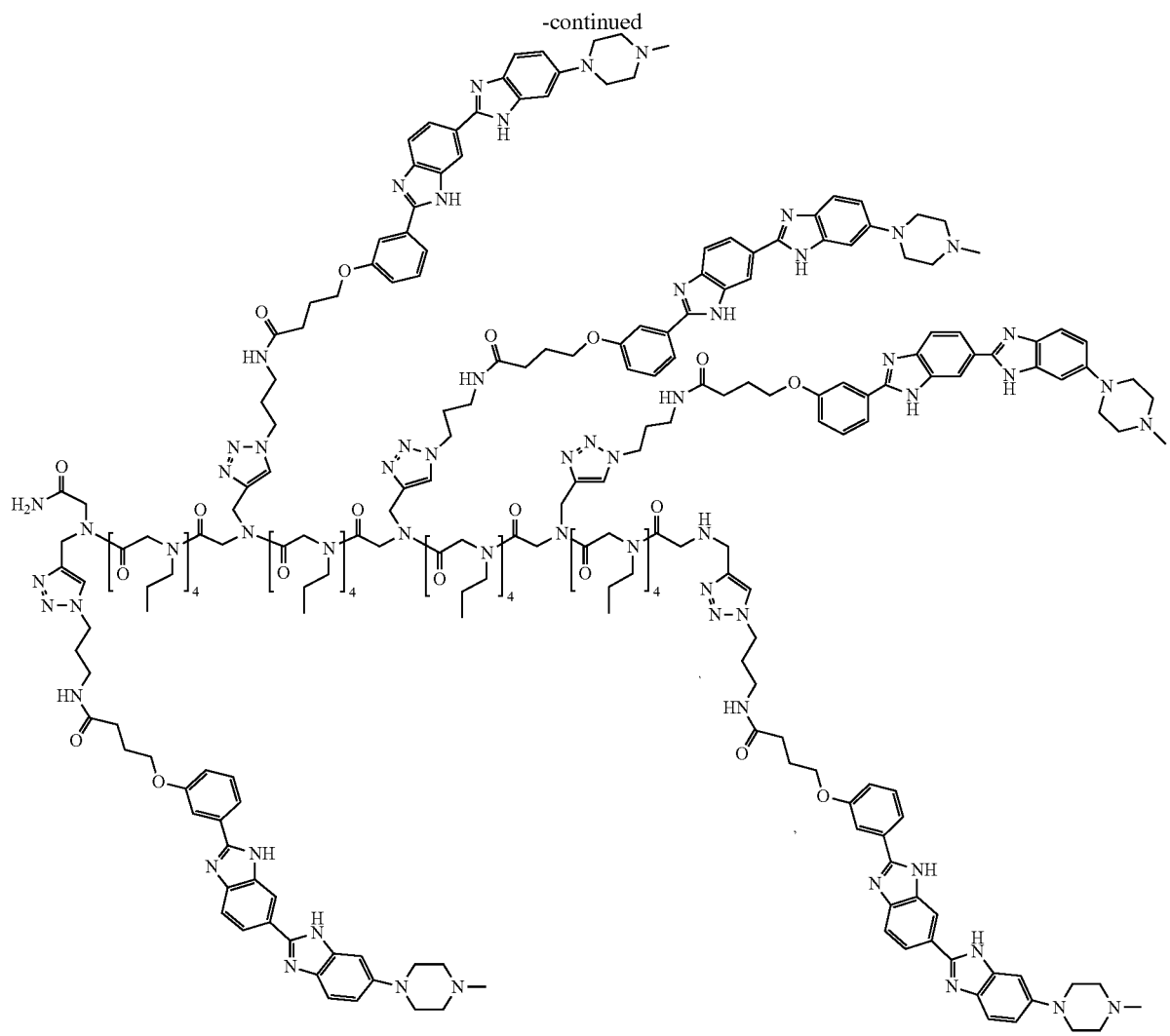
3. The compound according to claim 1, wherein $Q^3$ has the formula —C(O)—$R^4$, $R^4$ is
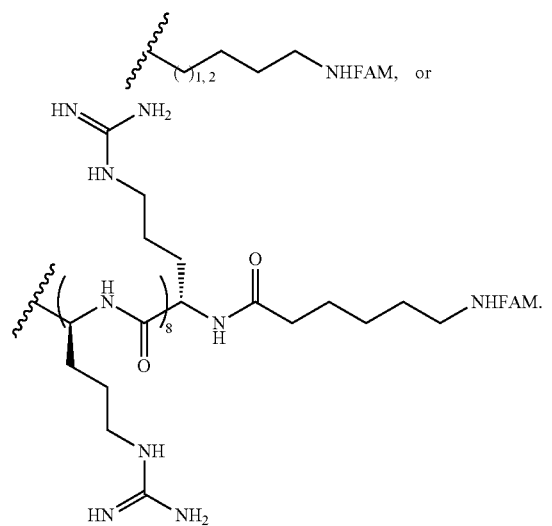

4. A compound according to claim 3, wherein the compound has the following structure:
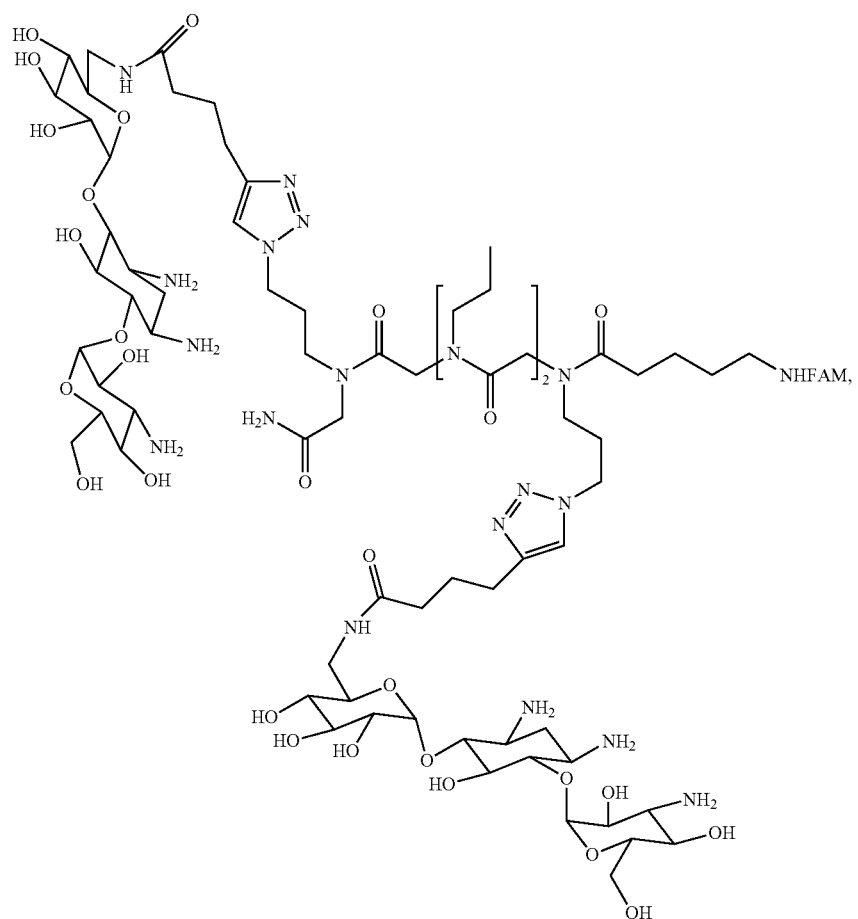

117
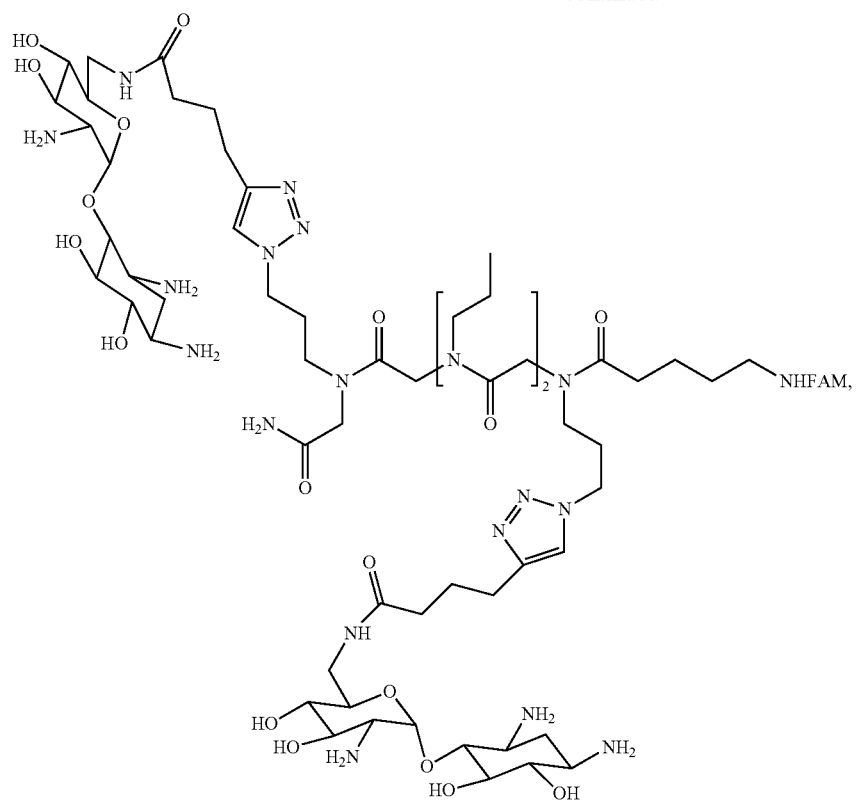
118
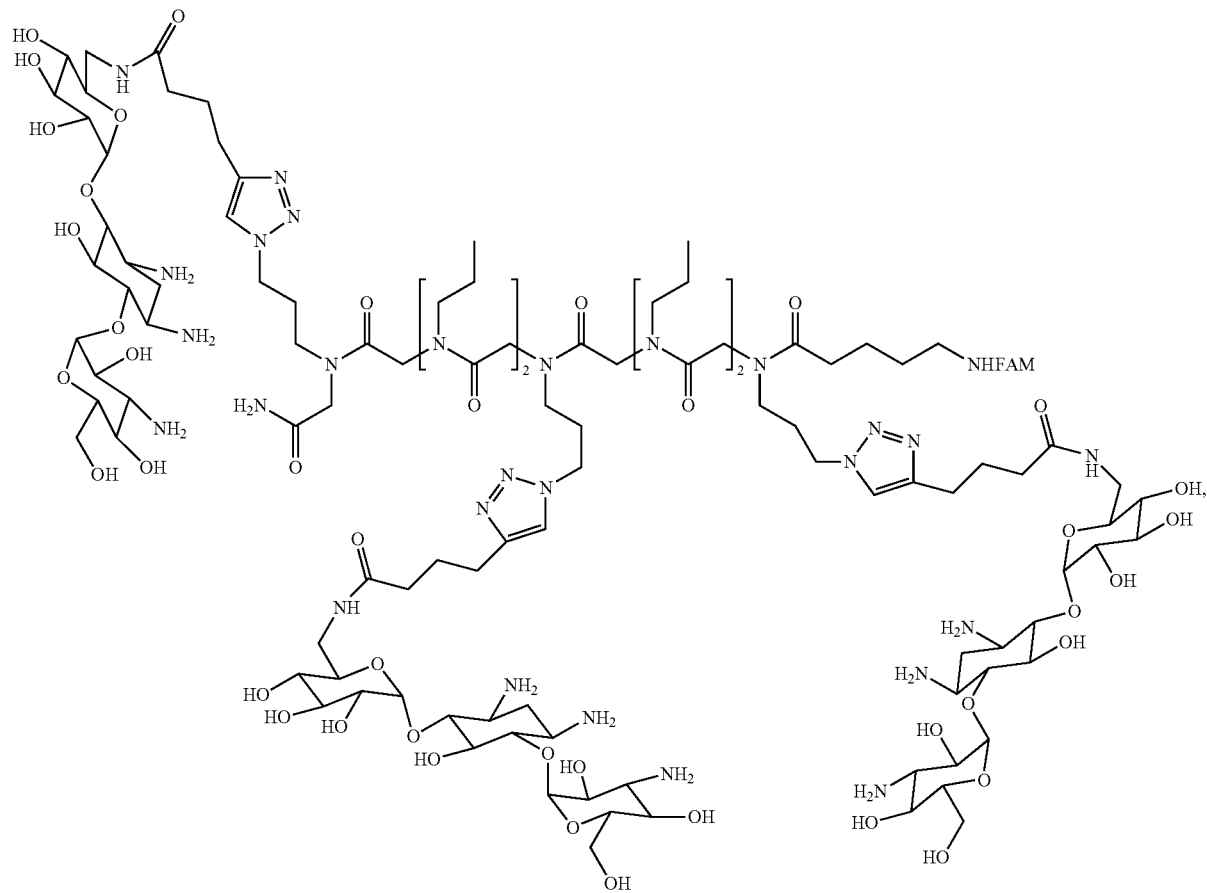

-continued
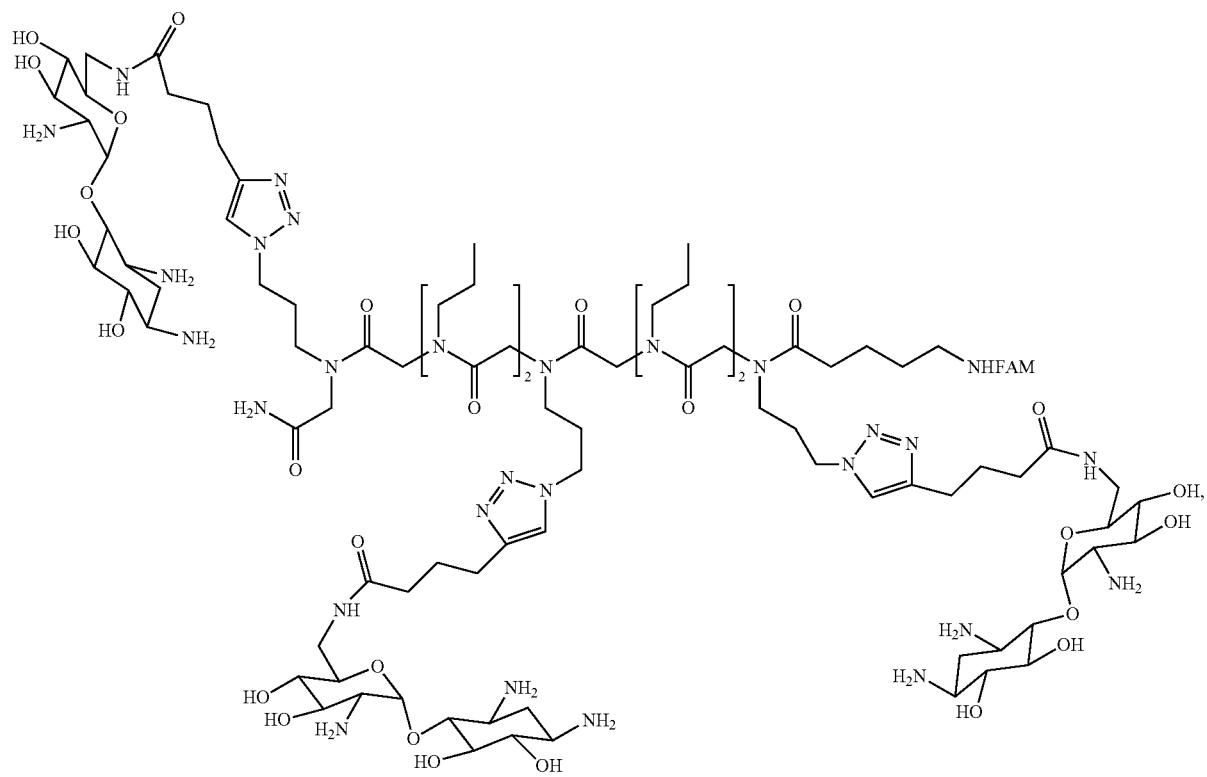
119
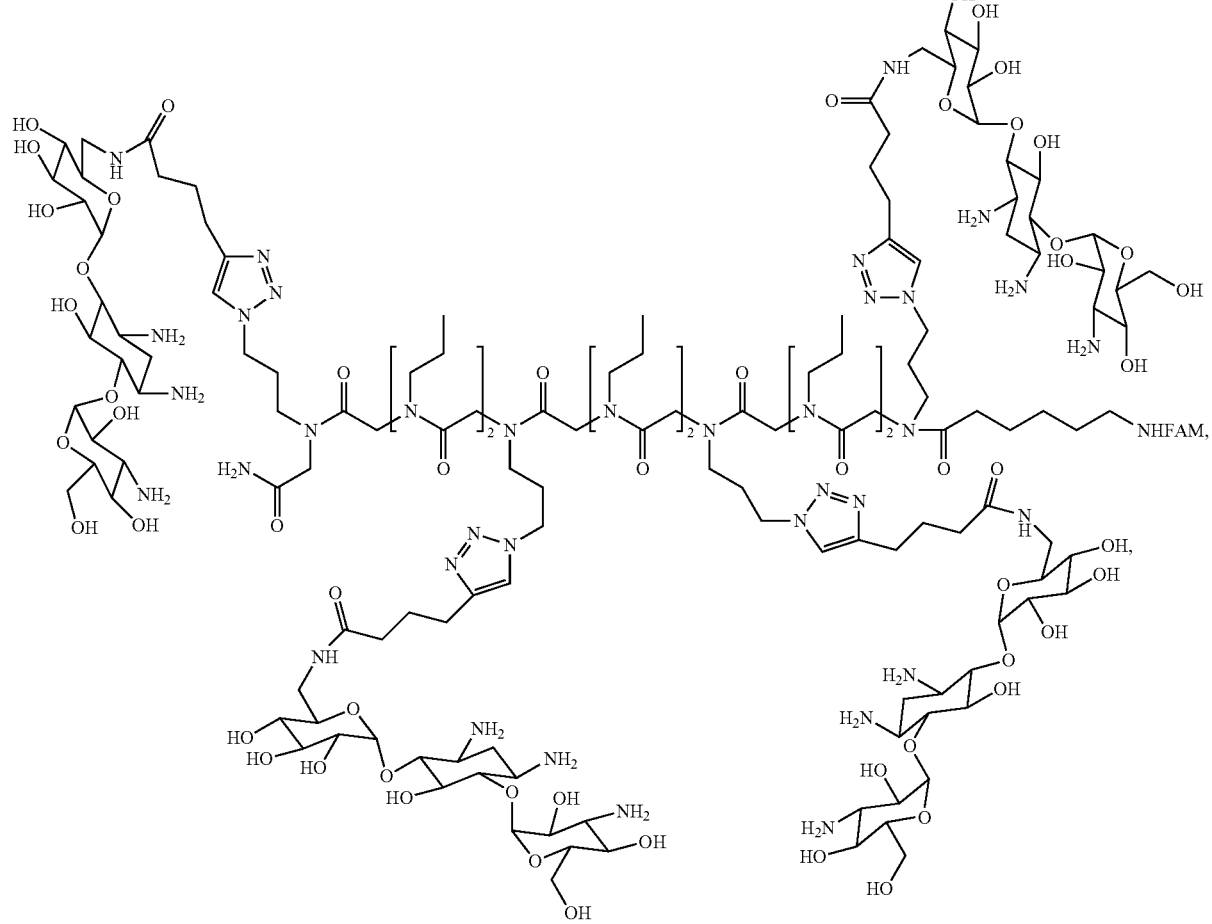
120

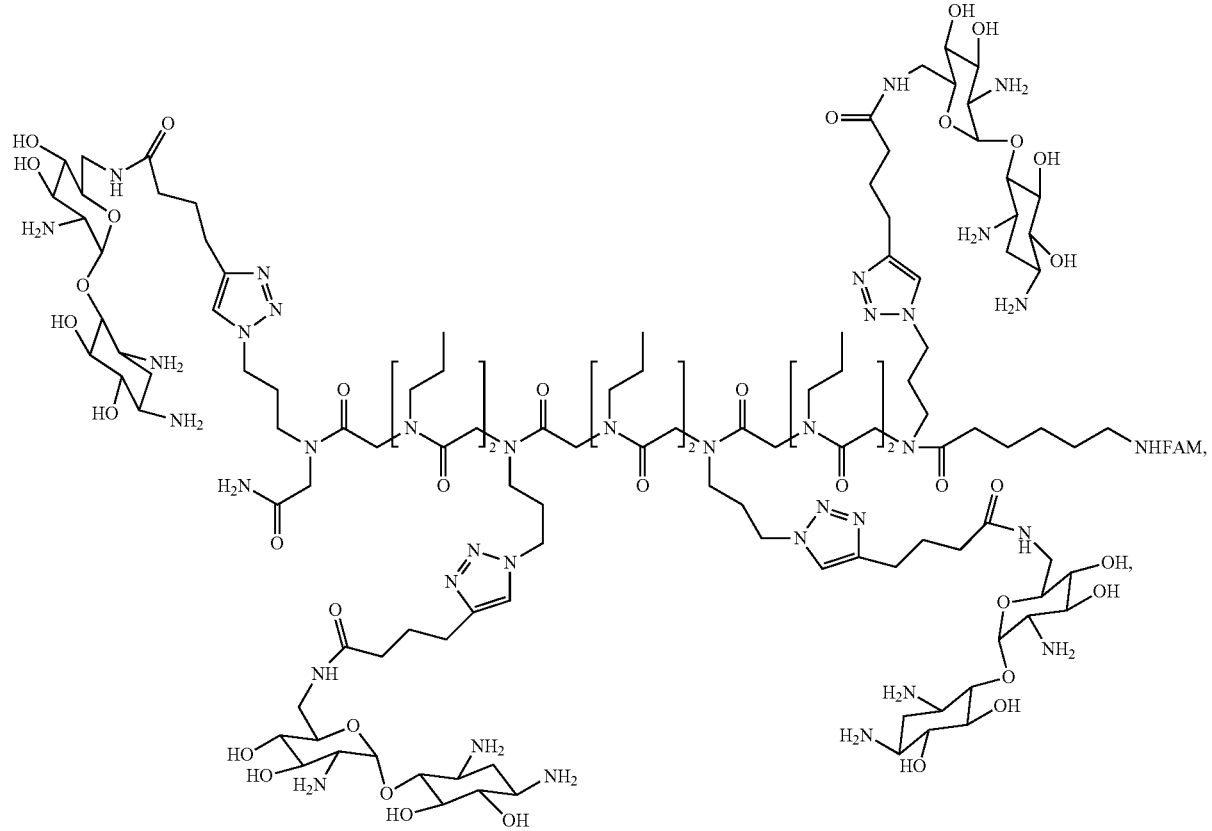

123
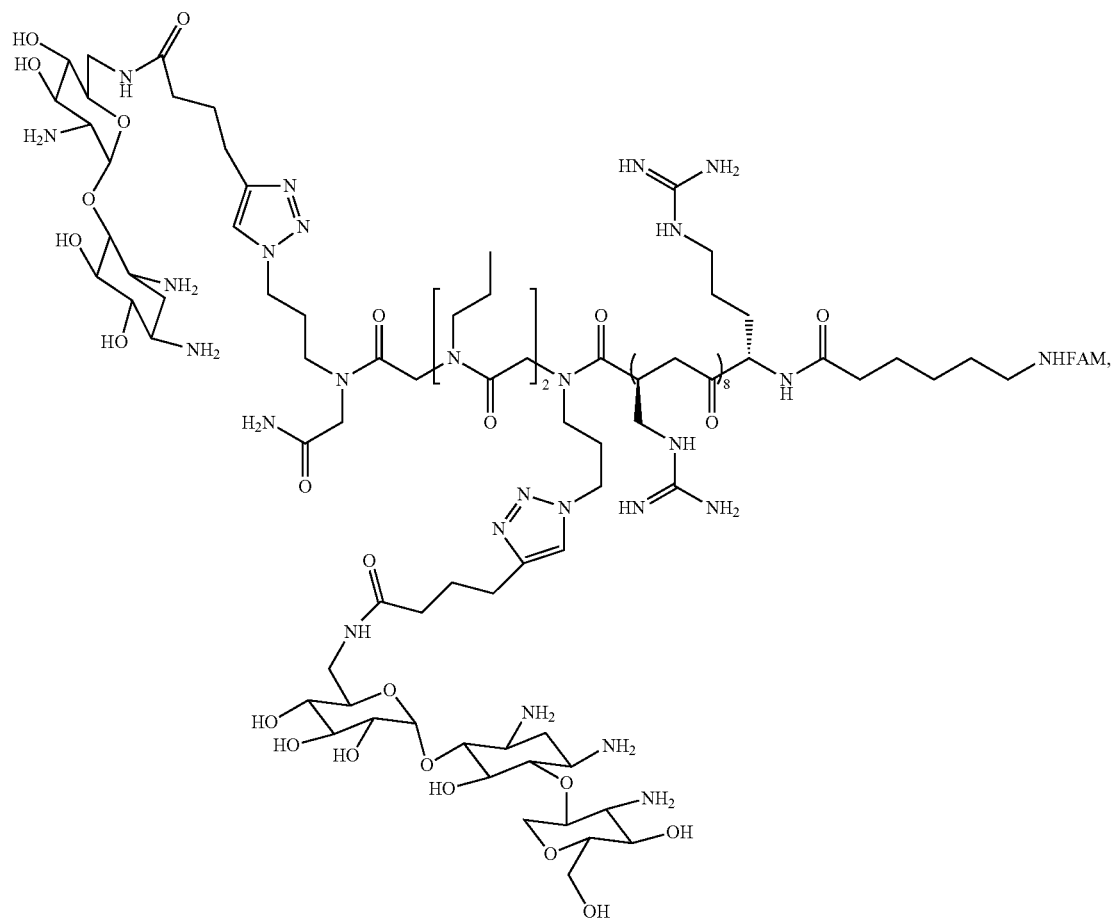
124
-continued
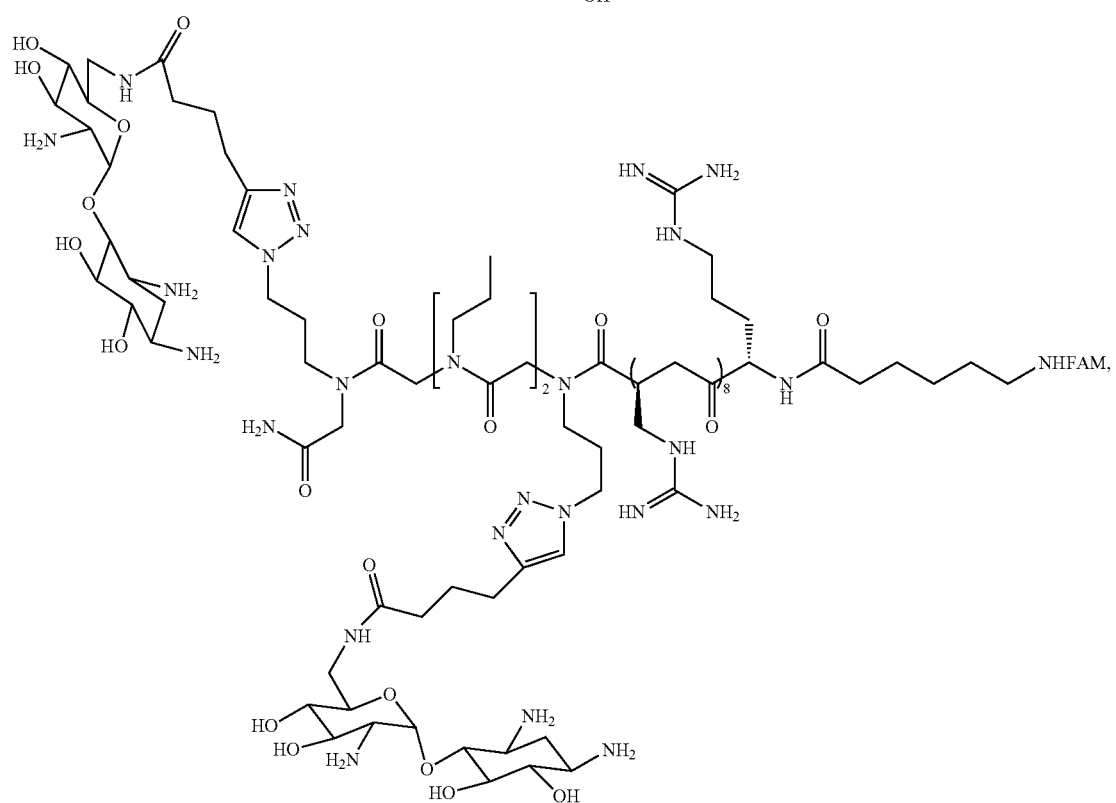

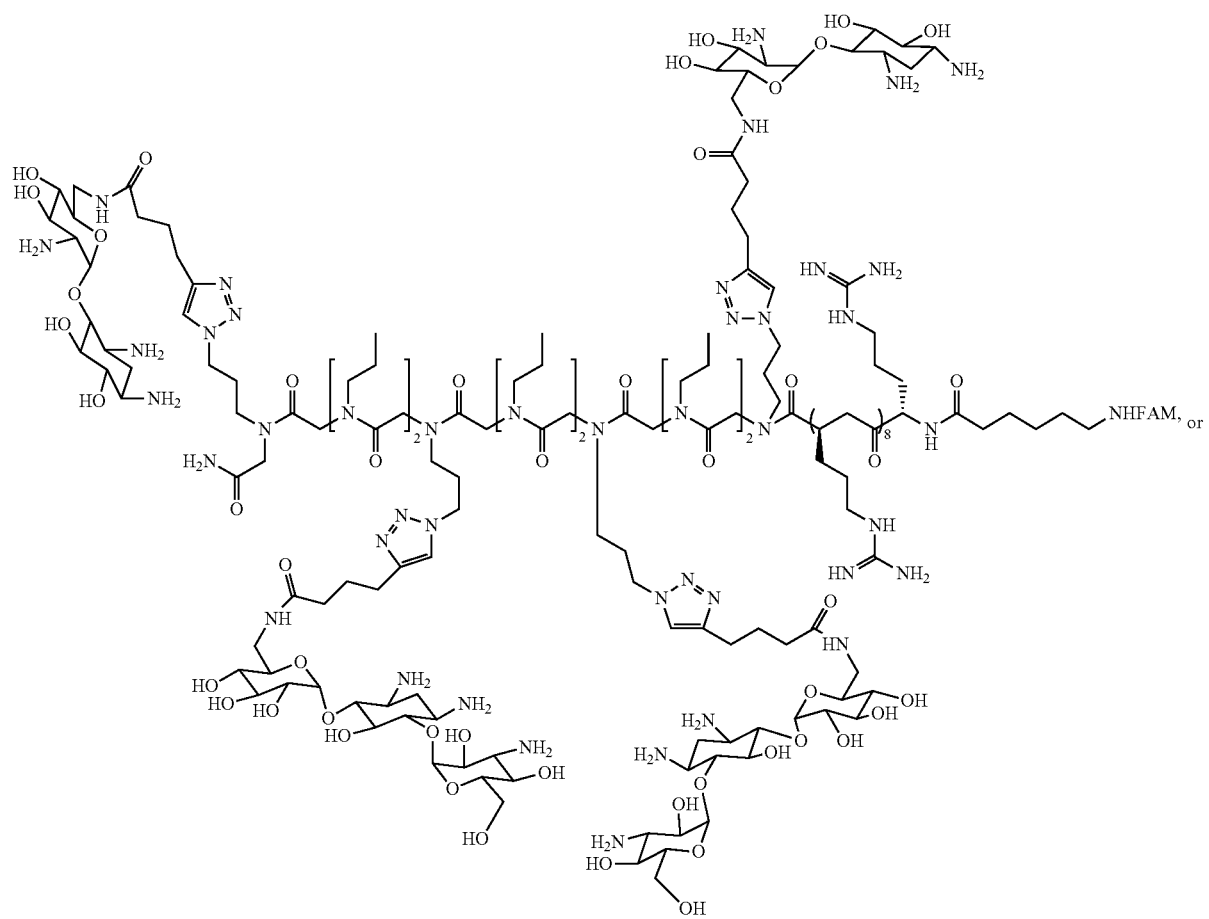

-continued

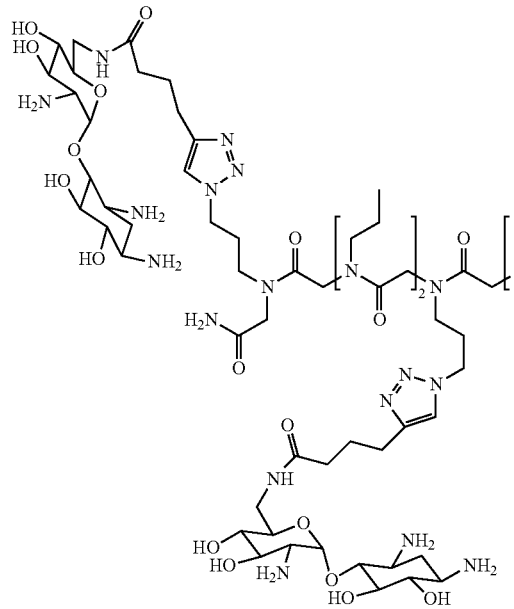
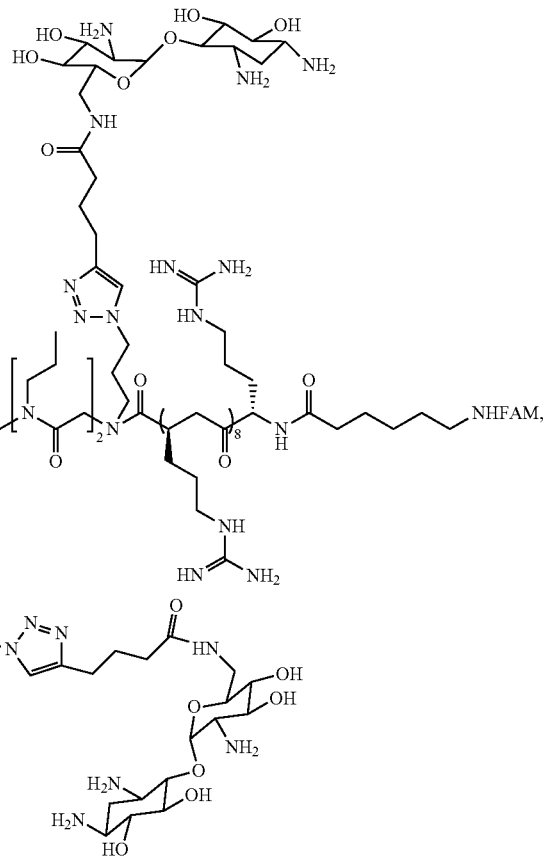

where FAM is a carboxyfluorescein.

5. A compound having the formula:

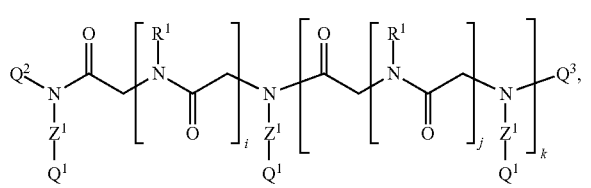

wherein i is an integer from 2 to 9; j is an integer from 0-4; k is an integer from 0-3; each $Z^1$ represents the same or different linking moiety; each $R^1$ is the same or different and represents an alkyl group or an aryl group; each $Q^1$ is the same or different and is selected from protein, polypeptides, carbohydrates, non-nucleic acid biopolymers, peptoids, whole cells, aminoglycoside sugars and bis-benzimidazoles; $Q^2$ is an unsubstituted or substituted alkyl group; and $Q^3$ is H or a substituted carbonyl group.

6. A compound having the formula:

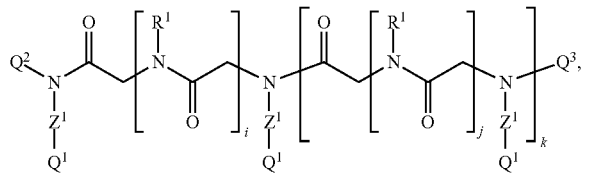

wherein i is an integer from 2 to 9; j is an integer from 0-4; k is an integer from 0-3; each $Z^1$ represents the same or different linking moiety and has one of the following structure:

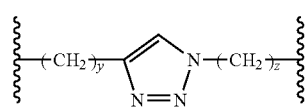

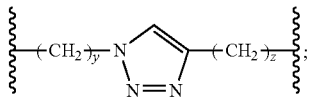

each $R^1$ is the same or different and represents an alkyl group or an aryl group; each $Q^1$ is the same or different and is selected from protein, polypeptides, carbohydrates, non-nucleic acid biopolymers, peptoids, whole cells, aminoglycoside sugars and bis-benzimidazoles; $Q^2$ is an unsubstituted or substituted alkyl group; and $Q^3$ is H or a substituted carbonyl group.

* * * * *

SEQUENCE LISTING

<160> NUMBER OF SEQ ID NOS: 19

<210> SEQ ID NO 1
<211> LENGTH: 46
<212> TYPE: RNA
<213> ORGANISM: artificial sequence
<220> FEATURE:
<223> OTHER INFORMATION: RNA sequence displaying internal loop motif

<400> SEQUENCE: 1
gggagagggu uuaaucugua cgaaaguacu gauuggaucc gcaagg    46

<210> SEQ ID NO 2
<211> LENGTH: 40
<212> TYPE: RNA
<213> ORGANISM: artificial sequence
<220> FEATURE:
<223> OTHER INFORMATION: Cassette sequence

<400> SEQUENCE: 2
gggagagggu uuaauuacga aaguaauugg auccgcaagg    40

<210> SEQ ID NO 3
<211> LENGTH: 18
<212> TYPE: RNA
<213> ORGANISM: artificial sequence
<220> FEATURE:
<223> OTHER INFORMATION: Stem sequence

<400> SEQUENCE: 3
gggagagggu uuaauuac    18

<210> SEQ ID NO 4
<211> LENGTH: 18
<212> TYPE: RNA
<213> ORGANISM: artificial sequence
<220> FEATURE:
<223> OTHER INFORMATION: Stem sequence

<400> SEQUENCE: 4
guaauuggau ccgcaagg    18

<210> SEQ ID NO 5
<211> LENGTH: 10
<212> TYPE: RNA
<213> ORGANISM: artificial sequence
<220> FEATURE:
<223> OTHER INFORMATION: Hairpin loop sequence

<400> SEQUENCE: 5
cgcgaaagcg    10

<210> SEQ ID NO 6
<211> LENGTH: 87
<212> TYPE: RNA
<213> ORGANISM: artificial sequence
<220> FEATURE:
<223> OTHER INFORMATION: CUG repeat

<400> SEQUENCE: 6
cugcugcugc ugcugcugcu gcugcugcug cugcugcugc ugcugcugcu gcugcugcug    60
cugcugcugc ugcugcugcu gcugcug    87

<210> SEQ ID NO 7
<211> LENGTH: 19

```
<212> TYPE: DNA
<213> ORGANISM: artificial sequence
<220> FEATURE:
<223> OTHER INFORMATION: Labeled probe

<400> SEQUENCE: 7
cagcagcagc agcagcagc                                                  19

<210> SEQ ID NO 8
<211> LENGTH: 24
<212> TYPE: DNA
<213> ORGANISM: artificial sequence
<220> FEATURE:
<223> OTHER INFORMATION: Primer

<400> SEQUENCE: 8
tgaaggaata cctcacactc aagg                                            24

<210> SEQ ID NO 9
<211> LENGTH: 20
<212> TYPE: DNA
<213> ORGANISM: artificial sequence
<220> FEATURE:
<223> OTHER INFORMATION: Primer

<400> SEQUENCE: 9
cacggaacac aaaggcactg                                                 20

<210> SEQ ID NO 10
<211> LENGTH: 23
<212> TYPE: DNA
<213> ORGANISM: artificial sequence
<220> FEATURE:
<223> OTHER INFORMATION: Primer

<400> SEQUENCE: 10
gctcatggtc ctcaagatct cac                                             23

<210> SEQ ID NO 11
<211> LENGTH: 20
<212> TYPE: DNA
<213> ORGANISM: artificial sequence
<220> FEATURE:
<223> OTHER INFORMATION: Primer

<400> SEQUENCE: 11
gggtcagtgc ctcagctttg                                                 20

<210> SEQ ID NO 12
<211> LENGTH: 25
<212> TYPE: DNA
<213> ORGANISM: artificial sequence
<220> FEATURE:
<223> OTHER INFORMATION: Oligonucleotide

<400> SEQUENCE: 12
gttcacaacc atctaaagca agatg                                           25

<210> SEQ ID NO 13
<211> LENGTH: 19
<212> TYPE: DNA
<213> ORGANISM: artificial sequence
<220> FEATURE:
<223> OTHER INFORMATION: Oligonucleotide

<400> SEQUENCE: 13
```

-continued

```
gttgcatggc tggtgcagg                                              19

<210> SEQ ID NO 14
<211> LENGTH: 30
<212> TYPE: DNA
<213> ORGANISM: artificial sequence
<220> FEATURE:
<223> OTHER INFORMATION: Primer

<400> SEQUENCE: 14
cggggtacca aatgctgcag ttgactctcc                                  30

<210> SEQ ID NO 15
<211> LENGTH: 29
<212> TYPE: DNA
<213> ORGANISM: artificial sequence
<220> FEATURE:
<223> OTHER INFORMATION: Primer

<400> SEQUENCE: 15
ccgctcgagc cattcatgaa gtgcacagg                                   29

<210> SEQ ID NO 16
<211> LENGTH: 22
<212> TYPE: DNA
<213> ORGANISM: artificial sequence
<220> FEATURE:
<223> OTHER INFORMATION: Primer

<400> SEQUENCE: 16
agctatttta ggcgcaggaa gt                                          22

<210> SEQ ID NO 17
<211> LENGTH: 22
<212> TYPE: DNA
<213> ORGANISM: artificial sequence
<220> FEATURE:
<223> OTHER INFORMATION: Primer

<400> SEQUENCE: 17
ttttcatcca gcatcatttc tg                                          22

<210> SEQ ID NO 18
<211> LENGTH: 21
<212> TYPE: DNA
<213> ORGANISM: artificial sequence
<220> FEATURE:
<223> OTHER INFORMATION: Primer

<400> SEQUENCE: 18
cctggtgaag accatgatac g                                           21

<210> SEQ ID NO 19
<211> LENGTH: 18
<212> TYPE: DNA
<213> ORGANISM: artificial sequence
<220> FEATURE:
<223> OTHER INFORMATION: Primer

<400> SEQUENCE: 19
ggcccagcaa ctttccac                                               18
```